(12) United States Patent
Guyenot et al.

(10) Patent No.: US 11,357,624 B2
(45) Date of Patent: *Jun. 14, 2022

(54) MEDICAL DEVICE FOR TREATING A HEART VALVE INSUFFICIENCY

(71) Applicant: JenaValve Technology, Inc., Irvine, CA (US)

(72) Inventors: Volker Guyenot, Jena (DE); Thomas Peschel, Jena (DE); Christoph Damm, Jena (DE); Hans-Reiner Figulla, Jena (DE); Markus Ferrari, Jena (DE); Johannes Jung, Pforzheim (DE)

(73) Assignee: JenaValve Technology, Inc., Irvine, CA (US)

( * ) Notice: Subject to any disclaimer, the term of this patent is extended or adjusted under 35 U.S.C. 154(b) by 260 days.

This patent is subject to a terminal disclaimer.

(21) Appl. No.: 16/708,920

(22) Filed: Dec. 10, 2019

(65) Prior Publication Data

US 2020/0179110 A1 Jun. 11, 2020

Related U.S. Application Data

(60) Continuation of application No. 15/889,959, filed on Feb. 6, 2018, now Pat. No. 10,543,084, which is a
(Continued)

(51) Int. Cl.
*A61F 2/24* (2006.01)

(52) U.S. Cl.
CPC .......... *A61F 2/2418* (2013.01); *A61F 2/2442* (2013.01); *A61F 2210/0014* (2013.01); *A61F 2220/0008* (2013.01); *A61F 2220/0016* (2013.01); *A61F 2220/0075* (2013.01); *A61F 2230/0013* (2013.01); *A61F 2230/0054* (2013.01); *Y10T 29/5116* (2015.01)

(58) Field of Classification Search
CPC .......... A61F 2/24; A61F 2/2418; A61F 2/2442
See application file for complete search history.

(56) References Cited

U.S. PATENT DOCUMENTS

| 15,192 A | 6/1856 | Peale |
| 388,776 A | 8/1888 | Hall |

(Continued)

FOREIGN PATENT DOCUMENTS

| AU | 757647 B2 | 2/2003 |
| AU | 776895 B2 | 9/2004 |

(Continued)

OTHER PUBLICATIONS

US 6,331,185 B1, 12/2001, Gambale et al. (withdrawn)
(Continued)

*Primary Examiner* — Matthew W Schall
(74) *Attorney, Agent, or Firm* — Eversheds Sutherland (US) LLP; Christopher C. Bolten; Robert D. Ward

(57) ABSTRACT

A medical device for treating a heart valve insufficiency, with an endoprosthesis which can be introduced into a patient's body and expanded to secure a heart valve prosthesis in the patient's aorta. In an embodiment, the endoprosthesis has a plurality of positioning arches configured to be positioned with respect to a patient's aorta and a plurality of retaining arches to support a heart valve prosthesis. The endoprosthesis includes a first collapsed mode during the process of introducing it into the patient's body and a second expanded mode when it is implanted.

20 Claims, 48 Drawing Sheets

Related U.S. Application Data continuation of application No. 15/098,410, filed on Apr. 14, 2016, now Pat. No. 9,918,835, which is a continuation of application No. 14/174,441, filed on Feb. 6, 2014, now Pat. No. 9,339,386, which is a continuation of application No. 13/030,708, filed on Feb. 18, 2011, now Pat. No. 8,685,085, which is a continuation of application No. 12/572,340, filed on Oct. 2, 2009, now Pat. No. 7,914,575, which is a division of application No. 11/785,072, filed on Apr. 13, 2007, now Pat. No. 7,896,915.

(56) References Cited

U.S. PATENT DOCUMENTS

| | | |
|---|---|---|
| 944,214 A | 12/1909 | Rydquist |
| 2,121,182 A | 6/1938 | Benjamin |
| 2,669,896 A | 2/1954 | Clough |
| 2,682,057 A | 6/1954 | Lord |
| 2,701,559 A | 2/1955 | Cooper |
| 2,832,078 A | 4/1958 | Williams |
| 3,029,819 A | 4/1962 | Edward et al. |
| 3,099,016 A | 7/1963 | Lowell et al. |
| 3,113,586 A | 12/1963 | Edmark, Jr. et al. |
| 3,130,418 A | 4/1964 | Head et al. |
| 3,143,742 A | 8/1964 | Cromie |
| 3,210,836 A | 10/1965 | Johanson et al. |
| 3,221,006 A | 11/1965 | Moore et al. |
| 3,334,629 A | 8/1967 | Cohn |
| 3,365,728 A | 1/1968 | Lowell et al. |
| 3,367,364 A | 2/1968 | Cruz, Jr. et al. |
| 3,409,013 A | 11/1968 | Henry et al. |
| 3,445,916 A | 5/1969 | Schulte et al. |
| 3,540,431 A | 11/1970 | Mobin-Uddin et al. |
| 3,548,417 A | 12/1970 | Kischer et al. |
| 3,570,014 A | 3/1971 | Hancock et al. |
| 3,574,865 A | 4/1971 | Hamaker |
| 3,587,115 A | 6/1971 | Shiley et al. |
| 3,592,184 A | 7/1971 | Watkins et al. |
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,725,961 A | 4/1973 | Magovern et al. |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 3,983,581 A | 10/1976 | Angell et al. |
| 3,997,923 A | 12/1976 | Possis |
| 4,035,849 A | 7/1977 | Angell et al. |
| 4,056,854 A | 11/1977 | Boretos et al. |
| 4,078,268 A | 3/1978 | Possis |
| 4,084,268 A | 4/1978 | Ionescu et al. |
| 4,106,126 A | 8/1978 | Traenkle |
| 4,106,129 A | 8/1978 | Carpentier et al. |
| 4,118,806 A | 10/1978 | Porier et al. |
| 4,164,046 A | 8/1979 | Cooley |
| 4,182,446 A | 1/1980 | Penny |
| 4,191,218 A | 3/1980 | Clark et al. |
| 4,214,587 A | 7/1980 | Sakura, Jr. |
| 4,215,871 A | 8/1980 | Hirsch et al. |
| 4,222,126 A | 9/1980 | Boretos et al. |
| 4,233,690 A | 11/1980 | Akins |
| 4,261,342 A | 4/1981 | Aranguren Duo |
| 4,263,680 A | 4/1981 | Reul et al. |
| 4,265,694 A | 5/1981 | Boretos et al. |
| 4,291,420 A | 9/1981 | Reul |
| 4,297,749 A | 11/1981 | Davis et al. |
| 4,319,831 A | 3/1982 | Matsui et al. |
| RE30,912 E | 4/1982 | Hancock |
| 4,323,358 A | 4/1982 | Lentz et al. |
| 4,326,306 A | 4/1982 | Poler |
| 4,339,831 A | 7/1982 | Johnson |
| 4,343,048 A | 8/1982 | Ross et al. |
| 4,345,340 A | 8/1982 | Rosen |
| 4,350,492 A | 9/1982 | Wright et al. |
| 4,373,216 A | 2/1983 | Klawitter |
| 4,388,735 A | 6/1983 | Ionescu et al. |
| 4,406,022 A | 9/1983 | Roy |
| 4,423,809 A | 1/1984 | Mazzocco |
| 4,425,908 A | 1/1984 | Simon |
| 4,441,215 A | 4/1984 | Kaster |
| 4,441,216 A | 4/1984 | Ionescu et al. |
| 4,470,157 A | 9/1984 | Love |
| 4,484,579 A | 11/1984 | Meno et al. |
| 4,485,816 A | 12/1984 | Krumme |
| 4,491,986 A | 1/1985 | Gabbay |
| 4,501,030 A | 2/1985 | Lane |
| 4,502,488 A | 3/1985 | Degironimo et al. |
| 4,531,943 A | 7/1985 | Van Tassel et al. |
| 4,535,483 A | 8/1985 | Klawitter et al. |
| 4,546,499 A | 10/1985 | Possis et al. |
| 4,562,597 A | 1/1986 | Possis et al. |
| 4,574,803 A | 3/1986 | Storz |
| 4,580,568 A | 4/1986 | Gianturco |
| 4,592,340 A | 6/1986 | Boyles |
| 4,602,911 A | 7/1986 | Ahmadi et al. |
| 4,605,407 A | 8/1986 | Black et al. |
| 4,610,688 A | 9/1986 | Silvestrini et al. |
| 4,612,011 A | 9/1986 | Kautzky |
| 4,617,932 A | 10/1986 | Kornberg |
| 4,619,246 A | 10/1986 | Molgaard-Nielsen et al. |
| 4,643,732 A | 2/1987 | Pietsch et al. |
| 4,647,283 A | 3/1987 | Carpentier et al. |
| 4,648,881 A | 3/1987 | Carpentier et al. |
| 4,655,218 A | 4/1987 | Kulik et al. |
| 4,655,771 A | 4/1987 | Wallsten |
| 4,662,885 A | 5/1987 | DiPisa, Jr. |
| 4,665,906 A | 5/1987 | Jervis |
| 4,665,918 A | 5/1987 | Garza et al. |
| 4,680,031 A | 7/1987 | Alonso |
| 4,681,908 A | 7/1987 | Broderick et al. |
| 4,687,483 A | 8/1987 | Fisher et al. |
| 4,692,164 A | 9/1987 | Dzemeshkevich et al. |
| 4,705,516 A | 11/1987 | Barone et al. |
| 4,710,192 A | 12/1987 | Liotta et al. |
| 4,733,665 A | 3/1988 | Palmaz |
| 4,755,181 A | 7/1988 | Igoe |
| 4,759,758 A | 7/1988 | Gabbay |
| 4,769,029 A | 9/1988 | Patel |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,797,901 A | 1/1989 | Goerne et al. |
| 4,806,595 A | 2/1989 | Noishiki et al. |
| 4,819,751 A | 4/1989 | Shimada et al. |
| 4,829,990 A | 5/1989 | Thuroff et al. |
| 4,834,755 A | 5/1989 | Silvestrini et al. |
| 4,846,830 A | 7/1989 | Knoch et al. |
| 4,851,001 A | 7/1989 | Taheri |
| 4,856,516 A | 8/1989 | Hillstead |
| 4,865,600 A | 9/1989 | Carpentier et al. |
| 4,872,874 A | 10/1989 | Taheri |
| 4,873,978 A | 10/1989 | Ginsburg |
| 4,878,495 A | 11/1989 | Grayzel |
| 4,878,906 A | 11/1989 | Lindemann et al. |
| 4,883,458 A | 11/1989 | Shiber |
| 4,885,005 A | 12/1989 | Nashef et al. |
| 4,909,252 A | 3/1990 | Goldberger |
| 4,917,102 A | 4/1990 | Miller et al. |
| 4,922,905 A | 5/1990 | Strecker |
| 4,927,426 A | 5/1990 | Dretler |
| 4,950,227 A | 8/1990 | Savin et al. |
| 4,953,553 A | 9/1990 | Tremulis |
| 4,954,126 A | 9/1990 | Wallsten |
| 4,966,604 A | 10/1990 | Reiss |
| 4,969,890 A | 11/1990 | Sugita et al. |
| 4,979,939 A | 12/1990 | Shiber |
| 4,986,830 A | 1/1991 | Owens et al. |
| 4,994,077 A | 2/1991 | Dobben |

(56) References Cited

U.S. PATENT DOCUMENTS

| | | |
|---|---|---|
| 5,002,556 A | 3/1991 | Ishida et al. |
| 5,002,559 A | 3/1991 | Tower |
| 5,002,566 A | 3/1991 | Carpentier et al. |
| 5,007,896 A | 4/1991 | Shiber |
| 5,026,366 A | 6/1991 | Leckrone |
| 5,026,377 A | 6/1991 | Burton et al. |
| 5,032,128 A | 7/1991 | Alonso |
| 5,035,706 A | 7/1991 | Giantureo et al. |
| 5,037,434 A | 8/1991 | Lane |
| 5,047,041 A | 9/1991 | Samuels |
| 5,053,008 A | 10/1991 | Bajaj |
| 5,059,177 A | 10/1991 | Towne et al. |
| 5,061,273 A | 10/1991 | Yock |
| 5,061,277 A | 10/1991 | Carpentier et al. |
| 5,064,435 A | 11/1991 | Porter |
| 5,078,720 A | 1/1992 | Burton et al. |
| 5,080,668 A | 1/1992 | Bolz et al. |
| 5,085,635 A | 2/1992 | Cragg |
| 5,089,015 A | 2/1992 | Ross |
| 5,094,661 A | 3/1992 | Levy et al. |
| 5,104,399 A | 4/1992 | Lazarus |
| 5,104,407 A | 4/1992 | Lam et al. |
| 5,108,425 A | 4/1992 | Hwang |
| 5,122,154 A | 6/1992 | Rhodes |
| 5,132,473 A | 7/1992 | Furutaka et al. |
| 5,141,494 A | 8/1992 | Danforth et al. |
| 5,143,987 A | 9/1992 | Hansel et al. |
| 5,147,388 A | 9/1992 | Yamazaki |
| 5,152,771 A | 10/1992 | Sabbaghian et al. |
| 5,159,937 A | 11/1992 | Tremulis |
| 5,161,547 A | 11/1992 | Tower |
| 5,163,953 A | 11/1992 | Vince |
| 5,163,955 A | 11/1992 | Love et al. |
| 5,167,628 A | 12/1992 | Boyles |
| 5,178,632 A | 1/1993 | Hanson |
| 5,192,301 A | 3/1993 | Kamiya et al. |
| 5,193,546 A | 3/1993 | Shaknovich |
| 5,197,979 A | 3/1993 | Quintero et al. |
| 5,201,757 A | 4/1993 | Heyn et al. |
| 5,207,695 A | 5/1993 | Trout, III |
| 5,209,741 A | 5/1993 | Spaeth |
| 5,211,183 A | 5/1993 | Wilson |
| 5,215,541 A | 6/1993 | Nashef et al. |
| 5,217,481 A | 6/1993 | Barbara |
| 5,217,483 A | 6/1993 | Tower |
| 5,232,445 A | 8/1993 | Bonzel |
| 5,234,447 A | 8/1993 | Kaster et al. |
| 5,234,456 A | 8/1993 | Silvestrini |
| 5,238,004 A | 8/1993 | Sahatjian et al. |
| 5,258,008 A | 11/1993 | Wilk |
| 5,258,023 A | 11/1993 | Reger |
| 5,258,042 A | 11/1993 | Mehta |
| 5,272,909 A | 12/1993 | Nguyen et al. |
| 5,275,580 A | 1/1994 | Yamazaki |
| 5,279,612 A | 1/1994 | Eberhardt |
| 5,282,847 A | 2/1994 | Trescony et al. |
| 5,287,861 A | 2/1994 | Wilk |
| 5,295,958 A | 3/1994 | Shturman |
| 5,327,774 A | 7/1994 | Nguyen et al. |
| 5,330,486 A | 7/1994 | Wilk |
| 5,330,500 A | 7/1994 | Song |
| 5,332,402 A | 7/1994 | Teitelbaum |
| 5,336,258 A | 8/1994 | Quintero et al. |
| 5,342,348 A | 8/1994 | Kaplan |
| 5,344,426 A | 9/1994 | Lau et al. |
| 5,344,427 A | 9/1994 | Cottenceau et al. |
| 5,344,442 A | 9/1994 | Deac |
| 5,350,398 A | 9/1994 | Pavcnik et al. |
| 5,350,399 A | 9/1994 | Erlebacher et al. |
| 5,352,240 A | 10/1994 | Ross |
| 5,354,330 A | 10/1994 | Hanson et al. |
| 5,360,444 A | 11/1994 | Kusuhara |
| 5,368,608 A | 11/1994 | Levy et al. |
| 5,370,685 A | 12/1994 | Stevens |
| 5,380,054 A | 1/1995 | Galvis |
| 5,387,235 A | 2/1995 | Chuter |
| 5,389,096 A | 2/1995 | Aita et al. |
| 5,389,106 A | 2/1995 | Tower |
| 5,397,351 A | 3/1995 | Pavcnik et al. |
| 5,397,355 A | 3/1995 | Marin et al. |
| 5,409,019 A | 4/1995 | Wilk |
| 5,411,552 A | 5/1995 | Andersen et al. |
| 5,415,633 A | 5/1995 | Lazarus et al. |
| 5,425,739 A | 6/1995 | Jessen |
| 5,425,762 A | 6/1995 | Muller |
| 5,429,144 A | 7/1995 | Wilk |
| 5,431,676 A | 7/1995 | Dubrul et al. |
| 5,433,723 A | 7/1995 | Lindenberg et al. |
| 5,443,446 A | 8/1995 | Shturman |
| 5,443,449 A | 8/1995 | Buelna |
| 5,443,477 A | 8/1995 | Marin et al. |
| 5,443,495 A | 8/1995 | Buscemi et al. |
| 5,443,499 A | 8/1995 | Schmitt |
| 5,449,384 A | 9/1995 | Johnson |
| 5,456,712 A | 10/1995 | Maginot |
| 5,456,713 A | 10/1995 | Chuter |
| 5,464,449 A | 11/1995 | Ryan et al. |
| 5,469,868 A | 11/1995 | Reger |
| 5,470,320 A | 11/1995 | Tiefenbrun et al. |
| 5,476,506 A | 12/1995 | Lunn |
| 5,476,508 A | 12/1995 | Amstrup |
| 5,476,510 A | 12/1995 | Eberhardt et al. |
| 5,480,423 A | 1/1996 | Ravenscroft et al. |
| 5,480,424 A | 1/1996 | Cox |
| 5,486,193 A | 1/1996 | Bourne et al. |
| 5,487,760 A | 1/1996 | Villafana |
| 5,489,294 A | 2/1996 | McVenes et al. |
| 5,489,297 A | 2/1996 | Duran |
| 5,489,298 A | 2/1996 | Love et al. |
| 5,496,346 A | 3/1996 | Horzewski et al. |
| 5,499,995 A | 3/1996 | Teirstein |
| 5,500,014 A | 3/1996 | Quijano et al. |
| 5,500,015 A | 3/1996 | Deac |
| 5,507,767 A | 4/1996 | Maeda et al. |
| 5,509,930 A | 4/1996 | Love |
| 5,522,881 A | 6/1996 | Lentz |
| 5,527,337 A | 6/1996 | Stack et al. |
| 5,530,949 A | 6/1996 | Koda et al. |
| 5,534,007 A | 7/1996 | St. Germain et al. |
| 5,540,712 A | 7/1996 | Kleshinski et al. |
| 5,545,133 A | 8/1996 | Burns et al. |
| 5,545,209 A | 8/1996 | Roberts et al. |
| 5,545,211 A | 8/1996 | An et al. |
| 5,545,214 A | 8/1996 | Stevens |
| 5,549,665 A | 8/1996 | Vesely et al. |
| 5,549,666 A | 8/1996 | Hata et al. |
| 5,554,119 A | 9/1996 | Harrison et al. |
| 5,554,185 A | 9/1996 | Block et al. |
| 5,569,274 A | 10/1996 | Rapacki et al. |
| 5,571,167 A | 11/1996 | Maginot |
| 5,571,174 A | 11/1996 | Love et al. |
| 5,571,175 A | 11/1996 | Vanney et al. |
| 5,571,215 A | 11/1996 | Sterman et al. |
| 5,573,520 A | 11/1996 | Schwartz et al. |
| 5,575,818 A | 11/1996 | Pinchuk |
| 5,580,922 A | 12/1996 | Park et al. |
| 5,591,185 A | 1/1997 | Kilmer et al. |
| 5,591,195 A | 1/1997 | Taheri et al. |
| 5,593,434 A | 1/1997 | Williams |
| 5,595,571 A | 1/1997 | Jaffe et al. |
| 5,596,471 A | 1/1997 | Hanlin |
| 5,607,464 A | 3/1997 | Trescony et al. |
| 5,607,465 A | 3/1997 | Camilli |
| 5,609,626 A | 3/1997 | Quijano et al. |
| 5,613,982 A | 3/1997 | Goldstein |
| 5,618,299 A | 4/1997 | Khosravi et al. |
| 5,626,553 A | 5/1997 | Frassica et al. |
| 5,628,784 A | 5/1997 | Strecker |
| 5,632,778 A | 5/1997 | Goldstein |
| 5,634,942 A | 6/1997 | Chevillon et al. |
| 5,643,278 A | 7/1997 | Wijay |
| 5,645,559 A | 7/1997 | Hachtman et al. |
| 5,653,684 A | 8/1997 | Laptewicz et al. |
| 5,653,745 A | 8/1997 | Trescony et al. |

(56) References Cited

U.S. PATENT DOCUMENTS

| | | |
|---|---|---|
| 5,653,749 A | 8/1997 | Love et al. |
| 5,655,548 A | 8/1997 | Nelson et al. |
| 5,662,124 A | 9/1997 | Wilk |
| 5,662,671 A | 9/1997 | Barbut et al. |
| 5,662,703 A | 9/1997 | Yurek et al. |
| 5,665,115 A | 9/1997 | Cragg |
| 5,667,523 A | 9/1997 | Bynon et al. |
| 5,674,277 A | 10/1997 | Freitag |
| 5,674,298 A | 10/1997 | Levy et al. |
| 5,679,112 A | 10/1997 | Levy et al. |
| 5,681,345 A | 10/1997 | Euteneuer |
| 5,682,906 A | 11/1997 | Sterman et al. |
| 5,683,451 A | 11/1997 | Lenker et al. |
| 5,690,644 A | 11/1997 | Yurek et al. |
| 5,693,083 A | 12/1997 | Baker et al. |
| 5,693,088 A | 12/1997 | Lazarus |
| 5,693,310 A | 12/1997 | Gries et al. |
| 5,695,498 A | 12/1997 | Tower |
| 5,697,972 A | 12/1997 | Kim et al. |
| 5,700,269 A | 12/1997 | Pinchuk et al. |
| 5,702,368 A | 12/1997 | Stevens et al. |
| 5,709,713 A | 1/1998 | Evans et al. |
| 5,713,917 A | 2/1998 | Leonhardt et al. |
| 5,713,950 A | 2/1998 | Cox |
| 5,713,951 A | 2/1998 | Garrison et al. |
| 5,713,953 A | 2/1998 | Vallana et al. |
| 5,716,370 A | 2/1998 | Williamson, IV et al. |
| 5,716,417 A | 2/1998 | Girard et al. |
| 5,718,725 A | 2/1998 | Sterman et al. |
| 5,720,391 A | 2/1998 | Dohm et al. |
| 5,720,776 A | 2/1998 | Chuter et al. |
| 5,725,549 A | 3/1998 | Lam |
| 5,725,550 A | 3/1998 | Nadal |
| 5,728,068 A | 3/1998 | Leone et al. |
| 5,728,151 A | 3/1998 | Garrison et al. |
| 5,733,267 A | 3/1998 | Del Toro |
| 5,733,325 A | 3/1998 | Robinson et al. |
| 5,735,842 A | 4/1998 | Krueger et al. |
| 5,746,476 A | 5/1998 | Novak et al. |
| 5,746,709 A | 5/1998 | Rom et al. |
| 5,746,765 A | 5/1998 | Kleshinski et al. |
| 5,746,775 A | 5/1998 | Levy et al. |
| 5,749,890 A | 5/1998 | Shaknovich |
| 5,749,921 A | 5/1998 | Lenker et al. |
| 5,755,682 A | 5/1998 | Knudson et al. |
| 5,755,777 A | 5/1998 | Chuter |
| 5,755,783 A | 5/1998 | Stobie et al. |
| 5,756,476 A | 5/1998 | Epstein et al. |
| 5,758,663 A | 6/1998 | Wilk et al. |
| 5,766,151 A | 6/1998 | Valley et al. |
| 5,769,780 A | 6/1998 | Hata et al. |
| 5,769,812 A | 6/1998 | Stevens et al. |
| 5,769,882 A | 6/1998 | Fogarty et al. |
| 5,769,887 A | 6/1998 | Brown et al. |
| 5,772,609 A | 6/1998 | Nguyen et al. |
| 5,776,188 A | 7/1998 | Shepherd et al. |
| 5,782,809 A | 7/1998 | Umeno et al. |
| 5,782,904 A | 7/1998 | White et al. |
| 5,795,331 A | 8/1998 | Cragg et al. |
| 5,797,946 A | 8/1998 | Chin |
| 5,797,960 A | 8/1998 | Stevens et al. |
| 5,799,661 A | 9/1998 | Boyd et al. |
| 5,800,456 A | 9/1998 | Maeda et al. |
| 5,800,508 A | 9/1998 | Goicoechea et al. |
| 5,800,531 A | 9/1998 | Cosgrove et al. |
| 5,807,327 A | 9/1998 | Green et al. |
| 5,807,384 A | 9/1998 | Mueller |
| 5,807,405 A | 9/1998 | Vanney et al. |
| 5,810,836 A | 9/1998 | Hussein et al. |
| 5,814,016 A | 9/1998 | Valley et al. |
| 5,817,113 A | 10/1998 | Gifford, III et al. |
| 5,817,126 A | 10/1998 | Imran |
| 5,823,956 A | 10/1998 | Roth et al. |
| 5,824,037 A | 10/1998 | Fogarty et al. |
| 5,824,038 A | 10/1998 | Wall |
| 5,824,041 A | 10/1998 | Lenker et al. |
| 5,824,043 A | 10/1998 | Cottone, Jr. |
| 5,824,053 A | 10/1998 | Khosravi et al. |
| 5,824,055 A | 10/1998 | Spiridigliozzi et al. |
| 5,824,056 A | 10/1998 | Rosenberg |
| 5,824,061 A | 10/1998 | Quijano et al. |
| 5,824,063 A | 10/1998 | Cox |
| 5,824,064 A | 10/1998 | Taheri |
| 5,824,071 A | 10/1998 | Nelson et al. |
| 5,824,080 A | 10/1998 | Lamuraglia |
| 5,829,447 A | 11/1998 | Stevens et al. |
| 5,830,222 A | 11/1998 | Makower |
| 5,840,081 A | 11/1998 | Andersen et al. |
| 5,841,382 A | 11/1998 | Walden et al. |
| 5,843,158 A | 12/1998 | Lenker et al. |
| 5,843,161 A | 12/1998 | Solovay |
| 5,843,181 A | 12/1998 | Jaffe et al. |
| 5,851,232 A | 12/1998 | Lois |
| 5,853,419 A | 12/1998 | Imran |
| 5,853,420 A | 12/1998 | Chevillon et al. |
| 5,855,210 A | 1/1999 | Sterman et al. |
| 5,855,597 A | 1/1999 | Jayaraman |
| 5,855,600 A | 1/1999 | Alt |
| 5,855,601 A | 1/1999 | Bessler et al. |
| 5,855,602 A | 1/1999 | Angell |
| 5,860,966 A | 1/1999 | Tower |
| 5,860,996 A | 1/1999 | Urban et al. |
| 5,861,024 A | 1/1999 | Rashidi |
| 5,861,028 A | 1/1999 | Angell |
| 5,865,723 A | 2/1999 | Love |
| 5,868,783 A | 2/1999 | Tower |
| 5,873,812 A | 2/1999 | Ciana et al. |
| 5,873,906 A | 2/1999 | Lau et al. |
| 5,876,373 A | 3/1999 | Giba et al. |
| 5,876,419 A | 3/1999 | Carpenter et al. |
| 5,876,434 A | 3/1999 | Flomenblit et al. |
| 5,876,448 A | 3/1999 | Thompson et al. |
| 5,878,751 A | 3/1999 | Hussein et al. |
| 5,880,242 A | 3/1999 | Hu et al. |
| 5,885,228 A | 3/1999 | Rosenman et al. |
| 5,885,238 A | 3/1999 | Stevens et al. |
| 5,885,259 A | 3/1999 | Berg |
| 5,888,201 A | 3/1999 | Stinson et al. |
| 5,891,160 A | 4/1999 | Williamson, IV et al. |
| 5,891,191 A | 4/1999 | Stinson |
| 5,895,399 A | 4/1999 | Barbut et al. |
| 5,895,420 A | 4/1999 | Mirsch, II et al. |
| 5,899,936 A | 5/1999 | Goldstein |
| 5,906,619 A | 5/1999 | Olson et al. |
| 5,907,893 A | 6/1999 | Zadno-Azizi et al. |
| 5,908,028 A | 6/1999 | Wilk |
| 5,908,029 A | 6/1999 | Knudson et al. |
| 5,908,451 A | 6/1999 | Yeo |
| 5,908,452 A | 6/1999 | Bokros et al. |
| 5,910,144 A | 6/1999 | Hayashi |
| 5,910,154 A | 6/1999 | Tsugita et al. |
| 5,911,734 A | 6/1999 | Tsugita et al. |
| 5,911,752 A | 6/1999 | Dustrude et al. |
| 5,913,842 A | 6/1999 | Boyd et al. |
| 5,916,193 A | 6/1999 | Stevens et al. |
| 5,922,022 A | 7/1999 | Nash et al. |
| 5,924,424 A | 7/1999 | Stevens et al. |
| 5,925,012 A | 7/1999 | Murphy-Chutorian et al. |
| 5,925,063 A | 7/1999 | Khosravi |
| 5,928,281 A | 7/1999 | Huynh et al. |
| 5,931,848 A | 8/1999 | Saadat |
| 5,935,119 A | 8/1999 | Guy et al. |
| 5,935,161 A | 8/1999 | Robinson et al. |
| 5,935,163 A | 8/1999 | Gabbay |
| 5,938,632 A | 8/1999 | Ellis |
| 5,938,697 A | 8/1999 | Killion et al. |
| 5,941,908 A | 8/1999 | Goldsteen et al. |
| 5,944,019 A | 8/1999 | Knudson et al. |
| 5,944,738 A | 8/1999 | Amplatz et al. |
| B1 5,104,404 I5 | 9/1999 | Lam et al. |
| 5,948,017 A | 9/1999 | Taheri |
| 5,954,764 A | 9/1999 | Parodi |
| 5,954,766 A | 9/1999 | Zadno-Azizi et al. |
| 5,957,949 A | 9/1999 | Leonhardt et al. |

(56) References Cited

U.S. PATENT DOCUMENTS

| | | |
|---|---|---|
| 5,961,549 A | 10/1999 | Nguyen et al. |
| 5,964,405 A | 10/1999 | Benary et al. |
| 5,964,798 A | 10/1999 | Imran |
| 5,968,064 A | 10/1999 | Selmon et al. |
| 5,968,068 A | 10/1999 | Dehdashtian et al. |
| 5,968,070 A | 10/1999 | Bley et al. |
| 5,971,993 A | 10/1999 | Hussein et al. |
| 5,975,949 A | 11/1999 | Holliday et al. |
| 5,976,153 A | 11/1999 | Fischell et al. |
| 5,976,155 A | 11/1999 | Foreman et al. |
| 5,976,174 A | 11/1999 | Ruiz |
| 5,976,178 A | 11/1999 | Goldsteen et al. |
| 5,976,192 A | 11/1999 | McIntyre et al. |
| 5,976,650 A | 11/1999 | Campbell et al. |
| 5,979,455 A | 11/1999 | Maginot |
| 5,980,455 A | 11/1999 | Daniel et al. |
| 5,980,533 A | 11/1999 | Holman |
| 5,980,548 A | 11/1999 | Evans et al. |
| 5,984,956 A | 11/1999 | Tweden et al. |
| 5,984,957 A | 11/1999 | Laptewicz, Jr. et al. |
| 5,984,959 A | 11/1999 | Robertson et al. |
| 5,984,964 A | 11/1999 | Roberts et al. |
| 5,987,344 A | 11/1999 | West |
| 5,989,276 A | 11/1999 | Houser et al. |
| 5,989,287 A | 11/1999 | Yang et al. |
| 5,993,469 A | 11/1999 | McKenzie et al. |
| 5,993,481 A | 11/1999 | Marcade et al. |
| 5,997,525 A | 12/1999 | March et al. |
| 5,997,557 A | 12/1999 | Barbut et al. |
| 5,997,563 A | 12/1999 | Kretzers |
| 5,997,573 A | 12/1999 | Quijano et al. |
| 5,999,678 A | 12/1999 | Murphy-Chutorian et al. |
| 6,001,123 A | 12/1999 | Lau |
| 6,001,126 A | 12/1999 | Nguyen-Thien-Nhon |
| 6,004,261 A | 12/1999 | Sinofsky et al. |
| 6,004,347 A | 12/1999 | McNamara et al. |
| 6,004,348 A | 12/1999 | Banas et al. |
| 6,007,543 A | 12/1999 | Ellis et al. |
| 6,010,449 A | 1/2000 | Selmon et al. |
| 6,010,522 A | 1/2000 | Barbut et al. |
| 6,010,530 A | 1/2000 | Goicoechea |
| 6,010,531 A | 1/2000 | Donlon et al. |
| 6,012,457 A | 1/2000 | Lesh |
| 6,013,854 A | 1/2000 | Moriuchi |
| 6,015,431 A | 1/2000 | Thornton et al. |
| B150,612 I5 | 2/2000 | Carpentier et al. |
| 6,019,777 A | 2/2000 | Mackenzie |
| 6,019,778 A | 2/2000 | Wilson et al. |
| 6,022,370 A | 2/2000 | Tower |
| 6,026,814 A | 2/2000 | LaFontaine et al. |
| 6,027,476 A | 2/2000 | Sterman et al. |
| 6,027,520 A | 2/2000 | Tsugita et al. |
| 6,027,525 A | 2/2000 | Suh et al. |
| 6,029,671 A | 2/2000 | Stevens et al. |
| 6,029,672 A | 2/2000 | Vanney et al. |
| 6,033,582 A | 3/2000 | Lee et al. |
| 6,035,856 A | 3/2000 | LaFontaine et al. |
| 6,036,677 A | 3/2000 | Javier, Jr. et al. |
| 6,036,697 A | 3/2000 | DiCaprio |
| 6,042,554 A | 3/2000 | Rosenman et al. |
| 6,042,581 A | 3/2000 | Ryan et al. |
| 6,042,589 A | 3/2000 | Marianne |
| 6,042,598 A | 3/2000 | Tsugita et al. |
| 6,042,607 A | 3/2000 | Williamson, IV et al. |
| 6,045,565 A | 4/2000 | Ellis et al. |
| 6,051,014 A | 4/2000 | Jang |
| 6,051,104 A | 4/2000 | Oriaran et al. |
| 6,053,924 A | 4/2000 | Hussein |
| 6,053,942 A | 4/2000 | Eno et al. |
| 6,056,743 A | 5/2000 | Ellis et al. |
| 6,059,809 A | 5/2000 | Amor et al. |
| 6,059,827 A | 5/2000 | Fenton, Jr. |
| 6,066,160 A | 5/2000 | Colvin et al. |
| 6,067,988 A | 5/2000 | Mueller |
| 6,068,638 A | 5/2000 | Makower |
| 6,071,292 A | 6/2000 | Makower et al. |
| 6,074,416 A | 6/2000 | Berg et al. |
| 6,074,417 A | 6/2000 | Peredo |
| 6,074,418 A | 6/2000 | Buchanan et al. |
| 6,076,529 A | 6/2000 | Vanney et al. |
| 6,076,742 A | 6/2000 | Benary |
| 6,077,297 A | 6/2000 | Robinson et al. |
| 6,079,414 A | 6/2000 | Roth |
| 6,080,163 A | 6/2000 | Hussein et al. |
| 6,080,170 A | 6/2000 | Nash et al. |
| 6,083,257 A | 7/2000 | Taylor et al. |
| 6,091,042 A | 7/2000 | Benary |
| 6,092,526 A | 7/2000 | LaFontaine et al. |
| 6,092,529 A | 7/2000 | Cox |
| 6,093,166 A | 7/2000 | Knudson et al. |
| 6,093,177 A | 7/2000 | Javier, Jr. et al. |
| 6,093,185 A | 7/2000 | Ellis et al. |
| 6,093,203 A | 7/2000 | Uflacker |
| 6,093,530 A | 7/2000 | McIlroy et al. |
| 6,096,074 A | 8/2000 | Pedros |
| 6,102,941 A | 8/2000 | Tweden et al. |
| 6,102,944 A | 8/2000 | Huynh et al. |
| 6,106,550 A | 8/2000 | Magovern et al. |
| 6,110,191 A | 8/2000 | Dehdashtian et al. |
| 6,110,198 A | 8/2000 | Fogarty et al. |
| 6,110,201 A | 8/2000 | Quijano et al. |
| 6,113,612 A | 9/2000 | Swanson et al. |
| 6,113,630 A | 9/2000 | Vanney et al. |
| 6,113,823 A | 9/2000 | Eno |
| 6,117,169 A | 9/2000 | Moe |
| 6,120,520 A | 9/2000 | Saadat et al. |
| 6,120,534 A | 9/2000 | Ruiz |
| 6,123,682 A | 9/2000 | Knudson et al. |
| 6,123,723 A | 9/2000 | Konya et al. |
| 6,125,852 A | 10/2000 | Stevens et al. |
| 6,126,649 A | 10/2000 | Vantassel et al. |
| 6,126,654 A | 10/2000 | Giba et al. |
| 6,126,685 A | 10/2000 | Lenker et al. |
| 6,126,686 A | 10/2000 | Badylak et al. |
| 6,132,451 A | 10/2000 | Payne et al. |
| 6,132,473 A | 10/2000 | Williams et al. |
| 6,132,986 A | 10/2000 | Pathak et al. |
| 6,139,510 A | 10/2000 | Palermo |
| 6,139,541 A | 10/2000 | Vanney et al. |
| 6,142,987 A | 11/2000 | Tsugita |
| 6,143,021 A | 11/2000 | Staehle |
| 6,143,987 A | 11/2000 | Makita |
| 6,146,366 A | 11/2000 | Schachar |
| 6,146,415 A | 11/2000 | Fitz |
| 6,146,417 A | 11/2000 | Ischinger |
| 6,152,937 A | 11/2000 | Peterson et al. |
| 6,152,956 A | 11/2000 | Pierce |
| 6,155,264 A | 12/2000 | Ressemann et al. |
| 6,156,031 A | 12/2000 | Aita et al. |
| 6,156,055 A | 12/2000 | Ravenscroft |
| 6,156,531 A | 12/2000 | Pathak et al. |
| 6,157,852 A | 12/2000 | Selmon et al. |
| 6,159,225 A | 12/2000 | Makower |
| 6,159,239 A | 12/2000 | Greenhalgh |
| 6,162,208 A | 12/2000 | Hipps |
| 6,162,245 A | 12/2000 | Jayaraman |
| 6,165,185 A | 12/2000 | Shennib et al. |
| 6,165,188 A | 12/2000 | Saadat et al. |
| 6,165,200 A | 12/2000 | Tsugita et al. |
| 6,165,209 A | 12/2000 | Patterson et al. |
| 6,167,605 B1 | 1/2001 | Morales |
| 6,168,579 B1 | 1/2001 | Tsugita |
| 6,168,614 B1 | 1/2001 | Andersen et al. |
| 6,168,616 B1 | 1/2001 | Brown, III |
| 6,171,251 B1 | 1/2001 | Mueller et al. |
| 6,171,327 B1 | 1/2001 | Daniel et al. |
| 6,171,335 B1 | 1/2001 | Wheatley et al. |
| 6,177,514 B1 | 1/2001 | Pathak et al. |
| 6,179,859 B1 | 1/2001 | Bates et al. |
| 6,182,664 B1 | 2/2001 | Cosgrove |
| 6,182,668 B1 | 2/2001 | Tweden et al. |
| 6,183,481 B1 | 2/2001 | Lee et al. |
| 6,186,972 B1 | 2/2001 | Nelson et al. |
| 6,187,016 B1 | 2/2001 | Hedges et al. |

(56) References Cited

U.S. PATENT DOCUMENTS

| | | |
|---|---|---|
| 6,190,353 B1 | 2/2001 | Makower et al. |
| 6,190,393 B1 | 2/2001 | Bevier et al. |
| 6,190,405 B1 | 2/2001 | Culombo et al. |
| 6,193,726 B1 | 2/2001 | Vanney |
| 6,193,734 B1 | 2/2001 | Bolduc et al. |
| 6,196,230 B1 | 3/2001 | Hall et al. |
| 6,197,050 B1 | 3/2001 | Eno et al. |
| 6,197,053 B1 | 3/2001 | Cosgrove et al. |
| 6,197,296 B1 | 3/2001 | Davies et al. |
| 6,197,324 B1 | 3/2001 | Crittenden |
| 6,200,311 B1 | 3/2001 | Danek et al. |
| 6,200,336 B1 | 3/2001 | Pavcnik et al. |
| 6,203,550 B1 | 3/2001 | Olson |
| 6,203,556 B1 | 3/2001 | Evans et al. |
| 6,206,888 B1 | 3/2001 | Bicek et al. |
| 6,206,911 B1 | 3/2001 | Milo |
| 6,210,408 B1 | 4/2001 | Chandrasekaran et al. |
| 6,210,957 B1 | 4/2001 | Carpentier et al. |
| 6,213,126 B1 | 4/2001 | LaFontaine et al. |
| 6,214,036 B1 | 4/2001 | Letendre et al. |
| 6,214,041 B1 | 4/2001 | Tweden et al. |
| 6,214,054 B1 | 4/2001 | Cunanan et al. |
| 6,214,055 B1 | 4/2001 | Simionescu et al. |
| 6,217,527 B1 | 4/2001 | Selmon et al. |
| 6,217,549 B1 | 4/2001 | Selmon et al. |
| 6,217,575 B1 | 4/2001 | DeVore et al. |
| 6,217,609 B1 | 4/2001 | Haverkost |
| 6,218,662 B1 | 4/2001 | Tchakarov et al. |
| 6,221,006 B1 | 4/2001 | Dubrul et al. |
| 6,221,049 B1 | 4/2001 | Selmon et al. |
| 6,221,091 B1 | 4/2001 | Khosravi |
| 6,221,096 B1 | 4/2001 | Aiba et al. |
| 6,221,100 B1 | 4/2001 | Strecker |
| 6,223,752 B1 | 5/2001 | Vanney et al. |
| 6,224,584 B1 | 5/2001 | March et al. |
| 6,231,544 B1 | 5/2001 | Tsugita et al. |
| 6,231,546 B1 | 5/2001 | Milo et al. |
| 6,231,551 B1 | 5/2001 | Barbut |
| 6,231,587 B1 | 5/2001 | Makower |
| 6,231,602 B1 | 5/2001 | Carpentier et al. |
| 6,235,000 B1 | 5/2001 | Milo et al. |
| 6,237,607 B1 | 5/2001 | Vanney et al. |
| 6,238,406 B1 | 5/2001 | Ellis et al. |
| 6,241,667 B1 | 6/2001 | Vetter et al. |
| 6,241,738 B1 | 6/2001 | Dereume |
| 6,241,741 B1 | 6/2001 | Duhaylongsod et al. |
| 6,241,757 B1 | 6/2001 | An et al. |
| 6,245,102 B1 | 6/2001 | Jayaraman |
| 6,245,103 B1 | 6/2001 | Stinson |
| 6,245,105 B1 | 6/2001 | Nguyen et al. |
| 6,248,112 B1 | 6/2001 | Gambale et al. |
| 6,248,116 B1 | 6/2001 | Chevillon et al. |
| 6,250,305 B1 | 6/2001 | Tweden |
| 6,251,079 B1 | 6/2001 | Gambale et al. |
| 6,251,104 B1 | 6/2001 | Kesten et al. |
| 6,251,116 B1 | 6/2001 | Shennib et al. |
| 6,251,135 B1 | 6/2001 | Stinson et al. |
| 6,251,418 B1 | 6/2001 | Ahern et al. |
| 6,253,768 B1 | 7/2001 | Wilk |
| 6,253,769 B1 | 7/2001 | LaFontaine et al. |
| 6,254,564 B1 | 7/2001 | Wilk et al. |
| 6,254,635 B1 | 7/2001 | Schroeder et al. |
| 6,254,636 B1 | 7/2001 | Peredo |
| 6,257,634 B1 | 7/2001 | Wei |
| 6,258,052 B1 | 7/2001 | Milo |
| 6,258,087 B1 | 7/2001 | Edwards et al. |
| 6,258,114 B1 | 7/2001 | Konya et al. |
| 6,258,115 B1 | 7/2001 | Dubrul |
| 6,258,119 B1 | 7/2001 | Hussein et al. |
| 6,258,120 B1 | 7/2001 | McKenzie et al. |
| 6,258,129 B1 | 7/2001 | Dybdal et al. |
| 6,258,150 B1 | 7/2001 | Mackellar |
| 6,261,304 B1 | 7/2001 | Hall et al. |
| 6,267,783 B1 | 7/2001 | Letendre et al. |
| 6,269,819 B1 | 8/2001 | Oz et al. |
| 6,270,513 B1 | 8/2001 | Tsugita et al. |
| 6,270,521 B1 | 8/2001 | Fischell et al. |
| 6,270,526 B1 | 8/2001 | Cox |
| 6,273,876 B1 | 8/2001 | Klima et al. |
| 6,273,895 B1 | 8/2001 | Pinchuk et al. |
| 6,276,661 B1 | 8/2001 | Laird |
| 6,277,555 B1 | 8/2001 | Duran et al. |
| 6,283,127 B1 | 9/2001 | Sterman et al. |
| 6,283,951 B1 | 9/2001 | Flaherty et al. |
| 6,283,983 B1 | 9/2001 | Makower et al. |
| 6,283,995 B1 | 9/2001 | Moe et al. |
| 6,285,903 B1 | 9/2001 | Rosenthal et al. |
| 6,287,317 B1 | 9/2001 | Makower et al. |
| 6,287,334 B1 | 9/2001 | Moll et al. |
| 6,287,338 B1 | 9/2001 | Sarnowski et al. |
| 6,287,339 B1 | 9/2001 | Vazquez et al. |
| 6,290,709 B1 | 9/2001 | Ellis et al. |
| 6,290,728 B1 | 9/2001 | Phelps et al. |
| 6,296,662 B1 | 10/2001 | Caffey |
| 6,299,637 B1 | 10/2001 | Shaolian et al. |
| 6,302,875 B1 | 10/2001 | Makower et al. |
| 6,302,892 B1 | 10/2001 | Wilk |
| 6,302,906 B1 | 10/2001 | Goicoechea et al. |
| 6,306,164 B1 | 10/2001 | Kujawski |
| 6,309,382 B1 | 10/2001 | Garrison et al. |
| 6,309,417 B1 | 10/2001 | Spence et al. |
| 6,311,693 B1 | 11/2001 | Sterman et al. |
| 6,312,465 B1 | 11/2001 | Griffin et al. |
| 6,319,281 B1 | 11/2001 | Patel |
| 6,322,548 B1 | 11/2001 | Payne et al. |
| 6,322,593 B1 | 11/2001 | Pathak et al. |
| 6,325,067 B1 | 12/2001 | Sterman et al. |
| 6,327,772 B1 | 12/2001 | Zadno-Azizi et al. |
| 6,330,884 B1 | 12/2001 | Kim |
| 6,331,189 B1 | 12/2001 | Wolinsky et al. |
| 6,334,873 B1 | 1/2002 | Lane et al. |
| 6,336,934 B1 | 1/2002 | Gilson et al. |
| 6,336,937 B1 | 1/2002 | Vonesh et al. |
| 6,338,735 B1 | 1/2002 | Stevens |
| 6,338,740 B1 | 1/2002 | Carpentier |
| 6,342,070 B1 | 1/2002 | Nguyen-Thien-Nhon |
| 6,344,044 B1 | 2/2002 | Fulkerson et al. |
| 6,346,074 B1 | 2/2002 | Roth |
| 6,346,116 B1 | 2/2002 | Brooks et al. |
| 6,348,063 B1 | 2/2002 | Yassour et al. |
| 6,350,248 B1 | 2/2002 | Knudson et al. |
| 6,350,277 B1 | 2/2002 | Kocur |
| 6,350,278 B1 | 2/2002 | Lenker et al. |
| 6,352,547 B1 | 3/2002 | Brown et al. |
| 6,352,554 B2 | 3/2002 | De Paulis |
| 6,352,708 B1 | 3/2002 | Duran et al. |
| 6,357,104 B1 | 3/2002 | Myers |
| 6,358,277 B1 | 3/2002 | Duran |
| 6,361,519 B1 | 3/2002 | Knudson et al. |
| 6,361,545 B1 | 3/2002 | Macoviak et al. |
| 6,363,938 B2 | 4/2002 | Saadat et al. |
| 6,363,939 B1 | 4/2002 | Wilk |
| 6,364,895 B1 | 4/2002 | Greenhalgh |
| 6,368,338 B1 | 4/2002 | Konya et al. |
| 6,371,970 B1 | 4/2002 | Khosravi et al. |
| 6,371,983 B1 | 4/2002 | Lane |
| 6,375,615 B1 | 4/2002 | Flaherty et al. |
| 6,378,221 B1 | 4/2002 | Ekholm, Jr. et al. |
| 6,379,319 B1 | 4/2002 | Garibotto et al. |
| 6,379,365 B1 | 4/2002 | Diaz |
| 6,379,372 B1 | 4/2002 | Dehdashtian et al. |
| 6,379,383 B1 | 4/2002 | Palmaz et al. |
| 6,379,740 B1 | 4/2002 | Rinaldi et al. |
| 6,380,457 B1 | 4/2002 | Yurek et al. |
| 6,383,193 B1 | 5/2002 | Cathcart et al. |
| 6,387,119 B2 | 5/2002 | Wolf et al. |
| 6,387,122 B1 | 5/2002 | Cragg |
| 6,390,098 B1 | 5/2002 | LaFontaine et al. |
| 6,391,051 B2 | 5/2002 | Sullivan, III et al. |
| 6,391,538 B1 | 5/2002 | Vyavahare et al. |
| 6,395,208 B1 | 5/2002 | Herweck et al. |
| 6,398,807 B1 | 6/2002 | Chouinard et al. |
| 6,401,720 B1 | 6/2002 | Stevens et al. |
| 6,402,736 B1 | 6/2002 | Brown et al. |

(56) References Cited

U.S. PATENT DOCUMENTS

| | | |
|---|---|---|
| 6,402,740 B1 | 6/2002 | Ellis et al. |
| 6,406,488 B1 | 6/2002 | Tweden et al. |
| 6,406,491 B1 | 6/2002 | Vanney |
| 6,406,493 B1 | 6/2002 | Tu et al. |
| 6,409,697 B2 | 6/2002 | Eno et al. |
| 6,409,750 B1 | 6/2002 | Hyodoh et al. |
| 6,409,751 B1 | 6/2002 | Hall et al. |
| 6,409,755 B1 | 6/2002 | Vrba |
| 6,409,759 B1 | 6/2002 | Peredo |
| 6,413,275 B1 | 7/2002 | Nguyen et al. |
| 6,416,490 B1 | 7/2002 | Ellis et al. |
| 6,416,510 B1 | 7/2002 | Altman et al. |
| 6,423,089 B1 | 7/2002 | Gingras et al. |
| 6,425,916 B1 | 7/2002 | Garrison et al. |
| 6,432,119 B1 | 8/2002 | Saadat |
| 6,432,126 B1 | 8/2002 | Gambale et al. |
| 6,432,127 B1 | 8/2002 | Kim et al. |
| 6,432,132 B1 | 8/2002 | Cottone et al. |
| 6,440,164 B1 | 8/2002 | DiMatteo et al. |
| 6,443,158 B1 | 9/2002 | LaFontaine et al. |
| 6,447,522 B2 | 9/2002 | Gambale et al. |
| 6,447,539 B1 | 9/2002 | Nelson et al. |
| 6,451,025 B1 | 9/2002 | Jervis |
| 6,451,054 B1 | 9/2002 | Stevens |
| 6,454,760 B2 | 9/2002 | Vanney |
| 6,454,794 B1 | 9/2002 | Knudson et al. |
| 6,454,799 B1 | 9/2002 | Schreck |
| 6,458,092 B1 | 10/2002 | Gambale et al. |
| 6,458,140 B2 | 10/2002 | Akin et al. |
| 6,458,153 B1 | 10/2002 | Bailey et al. |
| 6,458,323 B1 | 10/2002 | Boekstegers |
| 6,461,382 B1 | 10/2002 | Cao |
| 6,464,709 B1 | 10/2002 | Shennib et al. |
| 6,468,303 B1 | 10/2002 | Amplatz et al. |
| 6,468,660 B2 | 10/2002 | Ogle et al. |
| 6,471,723 B1 | 10/2002 | Ashworth et al. |
| 6,475,169 B2 | 11/2002 | Ferrera |
| 6,475,226 B1 | 11/2002 | Belef et al. |
| 6,475,239 B1 | 11/2002 | Campbell et al. |
| 6,475,244 B2 | 11/2002 | Herweck et al. |
| 6,478,819 B2 | 11/2002 | Moe |
| 6,479,079 B1 | 11/2002 | Pathak et al. |
| 6,482,220 B1 | 11/2002 | Mueller |
| 6,482,228 B1 | 11/2002 | Norred |
| 6,485,501 B1 | 11/2002 | Green |
| 6,485,502 B2 | 11/2002 | Don Michael et al. |
| 6,485,513 B1 | 11/2002 | Fan |
| 6,485,524 B2 | 11/2002 | Strecker |
| 6,487,581 B1 | 11/2002 | Spence et al. |
| 6,488,704 B1 | 12/2002 | Connelly et al. |
| 6,491,689 B1 | 12/2002 | Ellis et al. |
| 6,491,707 B2 | 12/2002 | Makower et al. |
| 6,494,211 B1 | 12/2002 | Boyd et al. |
| 6,494,897 B2 | 12/2002 | Sterman et al. |
| 6,494,909 B2 | 12/2002 | Greenhalgh |
| 6,503,272 B2 | 1/2003 | Duerig et al. |
| 6,508,496 B1 | 1/2003 | Huang |
| 6,508,803 B1 | 1/2003 | Horikawa et al. |
| 6,508,825 B1 | 1/2003 | Selmon et al. |
| 6,508,833 B2 | 1/2003 | Pavcnik et al. |
| 6,509,145 B1 | 1/2003 | Torrianni |
| 6,511,458 B2 | 1/2003 | Milo et al. |
| 6,511,491 B2 | 1/2003 | Grudem et al. |
| 6,514,217 B1 | 2/2003 | Selmon et al. |
| 6,514,271 B2 | 2/2003 | Evans et al. |
| 6,517,527 B2 | 2/2003 | Gambale et al. |
| 6,517,558 B2 | 2/2003 | Gittings et al. |
| 6,517,573 B1 | 2/2003 | Pollock et al. |
| 6,521,179 B1 | 2/2003 | Girardot et al. |
| 6,524,323 B1 | 2/2003 | Nash et al. |
| 6,524,335 B1 | 2/2003 | Hartley et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,533,807 B2 | 3/2003 | Wolinsky et al. |
| 6,537,297 B2 | 3/2003 | Tsugita et al. |
| 6,537,310 B1 | 3/2003 | Palmaz et al. |
| 6,540,768 B1 | 4/2003 | Diaz et al. |
| 6,540,782 B1 | 4/2003 | Snyders |
| 6,544,230 B1 | 4/2003 | Flaherty et al. |
| 6,547,827 B2 | 4/2003 | Carpentier et al. |
| 6,551,303 B1 | 4/2003 | Van Tassel et al. |
| 6,558,318 B1 | 5/2003 | Daniel et al. |
| 6,558,417 B2 | 5/2003 | Peredo |
| 6,558,418 B2 | 5/2003 | Carpentier et al. |
| 6,558,429 B2 | 5/2003 | Taylor |
| 6,559,132 B1 | 5/2003 | Holmer |
| 6,561,998 B1 | 5/2003 | Roth et al. |
| 6,562,031 B2 | 5/2003 | Chandrasekaran et al. |
| 6,562,058 B2 | 5/2003 | Seguin et al. |
| 6,562,063 B1 | 5/2003 | Euteneuer et al. |
| 6,562,069 B2 | 5/2003 | Cai et al. |
| 6,564,805 B2 | 5/2003 | Garrison et al. |
| 6,565,528 B1 | 5/2003 | Mueller |
| 6,565,594 B1 | 5/2003 | Herweck et al. |
| 6,569,145 B1 | 5/2003 | Shmulewitz et al. |
| 6,569,147 B1 | 5/2003 | Evans et al. |
| 6,569,196 B1 | 5/2003 | Vesely |
| 6,572,642 B2 | 6/2003 | Rinaldi et al. |
| 6,572,643 B1 | 6/2003 | Gharibadeh |
| 6,572,652 B2 | 6/2003 | Shaknovich |
| 6,575,168 B2 | 6/2003 | LaFontaine et al. |
| 6,579,311 B1 | 6/2003 | Makower |
| 6,582,444 B2 | 6/2003 | Wilk |
| 6,582,460 B1 | 6/2003 | Cryer |
| 6,582,462 B1 | 6/2003 | Andersen et al. |
| 6,585,756 B1 | 7/2003 | Strecker |
| 6,585,758 B1 | 7/2003 | Chouinard et al. |
| 6,585,766 B1 | 7/2003 | Huynh et al. |
| 6,589,279 B1 | 7/2003 | Anderson et al. |
| 6,592,546 B1 | 7/2003 | Barbut et al. |
| 6,592,614 B2 | 7/2003 | Lenker et al. |
| 6,599,304 B1 | 7/2003 | Selmon et al. |
| 6,600,803 B2 | 7/2003 | Bruder et al. |
| 6,605,053 B1 | 8/2003 | Kamm et al. |
| 6,605,112 B1 | 8/2003 | Moll et al. |
| 6,605,113 B2 | 8/2003 | Wilk |
| 6,608,040 B1 | 8/2003 | Lin et al. |
| 6,610,077 B1 | 8/2003 | Hancock et al. |
| 6,610,085 B1 | 8/2003 | Lazarus |
| 6,610,100 B2 | 8/2003 | Phelps et al. |
| 6,613,069 B2 | 9/2003 | Boyd et al. |
| 6,613,077 B2 | 9/2003 | Gilligan et al. |
| 6,613,079 B1 | 9/2003 | Wolinsky et al. |
| 6,613,081 B2 | 9/2003 | Kim et al. |
| 6,613,086 B1 | 9/2003 | Moe et al. |
| 6,616,675 B1 | 9/2003 | Evard et al. |
| 6,616,682 B2 | 9/2003 | Joergensen et al. |
| 6,622,604 B1 | 9/2003 | Chouinard et al. |
| 6,623,491 B2 | 9/2003 | Thompson |
| 6,623,518 B2 | 9/2003 | Thompson et al. |
| 6,623,521 B2 | 9/2003 | Steinke et al. |
| 6,626,938 B1 | 9/2003 | Butaric et al. |
| 6,626,939 B1 | 9/2003 | Burnside et al. |
| 6,632,241 B1 | 10/2003 | Hancock et al. |
| 6,632,243 B1 | 10/2003 | Zadno-Azizi et al. |
| 6,632,470 B2 | 10/2003 | Morra et al. |
| 6,635,068 B1 | 10/2003 | Dubrul et al. |
| 6,635,079 B2 | 10/2003 | Unsworth et al. |
| 6,635,080 B1 | 10/2003 | Lauterjung et al. |
| 6,635,085 B1 | 10/2003 | Caffey et al. |
| 6,638,237 B1 | 10/2003 | Guiles et al. |
| 6,638,247 B1 | 10/2003 | Selmon et al. |
| 6,638,293 B1 | 10/2003 | Makower et al. |
| 6,641,610 B2 | 11/2003 | Wolf et al. |
| 6,651,670 B2 | 11/2003 | Rapacki et al. |
| 6,651,672 B2 | 11/2003 | Roth |
| 6,652,540 B1 | 11/2003 | Cole et al. |
| 6,652,546 B1 | 11/2003 | Nash et al. |
| 6,652,555 B1 | 11/2003 | Vantassel et al. |
| 6,652,571 B1 | 11/2003 | White et al. |
| 6,652,578 B2 | 11/2003 | Bailey et al. |
| 6,655,386 B1 | 12/2003 | Makower et al. |
| 6,656,213 B2 | 12/2003 | Solem |

(56) References Cited

U.S. PATENT DOCUMENTS

| | | |
|---|---|---|
| 6,660,003 B1 | 12/2003 | DeVore et al. |
| 6,660,024 B1 | 12/2003 | Flaherty et al. |
| 6,663,588 B2 | 12/2003 | DuBois et al. |
| 6,663,663 B2 | 12/2003 | Kim et al. |
| 6,663,667 B2 | 12/2003 | Dehdashtian et al. |
| 6,666,863 B2 | 12/2003 | Wentzel et al. |
| 6,669,709 B1 | 12/2003 | Cohn et al. |
| 6,669,724 B2 | 12/2003 | Park et al. |
| 6,673,089 B1 | 1/2004 | Yassour et al. |
| 6,673,101 B1 | 1/2004 | Fitzgerald et al. |
| 6,673,106 B2 | 1/2004 | Mitelberg et al. |
| 6,673,109 B2 | 1/2004 | Cox |
| 6,676,668 B2 | 1/2004 | Mercereau et al. |
| 6,676,692 B2 | 1/2004 | Rabkin et al. |
| 6,676,693 B1 | 1/2004 | Belding et al. |
| 6,676,698 B2 | 1/2004 | McGuckin, Jr. et al. |
| 6,679,268 B2 | 1/2004 | Stevens et al. |
| 6,682,543 B2 | 1/2004 | Barbut et al. |
| 6,682,558 B2 | 1/2004 | Tu et al. |
| 6,682,559 B2 | 1/2004 | Myers et al. |
| 6,685,648 B2 | 2/2004 | Flaherty et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,694,983 B2 | 2/2004 | Wolf et al. |
| 6,695,864 B2 | 2/2004 | Macoviak et al. |
| 6,695,865 B2 | 2/2004 | Boyle et al. |
| 6,695,875 B2 | 2/2004 | Stelter et al. |
| 6,695,878 B2 | 2/2004 | McGuckin, Jr. et al. |
| 6,699,274 B2 | 3/2004 | Stinson |
| 6,701,932 B2 | 3/2004 | Knudson et al. |
| 6,702,851 B1 | 3/2004 | Chinn et al. |
| 6,709,425 B2 | 3/2004 | Gambale et al. |
| 6,709,444 B1 | 3/2004 | Makower |
| 6,712,842 B1 | 3/2004 | Gifford, III et al. |
| 6,712,843 B2 | 3/2004 | Elliott |
| 6,714,842 B1 | 3/2004 | Ito |
| 6,719,770 B2 | 4/2004 | Laufer et al. |
| 6,719,787 B2 | 4/2004 | Cox |
| 6,719,788 B2 | 4/2004 | Cox |
| 6,719,789 B2 | 4/2004 | Cox |
| 6,723,116 B2 | 4/2004 | Taheri |
| 6,723,122 B2 | 4/2004 | Yang et al. |
| 6,726,677 B1 | 4/2004 | Flaherty et al. |
| 6,729,356 B1 | 5/2004 | Baker et al. |
| 6,730,118 B2 | 5/2004 | Spenser et al. |
| 6,730,121 B2 | 5/2004 | Ortiz et al. |
| 6,730,377 B2 | 5/2004 | Wang |
| 6,733,513 B2 | 5/2004 | Boyle et al. |
| 6,733,525 B2 | 5/2004 | Yang et al. |
| 6,736,827 B1 | 5/2004 | McAndrew et al. |
| 6,736,839 B2 | 5/2004 | Cummings |
| 6,736,845 B2 | 5/2004 | Marquez et al. |
| 6,736,846 B2 | 5/2004 | Cox |
| 6,743,252 B1 | 6/2004 | Bates et al. |
| 6,746,464 B1 | 6/2004 | Makower |
| 6,752,828 B2 | 6/2004 | Thornton |
| 6,755,854 B2 | 6/2004 | Gillick et al. |
| 6,755,855 B2 | 6/2004 | Yurek et al. |
| 6,758,855 B2 | 7/2004 | Fulton, III et al. |
| 6,764,503 B1 | 7/2004 | Ishimaru |
| 6,764,509 B2 | 7/2004 | Chinn et al. |
| 6,767,345 B2 | 7/2004 | St. Germain et al. |
| 6,767,362 B2 | 7/2004 | Schreck |
| 6,769,434 B2 | 8/2004 | Liddicoat et al. |
| 6,773,454 B2 | 8/2004 | Wholey et al. |
| 6,773,455 B2 | 8/2004 | Allen et al. |
| 6,773,456 B1 | 8/2004 | Gordon et al. |
| 6,774,278 B1 | 8/2004 | Ragheb et al. |
| 6,776,791 B1 | 8/2004 | Stallings et al. |
| 6,786,925 B1 | 9/2004 | Schoon et al. |
| 6,786,929 B2 | 9/2004 | Gambale et al. |
| 6,790,229 B1 | 9/2004 | Berreklouw |
| 6,790,230 B2 | 9/2004 | Beyersdorf et al. |
| 6,790,237 B2 | 9/2004 | Stinson |
| 6,792,979 B2 | 9/2004 | Konya et al. |
| 6,797,000 B2 | 9/2004 | Simpson et al. |
| 6,797,002 B2 | 9/2004 | Spence et al. |
| 6,802,319 B2 | 10/2004 | Stevens et al. |
| 6,802,858 B2 | 10/2004 | Gambale et al. |
| 6,805,711 B2 | 10/2004 | Quijano et al. |
| 6,808,498 B2 | 10/2004 | Laroya et al. |
| 6,808,504 B2 | 10/2004 | Schorgl et al. |
| 6,808,529 B2 | 10/2004 | Fulkerson |
| 6,814,746 B2 | 11/2004 | Thompson et al. |
| 6,814,754 B2 | 11/2004 | Greenhalgh |
| 6,820,676 B2 | 11/2004 | Palmaz et al. |
| 6,821,211 B2 | 11/2004 | Otten et al. |
| 6,821,297 B2 | 11/2004 | Snyders |
| 6,824,041 B2 | 11/2004 | Grieder et al. |
| 6,824,970 B2 | 11/2004 | Vyavahare et al. |
| 6,830,568 B1 | 12/2004 | Kesten et al. |
| 6,830,575 B2 | 12/2004 | Stenzel et al. |
| 6,830,584 B1 | 12/2004 | Seguin |
| 6,830,585 B1 | 12/2004 | Artof et al. |
| 6,830,586 B2 | 12/2004 | Quijano et al. |
| 6,837,901 B2 | 1/2005 | Rabkin et al. |
| 6,837,902 B2 | 1/2005 | Nguyen et al. |
| 6,840,957 B2 | 1/2005 | DiMatteo et al. |
| 6,843,802 B1 | 1/2005 | Villalobos et al. |
| 6,846,325 B2 | 1/2005 | Liddicoat |
| 6,849,084 B2 | 2/2005 | Rabkin et al. |
| 6,849,085 B2 | 2/2005 | Marton |
| 6,854,467 B2 | 2/2005 | Boekstegers |
| 6,860,898 B2 | 3/2005 | Stack et al. |
| 6,861,211 B2 | 3/2005 | Levy et al. |
| 6,863,668 B2 | 3/2005 | Gillespie et al. |
| 6,863,684 B2 | 3/2005 | Kim et al. |
| 6,863,688 B2 | 3/2005 | Ralph et al. |
| 6,866,650 B2 | 3/2005 | Stevens et al. |
| 6,866,669 B2 | 3/2005 | Buzzard et al. |
| 6,872,223 B2 | 3/2005 | Roberts et al. |
| 6,872,226 B2 | 3/2005 | Cali et al. |
| 6,875,231 B2 | 4/2005 | Anduiza et al. |
| 6,881,199 B2 | 4/2005 | Wilk et al. |
| 6,881,220 B2 | 4/2005 | Edwin et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,890,340 B2 | 5/2005 | Duane |
| 6,893,459 B1 | 5/2005 | Macoviak |
| 6,893,460 B2 | 5/2005 | Spenser et al. |
| 6,896,690 B1 | 5/2005 | Lambrecht et al. |
| 6,899,704 B2 | 5/2005 | Sterman et al. |
| 6,905,743 B1 | 6/2005 | Chen et al. |
| 6,908,481 B2 | 6/2005 | Cribier |
| 6,911,036 B2 | 6/2005 | Douk et al. |
| 6,911,040 B2 | 6/2005 | Johnson et al. |
| 6,911,043 B2 | 6/2005 | Myers et al. |
| 6,913,021 B2 | 7/2005 | Knudson et al. |
| 6,913,600 B2 | 7/2005 | Valley et al. |
| 6,916,304 B2 | 7/2005 | Eno et al. |
| 6,920,674 B2 | 7/2005 | Thornton |
| 6,920,732 B2 | 7/2005 | Mårtensson |
| 6,926,690 B2 | 8/2005 | Renati |
| 6,926,732 B2 | 8/2005 | Derus et al. |
| 6,929,009 B2 | 8/2005 | Makower et al. |
| 6,929,011 B2 | 8/2005 | Knudson et al. |
| 6,929,653 B2 | 8/2005 | Strecter |
| 6,936,058 B2 | 8/2005 | Forde et al. |
| 6,936,066 B2 | 8/2005 | Palmaz et al. |
| 6,936,067 B2 | 8/2005 | Buchanan |
| 6,939,352 B2 | 9/2005 | Buzzard et al. |
| 6,939,359 B2 | 9/2005 | Tu et al. |
| 6,939,365 B1 | 9/2005 | Fogarty et al. |
| 6,939,370 B2 | 9/2005 | Hartley et al. |
| 6,942,682 B2 | 9/2005 | Vrba et al. |
| 6,945,949 B2 | 9/2005 | Wilk |
| 6,945,997 B2 | 9/2005 | Huynh et al. |
| 6,949,080 B2 | 9/2005 | Wolf et al. |
| 6,949,118 B2 | 9/2005 | Kohler et al. |
| 6,951,571 B1 | 10/2005 | Srivastava |

(56) References Cited

U.S. PATENT DOCUMENTS

| | | |
|---|---|---|
| 6,953,332 B1 | 10/2005 | Kurk et al. |
| 6,953,481 B2 | 10/2005 | Phelps et al. |
| 6,955,175 B2 | 10/2005 | Stevens et al. |
| 6,955,681 B2 | 10/2005 | Evans et al. |
| 6,964,652 B2 | 11/2005 | Guiles et al. |
| 6,964,673 B2 | 11/2005 | Tsugita et al. |
| 6,964,676 B1 | 11/2005 | Gerberding et al. |
| 6,969,395 B2 | 11/2005 | Eskuri |
| 6,972,025 B2 | 12/2005 | Wasdyke |
| 6,972,029 B2 | 12/2005 | Mayrhofer et al. |
| 6,974,464 B2 | 12/2005 | Quijano et al. |
| 6,974,474 B2 | 12/2005 | Pavcnik et al. |
| 6,974,476 B2 | 12/2005 | McGuckin, Jr. et al. |
| 6,976,990 B2 | 12/2005 | Mowry |
| 6,979,350 B2 | 12/2005 | Moll et al. |
| 6,984,242 B2 | 1/2006 | Campbell et al. |
| 6,984,244 B2 | 1/2006 | Perez et al. |
| 6,986,742 B2 | 1/2006 | Hart et al. |
| 6,986,784 B1 | 1/2006 | Weiser et al. |
| 6,988,949 B2 | 1/2006 | Wang |
| 6,989,027 B2 | 1/2006 | Allen et al. |
| 6,989,028 B2 | 1/2006 | Lashinski et al. |
| 6,991,649 B2 | 1/2006 | Sievers |
| 7,001,425 B2 | 2/2006 | McCullagh et al. |
| 7,004,176 B2 | 2/2006 | Lau |
| 7,008,397 B2 | 3/2006 | Tweden et al. |
| 7,011,095 B2 | 3/2006 | Wolf et al. |
| 7,011,681 B2 | 3/2006 | Vesely |
| 7,014,655 B2 | 3/2006 | Barbarash et al. |
| 7,018,401 B1 | 3/2006 | Hyodoh et al. |
| 7,018,406 B2 | 3/2006 | Seguin et al. |
| 7,018,408 B2 | 3/2006 | Bailey et al. |
| 7,022,134 B1 | 4/2006 | Quijano et al. |
| 7,025,773 B2 | 4/2006 | Gittings et al. |
| 7,025,780 B2 | 4/2006 | Gabbay |
| 7,025,791 B2 | 4/2006 | Levine et al. |
| 7,028,692 B2 | 4/2006 | Sterman et al. |
| 7,037,331 B2 | 5/2006 | Mitelberg et al. |
| 7,037,333 B2 | 5/2006 | Myers et al. |
| 7,041,128 B2 | 5/2006 | McGuckin, Jr. et al. |
| 7,041,132 B2 | 5/2006 | Quijano et al. |
| 7,044,966 B2 | 5/2006 | Svanidze et al. |
| 7,048,014 B2 | 5/2006 | Hyodoh et al. |
| 7,048,757 B2 | 5/2006 | Shaknovich |
| 7,050,276 B2 | 5/2006 | Nishiyama |
| 7,074,236 B2 | 7/2006 | Rabkin et al. |
| 7,078,163 B2 | 7/2006 | Torrianni |
| 7,081,132 B2 | 7/2006 | Cook et al. |
| 7,097,658 B2 | 8/2006 | Oktay |
| 7,097,659 B2 | 8/2006 | Woolfson et al. |
| 7,101,396 B2 | 9/2006 | Artof et al. |
| 7,105,016 B2 | 9/2006 | Shiu et al. |
| 7,108,715 B2 | 9/2006 | Lawrence-Brown et al. |
| 7,115,141 B2 | 10/2006 | Menz et al. |
| 7,118,585 B2 | 10/2006 | Addis |
| 7,122,020 B2 | 10/2006 | Mogul |
| 7,125,418 B2 | 10/2006 | Duran et al. |
| 7,128,759 B2 | 10/2006 | Osborne et al. |
| 7,137,184 B2 | 11/2006 | Schreck et al. |
| 7,141,063 B2 | 11/2006 | White et al. |
| 7,141,064 B2 | 11/2006 | Scott et al. |
| 7,143,312 B1 | 11/2006 | Wang et al. |
| 7,147,662 B1 | 12/2006 | Pollock et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,163,556 B2 | 1/2007 | Xie et al. |
| 7,166,097 B2 | 1/2007 | Barbut |
| 7,175,652 B2 | 2/2007 | Cook et al. |
| 7,175,653 B2 | 2/2007 | Gaber |
| 7,175,654 B2 | 2/2007 | Bonsignore et al. |
| 7,175,656 B2 | 2/2007 | Khairkhahan |
| 7,179,290 B2 | 2/2007 | Cao |
| 7,186,265 B2 | 3/2007 | Sharkawy et al. |
| 7,189,258 B2 | 3/2007 | Johnson et al. |
| 7,189,259 B2 | 3/2007 | Simionescu et al. |
| 7,191,018 B2 | 3/2007 | Gielen et al. |
| 7,191,406 B1 | 3/2007 | Barber et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,214,344 B2 | 5/2007 | Carpentier et al. |
| 7,217,287 B2 | 5/2007 | Wilson et al. |
| 7,235,092 B2 | 6/2007 | Banas et al. |
| 7,235,093 B2 | 6/2007 | Gregorich |
| 7,238,200 B2 | 7/2007 | Lee et al. |
| 7,241,257 B1 | 7/2007 | Ainsworth et al. |
| 7,252,682 B2 | 8/2007 | Seguin |
| 7,258,696 B2 | 8/2007 | Rabkin et al. |
| 7,258,891 B2 | 8/2007 | Pacetti et al. |
| 7,261,732 B2 | 8/2007 | Justino |
| 7,264,632 B2 | 9/2007 | Wright et al. |
| 7,267,686 B2 | 9/2007 | DiMatteo et al. |
| 7,276,078 B2 | 10/2007 | Spenser et al. |
| 7,276,084 B2 | 10/2007 | Yang et al. |
| 7,285,130 B2 | 10/2007 | Austin |
| 7,297,150 B2 | 11/2007 | Cartledge et al. |
| 7,300,457 B2 | 11/2007 | Palmaz |
| 7,300,463 B2 | 11/2007 | Liddicoat |
| 7,311,730 B2 | 12/2007 | Gabbay |
| 7,314,449 B2 | 1/2008 | Pfeiffer et al. |
| 7,314,485 B2 | 1/2008 | Mathis |
| 7,314,880 B2 | 1/2008 | Chang et al. |
| 7,316,706 B2 | 1/2008 | Bloom et al. |
| 7,316,712 B2 | 1/2008 | Peredo |
| 7,317,005 B2 | 1/2008 | Hoekstra et al. |
| 7,317,942 B2 | 1/2008 | Brown |
| 7,317,950 B2 | 1/2008 | Lee |
| 7,318,278 B2 | 1/2008 | Zhang et al. |
| 7,318,998 B2 | 1/2008 | Goldstein et al. |
| 7,319,096 B2 | 1/2008 | Malm et al. |
| 7,320,692 B1 | 1/2008 | Bender et al. |
| 7,320,704 B2 | 1/2008 | Lashinski et al. |
| 7,320,705 B2 | 1/2008 | Quintessenza |
| 7,320,706 B2 | 1/2008 | Al-Najjar |
| 7,322,932 B2 | 1/2008 | Xie et al. |
| 7,323,006 B2 | 1/2008 | Andreas et al. |
| 7,323,066 B1 | 1/2008 | Budron |
| 7,326,174 B2 | 2/2008 | Cox et al. |
| 7,326,219 B2 | 2/2008 | Mowry et al. |
| 7,326,236 B2 | 2/2008 | Andreas et al. |
| 7,327,862 B2 | 2/2008 | Murphy et al. |
| 7,329,278 B2 | 2/2008 | Seguin et al. |
| 7,329,279 B2 | 2/2008 | Haug et al. |
| 7,329,280 B2 | 2/2008 | Bolling et al. |
| 7,329,777 B2 | 2/2008 | Harter et al. |
| 7,331,991 B2 | 2/2008 | Kheradvar et al. |
| 7,331,993 B2 | 2/2008 | White |
| 7,333,643 B2 | 2/2008 | Murphy et al. |
| 7,335,158 B2 | 2/2008 | Taylor |
| 7,335,213 B1 | 2/2008 | Hyde et al. |
| 7,335,218 B2 | 2/2008 | Wilson et al. |
| 7,335,490 B2 | 2/2008 | Van Gilst et al. |
| 7,338,484 B2 | 3/2008 | Schoon et al. |
| 7,338,520 B2 | 3/2008 | Bailey et al. |
| 7,361,189 B2 | 4/2008 | Case et al. |
| 7,361,190 B2 | 4/2008 | Shaoulian et al. |
| 7,364,588 B2 | 4/2008 | Mathis et al. |
| 7,371,258 B2 | 5/2008 | Woo et al. |
| 7,374,560 B2 | 5/2008 | Ressemann et al. |
| 7,374,571 B2 | 5/2008 | Pease et al. |
| 7,377,895 B2 | 5/2008 | Spence et al. |
| 7,377,938 B2 | 5/2008 | Sarac et al. |
| 7,377,940 B2 | 5/2008 | Ryan et al. |
| 7,381,210 B2 | 6/2008 | Zarbatany et al. |
| 7,381,216 B2 | 6/2008 | Buzzard et al. |
| 7,381,218 B2 | 6/2008 | Schreck |
| 7,381,219 B2 | 6/2008 | Salahieh et al. |
| 7,381,220 B2 | 6/2008 | Macoviak et al. |
| 7,384,411 B1 | 6/2008 | Condado |
| 7,387,640 B2 | 6/2008 | Cummings |
| 7,389,874 B2 | 6/2008 | Quest et al. |
| 7,390,325 B2 | 6/2008 | Wang et al. |

(56) References Cited

U.S. PATENT DOCUMENTS

| | | |
|---|---|---|
| 7,393,358 B2 | 7/2008 | Malewicz |
| 7,393,360 B2 | 7/2008 | Spenser et al. |
| 7,396,364 B2 | 7/2008 | Moaddeb et al. |
| 7,399,315 B2 | 7/2008 | Iobbi |
| 7,402,171 B2 | 7/2008 | Osborne et al. |
| 7,404,792 B2 | 7/2008 | Spence et al. |
| 7,404,793 B2 | 7/2008 | Lau et al. |
| 7,405,259 B2 | 7/2008 | Frye et al. |
| 7,410,499 B2 | 8/2008 | Bicer |
| 7,412,274 B2 | 8/2008 | Mejia |
| 7,412,290 B2 | 8/2008 | Janke et al. |
| 7,415,861 B2 | 8/2008 | Sokel |
| 7,416,530 B2 | 8/2008 | Turner et al. |
| 7,422,603 B2 | 9/2008 | Lane |
| 7,422,606 B2 | 9/2008 | Ung-Chhun et al. |
| 7,423,032 B2 | 9/2008 | Ozaki et al. |
| 7,426,413 B2 | 9/2008 | Balczewski et al. |
| 7,427,279 B2 | 9/2008 | Frazier et al. |
| 7,427,287 B2 | 9/2008 | Turovskiy et al. |
| 7,427,291 B2 | 9/2008 | Liddicoat et al. |
| 7,429,269 B2 | 9/2008 | Schwammenthal et al. |
| 7,430,448 B1 | 9/2008 | Zimmer et al. |
| 7,430,484 B2 | 9/2008 | Ohara |
| 7,431,691 B1 | 10/2008 | Wilk |
| 7,431,733 B2 | 10/2008 | Knight |
| 7,435,059 B2 | 10/2008 | Smith et al. |
| 7,435,257 B2 | 10/2008 | Lashinski et al. |
| 7,442,204 B2 | 10/2008 | Schwammenthal et al. |
| RE40,570 E | 11/2008 | Carpentier et al. |
| 7,445,630 B2 | 11/2008 | Lashinski et al. |
| 7,445,631 B2 | 11/2008 | Salahieh et al. |
| 7,445,632 B2 | 11/2008 | McGuckin, Jr. et al. |
| 7,452,371 B2 | 11/2008 | Pavcnik et al. |
| 7,455,689 B2 | 11/2008 | Johnson |
| 7,462,156 B2 | 12/2008 | Mitrev |
| 7,462,184 B2 | 12/2008 | Worley et al. |
| 7,462,191 B2 | 12/2008 | Spenser et al. |
| 7,468,050 B1 | 12/2008 | Kantrowitz |
| 7,470,284 B2 | 12/2008 | Lambrecht et al. |
| 7,470,285 B2 | 12/2008 | Nugent et al. |
| 7,473,271 B2 | 1/2009 | Gunderson |
| 7,473,275 B2 | 1/2009 | Marquez |
| 7,473,417 B2 | 1/2009 | Zeltinger et al. |
| 7,476,196 B2 | 1/2009 | Spence et al. |
| 7,476,199 B2 | 1/2009 | Spence et al. |
| 7,476,200 B2 | 1/2009 | Tal |
| 7,476,244 B2 | 1/2009 | Buzzard et al. |
| 7,481,838 B2 | 1/2009 | Carpentier et al. |
| 7,485,088 B2 | 2/2009 | Murphy et al. |
| 7,485,143 B2 | 2/2009 | Webler et al. |
| 7,488,346 B2 | 2/2009 | Navia |
| 7,491,232 B2 | 2/2009 | Bolduc et al. |
| 7,493,869 B1 | 2/2009 | Foster et al. |
| 7,497,824 B2 | 3/2009 | Taylor |
| 7,500,949 B2 | 3/2009 | Gottlieb et al. |
| 7,500,989 B2 | 3/2009 | Solem et al. |
| 7,503,929 B2 | 3/2009 | Johnson et al. |
| 7,503,930 B2 | 3/2009 | Sharkawy et al. |
| 7,507,199 B2 | 3/2009 | Wang et al. |
| 7,510,572 B2 | 3/2009 | Gabbay |
| 7,510,574 B2 | 3/2009 | L et al. |
| 7,510,575 B2 | 3/2009 | Spenser et al. |
| 7,510,577 B2 | 3/2009 | Moaddeb et al. |
| 7,513,863 B2 | 4/2009 | Bolling et al. |
| 7,513,909 B2 | 4/2009 | Lane et al. |
| 7,522,950 B2 | 4/2009 | Fuimaono et al. |
| 7,524,330 B2 | 4/2009 | Berreklouw |
| 7,530,253 B2 | 5/2009 | Spenser et al. |
| 7,530,995 B2 | 5/2009 | Quijano et al. |
| 7,534,261 B2 | 5/2009 | Friedman |
| 7,544,206 B2 | 6/2009 | Cohn |
| 7,547,322 B2 | 6/2009 | Sarac et al. |
| 7,553,324 B2 | 6/2009 | Andreas et al. |
| 7,556,386 B2 | 7/2009 | Smith |
| 7,556,646 B2 | 7/2009 | Yang et al. |
| 7,569,071 B2 | 8/2009 | Haverkost et al. |
| 7,578,828 B2 | 8/2009 | Gittings et al. |
| 7,585,321 B2 | 9/2009 | Cribier |
| 7,591,848 B2 | 9/2009 | Allen |
| 7,594,974 B2 | 9/2009 | Cali et al. |
| 7,601,159 B2 | 10/2009 | Ewers et al. |
| 7,601,195 B2 | 10/2009 | Ichikawa |
| 7,608,099 B2 | 10/2009 | Johnson et al. |
| 7,611,534 B2 | 11/2009 | Kapadia et al. |
| 7,618,446 B2 | 11/2009 | Andersen et al. |
| 7,622,276 B2 | 11/2009 | Cunanan et al. |
| 7,625,403 B2 | 12/2009 | Krivoruchko |
| 7,628,802 B2 | 12/2009 | White et al. |
| 7,628,803 B2 | 12/2009 | Pavcnik et al. |
| 7,632,296 B2 | 12/2009 | Malewicz |
| 7,632,298 B2 | 12/2009 | Hijlkema et al. |
| 7,635,386 B1 | 12/2009 | Gammie |
| 7,641,687 B2 | 1/2010 | Chinn et al. |
| 7,651,519 B2 | 1/2010 | Dittman |
| 7,655,034 B2 | 2/2010 | Mitchell et al. |
| 7,674,282 B2 | 3/2010 | Wu et al. |
| 7,682,390 B2 | 3/2010 | Seguin |
| 7,704,222 B2 | 4/2010 | Wilk et al. |
| 7,704,277 B2 | 4/2010 | Zakay et al. |
| 7,712,606 B2 | 5/2010 | Salahieh et al. |
| 7,717,955 B2 | 5/2010 | Lane et al. |
| 7,722,638 B2 | 5/2010 | Deyette, Jr. et al. |
| 7,722,662 B2 | 5/2010 | Steinke et al. |
| 7,722,666 B2 | 5/2010 | Lafontaine |
| 7,722,671 B1 | 5/2010 | Carlyle et al. |
| 7,731,742 B2 | 6/2010 | Schlick et al. |
| 7,735,493 B2 | 6/2010 | Van Der Burg et al. |
| 7,736,327 B2 | 6/2010 | Wilk et al. |
| 7,736,388 B2 | 6/2010 | Goldfarb et al. |
| 7,743,481 B2 | 6/2010 | Lafont et al. |
| 7,748,389 B2 | 7/2010 | Salahieh et al. |
| 7,758,625 B2 | 7/2010 | Wu et al. |
| 7,763,065 B2 | 7/2010 | Schmid et al. |
| 7,771,463 B2 | 8/2010 | Ton et al. |
| 7,771,467 B2 | 8/2010 | Svensson |
| 7,776,083 B2 | 8/2010 | Vesely |
| 7,780,725 B2 | 8/2010 | Haug et al. |
| 7,780,726 B2 | 8/2010 | Seguin |
| 7,785,360 B2 | 8/2010 | Freitag |
| 7,794,487 B2 | 9/2010 | Majercak et al. |
| 7,799,046 B2 | 9/2010 | White et al. |
| 7,799,065 B2 | 9/2010 | Pappas |
| 7,803,185 B2 | 9/2010 | Gabbay |
| 7,806,919 B2 | 10/2010 | Bloom et al. |
| 7,823,267 B2 | 11/2010 | Bolduc |
| 7,824,442 B2 | 11/2010 | Salahieh et al. |
| 7,824,443 B2 | 11/2010 | Salahieh et al. |
| 7,833,262 B2 | 11/2010 | McGuckin, Jr. et al. |
| 7,837,727 B2 | 11/2010 | Goetz et al. |
| 7,846,203 B2 | 12/2010 | Cribier |
| 7,846,204 B2 | 12/2010 | Letac et al. |
| 7,854,758 B2 | 12/2010 | Taheri |
| 7,857,845 B2 | 12/2010 | Stacchino et al. |
| 7,862,602 B2 | 1/2011 | Licata et al. |
| 7,867,274 B2 | 1/2011 | Hill et al. |
| 7,887,583 B2 | 2/2011 | Macoviak |
| 7,892,276 B2 | 2/2011 | Stocker et al. |
| 7,892,292 B2 | 2/2011 | Stack et al. |
| 7,896,913 B2 | 3/2011 | Damm et al. |
| 7,896,915 B2 | 3/2011 | Guyenot et al. |
| 7,914,569 B2 | 3/2011 | Nguyen et al. |
| 7,914,574 B2 | 3/2011 | Schmid et al. |
| 7,914,575 B2 | 3/2011 | Guyenot et al. |
| 7,918,880 B2 | 4/2011 | Austin |
| 7,927,363 B2 | 4/2011 | Perouse |
| 7,938,851 B2 | 5/2011 | Olson et al. |
| 7,947,071 B2 | 5/2011 | Schmid et al. |
| 7,947,075 B2 | 5/2011 | Goetz et al. |
| 7,951,189 B2 | 5/2011 | Haverkost et al. |
| 7,959,666 B2 | 6/2011 | Salahieh et al. |
| 7,959,672 B2 | 6/2011 | Salahieh et al. |
| 7,967,853 B2 | 6/2011 | Eidenschink et al. |
| 7,972,359 B2 | 7/2011 | Kreidler |
| 7,972,376 B1 | 7/2011 | Dove et al. |

(56) References Cited

U.S. PATENT DOCUMENTS

| | | |
|---|---|---|
| 7,972,378 B2 | 7/2011 | Tabor et al. |
| 7,988,724 B2 | 8/2011 | Salahieh et al. |
| 7,993,386 B2 | 8/2011 | Elliott |
| 8,002,824 B2 | 8/2011 | Jenson et al. |
| 8,002,825 B2 | 8/2011 | Letac et al. |
| 8,012,198 B2 | 9/2011 | Hill et al. |
| 8,021,421 B2 | 9/2011 | Fogarty et al. |
| RE42,818 E | 10/2011 | Cali et al. |
| RE42,857 E | 10/2011 | Cali et al. |
| 8,038,704 B2 | 10/2011 | Sherburne |
| 8,038,709 B2 | 10/2011 | Palasis et al. |
| 8,043,450 B2 | 10/2011 | Cali et al. |
| 8,048,153 B2 | 11/2011 | Salahieh et al. |
| 8,052,715 B2 | 11/2011 | Quinn et al. |
| 8,052,749 B2 | 11/2011 | Salahieh et al. |
| 8,052,750 B2 | 11/2011 | Tuval et al. |
| 8,057,540 B2 | 11/2011 | Letac et al. |
| 8,062,355 B2 | 11/2011 | Figulla et al. |
| 8,062,536 B2 | 11/2011 | Liu et al. |
| 8,062,537 B2 | 11/2011 | Tuominen et al. |
| 8,062,749 B2 | 11/2011 | Shelestak et al. |
| 8,070,799 B2 | 12/2011 | Righini et al. |
| 8,075,641 B2 | 12/2011 | Aravanis et al. |
| 8,083,788 B2 | 12/2011 | Acosta et al. |
| 8,092,518 B2 | 1/2012 | Schreck |
| 8,092,520 B2 | 1/2012 | Quadri |
| 8,092,521 B2 | 1/2012 | Figulla et al. |
| 8,128,676 B2 | 3/2012 | Cummings |
| 8,128,681 B2 | 3/2012 | Shoemaker et al. |
| 8,133,217 B2 | 3/2012 | Stokes et al. |
| 8,133,270 B2 | 3/2012 | Kheradvar et al. |
| 8,136,659 B2 | 3/2012 | Salahieh et al. |
| 8,137,394 B2 | 3/2012 | Stocker et al. |
| 8,137,398 B2 | 3/2012 | Tuval et al. |
| 8,147,534 B2 | 4/2012 | Berez et al. |
| 8,157,853 B2 | 4/2012 | Laske et al. |
| 8,167,894 B2 | 5/2012 | Miles et al. |
| 8,172,896 B2 | 5/2012 | McNamara et al. |
| 8,182,528 B2 | 5/2012 | Salahieh et al. |
| 8,192,351 B2 | 6/2012 | Fishler et al. |
| 8,206,437 B2 | 6/2012 | Bonhoeffer et al. |
| 8,211,107 B2 | 7/2012 | Parks et al. |
| 8,216,174 B2 | 7/2012 | Wilk et al. |
| 8,216,301 B2 | 7/2012 | Bonhoeffer et al. |
| 8,221,493 B2 | 7/2012 | Boyle et al. |
| 8,226,707 B2 | 7/2012 | White |
| 8,226,710 B2 | 7/2012 | Nguyen et al. |
| 8,231,670 B2 | 7/2012 | Salahieh et al. |
| 8,236,049 B2 | 8/2012 | Rowe et al. |
| 8,236,241 B2 | 8/2012 | Carpentier et al. |
| 8,246,675 B2 | 8/2012 | Zegdi |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,277,500 B2 | 10/2012 | Schmid et al. |
| 8,287,584 B2 | 10/2012 | Salahieh et al. |
| 8,303,653 B2 | 11/2012 | Bonhoeffer et al. |
| 8,308,798 B2 | 11/2012 | Pintor et al. |
| 8,317,858 B2 | 11/2012 | Straubinger et al. |
| 8,323,335 B2 | 12/2012 | Rowe et al. |
| 8,328,868 B2 | 12/2012 | Paul et al. |
| 8,343,136 B2 | 1/2013 | How et al. |
| 8,343,213 B2 | 1/2013 | Salahieh et al. |
| 8,348,995 B2 | 1/2013 | Tuval et al. |
| 8,348,996 B2 | 1/2013 | Tuval et al. |
| 8,348,999 B2 | 1/2013 | Kheradvar et al. |
| 8,357,387 B2 | 1/2013 | Dove et al. |
| 8,366,767 B2 | 2/2013 | Zhang |
| 8,372,134 B2 | 2/2013 | Schlick et al. |
| 8,376,865 B2 | 2/2013 | Forster et al. |
| 8,377,117 B2 | 2/2013 | Keidar et al. |
| 8,382,822 B2 | 2/2013 | Pavcnik et al. |
| 8,398,704 B2 | 3/2013 | Straubinger et al. |
| 8,398,708 B2 | 3/2013 | Meiri et al. |
| 8,403,983 B2 | 3/2013 | Quadri et al. |
| 8,414,641 B2 | 4/2013 | Stocker et al. |
| 8,414,643 B2 | 4/2013 | Tuval et al. |
| 8,414,644 B2 | 4/2013 | Quadri et al. |
| 8,414,645 B2 | 4/2013 | Dwork et al. |
| 8,439,961 B2 | 5/2013 | Jagger et al. |
| 8,445,278 B2 | 5/2013 | Everaerts et al. |
| 8,460,365 B2 | 6/2013 | Haverkost et al. |
| 8,465,540 B2 | 6/2013 | Straubinger et al. |
| 8,468,667 B2 | 6/2013 | Straubinger et al. |
| 8,470,023 B2 | 6/2013 | Eidenschink et al. |
| 8,491,650 B2 | 7/2013 | Wiemeyer et al. |
| 8,512,394 B2 | 8/2013 | Schmid et al. |
| 8,512,399 B2 | 8/2013 | Lafontaine |
| 8,512,400 B2 | 8/2013 | Tran et al. |
| 8,512,401 B2 | 8/2013 | Murray, III et al. |
| 8,523,936 B2 | 9/2013 | Schmid et al. |
| 8,535,368 B2 | 9/2013 | Headley, Jr. et al. |
| 8,540,762 B2 | 9/2013 | Schmid et al. |
| 8,545,547 B2 | 10/2013 | Schmid et al. |
| 8,551,160 B2 | 10/2013 | Figulla et al. |
| 8,556,880 B2 | 10/2013 | Freyman et al. |
| 8,556,966 B2 | 10/2013 | Jenson |
| 8,568,475 B2 | 10/2013 | Nguyen et al. |
| 8,579,962 B2 | 11/2013 | Salahieh et al. |
| 8,579,965 B2 | 11/2013 | Bonhoeffer et al. |
| 8,585,756 B2 | 11/2013 | Bonhoeffer et al. |
| 8,585,759 B2 | 11/2013 | Bumbalough |
| 8,591,570 B2 | 11/2013 | Revuelta et al. |
| 8,597,226 B2 | 12/2013 | Wilk et al. |
| 8,603,159 B2 | 12/2013 | Seguin et al. |
| 8,603,160 B2 | 12/2013 | Salahieh et al. |
| 8,617,235 B2 | 12/2013 | Schmid et al. |
| 8,617,236 B2 | 12/2013 | Paul et al. |
| 8,623,074 B2 | 1/2014 | Ryan |
| 8,623,075 B2 | 1/2014 | Murray, III et al. |
| 8,623,076 B2 | 1/2014 | Salahieh et al. |
| 8,623,078 B2 | 1/2014 | Salahieh et al. |
| 8,628,562 B2 | 1/2014 | Cummings |
| 8,628,571 B1 | 1/2014 | Hacohen et al. |
| 8,647,381 B2 | 2/2014 | Essinger et al. |
| 8,668,733 B2 | 3/2014 | Haug et al. |
| 8,672,997 B2 | 3/2014 | Drasler et al. |
| 8,679,174 B2 | 3/2014 | Ottma et al. |
| 8,685,077 B2 | 4/2014 | Laske et al. |
| 8,696,743 B2 | 4/2014 | Holecek et al. |
| 8,721,713 B2 | 5/2014 | Tower et al. |
| 8,721,717 B2 | 5/2014 | Shoemaker et al. |
| 8,734,508 B2 | 5/2014 | Hastings et al. |
| 8,758,430 B2 | 6/2014 | Ferrari et al. |
| 8,764,818 B2 | 7/2014 | Gregg |
| 8,778,020 B2 | 7/2014 | Gregg et al. |
| 8,790,395 B2 | 7/2014 | Straubinger et al. |
| 8,795,305 B2 | 8/2014 | Martin et al. |
| 8,795,356 B2 | 8/2014 | Quadri et al. |
| 8,808,356 B2 | 8/2014 | Braido et al. |
| 8,808,364 B2 | 8/2014 | Palasis et al. |
| 8,828,078 B2 | 9/2014 | Salahieh et al. |
| 8,828,079 B2 | 9/2014 | Thielen et al. |
| 8,840,662 B2 | 9/2014 | Salahieh et al. |
| 8,840,663 B2 | 9/2014 | Salahieh et al. |
| 8,845,721 B2 | 9/2014 | Braido et al. |
| 8,851,286 B2 | 10/2014 | Chang et al. |
| 8,852,272 B2 | 10/2014 | Gross et al. |
| 8,858,620 B2 | 10/2014 | Salahieh et al. |
| 8,894,703 B2 | 11/2014 | Salahieh et al. |
| 8,932,349 B2 | 1/2015 | Jenson et al. |
| 8,940,014 B2 | 1/2015 | Gamarra et al. |
| 8,951,243 B2 | 2/2015 | Crisostomo et al. |
| 8,951,299 B2 | 2/2015 | Paul et al. |
| 8,956,383 B2 | 2/2015 | Aklog et al. |
| 8,992,608 B2 | 3/2015 | Haug et al. |
| 8,998,976 B2 | 4/2015 | Gregg et al. |
| 9,005,273 B2 | 4/2015 | Salahieh et al. |
| 9,011,521 B2 | 4/2015 | Haug et al. |
| 9,023,099 B2 | 5/2015 | Duffy et al. |
| 9,028,542 B2 | 5/2015 | Hill et al. |
| 9,039,756 B2 | 5/2015 | White |
| 9,044,318 B2 | 6/2015 | Straubinger et al. |
| 9,131,926 B2 | 9/2015 | Crisostomo et al. |

(56) References Cited

U.S. PATENT DOCUMENTS

| | | |
|---|---|---|
| 9,149,358 B2 | 10/2015 | Tabor et al. |
| 9,168,130 B2 | 10/2015 | Straubinger et al. |
| 9,168,131 B2 | 10/2015 | Yohanan et al. |
| 9,168,136 B2 | 10/2015 | Yang et al. |
| 9,180,005 B1 | 11/2015 | Lashinski et al. |
| 9,186,482 B2 | 11/2015 | Dorn |
| 9,211,266 B2 | 12/2015 | Iwazawa et al. |
| 9,216,082 B2 | 12/2015 | Von Segesser et al. |
| 9,248,037 B2 | 2/2016 | Roeder et al. |
| 9,265,608 B2 | 2/2016 | Miller et al. |
| 9,277,991 B2 | 3/2016 | Salahieh et al. |
| 9,277,993 B2 | 3/2016 | Gamarra et al. |
| 9,301,840 B2 | 4/2016 | Nguyen et al. |
| 9,301,843 B2 | 4/2016 | Richardson et al. |
| 9,308,085 B2 | 4/2016 | Salahieh et al. |
| 9,320,599 B2 | 4/2016 | Salahieh et al. |
| 9,326,853 B2 | 5/2016 | Olson et al. |
| 9,358,106 B2 | 6/2016 | Salahieh et al. |
| 9,358,110 B2 | 6/2016 | Paul et al. |
| 9,370,419 B2 | 6/2016 | Hill et al. |
| 9,370,421 B2 | 6/2016 | Crisostomo et al. |
| 9,387,076 B2 | 7/2016 | Paul et al. |
| 9,393,094 B2 | 7/2016 | Salahieh et al. |
| 9,393,113 B2 | 7/2016 | Salahieh et al. |
| 9,393,114 B2 | 7/2016 | Sutton et al. |
| 9,393,115 B2 | 7/2016 | Tabor et al. |
| 9,415,567 B2 | 8/2016 | Sogard et al. |
| 9,421,083 B2 | 8/2016 | Eidenschink et al. |
| 9,439,759 B2 | 9/2016 | Straubinger et al. |
| 9,463,084 B2 | 10/2016 | Stinson |
| 9,474,598 B2 | 10/2016 | Gregg et al. |
| 9,474,609 B2 | 10/2016 | Haverkost et al. |
| 9,492,276 B2 | 11/2016 | Lee et al. |
| 9,510,945 B2 | 12/2016 | Sutton et al. |
| 9,526,609 B2 | 12/2016 | Salahieh et al. |
| 9,532,872 B2 | 1/2017 | Salahieh et al. |
| 9,539,091 B2 | 1/2017 | Yang et al. |
| 9,554,924 B2 | 1/2017 | Schlick et al. |
| 9,597,432 B2 | 3/2017 | Nakamura |
| 9,649,212 B2 | 5/2017 | Fargahi |
| 9,717,593 B2 | 8/2017 | Alkhatib et al. |
| D800,908 S | 10/2017 | Hariton et al. |
| 9,775,709 B2 | 10/2017 | Miller et al. |
| 9,788,945 B2 | 10/2017 | Ottma et al. |
| 9,861,476 B2 | 1/2018 | Salahieh et al. |
| 9,867,694 B2 | 1/2018 | Girard et al. |
| 9,867,699 B2 | 1/2018 | Straubinger et al. |
| 9,872,768 B2 | 1/2018 | Paul et al. |
| 9,889,002 B2 | 2/2018 | Bonhoeffer et al. |
| 9,901,445 B2 | 2/2018 | Backus et al. |
| 9,949,824 B2 | 4/2018 | Bonhoeffer et al. |
| 9,956,075 B2 | 5/2018 | Salahieh et al. |
| 9,987,133 B2 | 6/2018 | Straubinger et al. |
| 10,092,324 B2 | 10/2018 | Gillespie et al. |
| 10,143,552 B2 | 12/2018 | Wallace et al. |
| 10,154,901 B2 | 12/2018 | Straubinger et al. |
| 10,321,987 B2 | 6/2019 | Wang et al. |
| 10,363,134 B2 | 7/2019 | Figulla et al. |
| 10,543,084 B2 | 1/2020 | Guyenot et al. |
| 10,702,382 B2 | 7/2020 | Straubinger et al. |
| 10,709,555 B2 | 7/2020 | Schreck et al. |
| 2001/0000041 A1 | 3/2001 | Selmon et al. |
| 2001/0001314 A1 | 5/2001 | Davison et al. |
| 2001/0002445 A1 | 5/2001 | Vesely |
| 2001/0004683 A1 | 6/2001 | Gambale et al. |
| 2001/0004690 A1 | 6/2001 | Gambale et al. |
| 2001/0004699 A1 | 6/2001 | Gittings et al. |
| 2001/0007956 A1 | 7/2001 | Letac et al. |
| 2001/0008969 A1 | 7/2001 | Evans et al. |
| 2001/0010017 A1 | 7/2001 | Letac et al. |
| 2001/0011187 A1 | 8/2001 | Pavcnik et al. |
| 2001/0011189 A1 | 8/2001 | Drasler et al. |
| 2001/0012948 A1 | 8/2001 | Vanney |
| 2001/0014813 A1 | 8/2001 | Saadat et al. |
| 2001/0016700 A1 | 8/2001 | Eno et al. |
| 2001/0018596 A1 | 8/2001 | Selmon et al. |
| 2001/0020172 A1 | 9/2001 | Selmon et al. |
| 2001/0021872 A1 | 9/2001 | Bailey et al. |
| 2001/0025196 A1 | 9/2001 | Chinn et al. |
| 2001/0025643 A1 | 10/2001 | Foley |
| 2001/0027287 A1 | 10/2001 | Shmulewitz et al. |
| 2001/0027338 A1 | 10/2001 | Greenberg |
| 2001/0027339 A1 | 10/2001 | Boatman et al. |
| 2001/0029385 A1 | 10/2001 | Shennib et al. |
| 2001/0032013 A1 | 10/2001 | Marton |
| 2001/0034547 A1 | 10/2001 | Hall et al. |
| 2001/0037117 A1 | 11/2001 | Gambale et al. |
| 2001/0037141 A1 | 11/2001 | Yee et al. |
| 2001/0037149 A1 | 11/2001 | Wilk |
| 2001/0039426 A1 | 11/2001 | Makower et al. |
| 2001/0039445 A1 | 11/2001 | Hall et al. |
| 2001/0039450 A1 | 11/2001 | Pavcnik et al. |
| 2001/0041902 A1 | 11/2001 | Lepulu et al. |
| 2001/0041928 A1 | 11/2001 | Pavcnik et al. |
| 2001/0041930 A1 | 11/2001 | Globerman et al. |
| 2001/0044631 A1 | 11/2001 | Akin et al. |
| 2001/0044634 A1 | 11/2001 | Don Michael et al. |
| 2001/0044647 A1 | 11/2001 | Pinchuk et al. |
| 2001/0044652 A1 | 11/2001 | Moore |
| 2001/0044656 A1 | 11/2001 | Williamson, IV et al. |
| 2001/0047165 A1 | 11/2001 | Makower et al. |
| 2001/0049523 A1 | 12/2001 | DeVore et al. |
| 2001/0051822 A1 | 12/2001 | Stack et al. |
| 2001/0053932 A1 | 12/2001 | Phelps et al. |
| 2002/0002349 A1 | 1/2002 | Flaherty et al. |
| 2002/0002396 A1 | 1/2002 | Fulkerson |
| 2002/0002401 A1 | 1/2002 | McGuckin, Jr. et al. |
| 2002/0004662 A1 | 1/2002 | Wilk |
| 2002/0004663 A1 | 1/2002 | Gittings et al. |
| 2002/0007138 A1 | 1/2002 | Wilk et al. |
| 2002/0010489 A1 | 1/2002 | Grayzel et al. |
| 2002/0010508 A1 | 1/2002 | Chobotov |
| 2002/0026233 A1 | 2/2002 | Shaknovich |
| 2002/0029014 A1 | 3/2002 | Jayaraman |
| 2002/0029079 A1 | 3/2002 | Kim et al. |
| 2002/0029981 A1 | 3/2002 | Nigam |
| 2002/0032476 A1 | 3/2002 | Gambale et al. |
| 2002/0032478 A1 | 3/2002 | Boekstegers et al. |
| 2002/0032480 A1 | 3/2002 | Spence et al. |
| 2002/0032481 A1 | 3/2002 | Gabbay |
| 2002/0035390 A1 | 3/2002 | Schaldach et al. |
| 2002/0035396 A1 | 3/2002 | Heath |
| 2002/0042650 A1 | 4/2002 | Vardi et al. |
| 2002/0042651 A1 | 4/2002 | Liddicoat et al. |
| 2002/0045846 A1 | 4/2002 | Kaplon et al. |
| 2002/0045928 A1 | 4/2002 | Boekstegers |
| 2002/0045929 A1 | 4/2002 | Diaz |
| 2002/0049486 A1 | 4/2002 | Knudson et al. |
| 2002/0052651 A1 | 5/2002 | Myers et al. |
| 2002/0055767 A1 | 5/2002 | Forde et al. |
| 2002/0055769 A1 | 5/2002 | Wang |
| 2002/0055772 A1 | 5/2002 | McGuckin, Jr. et al. |
| 2002/0055774 A1 | 5/2002 | Liddicoat |
| 2002/0055775 A1 | 5/2002 | Carpentier et al. |
| 2002/0058897 A1 | 5/2002 | Renati |
| 2002/0058987 A1 | 5/2002 | Butaric et al. |
| 2002/0058993 A1 | 5/2002 | Landau et al. |
| 2002/0058995 A1 | 5/2002 | Stevens |
| 2002/0062146 A1 | 5/2002 | Makower et al. |
| 2002/0065478 A1 | 5/2002 | Knudson et al. |
| 2002/0065485 A1 | 5/2002 | DuBois et al. |
| 2002/0072699 A1 | 6/2002 | Knudson et al. |
| 2002/0072789 A1 | 6/2002 | Hackett et al. |
| 2002/0077566 A1 | 6/2002 | Laroya et al. |
| 2002/0077654 A1 | 6/2002 | Javier, Jr. et al. |
| 2002/0077696 A1 | 6/2002 | Zadno-Azizi et al. |
| 2002/0082584 A1 | 6/2002 | Rosenman et al. |
| 2002/0082609 A1 | 6/2002 | Green |
| 2002/0092535 A1 | 7/2002 | Wilk |
| 2002/0092536 A1 | 7/2002 | LaFontaine et al. |
| 2002/0095111 A1 | 7/2002 | Tweden et al. |
| 2002/0095173 A1 | 7/2002 | Mazzocchi et al. |
| 2002/0095206 A1 | 7/2002 | Addonizio et al. |
| 2002/0095209 A1 | 7/2002 | Zadno-Azizi et al. |

(56) References Cited

U.S. PATENT DOCUMENTS

| | | |
|---|---|---|
| 2002/0099439 A1 | 7/2002 | Schwartz et al. |
| 2002/0100484 A1 | 8/2002 | Hall et al. |
| 2002/0103533 A1 | 8/2002 | Langberg et al. |
| 2002/0107565 A1 | 8/2002 | Greenhalgh |
| 2002/0111627 A1 | 8/2002 | Vincent-Prestigiacomo |
| 2002/0111665 A1 | 8/2002 | Lauterjung |
| 2002/0111668 A1 | 8/2002 | Smith |
| 2002/0111672 A1 | 8/2002 | Kim et al. |
| 2002/0111674 A1 | 8/2002 | Chouinard et al. |
| 2002/0117789 A1 | 8/2002 | Childers et al. |
| 2002/0120322 A1 | 8/2002 | Thompson et al. |
| 2002/0120323 A1 | 8/2002 | Thompson et al. |
| 2002/0120328 A1 | 8/2002 | Pathak et al. |
| 2002/0123698 A1 | 9/2002 | Garibotto et al. |
| 2002/0123786 A1 | 9/2002 | Gittings et al. |
| 2002/0123790 A1 | 9/2002 | White et al. |
| 2002/0123802 A1 | 9/2002 | Snyders |
| 2002/0133183 A1 | 9/2002 | Lentz et al. |
| 2002/0133226 A1 | 9/2002 | Marquez et al. |
| 2002/0138087 A1 | 9/2002 | Shennib et al. |
| 2002/0138138 A1 | 9/2002 | Yang |
| 2002/0143285 A1 | 10/2002 | Eno et al. |
| 2002/0143289 A1 | 10/2002 | Ellis et al. |
| 2002/0143387 A1 | 10/2002 | Soetikno et al. |
| 2002/0144696 A1 | 10/2002 | Sharkawy et al. |
| 2002/0151913 A1 | 10/2002 | Berg et al. |
| 2002/0151970 A1 | 10/2002 | Garrison et al. |
| 2002/0156522 A1 | 10/2002 | Ivancev et al. |
| 2002/0161377 A1 | 10/2002 | Rabkin |
| 2002/0161383 A1 | 10/2002 | Akin et al. |
| 2002/0161390 A1 | 10/2002 | Mouw |
| 2002/0161392 A1 | 10/2002 | Dubrul |
| 2002/0161394 A1 | 10/2002 | Macoviak et al. |
| 2002/0161424 A1 | 10/2002 | Rapacki et al. |
| 2002/0161426 A1 | 10/2002 | Iancea |
| 2002/0165479 A1 | 11/2002 | Wilk |
| 2002/0165576 A1 | 11/2002 | Boyle et al. |
| 2002/0165606 A1 | 11/2002 | Wolf et al. |
| 2002/0173842 A1 | 11/2002 | Buchanan |
| 2002/0177766 A1 | 11/2002 | Mogul |
| 2002/0177772 A1 | 11/2002 | Altman et al. |
| 2002/0177840 A1 | 11/2002 | Farnholtz |
| 2002/0177894 A1 | 11/2002 | Acosta et al. |
| 2002/0179098 A1 | 12/2002 | Makower et al. |
| 2002/0183716 A1 | 12/2002 | Herweck et al. |
| 2002/0183781 A1 | 12/2002 | Casey et al. |
| 2002/0186558 A1 | 12/2002 | Plank et al. |
| 2002/0188341 A1 | 12/2002 | Elliott |
| 2002/0188344 A1 | 12/2002 | Bolea et al. |
| 2002/0193782 A1 | 12/2002 | Ellis et al. |
| 2002/0193871 A1 | 12/2002 | Beyersdorf et al. |
| 2002/0198594 A1 | 12/2002 | Schreck |
| 2003/0004541 A1 | 1/2003 | Linder et al. |
| 2003/0004560 A1 | 1/2003 | Chobotov et al. |
| 2003/0009189 A1 | 1/2003 | Gilson et al. |
| 2003/0014104 A1 | 1/2003 | Cribier |
| 2003/0018377 A1 | 1/2003 | Berg et al. |
| 2003/0018379 A1 | 1/2003 | Knudson et al. |
| 2003/0023300 A1 | 1/2003 | Bailey et al. |
| 2003/0023303 A1 | 1/2003 | Palmaz et al. |
| 2003/0027332 A1 | 2/2003 | Lafrance et al. |
| 2003/0028213 A1 | 2/2003 | Thill et al. |
| 2003/0028247 A1 | 2/2003 | Cali |
| 2003/0033001 A1 | 2/2003 | Igaki |
| 2003/0036791 A1 | 2/2003 | Philipp et al. |
| 2003/0036795 A1 | 2/2003 | Andersen et al. |
| 2003/0040736 A1 | 2/2003 | Stevens et al. |
| 2003/0040771 A1 | 2/2003 | Hyodoh et al. |
| 2003/0040772 A1 | 2/2003 | Hyodoh et al. |
| 2003/0040791 A1 | 2/2003 | Oktay |
| 2003/0040792 A1 | 2/2003 | Gabbay |
| 2003/0042186 A1 | 3/2003 | Boyle |
| 2003/0044315 A1 | 3/2003 | Boekstegers |
| 2003/0045828 A1 | 3/2003 | Wilk |
| 2003/0050694 A1 | 3/2003 | Yang et al. |
| 2003/0055371 A1 | 3/2003 | Wolf et al. |
| 2003/0055495 A1 | 3/2003 | Pease et al. |
| 2003/0057156 A1 | 3/2003 | Peterson et al. |
| 2003/0060844 A1 | 3/2003 | Borillo et al. |
| 2003/0065386 A1 | 4/2003 | Weadock |
| 2003/0069492 A1 | 4/2003 | Abrams et al. |
| 2003/0069646 A1 | 4/2003 | Stinson |
| 2003/0070944 A1 | 4/2003 | Nigam |
| 2003/0073973 A1 | 4/2003 | Evans et al. |
| 2003/0074058 A1 | 4/2003 | Sherry |
| 2003/0078561 A1 | 4/2003 | Gambale et al. |
| 2003/0078652 A1 | 4/2003 | Sutherland |
| 2003/0083730 A1 | 5/2003 | Stinson |
| 2003/0093145 A1 | 5/2003 | Lawrence-Brown et al. |
| 2003/0100918 A1 | 5/2003 | Duane |
| 2003/0100919 A1 | 5/2003 | Hopkins et al. |
| 2003/0100920 A1 | 5/2003 | Akin et al. |
| 2003/0105514 A1 | 6/2003 | Phelps et al. |
| 2003/0109924 A1 | 6/2003 | Cribier |
| 2003/0109930 A1 | 6/2003 | Bluni et al. |
| 2003/0114912 A1 | 6/2003 | Sequin et al. |
| 2003/0114913 A1 | 6/2003 | Spenser et al. |
| 2003/0120195 A1 | 6/2003 | Milo et al. |
| 2003/0125795 A1 | 7/2003 | Pavcnik et al. |
| 2003/0130726 A1 | 7/2003 | Thorpe et al. |
| 2003/0130727 A1 | 7/2003 | Drasler et al. |
| 2003/0130729 A1 | 7/2003 | Paniagua et al. |
| 2003/0130746 A1 | 7/2003 | Ashworth et al. |
| 2003/0135257 A1 | 7/2003 | Taheri |
| 2003/0139796 A1 | 7/2003 | Sequin et al. |
| 2003/0139798 A1 | 7/2003 | Brown et al. |
| 2003/0139803 A1 | 7/2003 | Sequin et al. |
| 2003/0139804 A1 | 7/2003 | Hankh et al. |
| 2003/0144657 A1 | 7/2003 | Bowe et al. |
| 2003/0144732 A1 | 7/2003 | Cosgrove et al. |
| 2003/0149474 A1 | 8/2003 | Becker |
| 2003/0149475 A1 | 8/2003 | Hyodoh et al. |
| 2003/0149476 A1 | 8/2003 | Damm et al. |
| 2003/0149477 A1 | 8/2003 | Gabbay |
| 2003/0149478 A1 | 8/2003 | Figulla et al. |
| 2003/0153971 A1 | 8/2003 | Chandrasekaran |
| 2003/0153974 A1 | 8/2003 | Spenser et al. |
| 2003/0158573 A1 | 8/2003 | Gittings et al. |
| 2003/0158595 A1 | 8/2003 | Randall et al. |
| 2003/0163193 A1 | 8/2003 | Widenhouse |
| 2003/0163198 A1 | 8/2003 | Morra et al. |
| 2003/0165352 A1 | 9/2003 | Ibrahim et al. |
| 2003/0171803 A1 | 9/2003 | Shimon |
| 2003/0171805 A1 | 9/2003 | Berg et al. |
| 2003/0176884 A1 | 9/2003 | Berrada et al. |
| 2003/0181850 A1 | 9/2003 | Diamond et al. |
| 2003/0181938 A1 | 9/2003 | Roth et al. |
| 2003/0181942 A1 | 9/2003 | Sutton et al. |
| 2003/0187495 A1 | 10/2003 | Cully et al. |
| 2003/0191449 A1 | 10/2003 | Nash et al. |
| 2003/0191516 A1 | 10/2003 | Weldon et al. |
| 2003/0191519 A1 | 10/2003 | Lombardi et al. |
| 2003/0191526 A1 | 10/2003 | Van Tassel et al. |
| 2003/0195457 A1 | 10/2003 | LaFontaine et al. |
| 2003/0195458 A1 | 10/2003 | Phelps et al. |
| 2003/0195609 A1 | 10/2003 | Berenstein et al. |
| 2003/0195620 A1 | 10/2003 | Huynh et al. |
| 2003/0198722 A1 | 10/2003 | Johnston, Jr. et al. |
| 2003/0199759 A1 | 10/2003 | Richard |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0199972 A1 | 10/2003 | Zadno-Azizi et al. |
| 2003/0204160 A1 | 10/2003 | Kamm et al. |
| 2003/0204249 A1 | 10/2003 | Letort |
| 2003/0208224 A1 | 11/2003 | Broome |
| 2003/0212410 A1 | 11/2003 | Stenzel et al. |
| 2003/0212413 A1 | 11/2003 | Wilk |
| 2003/0212429 A1 | 11/2003 | Keegan et al. |
| 2003/0212452 A1 | 11/2003 | Zadno-Azizi et al. |
| 2003/0212454 A1 | 11/2003 | Scott et al. |
| 2003/0216678 A1 | 11/2003 | March et al. |
| 2003/0216679 A1 | 11/2003 | Wolf et al. |
| 2003/0216774 A1 | 11/2003 | Larson |

(56) References Cited

U.S. PATENT DOCUMENTS

| | | |
|---|---|---|
| 2003/0220661 A1 | 11/2003 | Mowry et al. |
| 2003/0220667 A1 | 11/2003 | Van Der Burg et al. |
| 2003/0225445 A1 | 12/2003 | Derus et al. |
| 2003/0229366 A1 | 12/2003 | Reggie et al. |
| 2003/0229390 A1 | 12/2003 | Ashton et al. |
| 2003/0233117 A1 | 12/2003 | Adams et al. |
| 2003/0236542 A1 | 12/2003 | Makower |
| 2003/0236567 A1 | 12/2003 | Elliot |
| 2003/0236568 A1 | 12/2003 | Hojeibane et al. |
| 2003/0236570 A1 | 12/2003 | Cook et al. |
| 2004/0004926 A1 | 1/2004 | Maeda |
| 2004/0006298 A1 | 1/2004 | Wilk |
| 2004/0006380 A1 | 1/2004 | Buck et al. |
| 2004/0015225 A1 | 1/2004 | Kim et al. |
| 2004/0015228 A1 | 1/2004 | Lombardi et al. |
| 2004/0018651 A1 | 1/2004 | Nadeau |
| 2004/0019348 A1 | 1/2004 | Stevens et al. |
| 2004/0019374 A1 | 1/2004 | Hojeibane et al. |
| 2004/0026389 A1 | 2/2004 | Kessler et al. |
| 2004/0033364 A1 | 2/2004 | Spiridigliozzi et al. |
| 2004/0034411 A1 | 2/2004 | Quijano et al. |
| 2004/0037946 A1 | 2/2004 | Morra et al. |
| 2004/0039343 A1 | 2/2004 | Eppstein et al. |
| 2004/0039436 A1 | 2/2004 | Spenser et al. |
| 2004/0044350 A1 | 3/2004 | Martin et al. |
| 2004/0044361 A1 | 3/2004 | Frazier et al. |
| 2004/0044392 A1 | 3/2004 | Von Oepen |
| 2004/0044400 A1 | 3/2004 | Cheng et al. |
| 2004/0044402 A1 | 3/2004 | Jung et al. |
| 2004/0049204 A1 | 3/2004 | Harari et al. |
| 2004/0049207 A1 | 3/2004 | Goldfarb et al. |
| 2004/0049224 A1 | 3/2004 | Buehlmann et al. |
| 2004/0049226 A1 | 3/2004 | Keegan et al. |
| 2004/0049262 A1 | 3/2004 | Obermiller et al. |
| 2004/0049266 A1 | 3/2004 | Anduiza et al. |
| 2004/0058097 A1 | 3/2004 | Weder |
| 2004/0059280 A1 | 3/2004 | Makower et al. |
| 2004/0059407 A1 | 3/2004 | Escamilla et al. |
| 2004/0059409 A1 | 3/2004 | Stenzel |
| 2004/0059429 A1 | 3/2004 | Amin et al. |
| 2004/0073157 A1 | 4/2004 | Knudson et al. |
| 2004/0073198 A1 | 4/2004 | Gilson et al. |
| 2004/0073238 A1 | 4/2004 | Makower |
| 2004/0073289 A1 | 4/2004 | Hartley et al. |
| 2004/0077987 A1 | 4/2004 | Rapacki et al. |
| 2004/0077988 A1 | 4/2004 | Tweden et al. |
| 2004/0077990 A1 | 4/2004 | Knudson et al. |
| 2004/0078950 A1 | 4/2004 | Schreck et al. |
| 2004/0082904 A1 | 4/2004 | Houde et al. |
| 2004/0082967 A1 | 4/2004 | Broome et al. |
| 2004/0082989 A1 | 4/2004 | Cook et al. |
| 2004/0087982 A1 | 5/2004 | Eskuri |
| 2004/0088042 A1 | 5/2004 | Kim et al. |
| 2004/0088045 A1 | 5/2004 | Cox |
| 2004/0092858 A1 | 5/2004 | Wilson et al. |
| 2004/0092989 A1 | 5/2004 | Wilson et al. |
| 2004/0093005 A1 | 5/2004 | Durcan |
| 2004/0093016 A1 | 5/2004 | Root et al. |
| 2004/0093060 A1 | 5/2004 | Seguin et al. |
| 2004/0093063 A1 | 5/2004 | Wright et al. |
| 2004/0093070 A1 | 5/2004 | Hojeibane et al. |
| 2004/0093075 A1 | 5/2004 | Kuehne |
| 2004/0097788 A1 | 5/2004 | Mourlas et al. |
| 2004/0098022 A1 | 5/2004 | Barone |
| 2004/0098098 A1 | 5/2004 | McGuckin, Jr. et al. |
| 2004/0098099 A1 | 5/2004 | McCullagh et al. |
| 2004/0098112 A1 | 5/2004 | DiMatteo et al. |
| 2004/0102855 A1 | 5/2004 | Shank |
| 2004/0106931 A1 | 6/2004 | Guiles et al. |
| 2004/0106976 A1 | 6/2004 | Bailey et al. |
| 2004/0106990 A1 | 6/2004 | Spence et al. |
| 2004/0107004 A1 | 6/2004 | Levine et al. |
| 2004/0111096 A1 | 6/2004 | Tu et al. |
| 2004/0113306 A1 | 6/2004 | Rapacki et al. |
| 2004/0116951 A1 | 6/2004 | Rosengart |
| 2004/0116999 A1 | 6/2004 | Ledergerber |
| 2004/0117004 A1 | 6/2004 | Osborne et al. |
| 2004/0117009 A1 | 6/2004 | Cali et al. |
| 2004/0118415 A1 | 6/2004 | Hall et al. |
| 2004/0122318 A1 | 6/2004 | Flaherty et al. |
| 2004/0122347 A1 | 6/2004 | Knudson et al. |
| 2004/0122468 A1 | 6/2004 | Yodfat et al. |
| 2004/0122514 A1 | 6/2004 | Fogarty et al. |
| 2004/0122516 A1 | 6/2004 | Fogarty et al. |
| 2004/0127847 A1 | 7/2004 | DuBois et al. |
| 2004/0127912 A1 | 7/2004 | Rabkin et al. |
| 2004/0127936 A1 | 7/2004 | Salahieh et al. |
| 2004/0127979 A1 | 7/2004 | Wilson et al. |
| 2004/0127982 A1 | 7/2004 | Machold et al. |
| 2004/0133154 A1 | 7/2004 | Flaherty et al. |
| 2004/0133225 A1 | 7/2004 | Makower |
| 2004/0133274 A1 | 7/2004 | Webler et al. |
| 2004/0138694 A1 | 7/2004 | Tran et al. |
| 2004/0138742 A1 | 7/2004 | Myers et al. |
| 2004/0138743 A1 | 7/2004 | Myers et al. |
| 2004/0138745 A1 | 7/2004 | Macoviak et al. |
| 2004/0147868 A1 | 7/2004 | Bardsley et al. |
| 2004/0147869 A1 | 7/2004 | Wolf et al. |
| 2004/0148018 A1 | 7/2004 | Carpentier et al. |
| 2004/0148021 A1 | 7/2004 | Cartledge et al. |
| 2004/0153094 A1 | 8/2004 | Dunfee et al. |
| 2004/0153145 A1 | 8/2004 | Simionescu et al. |
| 2004/0153146 A1 | 8/2004 | Lashinski et al. |
| 2004/0158143 A1 | 8/2004 | Flaherty et al. |
| 2004/0158277 A1 | 8/2004 | Lowe et al. |
| 2004/0163094 A1 | 8/2004 | Matsui et al. |
| 2004/0167444 A1 | 8/2004 | Laroya et al. |
| 2004/0167565 A1 | 8/2004 | Beulke et al. |
| 2004/0167573 A1 | 8/2004 | Williamson, IV et al. |
| 2004/0167620 A1 | 8/2004 | Ortiz et al. |
| 2004/0168691 A1 | 9/2004 | Sharkawy et al. |
| 2004/0176791 A1 | 9/2004 | Lim et al. |
| 2004/0181140 A1 | 9/2004 | Falwell et al. |
| 2004/0186507 A1 | 9/2004 | Hall et al. |
| 2004/0186557 A1 | 9/2004 | Gambale et al. |
| 2004/0186558 A1 | 9/2004 | Pavcnik et al. |
| 2004/0186563 A1 | 9/2004 | Lobbi |
| 2004/0186565 A1 | 9/2004 | Schreck |
| 2004/0186587 A1 | 9/2004 | Ahern |
| 2004/0193180 A1 | 9/2004 | Buzzard et al. |
| 2004/0193244 A1 | 9/2004 | Hartley et al. |
| 2004/0193252 A1 | 9/2004 | Perez et al. |
| 2004/0193261 A1 | 9/2004 | Berreklouw |
| 2004/0197695 A1 | 10/2004 | Aono |
| 2004/0199245 A1 | 10/2004 | Lauterjung |
| 2004/0204683 A1 | 10/2004 | McGuckin, Jr. et al. |
| 2004/0204755 A1 | 10/2004 | Robin |
| 2004/0206363 A1 | 10/2004 | McCarthy et al. |
| 2004/0210104 A1 | 10/2004 | Lau et al. |
| 2004/0210190 A1 | 10/2004 | Kohler et al. |
| 2004/0210240 A1 | 10/2004 | Saint |
| 2004/0210301 A1 | 10/2004 | Obermiller et al. |
| 2004/0210304 A1 | 10/2004 | Seguin et al. |
| 2004/0210306 A1 | 10/2004 | Quijano et al. |
| 2004/0210307 A1 | 10/2004 | Khairkhahan |
| 2004/0215317 A1 | 10/2004 | Cummings |
| 2004/0215331 A1 | 10/2004 | Chew et al. |
| 2004/0215333 A1 | 10/2004 | Duran et al. |
| 2004/0215339 A1 | 10/2004 | Drasler et al. |
| 2004/0219180 A1 | 11/2004 | Gambale et al. |
| 2004/0220598 A1 | 11/2004 | Bolduc et al. |
| 2004/0220655 A1 | 11/2004 | Swanson et al. |
| 2004/0225321 A1 | 11/2004 | Krolik et al. |
| 2004/0225353 A1 | 11/2004 | McGuckin, Jr. et al. |
| 2004/0225354 A1 | 11/2004 | Allen et al. |
| 2004/0225355 A1 | 11/2004 | Stevens |
| 2004/0236411 A1 | 11/2004 | Sarac et al. |
| 2004/0236418 A1 | 11/2004 | Stevens |
| 2004/0243143 A1 | 12/2004 | Corcoran et al. |
| 2004/0243221 A1 | 12/2004 | Fawzi et al. |
| 2004/0249343 A1 | 12/2004 | Cioanta |
| 2004/0254594 A1 | 12/2004 | Alfaro |
| 2004/0254636 A1 | 12/2004 | Flagle et al. |
| 2004/0260389 A1 | 12/2004 | Case et al. |

(56) References Cited

U.S. PATENT DOCUMENTS

| | | |
|---|---|---|
| 2004/0260390 A1 | 12/2004 | Sarac et al. |
| 2004/0260393 A1 | 12/2004 | Rahdert et al. |
| 2004/0260394 A1 | 12/2004 | Douk et al. |
| 2004/0267357 A1 | 12/2004 | Allen et al. |
| 2005/0000858 A1 | 1/2005 | Roovers |
| 2005/0004505 A1 | 1/2005 | Phelps et al. |
| 2005/0004558 A1 | 1/2005 | Gambale et al. |
| 2005/0004648 A1 | 1/2005 | Boekstegers |
| 2005/0008589 A1 | 1/2005 | Legrand et al. |
| 2005/0009000 A1 | 1/2005 | Wilhelm et al. |
| 2005/0010246 A1 | 1/2005 | Streeter et al. |
| 2005/0010285 A1 | 1/2005 | Lambrecht et al. |
| 2005/0010287 A1 | 1/2005 | Macoviak et al. |
| 2005/0015112 A1 | 1/2005 | Cohn et al. |
| 2005/0021136 A1 | 1/2005 | Xie et al. |
| 2005/0025857 A1 | 2/2005 | Schoenherr et al. |
| 2005/0027305 A1 | 2/2005 | Shiu et al. |
| 2005/0027348 A1 | 2/2005 | Case et al. |
| 2005/0033220 A1 | 2/2005 | Wilk et al. |
| 2005/0033398 A1 | 2/2005 | Seguin |
| 2005/0033402 A1 | 2/2005 | Cully et al. |
| 2005/0038495 A1 | 2/2005 | Greenan |
| 2005/0038509 A1 | 2/2005 | Ashe |
| 2005/0043585 A1 | 2/2005 | Datta et al. |
| 2005/0043711 A1 | 2/2005 | Corcoran et al. |
| 2005/0043757 A1 | 2/2005 | Arad et al. |
| 2005/0043759 A1 | 2/2005 | Chanduszko |
| 2005/0043760 A1 | 2/2005 | Fogarty et al. |
| 2005/0043781 A1 | 2/2005 | Foley |
| 2005/0043790 A1 | 2/2005 | Seguin |
| 2005/0049674 A1 | 3/2005 | Berra et al. |
| 2005/0049692 A1 | 3/2005 | Numamoto et al. |
| 2005/0049696 A1 | 3/2005 | Siess et al. |
| 2005/0055088 A1 | 3/2005 | Liddicoat et al. |
| 2005/0060016 A1 | 3/2005 | Wu et al. |
| 2005/0060018 A1 | 3/2005 | Dittman |
| 2005/0060029 A1 | 3/2005 | Le et al. |
| 2005/0060030 A1 | 3/2005 | Lashinski et al. |
| 2005/0065594 A1 | 3/2005 | DiMatteo et al. |
| 2005/0070794 A1 | 3/2005 | Deal et al. |
| 2005/0070957 A1 | 3/2005 | Das |
| 2005/0075584 A1 | 4/2005 | Cali |
| 2005/0075662 A1 | 4/2005 | Pedersen et al. |
| 2005/0075712 A1 | 4/2005 | Biancucci et al. |
| 2005/0075717 A1 | 4/2005 | Nguyen et al. |
| 2005/0075719 A1 | 4/2005 | Bergheim |
| 2005/0075720 A1 | 4/2005 | Nguyen et al. |
| 2005/0075724 A1 | 4/2005 | Svanidze et al. |
| 2005/0075725 A1 | 4/2005 | Rowe |
| 2005/0075726 A1 | 4/2005 | Svanidze et al. |
| 2005/0075727 A1 | 4/2005 | Wheatley |
| 2005/0075730 A1 | 4/2005 | Myers et al. |
| 2005/0075731 A1 | 4/2005 | Artof et al. |
| 2005/0075776 A1 | 4/2005 | Cho |
| 2005/0084595 A1 | 4/2005 | Shukla et al. |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0090846 A1 | 4/2005 | Pedersen et al. |
| 2005/0090890 A1 | 4/2005 | Wu et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096726 A1 | 5/2005 | Sequin et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0096768 A1 | 5/2005 | Huang et al. |
| 2005/0098547 A1 | 5/2005 | Cali et al. |
| 2005/0100580 A1 | 5/2005 | Osborne et al. |
| 2005/0101903 A1 | 5/2005 | Kohler et al. |
| 2005/0101904 A1 | 5/2005 | Wilk |
| 2005/0101968 A1 | 5/2005 | Dadourian |
| 2005/0107822 A1 | 5/2005 | Wasdyke |
| 2005/0107871 A1 | 5/2005 | Realyvasquez et al. |
| 2005/0113902 A1 | 5/2005 | Geiser et al. |
| 2005/0113904 A1 | 5/2005 | Shank et al. |
| 2005/0113910 A1 | 5/2005 | Paniagua et al. |
| 2005/0119688 A1 | 6/2005 | Bergheim |
| 2005/0119728 A1 | 6/2005 | Sarac |
| 2005/0119736 A1 | 6/2005 | Zilla et al. |
| 2005/0125075 A1 | 6/2005 | Meade et al. |
| 2005/0131438 A1 | 6/2005 | Cohn |
| 2005/0137499 A1 | 6/2005 | Sheets et al. |
| 2005/0137609 A1 | 6/2005 | Guiraudon |
| 2005/0137681 A1 | 6/2005 | Shoemaker et al. |
| 2005/0137682 A1 | 6/2005 | Justino |
| 2005/0137683 A1 | 6/2005 | Hezi-Yamit et al. |
| 2005/0137686 A1 | 6/2005 | Salahieh et al. |
| 2005/0137687 A1 | 6/2005 | Salahieh et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137691 A1 | 6/2005 | Salahieh et al. |
| 2005/0137692 A1 | 6/2005 | Haug et al. |
| 2005/0137693 A1 | 6/2005 | Haug et al. |
| 2005/0137694 A1 | 6/2005 | Haug et al. |
| 2005/0137695 A1 | 6/2005 | Salahieh et al. |
| 2005/0137696 A1 | 6/2005 | Salahieh et al. |
| 2005/0137697 A1 | 6/2005 | Salahieh et al. |
| 2005/0137698 A1 | 6/2005 | Salahieh et al. |
| 2005/0137699 A1 | 6/2005 | Salahieh et al. |
| 2005/0137701 A1 | 6/2005 | Salahieh et al. |
| 2005/0137702 A1 | 6/2005 | Haug et al. |
| 2005/0138689 A1 | 6/2005 | Aukerman |
| 2005/0143804 A1 | 6/2005 | Haverkost |
| 2005/0143807 A1 | 6/2005 | Pavcnik et al. |
| 2005/0143809 A1 | 6/2005 | Salahieh et al. |
| 2005/0148997 A1 | 7/2005 | Valley et al. |
| 2005/0149159 A1 | 7/2005 | Andreas et al. |
| 2005/0149166 A1 | 7/2005 | Schaeffer et al. |
| 2005/0149181 A1 | 7/2005 | Eberhardt |
| 2005/0150775 A1 | 7/2005 | Zhang et al. |
| 2005/0159726 A1 | 7/2005 | Evans et al. |
| 2005/0165352 A1 | 7/2005 | Henry et al. |
| 2005/0165477 A1 | 7/2005 | Anduiza et al. |
| 2005/0165479 A1 | 7/2005 | Drews et al. |
| 2005/0171597 A1 | 8/2005 | Boatman et al. |
| 2005/0171598 A1 | 8/2005 | Schaeffer |
| 2005/0177227 A1 | 8/2005 | Heim et al. |
| 2005/0182483 A1 | 8/2005 | Osborne et al. |
| 2005/0182486 A1 | 8/2005 | Gabbay |
| 2005/0186349 A1 | 8/2005 | Loper et al. |
| 2005/0187616 A1 | 8/2005 | Realyvasquez |
| 2005/0192527 A1 | 9/2005 | Gharib et al. |
| 2005/0192665 A1 | 9/2005 | Spenser et al. |
| 2005/0197694 A1 | 9/2005 | Pai et al. |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203614 A1 | 9/2005 | Forster et al. |
| 2005/0203615 A1 | 9/2005 | Forster et al. |
| 2005/0203616 A1 | 9/2005 | Cribier |
| 2005/0203617 A1 | 9/2005 | Forster et al. |
| 2005/0203618 A1 | 9/2005 | Sharkawy et al. |
| 2005/0203818 A9 | 9/2005 | Rotman et al. |
| 2005/0209580 A1 | 9/2005 | Freyman |
| 2005/0214342 A1 | 9/2005 | Tweden et al. |
| 2005/0222664 A1 | 10/2005 | Parker |
| 2005/0222668 A1 | 10/2005 | Schaeffer et al. |
| 2005/0222674 A1 | 10/2005 | Paine |
| 2005/0228334 A1 | 10/2005 | Knudson et al. |
| 2005/0228472 A1 | 10/2005 | Case et al. |
| 2005/0228495 A1 | 10/2005 | Macoviak |
| 2005/0228496 A1 | 10/2005 | Mensah et al. |
| 2005/0234546 A1 | 10/2005 | Nugent et al. |
| 2005/0240200 A1 | 10/2005 | Bergheim |
| 2005/0240262 A1 | 10/2005 | White |
| 2005/0240263 A1 | 10/2005 | Fogarty et al. |
| 2005/0251243 A1 | 11/2005 | Seppala et al. |
| 2005/0251250 A1 | 11/2005 | Verhoeven et al. |

(56) References Cited

U.S. PATENT DOCUMENTS

| | | |
|---|---|---|
| 2005/0251251 A1 | 11/2005 | Cribier |
| 2005/0251252 A1 | 11/2005 | Stobie |
| 2005/0256532 A1 | 11/2005 | Nayak et al. |
| 2005/0261759 A1 | 11/2005 | Lambrecht et al. |
| 2005/0267523 A1 | 12/2005 | Devellian et al. |
| 2005/0267560 A1 | 12/2005 | Bates |
| 2005/0267567 A1 | 12/2005 | Shalev |
| 2005/0267573 A9 | 12/2005 | Macoviak et al. |
| 2005/0283231 A1 | 12/2005 | Haug et al. |
| 2005/0283962 A1 | 12/2005 | Boudjemline |
| 2005/0288627 A1 | 12/2005 | Mogul |
| 2005/0288685 A1 | 12/2005 | Gulles et al. |
| 2005/0288706 A1 | 12/2005 | Widomski et al. |
| 2006/0004439 A1 | 1/2006 | Spenser et al. |
| 2006/0004442 A1 | 1/2006 | Spenser et al. |
| 2006/0004469 A1 | 1/2006 | Sokel |
| 2006/0009841 A1 | 1/2006 | McGuckin, Jr. et al. |
| 2006/0009842 A1 | 1/2006 | Huynh et al. |
| 2006/0015168 A1 | 1/2006 | Gunderson |
| 2006/0025855 A1 | 2/2006 | Lashinski et al. |
| 2006/0025857 A1 | 2/2006 | Bergheim et al. |
| 2006/0028766 A1 | 2/2006 | Khizroev |
| 2006/0041218 A1 | 2/2006 | Phelps et al. |
| 2006/0047338 A1 | 3/2006 | Jenson et al. |
| 2006/0047343 A1 | 3/2006 | Oviatt et al. |
| 2006/0052736 A1 | 3/2006 | Tweden et al. |
| 2006/0052867 A1 | 3/2006 | Revuelta et al. |
| 2006/0058775 A1 | 3/2006 | Stevens et al. |
| 2006/0058864 A1 | 3/2006 | Schaeffer et al. |
| 2006/0058871 A1 | 3/2006 | Zakay et al. |
| 2006/0058872 A1 | 3/2006 | Salahieh et al. |
| 2006/0064151 A1 | 3/2006 | Guterman et al. |
| 2006/0069424 A1 | 3/2006 | Acosta et al. |
| 2006/0074477 A1 | 4/2006 | Berthiaume et al. |
| 2006/0074484 A1 | 4/2006 | Huber |
| 2006/0074485 A1 | 4/2006 | Realyvasquez |
| 2006/0077447 A1 | 4/2006 | Sojian et al. |
| 2006/0085060 A1 | 4/2006 | Campbell |
| 2006/0089711 A1 | 4/2006 | Dolan |
| 2006/0100685 A1 | 5/2006 | Seguin et al. |
| 2006/0111770 A1 | 5/2006 | Pavcnik et al. |
| 2006/0116757 A1 | 6/2006 | Lashinski et al. |
| 2006/0122692 A1 | 6/2006 | Gilad et al. |
| 2006/0135961 A1 | 6/2006 | Rosenman et al. |
| 2006/0135964 A1 | 6/2006 | Vesely |
| 2006/0136034 A1 | 6/2006 | Modesitt et al. |
| 2006/0142846 A1 | 6/2006 | Pavcnik et al. |
| 2006/0142848 A1 | 6/2006 | Gabbay |
| 2006/0149360 A1 | 7/2006 | Schwammenthal et al. |
| 2006/0155312 A1 | 7/2006 | Levine et al. |
| 2006/0155363 A1 | 7/2006 | LaDuca et al. |
| 2006/0155366 A1 | 7/2006 | LaDuca et al. |
| 2006/0161248 A1 | 7/2006 | Case et al. |
| 2006/0161249 A1 | 7/2006 | Realyvasquez et al. |
| 2006/0161265 A1 | 7/2006 | Levine et al. |
| 2006/0167474 A1 | 7/2006 | Bloom et al. |
| 2006/0167543 A1 | 7/2006 | Bailey et al. |
| 2006/0173524 A1 | 8/2006 | Salahieh et al. |
| 2006/0178740 A1 | 8/2006 | Stacchino et al. |
| 2006/0190070 A1 | 8/2006 | Dieck et al. |
| 2006/0193885 A1 | 8/2006 | Neethling et al. |
| 2006/0195134 A1 | 8/2006 | Crittenden |
| 2006/0195183 A1 | 8/2006 | Navia et al. |
| 2006/0195186 A1 | 8/2006 | Drews et al. |
| 2006/0206192 A1 | 9/2006 | Tower et al. |
| 2006/0206202 A1 | 9/2006 | Bonhoeffer et al. |
| 2006/0210597 A1 | 9/2006 | Hiles |
| 2006/0212110 A1 | 9/2006 | Osborne et al. |
| 2006/0212111 A1 | 9/2006 | Case et al. |
| 2006/0217802 A1 | 9/2006 | Ruiz et al. |
| 2006/0224183 A1 | 10/2006 | Freudenthal |
| 2006/0229561 A1 | 10/2006 | Huszar |
| 2006/0229718 A1 | 10/2006 | Marquez |
| 2006/0229719 A1 | 10/2006 | Marquez et al. |
| 2006/0241745 A1 | 10/2006 | Solem |
| 2006/0246584 A1 | 11/2006 | Covelli |
| 2006/0247570 A1 | 11/2006 | Pokorney |
| 2006/0247763 A1 | 11/2006 | Slater |
| 2006/0253191 A1 | 11/2006 | Salahieh et al. |
| 2006/0259134 A1 | 11/2006 | Schwammenthal et al. |
| 2006/0259135 A1 | 11/2006 | Navia et al. |
| 2006/0259136 A1 | 11/2006 | Nguyen et al. |
| 2006/0259137 A1 | 11/2006 | Artof et al. |
| 2006/0265043 A1 | 11/2006 | Mandrusov et al. |
| 2006/0265056 A1 | 11/2006 | Nguyen et al. |
| 2006/0270958 A1 | 11/2006 | George |
| 2006/0271149 A1 | 11/2006 | Berez et al. |
| 2006/0271161 A1 | 11/2006 | Meyer et al. |
| 2006/0271166 A1 | 11/2006 | Thill et al. |
| 2006/0271175 A1 | 11/2006 | Woolfson et al. |
| 2006/0276873 A1 | 12/2006 | Sato |
| 2006/0276874 A1 | 12/2006 | Wilson et al. |
| 2006/0276882 A1 | 12/2006 | Case et al. |
| 2006/0276887 A1 | 12/2006 | Brady et al. |
| 2006/0282161 A1 | 12/2006 | Huynh et al. |
| 2006/0287668 A1 | 12/2006 | Fawzi et al. |
| 2006/0287717 A1 | 12/2006 | Rowe et al. |
| 2006/0287719 A1 | 12/2006 | Rowe et al. |
| 2006/0290027 A1 | 12/2006 | O'Connor et al. |
| 2006/0293745 A1 | 12/2006 | Carpentier et al. |
| 2007/0005129 A1 | 1/2007 | Damm et al. |
| 2007/0005131 A1 | 1/2007 | Taylor |
| 2007/0005132 A1 | 1/2007 | Simionescu et al. |
| 2007/0010876 A1 | 1/2007 | Salahieh et al. |
| 2007/0010877 A1 | 1/2007 | Salahieh et al. |
| 2007/0010878 A1 | 1/2007 | Rafiee et al. |
| 2007/0010887 A1 | 1/2007 | Williams et al. |
| 2007/0016286 A1 | 1/2007 | Herrmann et al. |
| 2007/0016288 A1 | 1/2007 | Gurskis et al. |
| 2007/0020248 A1 | 1/2007 | Everaerts et al. |
| 2007/0021826 A1 | 1/2007 | Case et al. |
| 2007/0027518 A1 | 2/2007 | Case et al. |
| 2007/0027520 A1 | 2/2007 | Sherburne |
| 2007/0027533 A1 | 2/2007 | Douk |
| 2007/0027535 A1 | 2/2007 | Purdy, Jr. et al. |
| 2007/0032856 A1 | 2/2007 | Limon |
| 2007/0038291 A1 | 2/2007 | Case et al. |
| 2007/0038295 A1 | 2/2007 | Case et al. |
| 2007/0043420 A1 | 2/2007 | Lostetter |
| 2007/0043424 A1 | 2/2007 | Pryor |
| 2007/0043431 A1 | 2/2007 | Melsheimer |
| 2007/0043435 A1 | 2/2007 | Seguin et al. |
| 2007/0050014 A1 | 3/2007 | Johnson |
| 2007/0051377 A1 | 3/2007 | Douk et al. |
| 2007/0055340 A1 | 3/2007 | Pryor |
| 2007/0056346 A1 | 3/2007 | Spenser et al. |
| 2007/0060998 A1 | 3/2007 | Butterwick et al. |
| 2007/0061002 A1 | 3/2007 | Paul, Jr. et al. |
| 2007/0061008 A1 | 3/2007 | Salahieh et al. |
| 2007/0073389 A1 | 3/2007 | Bolduc et al. |
| 2007/0073392 A1 | 3/2007 | Heyninck-Jantz et al. |
| 2007/0078504 A1 | 4/2007 | Mialhe |
| 2007/0078509 A1 | 4/2007 | Lotfy |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0093887 A1 | 4/2007 | Case et al. |
| 2007/0100427 A1 | 5/2007 | Perouse |
| 2007/0100435 A1 | 5/2007 | Case et al. |
| 2007/0100439 A1 | 5/2007 | Cangialosi et al. |
| 2007/0100440 A1 | 5/2007 | Figulla et al. |
| 2007/0100449 A1 | 5/2007 | O'Neil et al. |
| 2007/0112355 A1 | 5/2007 | Salahieh et al. |
| 2007/0112358 A1 | 5/2007 | Abbott et al. |
| 2007/0112415 A1 | 5/2007 | Bartlett |
| 2007/0112422 A1 | 5/2007 | Dehdashtian |
| 2007/0118214 A1 | 5/2007 | Salahieh et al. |
| 2007/0123700 A1 | 5/2007 | Ueda et al. |
| 2007/0123979 A1 | 5/2007 | Perier et al. |
| 2007/0135889 A1 | 6/2007 | Moore et al. |
| 2007/0142906 A1 | 6/2007 | Figulla et al. |
| 2007/0142907 A1 | 6/2007 | Moaddeb et al. |
| 2007/0155010 A1 | 7/2007 | Farnsworth et al. |
| 2007/0156233 A1 | 7/2007 | Kapadia et al. |

(56) References Cited

U.S. PATENT DOCUMENTS

| | | |
|---|---|---|
| 2007/0162102 A1 | 7/2007 | Ryan et al. |
| 2007/0162103 A1 | 7/2007 | Case et al. |
| 2007/0162107 A1 | 7/2007 | Haug et al. |
| 2007/0162113 A1 | 7/2007 | Sharkawy et al. |
| 2007/0173918 A1 | 7/2007 | Dreher et al. |
| 2007/0173932 A1 | 7/2007 | Cali et al. |
| 2007/0179592 A1 | 8/2007 | Schaeffer |
| 2007/0179600 A1 | 8/2007 | Vardi |
| 2007/0185513 A1 | 8/2007 | Woolfson et al. |
| 2007/0185565 A1 | 8/2007 | Schwammenthal et al. |
| 2007/0185571 A1 | 8/2007 | Kapadia et al. |
| 2007/0198078 A1 | 8/2007 | Berra et al. |
| 2007/0198097 A1 | 8/2007 | Zegdi |
| 2007/0203391 A1 | 8/2007 | Bloom et al. |
| 2007/0203503 A1 | 8/2007 | Salahieh et al. |
| 2007/0203560 A1 | 8/2007 | Forster et al. |
| 2007/0203576 A1 | 8/2007 | Lee et al. |
| 2007/0208550 A1 | 9/2007 | Cao et al. |
| 2007/0213813 A1 | 9/2007 | Von Segesser et al. |
| 2007/0225681 A1 | 9/2007 | House |
| 2007/0225802 A1 | 9/2007 | Forsell |
| 2007/0232898 A1 | 10/2007 | Huynh et al. |
| 2007/0233222 A1 | 10/2007 | Roeder et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Chia et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239271 A1 | 10/2007 | Nguyen |
| 2007/0239273 A1 | 10/2007 | Allen |
| 2007/0244543 A1 | 10/2007 | Mitchell |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244551 A1 | 10/2007 | Stobie |
| 2007/0244552 A1 | 10/2007 | Salahieh et al. |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250151 A1 | 10/2007 | Pereira |
| 2007/0250160 A1 | 10/2007 | Rafiee |
| 2007/0255386 A1 | 11/2007 | Tenne |
| 2007/0255390 A1 | 11/2007 | Ducke et al. |
| 2007/0255394 A1 | 11/2007 | Ryan |
| 2007/0255396 A1 | 11/2007 | Douk et al. |
| 2007/0260301 A1 | 11/2007 | Chuter et al. |
| 2007/0260327 A1 | 11/2007 | Case et al. |
| 2007/0265701 A1 | 11/2007 | Gurskis et al. |
| 2007/0270751 A1 | 11/2007 | Stangenes et al. |
| 2007/0270943 A1 | 11/2007 | Solem et al. |
| 2007/0273813 A1 | 11/2007 | Yoshida et al. |
| 2007/0282436 A1 | 12/2007 | Pinchuk |
| 2007/0287717 A1 | 12/2007 | Fanning et al. |
| 2007/0288000 A1 | 12/2007 | Bonan |
| 2007/0288087 A1 | 12/2007 | Fearnot et al. |
| 2007/0288089 A1 | 12/2007 | Gurskis et al. |
| 2008/0004688 A1 | 1/2008 | Spenser et al. |
| 2008/0004696 A1 | 1/2008 | Vesely |
| 2008/0009934 A1 | 1/2008 | Schneider et al. |
| 2008/0009940 A1 | 1/2008 | Cribier |
| 2008/0015671 A1 | 1/2008 | Bonhoeffer |
| 2008/0021546 A1 | 1/2008 | Patz et al. |
| 2008/0021552 A1 | 1/2008 | Gabbay |
| 2008/0022504 A1 | 1/2008 | Melsheimer |
| 2008/0033534 A1 | 2/2008 | Cook et al. |
| 2008/0033541 A1 | 2/2008 | Gelbart et al. |
| 2008/0039925 A1 | 2/2008 | Ishimaru |
| 2008/0039934 A1 | 2/2008 | Styrc |
| 2008/0045921 A1 | 2/2008 | Anderson et al. |
| 2008/0048656 A1 | 2/2008 | Tan et al. |
| 2008/0065001 A1 | 3/2008 | DiNucci et al. |
| 2008/0065011 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077227 A1 | 3/2008 | Ouellette et al. |
| 2008/0077234 A1 | 3/2008 | Styrc |
| 2008/0077236 A1 | 3/2008 | Letac et al. |
| 2008/0082165 A1 | 4/2008 | Wilson et al. |
| 2008/0082166 A1 | 4/2008 | Styrc et al. |
| 2008/0086205 A1 | 4/2008 | Gordy et al. |
| 2008/0097586 A1 | 4/2008 | Pavcnik et al. |
| 2008/0102439 A1 | 5/2008 | Tian et al. |
| 2008/0109070 A1 | 5/2008 | Wagner et al. |
| 2008/0125859 A1 | 5/2008 | Salahieh et al. |
| 2008/0127707 A1 | 6/2008 | Kokish et al. |
| 2008/0133002 A1 | 6/2008 | Gelbart et al. |
| 2008/0133003 A1 | 6/2008 | Seguin et al. |
| 2008/0140188 A1 | 6/2008 | Rahdert et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichou et al. |
| 2008/0154356 A1 | 6/2008 | Obermiller et al. |
| 2008/0255660 A1 | 6/2008 | Straubinger et al. |
| 2008/0161909 A1 | 7/2008 | Kheradvar et al. |
| 2008/0161910 A1 | 7/2008 | Revuelta et al. |
| 2008/0161911 A1 | 7/2008 | Revuelta et al. |
| 2008/0172119 A1 | 7/2008 | Yamasaki et al. |
| 2008/0177381 A1 | 7/2008 | Navia et al. |
| 2008/0183273 A1 | 7/2008 | Mesana et al. |
| 2008/0188928 A1 | 8/2008 | Salahieh et al. |
| 2008/0195193 A1 | 8/2008 | Purdy et al. |
| 2008/0195199 A1 | 8/2008 | Kheradvar et al. |
| 2008/0200977 A1 | 8/2008 | Paul et al. |
| 2008/0208209 A1 | 8/2008 | Fischer et al. |
| 2008/0208327 A1 | 8/2008 | Rowe |
| 2008/0208328 A1 | 8/2008 | Antocci et al. |
| 2008/0208332 A1 | 8/2008 | Lamphere et al. |
| 2008/0215143 A1 | 9/2008 | Seguin |
| 2008/0215144 A1 | 9/2008 | Ryan et al. |
| 2008/0221672 A1 | 9/2008 | Lamphere et al. |
| 2008/0221703 A1 | 9/2008 | Que et al. |
| 2008/0228254 A1 | 9/2008 | Ryan |
| 2008/0228263 A1 | 9/2008 | Ryan |
| 2008/0234443 A1 | 9/2008 | Kiss et al. |
| 2008/0234797 A1 | 9/2008 | Styrc |
| 2008/0234814 A1 | 9/2008 | Salahieh et al. |
| 2008/0243246 A1 | 10/2008 | Ryan et al. |
| 2008/0255651 A1 | 10/2008 | Dwork |
| 2008/0255661 A1 | 10/2008 | Straubinger et al. |
| 2008/0262590 A1 | 10/2008 | Murray |
| 2008/0262592 A1 | 10/2008 | Jordan et al. |
| 2008/0262593 A1 | 10/2008 | Ryan et al. |
| 2008/0262602 A1 | 10/2008 | Wilk et al. |
| 2008/0264102 A1 | 10/2008 | Berra |
| 2008/0269878 A1 | 10/2008 | Iobbi |
| 2008/0275549 A1 | 11/2008 | Rowe |
| 2008/0275550 A1 | 11/2008 | Kheradvar et al. |
| 2008/0288054 A1 | 11/2008 | Pulnev et al. |
| 2009/0005863 A1 | 1/2009 | Goetz et al. |
| 2009/0012356 A1 | 1/2009 | Dann et al. |
| 2009/0012600 A1 | 1/2009 | Styrc et al. |
| 2009/0030512 A1 | 1/2009 | Thielen et al. |
| 2009/0048656 A1 | 2/2009 | Wen |
| 2009/0054968 A1 | 2/2009 | Bonhoeffer et al. |
| 2009/0054969 A1 | 2/2009 | Salahieh et al. |
| 2009/0054976 A1 | 2/2009 | Tuval et al. |
| 2009/0062908 A1 | 3/2009 | Bonhoeffer et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0069890 A1 | 3/2009 | Suri et al. |

(56) References Cited

U.S. PATENT DOCUMENTS

| | | |
|---|---|---|
| 2009/0076598 A1 | 3/2009 | Salahieh et al. |
| 2009/0082844 A1 | 3/2009 | Zacharias et al. |
| 2009/0082858 A1 | 3/2009 | Nugent et al. |
| 2009/0085900 A1 | 4/2009 | Weiner |
| 2009/0093876 A1 | 4/2009 | Nitzan et al. |
| 2009/0093877 A1 | 4/2009 | Keidar et al. |
| 2009/0099640 A1 | 4/2009 | Weng |
| 2009/0099641 A1 | 4/2009 | Wu et al. |
| 2009/0099643 A1 | 4/2009 | Hyodoh et al. |
| 2009/0099653 A1 | 4/2009 | Suri et al. |
| 2009/0112309 A1 | 4/2009 | Jaramillo et al. |
| 2009/0138079 A1 | 5/2009 | Tuval et al. |
| 2009/0157175 A1 | 6/2009 | Benichou |
| 2009/0163951 A1 | 6/2009 | Simmons et al. |
| 2009/0164004 A1 | 6/2009 | Cohn |
| 2009/0164006 A1 | 6/2009 | Seguin et al. |
| 2009/0171432 A1 | 7/2009 | Von Segesser et al. |
| 2009/0171447 A1 | 7/2009 | Von Segesser et al. |
| 2009/0171456 A1 | 7/2009 | Kveen et al. |
| 2009/0182405 A1 | 7/2009 | Arnault De La Menardiere et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0192601 A1 | 7/2009 | Rafiee et al. |
| 2009/0198316 A1 | 8/2009 | Laske et al. |
| 2009/0198323 A1 | 8/2009 | Johnson et al. |
| 2009/0210052 A1 | 8/2009 | Forster et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222076 A1 | 9/2009 | Figulla et al. |
| 2009/0222082 A1 | 9/2009 | Lock et al. |
| 2009/0234407 A1 | 9/2009 | Hastings et al. |
| 2009/0234443 A1 | 9/2009 | Ottma et al. |
| 2009/0240264 A1 | 9/2009 | Tuval et al. |
| 2009/0240320 A1 | 9/2009 | Tuval et al. |
| 2009/0248143 A1 | 10/2009 | Laham |
| 2009/0259306 A1 | 10/2009 | Rowe |
| 2009/0264759 A1 | 10/2009 | Byrd |
| 2009/0264997 A1 | 10/2009 | Salahieh et al. |
| 2009/0276040 A1 | 11/2009 | Rowe et al. |
| 2009/0281619 A1 | 11/2009 | Le et al. |
| 2009/0287290 A1 | 11/2009 | Macaulay et al. |
| 2009/0287296 A1 | 11/2009 | Manasse |
| 2009/0287299 A1 | 11/2009 | Tabor et al. |
| 2009/0299462 A1 | 12/2009 | Fawzi et al. |
| 2009/0319037 A1 | 12/2009 | Rowe et al. |
| 2010/0004739 A1 | 1/2010 | Vesely |
| 2010/0004740 A1 | 1/2010 | Seguin et al. |
| 2010/0011564 A1 | 1/2010 | Millwee et al. |
| 2010/0030328 A1 | 2/2010 | Seguin et al. |
| 2010/0036479 A1 | 2/2010 | Hill et al. |
| 2010/0036485 A1 | 2/2010 | Seguin |
| 2010/0049313 A1 | 2/2010 | Alon et al. |
| 2010/0057051 A1 | 3/2010 | How et al. |
| 2010/0057185 A1 | 3/2010 | Melsheimer et al. |
| 2010/0069852 A1 | 3/2010 | Kelley |
| 2010/0069916 A1 | 3/2010 | Cully et al. |
| 2010/0070027 A1 | 3/2010 | Bonhoeffer et al. |
| 2010/0082089 A1 | 4/2010 | Quadri et al. |
| 2010/0082094 A1 | 4/2010 | Quadri et al. |
| 2010/0087913 A1 | 4/2010 | Rabkin et al. |
| 2010/0094399 A1 | 4/2010 | Dorn et al. |
| 2010/0094411 A1 | 4/2010 | Tuval et al. |
| 2010/0100167 A1 | 4/2010 | Bortlein et al. |
| 2010/0121434 A1 | 5/2010 | Paul et al. |
| 2010/0131054 A1 | 5/2010 | Tuval et al. |
| 2010/0131057 A1 | 5/2010 | Subramanian et al. |
| 2010/0137979 A1 | 6/2010 | Tuval et al. |
| 2010/0145439 A1 | 6/2010 | Seguin et al. |
| 2010/0152840 A1 | 6/2010 | Seguin et al. |
| 2010/0160725 A1 | 6/2010 | Kiser et al. |
| 2010/0161045 A1 | 6/2010 | Righini |
| 2010/0168839 A1 | 7/2010 | Braido et al. |
| 2010/0174362 A1 | 7/2010 | Straubinger et al. |
| 2010/0185275 A1 | 7/2010 | Richter et al. |
| 2010/0185277 A1 | 7/2010 | Braido et al. |
| 2010/0191320 A1 | 7/2010 | Straubinger et al. |
| 2010/0191326 A1 | 7/2010 | Alkhatib |
| 2010/0198346 A1 | 8/2010 | Keogh et al. |
| 2010/0210991 A1 | 8/2010 | Wilk et al. |
| 2010/0219092 A1 | 9/2010 | Salahieh et al. |
| 2010/0234932 A1 | 9/2010 | Arbefeuille et al. |
| 2010/0234940 A1 | 9/2010 | Dolan |
| 2010/0239917 A1 | 9/2010 | Lee et al. |
| 2010/0249908 A1 | 9/2010 | Chau et al. |
| 2010/0249915 A1 | 9/2010 | Zhang |
| 2010/0249916 A1 | 9/2010 | Zhang |
| 2010/0249917 A1 | 9/2010 | Zhang |
| 2010/0249918 A1 | 9/2010 | Zhang |
| 2010/0256723 A1 | 10/2010 | Murray |
| 2010/0262231 A1 | 10/2010 | Tuval et al. |
| 2010/0268332 A1 | 10/2010 | Tuval et al. |
| 2010/0280459 A1 | 11/2010 | Werner |
| 2010/0280495 A1 | 11/2010 | Paul et al. |
| 2010/0286768 A1 | 11/2010 | Alkhatib |
| 2010/0292779 A1 | 11/2010 | Straubinger et al. |
| 2010/0292780 A1 | 11/2010 | Straubinger et al. |
| 2010/0292785 A1 | 11/2010 | Seguin et al. |
| 2010/0298931 A1 | 11/2010 | Quadri et al. |
| 2011/0004297 A1 | 1/2011 | Sogard et al. |
| 2011/0015616 A1 | 1/2011 | Straubinger et al. |
| 2011/0022157 A1 | 1/2011 | Essinger et al. |
| 2011/0029066 A1 | 2/2011 | Gilad et al. |
| 2011/0034852 A1 | 2/2011 | Hausler et al. |
| 2011/0040366 A1 | 2/2011 | Goetz et al. |
| 2011/0040374 A1 | 2/2011 | Goetz et al. |
| 2011/0071613 A1 | 3/2011 | Wood et al. |
| 2011/0093007 A1 | 4/2011 | Abbott et al. |
| 2011/0098805 A1 | 4/2011 | Dwork et al. |
| 2011/0106244 A1 | 5/2011 | Ferrari et al. |
| 2011/0137397 A1 | 6/2011 | Chau et al. |
| 2011/0166637 A1 | 7/2011 | Irwin et al. |
| 2011/0190862 A1 | 8/2011 | Bashiri et al. |
| 2011/0190874 A1 | 8/2011 | Celermajer et al. |
| 2011/0208290 A1 | 8/2011 | Straubinger et al. |
| 2011/0208297 A1 | 8/2011 | Tuval et al. |
| 2011/0224780 A1 | 9/2011 | Tabor et al. |
| 2011/0238159 A1 | 9/2011 | Guyenot et al. |
| 2011/0238167 A1 | 9/2011 | Dove et al. |
| 2011/0257729 A1 | 10/2011 | Spenser et al. |
| 2011/0257733 A1 | 10/2011 | Dwork |
| 2011/0257735 A1 | 10/2011 | Salahieh et al. |
| 2011/0264191 A1 | 10/2011 | Rothstein |
| 2011/0264196 A1 | 10/2011 | Savage et al. |
| 2011/0264203 A1 | 10/2011 | Dwork et al. |
| 2011/0276121 A1 | 11/2011 | Levine |
| 2011/0276129 A1 | 11/2011 | Salahieh et al. |
| 2011/0288626 A1 | 11/2011 | Straubinger et al. |
| 2011/0288634 A1 | 11/2011 | Tuval et al. |
| 2011/0295363 A1 | 12/2011 | Girard et al. |
| 2011/0319989 A1 | 12/2011 | Lane et al. |
| 2012/0016469 A1 | 1/2012 | Salahieh et al. |
| 2012/0016471 A1 | 1/2012 | Salahieh et al. |
| 2012/0022633 A1 | 1/2012 | Olson et al. |
| 2012/0022642 A1 | 1/2012 | Haug et al. |
| 2012/0029627 A1 | 2/2012 | Salahieh et al. |
| 2012/0035719 A1 | 2/2012 | Forster et al. |
| 2012/0035720 A1 | 2/2012 | Cali et al. |
| 2012/0041547 A1 | 2/2012 | Duffy et al. |
| 2012/0041549 A1 | 2/2012 | Salahieh et al. |
| 2012/0041550 A1 | 2/2012 | Salahieh et al. |
| 2012/0046740 A1 | 2/2012 | Paul et al. |
| 2012/0053683 A1 | 3/2012 | Salahieh et al. |
| 2012/0059447 A1 | 3/2012 | Zilla et al. |
| 2012/0065464 A1 | 3/2012 | Ellis et al. |
| 2012/0078347 A1 | 3/2012 | Braido et al. |
| 2012/0078357 A1 | 3/2012 | Conklin |
| 2012/0078360 A1 | 3/2012 | Rafiee |
| 2012/0089224 A1 | 4/2012 | Haug et al. |
| 2012/0100182 A1 | 4/2012 | Mooney et al. |
| 2012/0101571 A1 | 4/2012 | Thambar et al. |
| 2012/0101572 A1 | 4/2012 | Kovalsky et al. |
| 2012/0116496 A1 | 5/2012 | Chuter et al. |

(56) References Cited

U.S. PATENT DOCUMENTS

| | | |
|---|---|---|
| 2012/0123515 A1 | 5/2012 | Hosford et al. |
| 2012/0123529 A1 | 5/2012 | Levi et al. |
| 2012/0130468 A1 | 5/2012 | Khosravi et al. |
| 2012/0132547 A1 | 5/2012 | Salahieh et al. |
| 2012/0136430 A1 | 5/2012 | Sochman et al. |
| 2012/0165957 A1 | 6/2012 | Everland et al. |
| 2012/0172982 A1 | 7/2012 | Stacchino et al. |
| 2012/0179244 A1 | 7/2012 | Schankereli et al. |
| 2012/0185030 A1 | 7/2012 | Igaki et al. |
| 2012/0197379 A1 | 8/2012 | Laske et al. |
| 2012/0209374 A1 | 8/2012 | Bonhoeffer et al. |
| 2012/0209376 A1 | 8/2012 | Hauser et al. |
| 2012/0221100 A1 | 8/2012 | Huber |
| 2012/0226341 A1 | 9/2012 | Schreck et al. |
| 2012/0283715 A1 | 11/2012 | Mihalik et al. |
| 2012/0283823 A1 | 11/2012 | Bonhoeffer et al. |
| 2012/0303113 A1 | 11/2012 | Benichou et al. |
| 2012/0303116 A1 | 11/2012 | Gorman, III et al. |
| 2012/0305441 A1 | 12/2012 | Murray et al. |
| 2012/0310332 A1 | 12/2012 | Murray et al. |
| 2012/0316637 A1 | 12/2012 | Holm et al. |
| 2012/0330408 A1 | 12/2012 | Hillukka et al. |
| 2012/0330409 A1 | 12/2012 | Haug et al. |
| 2013/0013057 A1 | 1/2013 | Salahieh et al. |
| 2013/0018457 A1 | 1/2013 | Gregg et al. |
| 2013/0030519 A1 | 1/2013 | Tran et al. |
| 2013/0030520 A1 | 1/2013 | Lee et al. |
| 2013/0046373 A1 | 2/2013 | Cartledge et al. |
| 2013/0053949 A1 | 2/2013 | Pintor et al. |
| 2013/0066342 A1 | 3/2013 | Dell et al. |
| 2013/0066419 A1 | 3/2013 | Gregg |
| 2013/0071441 A1 | 3/2013 | Iwazawa et al. |
| 2013/0073037 A1 | 3/2013 | Gregg et al. |
| 2013/0079867 A1 | 3/2013 | Hoffman et al. |
| 2013/0079869 A1 | 3/2013 | Straubinger et al. |
| 2013/0089655 A1 | 4/2013 | Gregg |
| 2013/0090728 A1 | 4/2013 | Solem |
| 2013/0090729 A1 | 4/2013 | Gregg et al. |
| 2013/0096664 A1 | 4/2013 | Goetz et al. |
| 2013/0116778 A1 | 5/2013 | Gregg et al. |
| 2013/0118949 A1 | 5/2013 | Chang et al. |
| 2013/0123757 A1 | 5/2013 | Crisostomo et al. |
| 2013/0123795 A1 | 5/2013 | Gamarra et al. |
| 2013/0123796 A1 | 5/2013 | Sutton et al. |
| 2013/0123898 A1 | 5/2013 | Tung et al. |
| 2013/0138207 A1 | 5/2013 | Quadri et al. |
| 2013/0144203 A1 | 6/2013 | Wilk et al. |
| 2013/0144276 A1 | 6/2013 | Crisostomo et al. |
| 2013/0158653 A1 | 6/2013 | Gamarra et al. |
| 2013/0158655 A1 | 6/2013 | Sutton et al. |
| 2013/0158656 A1 | 6/2013 | Sutton et al. |
| 2013/0166017 A1 | 6/2013 | Cartledge et al. |
| 2013/0178930 A1 | 7/2013 | Straubinger et al. |
| 2013/0184813 A1 | 7/2013 | Quadri et al. |
| 2013/0190865 A1 | 7/2013 | Anderson |
| 2013/0204359 A1 | 8/2013 | Thubrikar et al. |
| 2013/0231735 A1 | 9/2013 | Deem et al. |
| 2013/0245752 A1 | 9/2013 | Goetz et al. |
| 2013/0253342 A1 | 9/2013 | Griswold et al. |
| 2013/0253635 A1 | 9/2013 | Straubinger et al. |
| 2013/0253640 A1 | 9/2013 | Meiri et al. |
| 2013/0268067 A1 | 10/2013 | Forster et al. |
| 2013/0274865 A1 | 10/2013 | Haverkost et al. |
| 2013/0274870 A1 | 10/2013 | Lombardi et al. |
| 2013/0289698 A1 | 10/2013 | Wang et al. |
| 2013/0296999 A1 | 11/2013 | Burriesci et al. |
| 2013/0304199 A1 | 11/2013 | Sutton et al. |
| 2013/0310917 A1 | 11/2013 | Richter et al. |
| 2013/0310923 A1 | 11/2013 | Kheradvar et al. |
| 2013/0310928 A1 | 11/2013 | Morriss et al. |
| 2013/0325101 A1 | 12/2013 | Goetz et al. |
| 2013/0338755 A1 | 12/2013 | Goetz et al. |
| 2013/0345799 A1 | 12/2013 | Lafontaine |
| 2014/0012368 A1 | 1/2014 | Sugimoto et al. |
| 2014/0012370 A1 | 1/2014 | Bonhoeffer et al. |
| 2014/0018911 A1 | 1/2014 | Zhou et al. |
| 2014/0052239 A1 | 2/2014 | Kong et al. |
| 2014/0058501 A1 | 2/2014 | Bonhoeffer et al. |
| 2014/0083190 A1 | 3/2014 | Kaack et al. |
| 2014/0088680 A1 | 3/2014 | Costello et al. |
| 2014/0094904 A1 | 4/2014 | Salahieh et al. |
| 2014/0114390 A1 | 4/2014 | Tobis et al. |
| 2014/0114405 A1 | 4/2014 | Paul et al. |
| 2014/0114406 A1 | 4/2014 | Salahieh et al. |
| 2014/0114407 A1 | 4/2014 | Rajamannan |
| 2014/0121763 A1 | 5/2014 | Duffy et al. |
| 2014/0121766 A1 | 5/2014 | Salahieh et al. |
| 2014/0128969 A1 | 5/2014 | Hill et al. |
| 2014/0135912 A1 | 5/2014 | Salahieh et al. |
| 2014/0207229 A1 | 7/2014 | Shoemaker et al. |
| 2014/0222142 A1 | 8/2014 | Kovalsky et al. |
| 2014/0236287 A1 | 8/2014 | Clague et al. |
| 2014/0243962 A1 | 8/2014 | Wilson et al. |
| 2014/0243963 A1 | 8/2014 | Sheps et al. |
| 2014/0243967 A1 | 8/2014 | Salahieh et al. |
| 2014/0249621 A1 | 9/2014 | Eidenschink |
| 2014/0257473 A1 | 9/2014 | Rajamannan |
| 2014/0277414 A1 | 9/2014 | Kheradvar |
| 2014/0296962 A1 | 10/2014 | Cartledge et al. |
| 2014/0309732 A1 | 10/2014 | Solem |
| 2014/0316518 A1 | 10/2014 | Kheradvar et al. |
| 2014/0330371 A1 | 11/2014 | Gloss et al. |
| 2014/0343669 A1 | 11/2014 | Lane et al. |
| 2014/0379068 A1 | 12/2014 | Thielen et al. |
| 2015/0012085 A1 | 1/2015 | Salahieh et al. |
| 2015/0032056 A1 | 1/2015 | Okamura et al. |
| 2015/0073540 A1 | 3/2015 | Salahieh et al. |
| 2015/0073541 A1 | 3/2015 | Salahieh et al. |
| 2015/0088252 A1 | 3/2015 | Jenson et al. |
| 2015/0094804 A1 | 4/2015 | Bonhoeffer et al. |
| 2015/0105857 A1 | 4/2015 | Bonhoeffer et al. |
| 2015/0127092 A1 | 5/2015 | Straubinger et al. |
| 2015/0127094 A1 | 5/2015 | Salahieh et al. |
| 2015/0142102 A1 | 5/2015 | Lafontaine et al. |
| 2015/0209142 A1 | 7/2015 | Paul et al. |
| 2015/0209146 A1 | 7/2015 | Hill et al. |
| 2015/0223933 A1 | 8/2015 | Haug et al. |
| 2015/0238315 A1 | 8/2015 | Rabito et al. |
| 2015/0245909 A1 | 9/2015 | Salahieh et al. |
| 2015/0272731 A1 | 10/2015 | Racchini et al. |
| 2015/0320557 A1 | 11/2015 | Sutton et al. |
| 2015/0335423 A1 | 11/2015 | Gregg et al. |
| 2015/0352252 A1 | 12/2015 | Nakamura et al. |
| 2015/0359997 A1 | 12/2015 | Crisostomo et al. |
| 2016/0022418 A1 | 1/2016 | Salahieh et al. |
| 2016/0045306 A1 | 2/2016 | Agrawal et al. |
| 2016/0045307 A1 | 2/2016 | Yohanan et al. |
| 2016/0051362 A1 | 2/2016 | Cooper et al. |
| 2016/0067040 A1 | 3/2016 | Agrawal et al. |
| 2016/0120645 A1 | 5/2016 | Alon |
| 2016/0135951 A1 | 5/2016 | Salahieh et al. |
| 2016/0143731 A1 | 5/2016 | Backus et al. |
| 2016/0158003 A1 | 6/2016 | Wallace et al. |
| 2016/0166384 A1 | 6/2016 | Olson et al. |
| 2016/0199184 A1 | 7/2016 | Ma et al. |
| 2016/0206423 A1 | 7/2016 | O'Connor et al. |
| 2016/0213467 A1 | 7/2016 | Backus et al. |
| 2016/0220359 A1 | 8/2016 | Backus et al. |
| 2016/0220360 A1 | 8/2016 | Lin et al. |
| 2016/0220365 A1 | 8/2016 | Backus et al. |
| 2016/0250024 A1 | 9/2016 | Hill et al. |
| 2016/0256271 A1 | 9/2016 | Backus et al. |
| 2016/0262878 A1 | 9/2016 | Backus et al. |
| 2016/0346107 A1 | 12/2016 | Matthison-Hansen et al. |
| 2016/0354203 A1 | 12/2016 | Tuval et al. |
| 2016/0374793 A1 | 12/2016 | Lafontaine et al. |
| 2016/0376063 A1 | 12/2016 | Salahieh et al. |
| 2017/0000609 A1 | 1/2017 | Gross et al. |
| 2017/0007400 A1 | 1/2017 | Sogard et al. |
| 2017/0027693 A1 | 2/2017 | Paul et al. |
| 2017/0049563 A1 | 2/2017 | Straubinger et al. |
| 2017/0049568 A1 | 2/2017 | Straubinger et al. |
| 2017/0056172 A1 | 3/2017 | Salahieh et al. |
| 2017/0065410 A1 | 3/2017 | Straubinger et al. |

(56) References Cited

U.S. PATENT DOCUMENTS

| | | | |
|---|---|---|---|
| 2017/0095595 | A1 | 4/2017 | Nakamura |
| 2017/0333230 | A1 | 11/2017 | Folan et al. |
| 2017/0348013 | A1 | 12/2017 | Mottola et al. |
| 2018/0368976 | A1 | 12/2018 | Bonhoeffer et al. |
| 2019/0328522 | A1 | 10/2019 | Straubinger et al. |
| 2020/0054449 | A1 | 2/2020 | Min et al. |

FOREIGN PATENT DOCUMENTS

| | | |
|---|---|---|
| AU | 777443 B2 | 10/2004 |
| AU | 778831 B2 | 12/2004 |
| AU | 2004231189 A1 | 12/2004 |
| AU | 2004242527 A1 | 1/2005 |
| AU | 2001281277 B2 | 9/2005 |
| AU | 2006308187 A1 | 5/2007 |
| AU | 2006310681 A1 | 5/2007 |
| AU | 2006328896 A1 | 6/2007 |
| AU | 2002329324 B2 | 7/2007 |
| AU | 2007294199 A1 | 3/2008 |
| AU | 2009200985 A1 | 4/2009 |
| AU | 2006328896 B2 | 8/2013 |
| CA | 2378589 A1 | 2/2001 |
| CA | 2381192 A1 | 2/2001 |
| CA | 2385662 A1 | 3/2001 |
| CA | 2407987 A1 | 11/2001 |
| CA | 2418958 A1 | 2/2002 |
| CA | 2435962 A1 | 8/2002 |
| CA | 2457755 A1 | 2/2003 |
| CA | 2436258 A1 | 1/2005 |
| CA | 2848485 A1 | 1/2005 |
| CA | 2848490 A1 | 1/2005 |
| CA | 2595233 A1 | 7/2006 |
| CA | 2627409 A1 | 5/2007 |
| CA | 2627555 | 5/2007 |
| CA | 2634358 A1 | 6/2007 |
| CA | 2657839 A1 | 3/2008 |
| CA | 2659690 A1 | 3/2008 |
| CN | 1338951 A | 3/2002 |
| CN | 1342443 A | 4/2002 |
| CN | 1745727 A | 3/2006 |
| CN | 2762776 Y | 3/2006 |
| CN | 1897892 A | 1/2007 |
| CN | 2933337 Y | 8/2007 |
| CN | 101011298 A | 8/2007 |
| CN | 101431963 A | 5/2009 |
| CN | 101605509 A | 12/2009 |
| CN | 101623217 A | 1/2010 |
| CN | 101700199 A | 5/2010 |
| CN | 101720211 A | 6/2010 |
| CN | 102271626 A | 12/2011 |
| CN | 102413793 A | 4/2012 |
| CN | 103118630 A | 5/2013 |
| DE | 2815756 A1 | 10/1979 |
| DE | 3640745 A1 | 6/1987 |
| DE | 3920657 A1 | 1/1991 |
| DE | 3640745 C2 | 3/1992 |
| DE | 4316971 A1 | 11/1994 |
| DE | 19532846 A1 | 3/1997 |
| DE | 19546692 A1 | 6/1997 |
| DE | 19633901 A1 | 2/1998 |
| DE | 20003874 U1 | 6/2000 |
| DE | 19857887 A1 | 7/2000 |
| DE | 19907646 A1 | 8/2000 |
| DE | 10010073 A1 | 9/2001 |
| DE | 10010074 A1 | 10/2001 |
| DE | 10034105 C1 | 4/2002 |
| DE | 10049812 A1 | 4/2002 |
| DE | 10049813 C1 | 4/2002 |
| DE | 10049814 A1 | 4/2002 |
| DE | 10049815 A1 | 4/2002 |
| DE | 10048814 A1 | 5/2002 |
| DE | 101 21 210 A1 | 11/2002 |
| DE | 19546692 C2 | 11/2002 |
| DE | 10301026 A1 | 2/2004 |
| DE | 10048814 B4 | 4/2004 |
| DE | 10049812 B4 | 6/2004 |
| DE | 10302447 A1 | 7/2004 |
| DE | 10335948 B3 | 2/2005 |
| DE | 10010074 B4 | 4/2005 |
| DE | 19857887 B4 | 5/2005 |
| DE | 10049815 B4 | 10/2005 |
| DE | 10010073 B4 | 12/2005 |
| DE | 102005003632 A1 | 8/2006 |
| DE | 10 2005 051 849 | 5/2007 |
| DE | 10 2005 052628 A1 | 5/2007 |
| DE | 20 2007 005 491 U1 | 7/2007 |
| DE | 20221871 U1 | 9/2008 |
| DE | 69937568 T2 | 9/2008 |
| DK | 1112042 T3 | 2/2008 |
| DK | 200800058 U1 | 6/2008 |
| DK | 200800058 U3 | 7/2008 |
| DK | 1259195 T3 | 2/2009 |
| DK | 1281375 T3 | 5/2012 |
| EP | 0084395 A1 | 7/1983 |
| EP | 0103546 A1 | 3/1984 |
| EP | 0103546 B1 | 5/1988 |
| EP | 0144167 B1 | 11/1989 |
| EP | 0402036 A1 | 12/1990 |
| EP | 0402036 B1 | 12/1990 |
| EP | 0402176 A2 | 12/1990 |
| EP | 0402176 B1 | 12/1990 |
| EP | 0411118 A1 | 2/1991 |
| EP | 0458877 B1 | 4/1991 |
| EP | 0458877 A1 | 12/1991 |
| EP | 0515324 A1 | 11/1992 |
| EP | 0547135 A1 | 6/1993 |
| EP | 0547135 B1 | 6/1993 |
| EP | 0579523 A1 | 1/1994 |
| EP | 0592410 A1 | 4/1994 |
| EP | 0597967 A1 | 5/1994 |
| EP | 0597967 A4 | 12/1994 |
| EP | 0657147 A2 | 6/1995 |
| EP | 0 592 410 B1 | 10/1995 |
| EP | 0 592 410 B1 | 11/1995 |
| EP | 0696447 A2 | 2/1996 |
| EP | 0729364 A1 | 9/1996 |
| EP | 0729364 B1 | 9/1996 |
| EP | 0732088 A2 | 9/1996 |
| EP | 0756498 A1 | 2/1997 |
| EP | 0409929 B1 | 4/1997 |
| EP | 0756498 B1 | 5/1997 |
| EP | 0778775 A1 | 6/1997 |
| EP | 0778775 B1 | 6/1997 |
| EP | 0786970 A1 | 8/1997 |
| EP | 0792624 A1 | 9/1997 |
| EP | 0797957 A1 | 10/1997 |
| EP | 0797958 A1 | 10/1997 |
| EP | 0799604 A1 | 10/1997 |
| EP | 0801928 A1 | 10/1997 |
| EP | 0815798 A2 | 1/1998 |
| EP | 0826346 A1 | 3/1998 |
| EP | 0829239 A1 | 3/1998 |
| EP | 0836834 A2 | 4/1998 |
| EP | 0850607 A1 | 7/1998 |
| EP | 0853921 A2 | 7/1998 |
| EP | 0858779 A1 | 8/1998 |
| EP | 0871414 A1 | 10/1998 |
| EP | 0876796 A2 | 11/1998 |
| EP | 0876803 A2 | 11/1998 |
| EP | 0888142 A1 | 1/1999 |
| EP | 0888750 A1 | 1/1999 |
| EP | 0895752 A1 | 2/1999 |
| EP | 0896813 A2 | 2/1999 |
| EP | 0903122 A2 | 3/1999 |
| EP | 0876796 A3 | 5/1999 |
| EP | 0928615 A1 | 7/1999 |
| EP | 0657147 B1 | 8/1999 |
| EP | 0934728 A2 | 8/1999 |
| EP | 0938877 A2 | 9/1999 |
| EP | 0943302 A2 | 9/1999 |
| EP | 0597967 B1 | 12/1999 |
| EP | 0696447 B1 | 1/2000 |
| EP | 0971649 A1 | 1/2000 |
| EP | 0986348 A1 | 3/2000 |

(56) References Cited

FOREIGN PATENT DOCUMENTS

| | | |
|---|---|---|
| EP | 0986348 B1 | 3/2000 |
| EP | 1000590 A1 | 5/2000 |
| EP | 1011523 A1 | 6/2000 |
| EP | 1020166 A1 | 7/2000 |
| EP | 1027870 A1 | 8/2000 |
| EP | 1 251 805 B1 | 10/2000 |
| EP | 1041942 A1 | 10/2000 |
| EP | 1041942 B1 | 10/2000 |
| EP | 1041943 A1 | 10/2000 |
| EP | 1041943 B1 | 10/2000 |
| EP | 1051204 A2 | 11/2000 |
| EP | 1057459 A1 | 12/2000 |
| EP | 1057460 A1 | 12/2000 |
| EP | 1078610 A2 | 2/2001 |
| EP | 1088529 A2 | 4/2001 |
| EP | 1089676 A2 | 4/2001 |
| EP | 1093771 A2 | 4/2001 |
| EP | 1097676 A1 | 5/2001 |
| EP | 1112042 A1 | 7/2001 |
| EP | 1112097 A1 | 7/2001 |
| EP | 1117446 A1 | 7/2001 |
| EP | 1117446 B1 | 7/2001 |
| EP | 1158937 A1 | 12/2001 |
| EP | 1164976 A1 | 1/2002 |
| EP | 1166721 A2 | 1/2002 |
| EP | 1171061 A1 | 1/2002 |
| EP | 1 233 731 B1 | 5/2002 |
| EP | 1206179 A1 | 5/2002 |
| EP | 1206179 B1 | 5/2002 |
| EP | 1233731 A1 | 8/2002 |
| EP | 1235537 A1 | 9/2002 |
| EP | 1248655 A1 | 10/2002 |
| EP | 1251804 A1 | 10/2002 |
| EP | 1251804 B1 | 10/2002 |
| EP | 1251805 A2 | 10/2002 |
| EP | 1255510 A1 | 11/2002 |
| EP | 1257305 A1 | 11/2002 |
| EP | 1259193 A1 | 11/2002 |
| EP | 1259195 A1 | 11/2002 |
| EP | 0 971 649 B1 | 12/2002 |
| EP | 0959815 B1 | 12/2002 |
| EP | 1262201 A1 | 12/2002 |
| EP | 1264582 A2 | 12/2002 |
| EP | 1281357 A2 | 2/2003 |
| EP | 1281375 A2 | 2/2003 |
| EP | 0888142 B1 | 5/2003 |
| EP | 1112097 B1 | 6/2003 |
| EP | 1330213 A1 | 7/2003 |
| EP | 1 017 868 B1 | 9/2003 |
| EP | 0937439 B1 | 9/2003 |
| EP | 1340473 A2 | 9/2003 |
| EP | 1347785 A1 | 10/2003 |
| EP | 1354569 A1 | 10/2003 |
| EP | 1356793 A2 | 10/2003 |
| EP | 1281375 A3 | 12/2003 |
| EP | 1340473 A3 | 2/2004 |
| EP | 1356793 A3 | 3/2004 |
| EP | 1395208 A1 | 3/2004 |
| EP | 1401359 A2 | 3/2004 |
| EP | 0871414 B1 | 4/2004 |
| EP | 1406561 A2 | 4/2004 |
| EP | 1408882 A1 | 4/2004 |
| EP | 1042045 B1 | 5/2004 |
| EP | 1414295 A2 | 5/2004 |
| EP | 0819013 B1 | 6/2004 |
| EP | 1430853 A2 | 6/2004 |
| EP | 1347785 B1 | 7/2004 |
| EP | 1435878 A1 | 7/2004 |
| EP | 1435879 A1 | 7/2004 |
| EP | 1439800 A2 | 7/2004 |
| EP | 1441672 A1 | 8/2004 |
| EP | 0954248 B1 | 9/2004 |
| EP | 1452153 A1 | 9/2004 |
| EP | 0987998 B1 | 10/2004 |
| EP | 1469797 A1 | 10/2004 |
| EP | 1 087 727 B1 | 11/2004 |
| EP | 1115452 B1 | 11/2004 |
| EP | 1472996 A1 | 11/2004 |
| EP | 1477202 A2 | 11/2004 |
| EP | 1107710 B1 | 12/2004 |
| EP | 1484081 A1 | 12/2004 |
| EP | 1494616 A2 | 1/2005 |
| EP | 1499366 A1 | 1/2005 |
| EP | 1499366 B1 | 1/2005 |
| EP | 1143879 B1 | 3/2005 |
| EP | 1516599 A2 | 3/2005 |
| EP | 1518518 A2 | 3/2005 |
| EP | 1 253 875 B1 | 4/2005 |
| EP | 1229864 B1 | 4/2005 |
| EP | 1519697 A1 | 4/2005 |
| EP | 1521414 A1 | 4/2005 |
| EP | 1522278 A2 | 4/2005 |
| EP | 1 251 803 B1 | 6/2005 |
| EP | 1088529 B1 | 6/2005 |
| EP | 1093771 B1 | 6/2005 |
| EP | 1430853 A3 | 6/2005 |
| EP | 1539047 A2 | 6/2005 |
| EP | 1547533 A2 | 6/2005 |
| EP | 1059894 B1 | 7/2005 |
| EP | 1551274 A2 | 7/2005 |
| EP | 1551336 A1 | 7/2005 |
| EP | 1000590 B1 | 8/2005 |
| EP | 1027013 B1 | 8/2005 |
| EP | 1078610 B1 | 8/2005 |
| EP | 1560542 A1 | 8/2005 |
| EP | 1562515 A1 | 8/2005 |
| EP | 1570809 A1 | 9/2005 |
| EP | 1576937 A2 | 9/2005 |
| EP | 0943302 B1 | 10/2005 |
| EP | 1267753 B1 | 10/2005 |
| EP | 1582178 A2 | 10/2005 |
| EP | 1582179 A2 | 10/2005 |
| EP | 1011523 B1 | 11/2005 |
| EP | 1067869 B1 | 11/2005 |
| EP | 1469797 B1 | 11/2005 |
| EP | 1589902 A1 | 11/2005 |
| EP | 1598031 A2 | 11/2005 |
| EP | 1600110 A1 | 11/2005 |
| EP | 1600121 A1 | 11/2005 |
| EP | 0786970 B1 | 12/2005 |
| EP | 1156757 B1 | 12/2005 |
| EP | 1603493 A2 | 12/2005 |
| EP | 1605871 A2 | 12/2005 |
| EP | 1021141 B1 | 1/2006 |
| EP | 1614400 A2 | 1/2006 |
| EP | 1616531 A2 | 1/2006 |
| EP | 1616536 A2 | 1/2006 |
| EP | 1441672 A4 | 6/2006 |
| EP | 1663070 A2 | 6/2006 |
| EP | 1667614 A1 | 6/2006 |
| EP | 1494616 A4 | 7/2006 |
| EP | 1 690 515 A1 | 8/2006 |
| EP | 1702247 A2 | 9/2006 |
| EP | 1051204 B1 | 12/2006 |
| EP | 1734902 A1 | 12/2006 |
| EP | 1395208 B1 | 1/2007 |
| EP | 1 255 510 B1 | 3/2007 |
| EP | 1600121 B1 | 7/2007 |
| EP | 1835948 A1 | 9/2007 |
| EP | 1112042 B1 | 11/2007 |
| EP | 1251797 B1 | 11/2007 |
| EP | 1616531 B1 | 12/2007 |
| EP | 1863545 A2 | 12/2007 |
| EP | 1878407 A1 | 1/2008 |
| EP | 1886649 A2 | 2/2008 |
| EP | 1 900 343 A2 | 3/2008 |
| EP | 1406561 A4 | 3/2008 |
| EP | 1893132 A2 | 3/2008 |
| EP | 1901681 A1 | 3/2008 |
| EP | 1435878 B1 | 4/2008 |
| EP | 1886649 A3 | 4/2008 |
| EP | 1605871 B1 | 7/2008 |
| EP | 1968491 A2 | 9/2008 |
| EP | 1259195 B1 | 10/2008 |

(56) References Cited

FOREIGN PATENT DOCUMENTS

| | | |
|---|---|---|
| EP | 1980220 A1 | 10/2008 |
| EP | 1994913 A2 | 11/2008 |
| EP | 2 000 115 A2 | 12/2008 |
| EP | 1994913 A3 | 12/2008 |
| EP | 1560542 A4 | 1/2009 |
| EP | 1408882 B1 | 2/2009 |
| EP | 1255510 B3 | 3/2009 |
| EP | 1330213 B1 | 3/2009 |
| EP | 2033593 A1 | 3/2009 |
| EP | 2047824 A1 | 4/2009 |
| EP | 2059192 A1 | 5/2009 |
| EP | 2074964 A1 | 7/2009 |
| EP | 1401359 B1 | 8/2009 |
| EP | 1968491 B1 | 7/2010 |
| EP | 1259193 B1 | 11/2010 |
| EP | 2257242 A1 | 12/2010 |
| EP | 2266503 A2 | 12/2010 |
| EP | 2266504 A2 | 12/2010 |
| EP | 1893132 B1 | 3/2011 |
| EP | 2266503 A3 | 4/2011 |
| EP | 2266504 A3 | 4/2011 |
| EP | 2059192 B1 | 7/2011 |
| EP | 1441672 B1 | 9/2011 |
| EP | 2364669 A2 | 9/2011 |
| EP | 2387977 A1 | 11/2011 |
| EP | 1603493 B1 | 12/2011 |
| EP | 1281375 B1 | 2/2012 |
| EP | 2364669 A3 | 3/2012 |
| EP | 2047824 B1 | 5/2012 |
| EP | 2474287 A1 | 7/2012 |
| EP | 2387977 B1 | 11/2013 |
| EP | 1551274 B1 | 12/2014 |
| EP | 2874812 A1 | 5/2015 |
| EP | 2749254 B1 | 6/2015 |
| EP | 1702247 B1 | 8/2015 |
| EP | 2926766 A1 | 10/2015 |
| EP | 1519697 B1 | 11/2015 |
| EP | 1863545 B1 | 11/2015 |
| EP | 1835948 B1 | 2/2016 |
| EP | 1734902 B1 | 6/2016 |
| EP | 3028668 A1 | 6/2016 |
| EP | 1539047 B1 | 11/2016 |
| EP | 1667614 B1 | 12/2016 |
| EP | 3181096 A1 | 6/2017 |
| EP | 2659861 B1 | 3/2019 |
| EP | 1667614 B2 | 4/2020 |
| ES | 2293734 T3 | 3/2008 |
| ES | 2313954 T3 | 3/2009 |
| ES | 2353733 T3 | 3/2011 |
| ES | 2381337 T3 | 5/2012 |
| ES | 2421438 T3 | 9/2013 |
| FI | 8311 U1 | 5/2009 |
| FR | 2432305 A1 | 2/1980 |
| FR | 2788217 A1 | 7/2000 |
| FR | 2815844 A1 | 5/2002 |
| FR | 2826863 A1 | 1/2003 |
| FR | 2828263 A1 | 2/2003 |
| FR | 2874812 A1 | 3/2006 |
| FR | 2828263 B1 | 5/2007 |
| GB | 2018950 A | 10/1979 |
| GB | 2056023 A | 3/1981 |
| GB | 2316322 A | 2/1998 |
| GB | 2316322 B | 10/1998 |
| GB | 2398214 A | 8/2004 |
| GB | 2398245 A | 8/2004 |
| GB | 2398245 B | 3/2007 |
| GB | 2433700 A | 7/2007 |
| GB | 2433700 B | 12/2007 |
| GB | 2440809 A | 2/2008 |
| GB | 2440809 B | 8/2011 |
| HK | 1053600 A1 | 7/2012 |
| JP | S5286296 A | 7/1977 |
| JP | S54137896 A | 9/1979 |
| JP | S62227352 A | 10/1987 |
| JP | S6449571 A | 2/1989 |
| JP | H0447576 B2 | 8/1992 |
| JP | H04505866 A | 10/1992 |
| JP | H06505187 A | 6/1994 |
| JP | H06343703 A | 12/1994 |
| JP | H07504091 A | 5/1995 |
| JP | H07505803 A | 6/1995 |
| JP | H07265339 A | 10/1995 |
| JP | H0833715 A | 2/1996 |
| JP | H1049571 A | 2/1998 |
| JP | H10507673 A | 7/1998 |
| JP | 2001000460 A | 1/2001 |
| JP | 2001504016 A | 3/2001 |
| JP | 2001-526574 A | 12/2001 |
| JP | 2002525168 A | 8/2002 |
| JP | 2002525169 A | 8/2002 |
| JP | 2002-536115 A | 10/2002 |
| JP | 2003515386 A | 5/2003 |
| JP | 2003518984 A | 6/2003 |
| JP | 2003-523262 | 8/2003 |
| JP | 2003-524504 | 8/2003 |
| JP | 2004504111 A | 2/2004 |
| JP | 2004130068 A | 4/2004 |
| JP | 2004514467 A | 5/2004 |
| JP | 2004255186 A | 9/2004 |
| JP | 2004267750 A | 9/2004 |
| JP | 2004283461 A | 10/2004 |
| JP | 2005505343 A | 2/2005 |
| JP | 2005-118585 | 5/2005 |
| JP | 2007521125 A | 8/2007 |
| JP | 2007-296375 | 11/2007 |
| JP | 2007298375 A | 11/2007 |
| JP | 2007534381 A | 11/2007 |
| JP | 2007536003 A | 12/2007 |
| JP | 2008506497 A | 3/2008 |
| JP | 2008514345 A | 5/2008 |
| JP | 2008535572 A | 9/2008 |
| JP | 2008-539305 | 11/2008 |
| JP | 2008539985 A | 11/2008 |
| JP | 2008541865 A | 11/2008 |
| JP | 2009034529 A | 2/2009 |
| JP | 2009061293 A | 3/2009 |
| JP | 2009509635 A | 3/2009 |
| JP | 4246433 B2 | 4/2009 |
| JP | 2009520535 A | 5/2009 |
| JP | 2009131397 A | 6/2009 |
| JP | 4295460 B2 | 7/2009 |
| JP | 2009528905 A | 8/2009 |
| JP | 2009534157 A | 9/2009 |
| JP | 2010525896 A | 7/2010 |
| JP | 2010526609 A | 8/2010 |
| JP | 4636794 B2 | 2/2011 |
| JP | 2011509805 A | 3/2011 |
| JP | 4739223 B2 | 8/2011 |
| JP | 2012500665 A | 1/2012 |
| JP | 4904362 B2 | 3/2012 |
| JP | 4912395 B2 | 4/2012 |
| JP | 2012518446 A | 8/2012 |
| JP | 2013520260 A | 6/2013 |
| JP | 2013521884 A | 6/2013 |
| JP | 2013526388 A | 6/2013 |
| JP | 5341455 B2 | 11/2013 |
| JP | 2013540495 A | 11/2013 |
| JP | 6144009 B2 | 6/2017 |
| JP | 6449571 B2 | 1/2019 |
| PT | 1112042 E | 1/2008 |
| PT | 1259195 E | 12/2008 |
| PT | 1259193 E | 1/2011 |
| PT | 1281375 E | 3/2012 |
| PT | 1994913 E | 8/2013 |
| RU | 2149037 C1 | 5/2000 |
| SE | 7901667 L | 10/1979 |
| SU | 1271508 A1 | 11/1986 |
| SU | 1371700 A1 | 2/1988 |
| WO | WO-8402266 A1 | 6/1984 |
| WO | WO-90/09102 | 8/1990 |
| WO | WO-9014804 A1 | 12/1990 |
| WO | WO-9117720 A1 | 11/1991 |
| WO | WO-9203990 A1 | 3/1992 |
| WO | WO-9212690 A1 | 8/1992 |

(56) References Cited

FOREIGN PATENT DOCUMENTS

| | | |
|---|---|---|
| WO | WO-9214419 A1 | 9/1992 |
| WO | WO-9217118 A1 | 10/1992 |
| WO | WO-9301768 A1 | 2/1993 |
| WO | WO-9315693 A1 | 8/1993 |
| WO | WO-9320757 A2 | 10/1993 |
| WO | WO-9504556 A2 | 2/1995 |
| WO | WO 95/11055 A1 | 4/1995 |
| WO | WO-9504556 A3 | 4/1995 |
| WO | WO-95/24873 | 9/1995 |
| WO | WO-95/28183 | 10/1995 |
| WO | WO-9528899 A1 | 11/1995 |
| WO | WO-9529640 A1 | 11/1995 |
| WO | WO-9529713 A1 | 11/1995 |
| WO | WO-96/13227 | 5/1996 |
| WO | WO-9614032 A1 | 5/1996 |
| WO | WO-9624306 A1 | 8/1996 |
| WO | WO-9630072 A1 | 10/1996 |
| WO | WO-9632972 A1 | 10/1996 |
| WO | WO-9635469 A1 | 11/1996 |
| WO | WO-9639962 A1 | 12/1996 |
| WO | WO-9639964 A1 | 12/1996 |
| WO | WO-9639965 A1 | 12/1996 |
| WO | WO-9640012 A1 | 12/1996 |
| WO | WO-9713463 A1 | 4/1997 |
| WO | WO-9713471 A1 | 4/1997 |
| WO | WO-9724082 A1 | 7/1997 |
| WO | WO-9727893 A1 | 8/1997 |
| WO | WO-9727897 A1 | 8/1997 |
| WO | WO-9727898 A1 | 8/1997 |
| WO | WO-9728839 A1 | 8/1997 |
| WO | WO-97/32615 | 9/1997 |
| WO | WO-9732551 A1 | 9/1997 |
| WO | WO-9743961 A1 | 11/1997 |
| WO | WO-9748350 A1 | 12/1997 |
| WO | WO-9803118 A1 | 1/1998 |
| WO | WO-9806356 A1 | 2/1998 |
| WO | WO-9808456 A1 | 3/1998 |
| WO | WO-9810714 A1 | 3/1998 |
| WO | WO-9811846 A1 | 3/1998 |
| WO | WO-9814137 A1 | 4/1998 |
| WO | WO-9816161 A1 | 4/1998 |
| WO | WO-9819633 A1 | 5/1998 |
| WO | WO-9824373 A1 | 6/1998 |
| WO | WO-9825533 A1 | 6/1998 |
| WO | WO-9825549 A1 | 6/1998 |
| WO | WO-9829057 A1 | 7/1998 |
| WO | WO-9836790 A1 | 8/1998 |
| WO | WO-9838916 A1 | 9/1998 |
| WO | WO-9838925 A1 | 9/1998 |
| WO | WO-9838939 A1 | 9/1998 |
| WO | WO-9838941 A1 | 9/1998 |
| WO | WO-9839038 A1 | 9/1998 |
| WO | WO 98/43556 | 10/1998 |
| WO | WO-98/46165 | 10/1998 |
| WO | WO-9844869 A1 | 10/1998 |
| WO | WO-9846115 A2 | 10/1998 |
| WO | WO-9846119 A1 | 10/1998 |
| WO | WO-9849964 A1 | 11/1998 |
| WO | WO-9850103 A1 | 11/1998 |
| WO | WO-9853759 A2 | 12/1998 |
| WO | WO-9853761 A1 | 12/1998 |
| WO | WO-9855027 A2 | 12/1998 |
| WO | WO-9855047 A1 | 12/1998 |
| WO | WO-9857590 A1 | 12/1998 |
| WO | WO-9857591 A1 | 12/1998 |
| WO | WO-9857592 A1 | 12/1998 |
| WO | WO-9857599 A2 | 12/1998 |
| WO | WO-9907296 A1 | 2/1999 |
| WO | WO-9908624 A1 | 2/1999 |
| WO | WO-9915112 A1 | 4/1999 |
| WO | WO-9915220 A1 | 4/1999 |
| WO | WO-9917671 A1 | 4/1999 |
| WO | WO-9917683 A1 | 4/1999 |
| WO | WO-9921490 A1 | 5/1999 |
| WO | WO-9921510 A1 | 5/1999 |
| WO | WO-9922655 A1 | 5/1999 |
| WO | WO-9922656 A1 | 5/1999 |
| WO | WO-9922658 A1 | 5/1999 |
| WO | WO-9925273 A1 | 5/1999 |
| WO | WO-9927985 A1 | 6/1999 |
| WO | WO-99/37337 | 7/1999 |
| WO | WO-9933414 A1 | 7/1999 |
| WO | WO-9935977 A1 | 7/1999 |
| WO | WO-9935979 A1 | 7/1999 |
| WO | WO-9935980 A1 | 7/1999 |
| WO | WO-9936000 A1 | 7/1999 |
| WO | WO-9936001 A1 | 7/1999 |
| WO | WO-9938459 A2 | 8/1999 |
| WO | WO-9940853 A1 | 8/1999 |
| WO | WO-9940868 A1 | 8/1999 |
| WO | WO-9940963 A1 | 8/1999 |
| WO | WO-9940964 A1 | 8/1999 |
| WO | WO-9942058 A1 | 8/1999 |
| WO | WO-9944524 A2 | 9/1999 |
| WO | WO-9944540 A2 | 9/1999 |
| WO | WO-9944542 A2 | 9/1999 |
| WO | WO-9947071 A1 | 9/1999 |
| WO | WO-9947075 A1 | 9/1999 |
| WO | WO-9948545 A1 | 9/1999 |
| WO | WO-9948549 A2 | 9/1999 |
| WO | WO-9949793 A1 | 10/1999 |
| WO | WO-9949910 A2 | 10/1999 |
| WO | WO-9951162 A1 | 10/1999 |
| WO | WO-9951165 A1 | 10/1999 |
| WO | WO-9953863 A1 | 10/1999 |
| WO | WO-9953987 A1 | 10/1999 |
| WO | WO-9955406 A1 | 11/1999 |
| WO | WO-99/66863 | 12/1999 |
| WO | WO-9960941 A1 | 12/1999 |
| WO | WO-9962430 A1 | 12/1999 |
| WO | WO-0002503 A1 | 1/2000 |
| WO | WO-0009059 A2 | 2/2000 |
| WO | WO-0009195 A1 | 2/2000 |
| WO | WO 00/15148 | 3/2000 |
| WO | WO-0010623 A1 | 3/2000 |
| WO | WO-0012029 A1 | 3/2000 |
| WO | WO-0013722 A1 | 3/2000 |
| WO | WO-0015146 A1 | 3/2000 |
| WO | WO-0015147 A1 | 3/2000 |
| WO | WO-0015149 A1 | 3/2000 |
| WO | WO-0015275 A2 | 3/2000 |
| WO | WO-0016848 A1 | 3/2000 |
| WO | WO-00/18445 | 4/2000 |
| WO | WO-0018302 A2 | 4/2000 |
| WO | WO-0018323 A2 | 4/2000 |
| WO | WO-0018325 A1 | 4/2000 |
| WO | WO-0018326 A1 | 4/2000 |
| WO | WO-0018330 A1 | 4/2000 |
| WO | WO-0018331 A2 | 4/2000 |
| WO | WO-0018333 A1 | 4/2000 |
| WO | WO-0018462 A2 | 4/2000 |
| WO | WO-0021436 A1 | 4/2000 |
| WO | WO-0021461 A2 | 4/2000 |
| WO | WO-0021463 A1 | 4/2000 |
| WO | WO-0021464 A1 | 4/2000 |
| WO | WO 2000/25702 A1 | 5/2000 |
| WO | WO-0024449 A1 | 5/2000 |
| WO | WO-0028922 A1 | 5/2000 |
| WO | WO-0028924 A2 | 5/2000 |
| WO | WO-0033725 A2 | 6/2000 |
| WO | WO-0035376 A1 | 6/2000 |
| WO | WO-0036997 A1 | 6/2000 |
| WO | WO-0041632 A1 | 7/2000 |
| WO | WO-0041633 A1 | 7/2000 |
| WO | WO-0041652 A1 | 7/2000 |
| WO | WO-0043051 A1 | 7/2000 |
| WO | WO-0044211 A1 | 7/2000 |
| WO | WO 00/47139 A1 | 8/2000 |
| WO | WO-0044308 A2 | 8/2000 |
| WO | WO-0044311 A2 | 8/2000 |
| WO | WO-0044313 A1 | 8/2000 |
| WO | WO-0044331 A1 | 8/2000 |
| WO | WO-0045711 A1 | 8/2000 |
| WO | WO-0045874 A1 | 8/2000 |

(56) References Cited

FOREIGN PATENT DOCUMENTS

| | | |
|---|---|---|
| WO | WO-0045886 A2 | 8/2000 |
| WO | WO-0047136 A1 | 8/2000 |
| WO | WO-0048531 A1 | 8/2000 |
| WO | WO-0049952 A1 | 8/2000 |
| WO | WO-0049954 A2 | 8/2000 |
| WO | WO-0049956 A1 | 8/2000 |
| WO | WO-0049970 A1 | 8/2000 |
| WO | WO-00/53125 | 9/2000 |
| WO | WO-0053122 A1 | 9/2000 |
| WO | WO-0054660 A1 | 9/2000 |
| WO | WO-0054661 A1 | 9/2000 |
| WO | WO-0056224 A1 | 9/2000 |
| WO | WO-0056225 A1 | 9/2000 |
| WO | WO-0056387 A1 | 9/2000 |
| WO | WO-00/62714 | 10/2000 |
| WO | WO-0060995 A2 | 10/2000 |
| WO | WO-0066007 A1 | 11/2000 |
| WO | WO-0066009 A1 | 11/2000 |
| WO | WO-0066035 A1 | 11/2000 |
| WO | WO-0067661 A2 | 11/2000 |
| WO | WO-0069345 A1 | 11/2000 |
| WO | WO-0069367 A1 | 11/2000 |
| WO | WO-0069504 A1 | 11/2000 |
| WO | WO-0071195 A1 | 11/2000 |
| WO | WO-0078226 A1 | 12/2000 |
| WO | WO-0105331 A1 | 1/2001 |
| WO | WO-01/10209 A1 | 2/2001 |
| WO | WO-0106959 A1 | 2/2001 |
| WO | WO-0108566 A1 | 2/2001 |
| WO | WO-0108596 A1 | 2/2001 |
| WO | WO-0108602 A1 | 2/2001 |
| WO | WO-0110320 A1 | 2/2001 |
| WO | WO-0110340 A1 | 2/2001 |
| WO | WO-0110341 A2 | 2/2001 |
| WO | WO-0110343 A1 | 2/2001 |
| WO | WO-0110347 A1 | 2/2001 |
| WO | WO-0110348 A1 | 2/2001 |
| WO | WO-0110349 A1 | 2/2001 |
| WO | WO-0110350 A1 | 2/2001 |
| WO | WO-0117440 A1 | 3/2001 |
| WO | WO-0117456 A1 | 3/2001 |
| WO | WO 2001/35870 A1 | 5/2001 |
| WO | WO-0135864 A1 | 5/2001 |
| WO | WO-0136870 A1 | 5/2001 |
| WO | WO-01/41679 A1 | 6/2001 |
| WO | WO-0139700 A1 | 6/2001 |
| WO | WO-01/51104 A1 | 7/2001 |
| WO | WO-0149185 A1 | 7/2001 |
| WO | WO-0149187 A1 | 7/2001 |
| WO | WO-0149213 A2 | 7/2001 |
| WO | WO 01/54625 A1 | 8/2001 |
| WO | WO 01/58503 A1 | 8/2001 |
| WO | WO 01/62189 A1 | 8/2001 |
| WO | WO 01/64137 A1 | 9/2001 |
| WO | WO-0047139 A9 | 9/2001 |
| WO | WO-0176510 A2 | 10/2001 |
| WO | WO-0182837 A2 | 11/2001 |
| WO | WO-0197715 A1 | 12/2001 |
| WO | WO-0211647 A2 | 2/2002 |
| WO | WO-0219926 A1 | 3/2002 |
| WO | WO-0222054 A1 | 3/2002 |
| WO | WO-0224118 A1 | 3/2002 |
| WO | WO 2002/36048 A1 | 5/2002 |
| WO | WO-0241789 A2 | 5/2002 |
| WO | WO-0243620 A1 | 6/2002 |
| WO | WO-0247575 A2 | 6/2002 |
| WO | WO-0249540 A2 | 6/2002 |
| WO | WO-02051489 A2 | 7/2002 |
| WO | WO-02056798 A2 | 7/2002 |
| WO | WO-02056955 A1 | 7/2002 |
| WO | WO-02/058745 A1 | 8/2002 |
| WO | WO-02060509 A1 | 8/2002 |
| WO | WO-02067782 A2 | 9/2002 |
| WO | WO-02069842 A2 | 9/2002 |
| WO | WO-02076349 A1 | 10/2002 |
| WO | WO-02/100301 A1 | 12/2002 |
| WO | WO-02/102286 A1 | 12/2002 |
| WO | WO-02100297 A2 | 12/2002 |
| WO | WO 03/003949 A2 | 1/2003 |
| WO | WO-03/007795 A2 | 1/2003 |
| WO | WO 2003/003949 A2 | 1/2003 |
| WO | WO-03003943 A2 | 1/2003 |
| WO | WO-03/009785 A1 | 2/2003 |
| WO | WO 03/013239 | 2/2003 |
| WO | WO 2003/011195 A2 | 2/2003 |
| WO | WO-03015851 A1 | 2/2003 |
| WO | WO 03/028592 A1 | 4/2003 |
| WO | WO-03030776 A2 | 4/2003 |
| WO | WO-03032869 A1 | 4/2003 |
| WO | WO-03032870 A1 | 4/2003 |
| WO | WO-03037222 A2 | 5/2003 |
| WO | WO-03037227 A2 | 5/2003 |
| WO | WO 03/047468 A1 | 6/2003 |
| WO | WO-03047460 A2 | 6/2003 |
| WO | WO-03047648 A2 | 6/2003 |
| WO | WO-03051231 A2 | 6/2003 |
| WO | WO-03063729 A2 | 8/2003 |
| WO | WO-03/079928 A2 | 10/2003 |
| WO | WO-03079932 A2 | 10/2003 |
| WO | WO-03079933 A1 | 10/2003 |
| WO | WO-03088873 A1 | 10/2003 |
| WO | WO 2003/096935 A1 | 11/2003 |
| WO | WO-03015851 B1 | 11/2003 |
| WO | WO-03063729 A3 | 11/2003 |
| WO | WO-03092554 A1 | 11/2003 |
| WO | WO-03094793 A1 | 11/2003 |
| WO | WO-03094797 A1 | 11/2003 |
| WO | WO-03096932 A1 | 11/2003 |
| WO | WO-03101195 A1 | 12/2003 |
| WO | WO-03103949 A1 | 12/2003 |
| WO | WO 2004/004597 A2 | 1/2004 |
| WO | WO-03003949 A3 | 1/2004 |
| WO | WO-2004006803 A1 | 1/2004 |
| WO | WO-2004006804 A1 | 1/2004 |
| WO | WO 2004/016200 A1 | 2/2004 |
| WO | WO 2004/016201 A2 | 2/2004 |
| WO | WO-2004014256 A1 | 2/2004 |
| WO | WO 2004/019825 A1 | 3/2004 |
| WO | WO-2004019811 A2 | 3/2004 |
| WO | WO-2004019817 A1 | 3/2004 |
| WO | WO-2004021922 A2 | 3/2004 |
| WO | WO-2004023980 A2 | 3/2004 |
| WO | WO-2004/026117 A2 | 4/2004 |
| WO | WO 2004/026173 A2 | 4/2004 |
| WO | WO 2004/028399 A2 | 4/2004 |
| WO | WO-2004019811 A9 | 4/2004 |
| WO | WO-2004030515 A2 | 4/2004 |
| WO | WO 2004/043301 A1 | 5/2004 |
| WO | WO-2004041126 A1 | 5/2004 |
| WO | WO-2004043293 A2 | 5/2004 |
| WO | WO-2004047681 A1 | 6/2004 |
| WO | WO-2004058106 A2 | 7/2004 |
| WO | WO-2004062980 A1 | 7/2004 |
| WO | WO-2004058106 A3 | 8/2004 |
| WO | WO-2004064671 A2 | 8/2004 |
| WO | WO-2004066876 A1 | 8/2004 |
| WO | WO-2004071352 A1 | 8/2004 |
| WO | WO 2004/082527 A2 | 9/2004 |
| WO | WO 2004/082528 A2 | 9/2004 |
| WO | WO-2004082536 A1 | 9/2004 |
| WO | WO-2004089250 A1 | 10/2004 |
| WO | WO-2004089253 A1 | 10/2004 |
| WO | WO 2004/096100 A1 | 11/2004 |
| WO | WO-2004093728 A2 | 11/2004 |
| WO | WO-2004103162 A2 | 12/2004 |
| WO | WO-2004105651 A1 | 12/2004 |
| WO | WO-2005002466 A2 | 1/2005 |
| WO | WO-2005004753 A1 | 1/2005 |
| WO | WO-2005007343 A1 | 1/2005 |
| WO | WO-2005009285 A2 | 2/2005 |
| WO | WO-2005011534 A1 | 2/2005 |
| WO | WO-2005011535 A2 | 2/2005 |
| WO | WO 2005/021063 A2 | 3/2005 |
| WO | WO-2005023155 A1 | 3/2005 |

(56) References Cited

FOREIGN PATENT DOCUMENTS

| | | |
|---|---|---|
| WO | WO-2005027790 A1 | 3/2005 |
| WO | WO-2005027797 A1 | 3/2005 |
| WO | WO 2005/034812 A1 | 4/2005 |
| WO | WO-2005032622 A2 | 4/2005 |
| WO | WO-2005010215 A3 | 5/2005 |
| WO | WO-2005046528 A1 | 5/2005 |
| WO | WO-2005046529 A1 | 5/2005 |
| WO | WO-2005048883 A1 | 6/2005 |
| WO | WO 2005/062980 A2 | 7/2005 |
| WO | WO 2005/063980 A1 | 7/2005 |
| WO | WO-2005065585 A1 | 7/2005 |
| WO | WO-2005065594 A1 | 7/2005 |
| WO | WO-2005/072654 A1 | 8/2005 |
| WO | WO-2005070343 A1 | 8/2005 |
| WO | WO-2005076890 A2 | 8/2005 |
| WO | WO-2005084595 A1 | 9/2005 |
| WO | WO-2005087140 A1 | 9/2005 |
| WO | WO-2005096993 A1 | 10/2005 |
| WO | WO 2005/102015 A2 | 11/2005 |
| WO | WO-2005110240 A1 | 11/2005 |
| WO | WO-2005112779 A1 | 12/2005 |
| WO | WO-2006005015 A2 | 1/2006 |
| WO | WO-2006009690 A1 | 1/2006 |
| WO | WO-2006026371 A1 | 3/2006 |
| WO | WO-2006027499 A2 | 3/2006 |
| WO | WO-2005062980 A3 | 5/2006 |
| WO | WO 2006/066327 | 6/2006 |
| WO | WO-2006/066327 A1 | 6/2006 |
| WO | WO-2006058163 A2 | 6/2006 |
| WO | WO-2006065949 A2 | 6/2006 |
| WO | WO-2006068944 A2 | 6/2006 |
| WO | WO 2006/070372 A2 | 7/2006 |
| WO | WO 2006/076890 | 7/2006 |
| WO | WO-2006083763 A1 | 8/2006 |
| WO | WO-2006086135 A2 | 8/2006 |
| WO | WO-2006086736 A2 | 8/2006 |
| WO | WO-2006089517 A1 | 8/2006 |
| WO | WO-2006/102063 A2 | 9/2006 |
| WO | WO-2006093795 A1 | 9/2006 |
| WO | WO 2006/108090 A2 | 10/2006 |
| WO | WO-2006/124649 A2 | 11/2006 |
| WO | WO 2006/124649 A2 | 11/2006 |
| WO | WO 2006/127756 A2 | 11/2006 |
| WO | WO 2006/127765 A1 | 11/2006 |
| WO | WO-2006118766 A1 | 11/2006 |
| WO | WO 2006/129441 A1 | 12/2006 |
| WO | WO-2006/132948 A1 | 12/2006 |
| WO | WO-2006133959 A1 | 12/2006 |
| WO | WO-2006138173 A2 | 12/2006 |
| WO | WO-2006138391 A2 | 12/2006 |
| WO | WO-2007009117 A1 | 1/2007 |
| WO | WO-2007009609 A1 | 1/2007 |
| WO | WO-2007013999 A2 | 2/2007 |
| WO | WO-2007033093 A2 | 3/2007 |
| WO | WO-2007035471 A2 | 3/2007 |
| WO | WO 2007/047488 A2 | 4/2007 |
| WO | WO 2007/047945 A2 | 4/2007 |
| WO | WO-2005102015 A3 | 4/2007 |
| WO | WO-2006138391 A9 | 4/2007 |
| WO | WO-2007044285 A2 | 4/2007 |
| WO | WO-2007/048529 A1 | 5/2007 |
| WO | WO 2007/051620 A1 | 5/2007 |
| WO | WO 2007/059252 A1 | 5/2007 |
| WO | WO-2007053243 A2 | 5/2007 |
| WO | WO-2007058847 A2 | 5/2007 |
| WO | WO-2007/071436 A2 | 6/2007 |
| WO | WO-2006086736 A3 | 6/2007 |
| WO | WO 2007/098232 A2 | 8/2007 |
| WO | WO-2007092354 A2 | 8/2007 |
| WO | WO-2007097983 A2 | 8/2007 |
| WO | WO-2007053243 A3 | 9/2007 |
| WO | WO 2007/120543 A1 | 10/2007 |
| WO | WO-2007071436 A3 | 11/2007 |
| WO | WO-2007123658 A1 | 11/2007 |
| WO | WO-2007123956 A2 | 11/2007 |
| WO | WO-2007033093 A3 | 1/2008 |
| WO | WO-2007071436 B1 | 1/2008 |
| WO | WO-2008/028569 A1 | 3/2008 |
| WO | WO 2008/031103 A2 | 3/2008 |
| WO | WO-2008/035337 A2 | 3/2008 |
| WO | WO 2008/045949 | 4/2008 |
| WO | WO-2008040555 A2 | 4/2008 |
| WO | WO-2008047354 A2 | 4/2008 |
| WO | WO-2008051554 A2 | 5/2008 |
| WO | WO 2008/070797 A2 | 6/2008 |
| WO | WO-2008070442 A1 | 6/2008 |
| WO | WO 2008/079962 A1 | 7/2008 |
| WO | WO 2008/101083 A2 | 8/2008 |
| WO | WO-2008098191 A2 | 8/2008 |
| WO | WO-2008100599 A1 | 8/2008 |
| WO | WO 2008/125153 A1 | 10/2008 |
| WO | WO 2008/138584 A1 | 11/2008 |
| WO | WO-2008137603 A2 | 11/2008 |
| WO | WO-2008/150529 A1 | 12/2008 |
| WO | WO-2009002548 A2 | 12/2008 |
| WO | WO-2009024859 A2 | 2/2009 |
| WO | WO-2009029199 A1 | 3/2009 |
| WO | WO-2009042196 A2 | 4/2009 |
| WO | WO-2009045334 A1 | 4/2009 |
| WO | WO-2009045338 A1 | 4/2009 |
| WO | WO-2009053497 A1 | 4/2009 |
| WO | WO-2009054397 A1 | 4/2009 |
| WO | WO-2007044285 A3 | 5/2009 |
| WO | WO-2009061389 A2 | 5/2009 |
| WO | WO-2009085206 A2 | 7/2009 |
| WO | WO-2009091509 A1 | 7/2009 |
| WO | WO-2009094188 A2 | 7/2009 |
| WO | WO-2009094501 A1 | 7/2009 |
| WO | WO-2009100198 A2 | 8/2009 |
| WO | WO-2009106545 A1 | 9/2009 |
| WO | WO-2009108615 A1 | 9/2009 |
| WO | WO-2009111241 A2 | 9/2009 |
| WO | WO-2009149462 A2 | 12/2009 |
| WO | WO-2009155561 A2 | 12/2009 |
| WO | WO-2010022138 A2 | 2/2010 |
| WO | WO-2010042950 A2 | 4/2010 |
| WO | WO-2010043950 A2 | 4/2010 |
| WO | WO-2010044851 A1 | 4/2010 |
| WO | WO-2010045238 A2 | 4/2010 |
| WO | WO-2010045297 A2 | 4/2010 |
| WO | WO-2010049160 A1 | 5/2010 |
| WO | WO-2010083558 A1 | 7/2010 |
| WO | WO-2010086460 A1 | 8/2010 |
| WO | WO-2010098857 A1 | 9/2010 |
| WO | WO-2010104638 A2 | 9/2010 |
| WO | WO-2010045238 A3 | 10/2010 |
| WO | WO-2010141626 A2 | 12/2010 |
| WO | WO-2011008812 A2 | 1/2011 |
| WO | WO-2011008853 A2 | 1/2011 |
| WO | WO-2011051043 A1 | 5/2011 |
| WO | WO-2011057087 A1 | 5/2011 |
| WO | WO-2011060386 A2 | 5/2011 |
| WO | WO-2011102968 A1 | 8/2011 |
| WO | WO-2011104269 A1 | 9/2011 |
| WO | WO-2011120050 A1 | 9/2011 |
| WO | WO-2011133368 A1 | 10/2011 |
| WO | WO-2011144351 A2 | 11/2011 |
| WO | WO-2011147849 A1 | 12/2011 |
| WO | WO-2012002228 A1 | 1/2012 |
| WO | WO-2012023980 A1 | 2/2012 |
| WO | WO-2012036742 A2 | 3/2012 |
| WO | WO-2012038550 A1 | 3/2012 |
| WO | WO-2012039748 A2 | 3/2012 |
| WO | WO-2012082952 A2 | 6/2012 |
| WO | WO-2012106491 A1 | 8/2012 |
| WO | WO-2012116368 A2 | 8/2012 |
| WO | WO-2012142189 A1 | 10/2012 |
| WO | WO-2012145546 A1 | 10/2012 |
| WO | WO-2012162228 A1 | 11/2012 |
| WO | WO-2013009975 A1 | 1/2013 |
| WO | WO-2013028387 A2 | 2/2013 |
| WO | WO-2013033791 A1 | 3/2013 |
| WO | WO-2013074671 A1 | 5/2013 |
| WO | WO-2013096545 A1 | 6/2013 |

(56) References Cited

FOREIGN PATENT DOCUMENTS

| | | |
|---|---|---|
| WO | WO-2013134214 A1 | 9/2013 |
| WO | WO-2014056644 A1 | 4/2014 |
| WO | WO-2014072439 A1 | 5/2014 |
| WO | WO-2014072439 A9 | 7/2014 |
| WO | WO-2015028209 A1 | 3/2015 |
| WO | WO-2016093877 A1 | 6/2016 |
| WO | WO-2016126511 A2 | 8/2016 |

OTHER PUBLICATIONS

US 8,062,356 B2, 11/2011, Salahieh et al. (withdrawn)
US 8,062,357 B2, 11/2011, Salahieh et al. (withdrawn)
US 8,075,614 B2, 12/2011, Salahieh et al. (withdrawn)
US 8,133,271 B2, 03/2012, Salahieh et al. (withdrawn)
US 8,211,170 B2, 07/2012, Paul et al. (withdrawn)
Aortenklappenbioprothese erfolgreich in der Entwicklung, May 16, 2003 (1 page).
English translation of Aortenklappenbioprothese erfolgreich in der Entwicklung (2 pages).
Screen shots from http://www.fraunhofer.de/presse/filme/2006/index.jsp, 2006 (2 pages).
Liang, Ma, et al., "Double-crowned valved stents for off-pump mitral valve replacement," Eur. J. Cardio-Thoracic Surgery, vol. 28, pp. 194-198 (2005) (5 pages).
Huber, Christoph H., et al. "Direct Access Valve Replacement (DAVR)—are we entering a new era in cardiac surgery?" Eur. J. Cardio-Thoracic Surgery, vol. 29, pp. 380-385 (2006) (6 pages).
English translation of DE 19546692 A1 (3 pages).
English translation of EP 1469797 B1 (15 pages).
File history for German Patent DE 195 46 692 filed Dec. 14, 1995 and patented Jul. 11, 2002 (111 pages).
English abstract for DE 19857887 A1 (1 page).
English abstract for DE 10335948 B3 (1 page).
Klein, Allan L. et al., "Age-related Prevalence of Valvular Regurgitation in Normal Subjects: A Comprehensive Color Flow Examination of 118 Volunteers," J. Am. Soc. Echocardiography, vol. 3, No. 1, pp. 54-63 (1990) (10 pages).
Gummert, J.F. et al., "Cardiac Surgery in Germany During 2007: A Report on Behalf of the German Society for Thoracic and Cardiovascular Surgery," Thorac. Cardiov. Surg., vol. 56, pp. 328-336 (2008) (9 pages).
Gummert, J.F. et al., "Cardiac Surgery in Germany During 2006: A Report on Behalf of the German Society for Thoracic and Cardiovascular Surgery," Thorac. Cardiov. Surg., vol. 55, pp. 343-350 (2007) (8 pages).
Akins C.W., et al., "Risk of Reoperative Valve Replacement for Failed Mitral and Aortic Bioprostheses," The Annals of Thoracic Surgery, 65:545-1552 (Jan. 1998). Retrieved from the Internet: URL: http://ats.ctsnetjournals.org/cgi/contenUfull/65/6/1545 (Jan. 1998).
Allen et al., "What are the characteristics of the ideal endovascular graft for abdominal aortic aneurysm exclusion?", J. Endovasc. Surg., vol. 4(2), May 1997, pp. 195-202.
Anabtawi I.N., et al., "Experimental evaluation of myocardial tunnelization as a method of myocardial revascularization," Journal of Thoracic and Cardiovascular Surgery, 58(5):638-646 (Nov. 1969).
Andersen H.R., et al., "Transluminal Implantation of Artificial Heart Valves. Description of a New Expandable Aortic Valve and Initial Results with Implantation by Catheter Technique in Closed Chest Pigs," European Heart Journal, May 1992, vol. 13, pp. 704-708.
Archie J.P., et al., "Intramyocardial Pressure: Effect of Preload on Transmural Distribution of Systolic Coronary Blood Flow," The American Journal of Cardiology, 35(6):904-911 (Jun. 1975).
Baba H., et al., "Hemodynamic effects of venous valves in aorta-coronary bypass grafts," The Journal of Thoracic and Cardiovascular Surgery, 71(5):774-778 (May 1976).
Babaliaros V., et al., "State of the Art Percutaneous Intervention for the Treatment of Valvular Heart Disease: A Review of the Current Technologies and Ongoing Research in the Field of Percutaneous Valve Replacement and Repair," Cardiology, 2007, vol. 107, pp. 87-96.
Bailey S.R., "Percutaneous Expandable Prosthetic Valves," Textbook of Interventional Cardiology, Second Edition, W.B. Saunders Company, 1994, vol. 2, pp. 1268-1276.
Block P.C., et al., "Percutaneous Approaches to Valvular Heart Disease," Current Cardiology Reports, Mar. 2005, vol. 7(2), pp. 108-113.
Blum et al., "Endoluminal Stent-Grafts for Intrarenal Abdominal Aortic Aneurysms." New Engl. J. Med., 336:13-20 (Jan. 1997).
Bonhoeffer et al., "Percutaneous Mitral Valve Dilatation with the Multi-Track System," Catheterization and Cardiovascular Interventions—Official Journal of the Society for Cardiac Angiograhy & Interventions, United States (Oct. 1999), pp. 178-183.
Bonhoeffer P., et al., "Percutaneous Insertion of the Pulmonary Valve," Journal of the American College of Cardiology, May 15, 2002, vol. 39, pp. 1664-1669.
Bonhoeffer P., et al., "Percutaneous Replacement of Pulmonary Valve in a Right-Ventricle to Pulmonary-Artery Prosthetic Conduit with Valve Dysfunction," Lancet, Oct. 2000, vol. 356, pp. 1403-1405.
Bonhoeffer P., et al., "Technique and Results of Percutaneous Mitral Valvuloplasty With the Multi-Track System," Journal of Interventional Cadiology, 13(4):263-268 (Aug. 2000).
Bonhoeffer P., et al., "Transcatheter Implantation of a Bovine Valve in Pulmonary Position: A Lamb Study," Circulation, Aug. 15, 2000, vol. 102, pp. 813-816.
Boudjemline et al., "Percutaneous Implantation of a Biological Valve in Aortic Position: Preliminary Results in a Sheep Study," European Heart Journal, vol. 22, p. 630, Abstract Only (Sep. 2001).
Boudjemline Y., et al., "Images in Cardiovascular Medicine: Percutaneous Aortic Valve Replacement in Animals," Circulation, United States, Mar. 16, 2004, vol. 109, p. e161.
Boudjemline Y., et al., "Is Percutaneous Implantation of a Bovine Venous Valve in the Inferior Vena Cava a Reliable Technique to Treat Chronic Venous Insufficiency Syndrome?," Medical Science Monitor, Poland, Mar. 2004, vol. 10(3), pp. BR61-BR66.
Boudjemline Y., et al., "Off-Pump Replacement of the Pulmonary Valve in Large Right Ventricular Outflow Tracts: A Hybrid Approach," Journal of Thoracic and Cardiovascular Surgery, United States, Apr. 2005, vol. 129(4), pp. 831-837.
Boudjemline Y., et al., "Percutaneous Aortic Valve Replacement: Will We Get There?," Heart, British Cardiac Society, England, Dec. 2001, vol. 86, pp. 705-706.
Boudjemline Y., et al., "Percutaneous Implantation of a Biological Valve in the Aorta to Treat Aortic Valve Insufficiency—A Sheep Study," Medical Science Monitor, Apr. 12, 2002, vol. 8(4), pp. BR113-BR116.
Boudjemline Y., et al., "Percutaneous Implantation of a Valve in the Descending Aorta in Lambs," European Heart Journal, Jul. 2002, vol. 23, pp. 1045-1049.
Boudjemline Y., et al., "Percutaneous Pulmonary Valve Replacement in a Large Right Ventricular Outflow Tract: An Experimental Study," Journal of the American College of Cardiology, Mar. 17, 2004, vol. 43(6), pp. 1082-1087.
Boudjemline Y., et al., "Percutaneous Valve Insertion: A New Approach?," Journal of Thoracic and Cardiovascular Surgery, United States, Mar. 2003, vol. 125(3), pp. 741-742.
Boudjemline Y., et al., "Stent Implantation Combined with a Valve Replacement to Treat Degenerated Right Ventricle to Pulmonary Artery Prosthetic Conduits," European Heart Journal, Sep. 2001, vol. 22, p. 355.
Boudjemline Y., et al., "Steps Toward Percutaneous Aortic Valve Replacement," Circulation, Feb. 12, 2002, vol. 105, pp. 775-778.
Boudjemline Y., et al., "The Percutaneous Implantable Heart Valve," Progress in Pediatric Cardiology, Ireland, 2001, vol. 14, pp. 89-93.
Boudjemline Y., et al., "Transcatheter Reconstruction of the Right Heart," Cardiology in the Young, England, 2003, vol. 13, pp. 308-311.
Bruce C.J., et al., "Right-sided Valve Disease Deserves Little More Respect," Circulation, 119(2):2726-2734 (May 2009).

(56) References Cited

OTHER PUBLICATIONS

Coats L., et al., "The Potential Impact of Percutaneous Pulmonary Valve Stent Implantation on Right Ventricular Outflow Tract Re-Intervention," European Journal of Cardio-Thoracic Surgery, England, Apr. 2005, vol. 27, pp. 536-543.
Commeau P et al., "Percutaneous Balloon Dilatation of calcific aortic Valve Stenosis: Anatomical and Haemodynamic Evaluation," British Heart Journal, 59:227-238 (Feb. 1988).
Cribier A., et al., "Percutaneous Transcatheter Implantation of an Aortic Valve Prosthesis for Calcific Aortic Stenosis: First Human Case Description," Circulation, 2002, vol. 10 6, pp. 3006-3008.
Cribier et al., "Early Experience with Percutaneous Transcatheter Implantation of Heart Valve Prosthesis for the Treatment of End-Stage Inoperable Patients with Calcific Aortic Stenosis", J. of Am. Coll. of Cardio, Feb. 18, 2004, 43(4), pp. 698-703.
Cribier et al., "Percutaneous Transluminal Valvuloplasty of Acquired Aortic Stenosis in Elderly Patients: An Alternative to Valve Replacement?", The Lancet, Jan. 11, 1986, pp. 63-67.
Cunanan et al., "Tissue Characterization and Calcification Potential of Commercial Bioprosthetic Heart Valves." Ann. Thorac. Surg., May 15, 2001, pp. S417-S421.
Cunliffe et al., "Glutaraldehyde Inactivation of Exotic Animal Viruses in Swine Heart Tissue," Applied and Environmental Microbiology, Greenport, New York, vol. 37, No. 5, May 1979, pp. 1044-1046.
Dake et al., "Transluminal Placement of Endovascular Stent-Grafts for the Treatment of Descending Thoracic Aortic Aneurysms." New Engl. J. of Med., 331 (26):1729-34 (Dec. 1994).
Dalby et al., "Non-Surgical Aortic Valve Replacement" Br. J. Cardiol., 10(6):450-452 (Nov. 2003).
Davidson M.J., et al., "Percutaneous Therapies for Valvular Heart Disease," Cardiovascular Pathology, Jan. 2006, vol. 15, pp. 123-129.
Dewey et al., "Transapical aortic valve implantation: An Animal Feasibility Study", The annals of thoracic surgery, 82:110-116 (Feb. 2006).
Dhasmana et al., "Factors Associated With Periprosthetic Leakage Following Primary Mitral Valve Replacement: With Special Consideration of Suture Technique." Annals of Thorac. Surg., (Feb. 1983), 35(2), pp. 170-178.
Dotter, "Transluminally-Placed Coilspring Endarterial Tube Grafts," Investigative Radiology, pp. 329-332 (Oct. 1969).
Emery et al., "Replacement of the Aortic Valve in Patients Under 50 Years of Age: Long-Term Follow-Up of the St. Jude Medical Prosthesis." Ann. Thorac. Surg., 75:1815-1819 (Jun. 2003).
European Search Report dated Aug. 10, 2011 for EP Application No. 06824992.9.
European Search Report for EP Patent Appl. Serial No. 12179049.7 (1257), dated Oct. 30, 2012, 4 pages.
European Search Report for EP Patent Appl. Serial No. 12179075.2 (1257), dated Oct. 29, 2012, 3 pages.
European Search Report for EP Patent Appl. Serial No. 12179141.2 (1257), dated Nov. 2, 2012, 3 pages.
European Search Report for EP Patent Appl. Serial No. 12179146.1 (1257), dated Nov. 7, 2012, 8 pages.
European Search Report for EP Patent Appl. Serial No. 12179330.1 (1257), dated Nov. 22, 2012, 3 pages.
European Search Report for EP Patent Appl. Serial No. 12179338.4 (1257), dated Nov. 2, 2012, 3 pages.
European Search Report for EP Patent Appl. Serial No. 12179339.2 (1257), dated Oct. 29, 2012, 4 pages.
European Search Report for EP Patent Appl. Serial No. 12179914.2 (1257), dated Nov. 7, 2012, 6 pages.
European Search Report for EP Patent Appl. Serial No. 13150337.7 (1257), dated Jul. 9, 2013, 3 pages.
European Search Report for EP Patent Appl. Serial No. 13183134.9 (1651), dated Nov. 19, 2013, 3 pages.
European Search Report for EP Patent Appl. Serial No. 14159630.4 (1651), dated May 22, 2014, 3 pages.
European Search Report for EP Patent Appl. Serial No. 14161991.6 (1651), dated Jun. 3, 2014, 3 pages.
European Search Report for EP Patent Appl. Serial No. 15167832.3 (1651), dated Jul. 23, 2015, 3 pages.
European Search Report for EP Patent Appl. Serial No. 15167847.1 (1651), dated Jul. 23, 2015, 3 pages.
European Search Report for EP Patent Appl. Serial No. 17196833.2, dated Mar. 6, 2018, 4 pages.
European Search Report for EP Patent Appl. Serial No. 18164490.7, dated Sep. 17, 2018 5 pages.
European Search Report from EP Patent Office for EP Application No. 15177718.2, dated Jan. 18, 2016, 4 pages.
European Search Report from EP Patent Office for EP Application No. 15177731.5, dated Apr. 14, 2016, 4 pages.
European Search Report from EP Patent Office for EP Application No. 16151726.3, dated Feb. 25, 2016, 4 pages.
Extended European Search Report dated Apr. 11, 2008 in EP Patent Appl. Serial No. 081630410, 5 pages.
Extended EP Search Report dated Sep. 24, 2020 in EP Patent Appl. Serial No. 20165841.6 (JVT-0280).
Extended European Search Report for Application No. 10183946.2.4-2320 dated Feb. 14, 2012, 7 pages.
Extended European Search Report dated Aug. 9, 2018 in EP Patent Appl. Serial No. 18158901.1 (1113).
Extended European Search Report dated Jun. 12, 2018 in EP Patent Appl. Serial No. 17209326.2 (1113).
Extended European Search Report dated May 16, 2012 in EP Patent Appl. Serial No. 11178135.7 (1257).
Extended European Search Report for Application No. 11178076.3-1257 dated Feb. 29, 2012, 5 pages.
Extended European Search Report from EP Patent Office for EP Application No. 17162616.1, dated Jul. 27, 2017, 7 pages.
Extended European Search Report dated Apr. 9, 2014 in EP Patent Appl. Serial No. 14164683.6.
Extended European Search Report dated May 9, 2013 in EP Patent Appl. Serial No. 130178309.4, 4 pages.
Extended European Search Report dated Aug. 19, 2011 in EP Patent Appl. Serial No. 07827132.7.
Extended European Search Report dated Feb. 27, 2017 in EP Patent Appl. Serial No. 16186773, 6 pages.
Extended European Search Report dated Sep. 29, 2014 in EP Patent Appl. U.S. Appl. No. 14/164,680, 5 pages.
Extended European Search Report for Application No. 07116242.4-2310 dated Mar. 31, 2008, 10 pages.
Extended European Search Report for Application No. 09154935.2, dated May 29, 2009, 7 pages.
Extended European Search Report for Application No. 10012198.7 dated Mar. 23, 2011, 7 pages.
Extended European Search Report for Application No. 10168525.3-1257 dated Feb. 3, 2011, 13 pages.
Extended European Search Report for Application No. 11153142.2-1257 dated Aug. 3, 2011, 10 pages.
Extended European Search Report for Application No. 11165093.3-1257 dated Aug. 30, 2011, 6 pages.
Extended European Search Report for Application No. 11178073.0-1257 dated Oct. 14, 2011, 5 pages.
Extended European Search Report for Application No. 11178145.6-1257 dated Feb. 29, 2012, 5 pages.
Extended European Search Report for Application No. 13188858.8-1651 dated Jan. 13, 2014, 6 pages.
Extended European Search Report for EP Patent Appl. Serial No. 19195062 dated Jan. 2, 2020, 7 pages.
Extended European Search Report for EP Patent Appl. Serial No. 06827630.2 dated Jun. 7, 2010, 5 pages.
Extended European Search Report for EP Patent Appl. Serial No. 07110318.8, dated May 29, 2008, 10 pages.
Extended European Search Report for EP Patent Appl. Serial No. 10163478.0, dated Mar. 22, 2011, 9 pages.
Extended European Search Report for EP Patent Appl. Serial No. 10184842.2, dated Mar. 23, 2011, 7 pages.
Extended European Search Report for EP Patent Appl. Serial No. 11162971.3, dated Jun. 30, 2011, 5 pages.

(56) References Cited

OTHER PUBLICATIONS

Extended European Search Report for EP Patent Appl. Serial No. 13163918.9, dated Jul. 24, 2013, 8 pages.
Extended European Search Report for EP Patent Appl. Serial No. 14179639.1, dated Mar. 9, 2015, 7 pages.
Extended European Search Report for EP Patent Appl. Serial No. 16201320.5, dated May 19, 2017, 6 pages.
Extended European Search Report for EP Patent Appl. Serial No. 18200191.7, dated May 6, 2019, 8 pages.
Ferrari, "Entwicklung eines Verfahrens zum transvaskularen Aortenklappenersatz," Habilitationsschrift, Medizinische Fakultat der Friedrich-Schiller-Universitat Jena, Sep. 2003, pp. 1-159. (With English Translation).
Ferrari, "Entwicklung eines Verfahrens zum transvaskulären Aortenklappenersatz," Habilitationsschrift, Medizinische Fakultát der Friedrich-Schiller-Universitát Jena, Sep. 2003, pp. 49-52. (With English Translation).
Ferrari M.W., "Transarterial Aortic Valve Replacement with a Self Expanding Stent in Pigs," Heart, vol. 90, No. 11, doi:10.1136/hrt.2003.028951, ISSN 1355-6037, XP055137208, Nov. 2004, pp. 1326-1331.
Filsoufi F., et al., "Long-term Outcomes of Tricuspid Valve Replacement in the Current Era," Ann. Thorac. Surg., 8(3):845-850 (Sep. 2005).
Fluency Vascular Stent Graft Instructions for Use, May 2014, 20 pages.
Greeenberg, "Abdominal Aortic Endografting: Fixation and Sealing." J. Am. Coll. Surg., 194(1):S79-S87 (Jan. 2002).
Grossi A.E. et al., "Impact of Minimally Invasive Valvular Heart Surgery: A Case-Control Study", Ann. Thorac. Surg., 71:807-810 (Mar. 2001).
Hanzel G.S., et al., "Complications of Percutaneous Aortic Valve Replacement: Experience with the Cribier-Edwards TM Percutaneous Heart Valve," EuroIntervention Supplements, 2006, vol. 1(A), pp. A3-A8.
Heinrich R.S., et al., "Experimental analysis of fluid mechanical energy losses in aortic valve stenosis: importance of pressure recovery", Ann Biomed Eng., Nov.-Dec. 1996, vol. 24(6), pp. 685-694.
Hijazi Z.M., "Transcatheter Valve Replacement: A New Era of Percutaneous Cardiac Intervention Begins", J. of Am. College of Cardio., Nov. 6, 2004, vol. 43, No. 6, pp. 1088-1089.
Hourihan M., et al., "Transcatheter Umbrella Closure of Valvular and Paravalvular Leaks", JACC, Boston, Massachusetts, 20(6):1371-1377 (Nov. 1992).
Huber C.H., et al., "Direct-Access Valve Replacement: A Novel Approach for Off-Pump Valve Implantation Using Valved Stents," Journal of the American College of Cardiology, Jul. 19, 2005, vol. 46(2), pp. 366-370.
Huber C.H., et al., "Do Valved Stents Compromise Coronary Flow?," European Journal of Cardio-thoracic Surgery, Jan. 23, 2004, vol. 25, pp. 754-759.
Ing F., "Stents: What's Available to the Pediatric Interventional Cardiologist?" Catheterization and Cardiovascular Interventions, 57:374-386 (Jun. 2002).
International Search Report dated Dec. 29, 2003 in Intl PCT Patent Appl. U.S. Appl. No. PCT/DE2003/002669.
International Search Report and Written Opinion for PCT Application No. PCT/EP2009/052230 dated Jun. 29, 2009, 12 pages.
International Search Report and Written Opinion for PCT Application No. PCT/EP2010/052429 dated Jun. 14, 2010, 12 pages.
International Search Report and Written Opinion for PCT Application No. PCT/EP2011/002524 dated Apr. 23, 2012, 15 pages.
International Search Report and Written Opinion for PCT Application No. PCT/EP2011/052674 dated Jul. 5, 2011, 12 pages.
International Search Report for PCT Application No. PCT/US1999/020736 dated Jan. 28, 2000, 3 pages.
International Search Report and Written Opinion for PCT Application No. PCT/EP2009/050762 dated Jun. 23, 2009, 12 pages.
International Search Report & Written Opinion dated Jul. 18, 2016 for PCT Patent Appl No. PCT/EP2016/059839, 10 pages.
International Search Report and Written Opinion for Appl. No. PCT/EP2016/055783, dated May 30, 2016, 15 pages.
International Search Report and Written Opinion for Application No. PCT/EP2013/057431 dated Jul. 26, 2013, 9 pages.
International Search Report and Written Opinion for Application No. PCT/IB2018/050438 dated Apr. 12, 2018, 11 pages.
International Search Report and Written Opinion for International Application No. PCT/EP2010/063306, dated Nov. 17, 2010, 9 pages.
International Search Report and Written Opinion for PCT Application No. PCT/EP2006/010519 dated Mar. 1, 2007, 13 pages.
International Search Report and Written Opinion for PCT Application No. PCT/US06/36286 dated Jul. 9, 2007, 4 pages.
International Search Report and Written Opinion for PCT Application No. PCT/US2004/041513 dated Jun. 10, 2005, 4 pages.
International Search Report and Written Opinion for PCT Application No. PCT/US2004/043607 dated Mar. 20, 2006, 4 pages.
International Search Report and Written Opinion for PCT Application No. PCT/US2005/020947 dated Oct. 6, 2005, 5 pages.
International Search Report and Written Opinion for PCT Application No. PCT/US2006/038352 dated May 19, 2008, 4 pages.
International Search Report and Written Opinion for PCT Application No. PCT/US2006/043484 dated Jun. 25, 2008, 4 pages.
International Search Report and Written Opinion for PCT Application No. PCT/US2007/003992 dated Jan. 10, 2008, 5 pages.
International Search Report and Written Opinion for PCT Application No. PCT/US2007/02970 dated Oct. 19, 2007, 7 pages.
International Search Report and Written Opinion for PCT Application No. PCT/US2009/060531 dated May 13, 2010, 6 pages.
International Search Report and Written Opinion for PCT/DE2006/000056 dated Jun. 7, 2006, 11 pages.
International Search Report and Written Opinion for PCT/EP2007/061117 dated May 20, 2008, 16 pages.
International Search Report and Written Opinion for PCT/EP2008/003803 dated Aug. 20, 2008, 10 pages.
International Search Report and Written Opinion for PCT/EP2009/055958 dated Oct. 21, 2009, 8 pages.
International Search Report and Written Opinion for PCT/EP2010/056558 dated Oct. 7, 2010, 14 pages.
International Search Report and Written Opinion for PCT/EP2012/067617 dated Dec. 19, 2012, 10 pages.
International Search Report and Written Opinion for PCT/IL2007/001149 dated May 1, 2008, 4 pages.
International Search Report and Written Opinion for PCT/US2011/027730 dated May 25, 2011, 9 pages.
International Search Report and Written Opinion of the International Search Authority for International Application No. PCT/EP2008/064558, date of completion of report is Mar. 18, 2009, 14 pages.
International Search Report dated Jan. 28, 2008 in Int'l PCT Application Serial No. PCT/EP2007/007413, 4 pages.
International Search Report dated Jul. 7, 2015 in Int'l PCT Application Serial No. PCT/EP2014/065817, 6 pages.
International Search Report dated Nov. 3, 2011 in Int'l PCT Application Serial No. PCT/EP2011/058506, 4 pages.
International Search Report dated Dec. 18, 2012 in Int'l PCT Patent Application Serial No. PCT/EP2012/067714, 3 pages.
International Search Report for Application No. PCT/DE2001/000837, dated Aug. 7, 2001, 4 pages.
International Search Report for Application No. PCT/EP2006/012455, dated Sep. 27, 2007, 5 pages.
International Search Report for Application No. PCT/EP2010/057798, dated Sep. 12, 2010, 6 pages.
International Search Report for Application No. PCT/EP2011/066677, dated Feb. 17, 2012, 7 pages.
International Search Report for Application No. PCT/EP2012/067617 dated Dec. 19, 2012, 3 pages.
International Search Report for Application No. PCT/EP2013/073318, dated Apr. 17, 2014, 5 pages.
International Search Report for Application No. PCT/EP2016/055783, dated May 30, 2016, 5 pages.

(56) References Cited

OTHER PUBLICATIONS

International Search Report for Application No. PCT/EP2016/058532, dated Jul. 11, 2016, 4 pages.
International Search Report for Application No. PCT/IB2008/002180, dated Apr. 15, 2009, 7 pages.
International Search Report for Application No. PCT/IB2018/050438 dated Apr. 12, 2018, 3 pages.
International Search Report for PCT/DE2001/000836 dated Jun. 13, 2001, 6 pages.
International Search Report for PCT/EP2006/010023 dated Mar. 30, 2007, 6 pages.
International Search Report for PCT/IB2017/052718, dated Sep. 5, 2017, 4 pages.
Kato et al., "Traumatic Thoracic Aortic Aneurysm: Treatment with Endovascular Stent-Grafts." Radiol., 205:657-662 (Dec. 1997).
Khambadkone S., et al., "Nonsurgical Pulmonary Valve Replacement: Why, When, and How?," Catheterization and Cardiovascular Interventions, United States, Jul. 2004, vol. 62, pp. 401-408.
Khambadkone S., et al., "Percutaneous Implantation of Pulmonary Valves," Expert Review of Cardiovascular Therapy (England), Nov. 2003, vol. 1(4), pp. 541-548.
Khambadkone S., et al., "Percutaneous Pulmonary Valve Implantation: Early and Medium Term Results," Circulation, Oct. 28, 2003, vol. 108(17), p. IV-375.
Knudsen et al., "Catheter-implanted prosthetic heart valves", Intl J. of Art. Organs, 16(5): 253-262, May 1993.
Kort et al., "Minimally Invasive Aortic Valve Replacement: Echocardiographic and Clinical Results." Am. Heart J., Sep. 2001, vol. 142(3), pp. 476-481.
Kuzela L., et al., "Experimental evaluation of direct transventricular revascularization," Journal of Thoracic and Cardiovascular Surgery, 57(6):770-773 (Jun. 1969).
Laborde et al., "Percutaneous Implantation of the Corevalve Aortic Valve Prosthesis for Patients Presenting High Risk for Surgical Valve Replacement," EuroIntervention, 1(4):472-474 (Feb. 2006).
Lawrence et al., "Percutaneous Endovascular Graft: Experimental Evaluation", Radiology, May 1987, vol. 163(2), pp. 357-360.
Levi et al., "Future of Interventional Cardiology in Pediactrics." Current Opinion in Cardiol., 18:79-90 (Mar. 2003).
Levy, "Mycobacterium chelonei Infection of Porcine Heart Valves." The New England Journal of Medicine, Washington DC, 297(12), Sep. 22, 1977, pp. 667-668.
Lichtenstein et al., "Transapical Transcatheter Aortic Valve Implantation in Humans: Initial Clinical Experience", circulation, American Heart Association vol. 114, Jul. 31, 2006, pp. 591-596.
Lichtenstein, S.V., "Closed heart surgery: Back to the future" The Journal of Thoracic and Cardiovascular Surgery, vol. 131(5), May 2006, pp. 941-943.
Liu et al., "Effect of Fiber Orientation on the Stress Distribution within a Leaflet of a Polymer Composite Heart Valve in be Closed Position", Journal of Biomechanics, 4:1099-1106 (Jan. 2007).
Ionescu et al., "Prevalence and Clinical Significance of Incidental Paraprosthetic Valvar Regurgitation: A prospective study using transesophageal echocardiography." Heart, 89:1316-21 (Oct. 2003).
Love S.C. et al., The Autogenous Tissue Heart Valve: Current Status, Journal of Cardiac Surgery, , Mar. 1991, vol. 6(4), pp. 499-507.
Lutter G., et al., "Percutaneous Aortic Valve Replacement: An Experimental Study. I. Studies on Implantation," Journal of Thoracic and Cardiovascular Surgery, Apr. 2002, vol. 123(4), pp. 768-776.
Lutter G., et al., "Percutaneous Valve Replacement: Current State and Future Prospects," Annals of Thoracic Surgery, Netherlands, Dec. 2004, vol. 78, pp. 2199-2206.
Mack, M.J., "Minimally invasive cardiac surgery", Surg Endosc, 20:S488-S492 (Mar. 2006).
Magovern et al., "Twenty-five-Year Review of the Magovern-Cromie Sutureless Aortic Valve", Ann. Thorac. Surg., 48:S33-S334 (Jan. 1989).
Maraj et al., Evaluation of Hemolysis in Patients with Prosthetic Heart Valves, Clin. Cardiol. 21:387-392 (Jun. 1998).
Marcus RH et al., "Assessment of small-diameter aortic mechanical prostheses: physiological relevance of the Doppler gradient, utility of flow augmentation, and limitations of orifice area estimation," Circulation, 98(9):866-872 (Sep. 1998).
Mckay G. R. et al., "The Mansfield Scientific Aortic Valvuloplasty Registry: Overview of Acute Hemodynamic Results and Procedural Complications." J. Am. Coll. Cardiol., 17(2):485-491 (Feb. 1991).
Mills N.L., et al., "Valvulotomy of valves in the saphenous vein graft before coronary artery bypass," The Journal of Thoracic and Cardiovascular Surgery, 71(6):878-879 (Jun. 1976).
Mirich et al., "Percutaneously Placed Endovascular Grafts for Aortic Aneurysms: Feasibility Study", Radiology, 170:1033-1037 (Mar. 1989).
Moazami N et al. "Transluminal Aortic Valve Placement: a Fesibility Study with a Newly Designed Collapsible Aortic Valve", ASAIO Journal, vol. 42, No. 2, Mar.-Apr. 1996.
Moulopoulos et al., "Catheter-Mounted Aortic Valves," Annals of Thoracic Surg., vol. 11, No. 5, May 1971, pp. 423-430.
Munro I., et al., "The possibility of myocardial revascularization by creation of a left ventriculocoronary artery fistula," The Journal of Thoracic and Cardiovascular Surgery, 58(1):25-32 (Jul. 1969).
Nath J., et al., Impact of Tricuspid Regurgitation on Long-term Survival, Journal of the American College of Cardiology, 43(3):405-406 (Feb. 2004).
Nietlispach F., et al., "Current Balloon-Expandable Transcatheter Heart Valve and Delivery Systems", Catheterization and Cardiovascular Interventions, 75:295-300 (Sep. 2009).
Palacios I.F., "Percutaneous Valve Replacement and Repair: Fiction or Reality?," Journal of American College of Cardiology, Oct. 2004, vol. 44(8), pp. 1662-1663.
Palmaz J.C., et al., "Expandable Intrahepatic Portacaval Shunt Stents: Early Experience in the Dog," American Journal of Roentgenology, 145 (4):821-825 (Oct. 1985).
Palmaz J.C., et al., "Expandable Intrahepatic Portacaval Shunt Stents in Dogs with Chronic Portal Hypertension," American Journal of Roentgenology, 147(6):1251-1254 (Dec. 1986).
Paniagua et al., "Percutaneous Heart Valve in the Chronic in Vitro Testing Model." Circulation, Sep. 17, 2002, vol. 106: e51-e52.
Parodi J.C., et al., "Transfemoral Intraluminal Graft Implantation for Abdominal Aortic Aneurysms", Ann. Vasc. Surg., 5(6):491-499 (Nov. 1991).
Partial European Search Report dated Feb. 28, 2012 in EP Patent Appl. Serial No. 11178135.7 (1257).
Partial European Search Report for Application No. 10168525.3-1269 dated Sep. 20, 2010, 5 pages.
Partial European Search Report for Application No. 07116242.4-2310 dated Jan. 14, 2008, 5 pages.
Partial European Search Report for Application No. 11153142.2-1257 dated Apr. 4, 2011, 5 pages.
Partial European Search Report for EP Patent Appl. Serial No. 07110318.8, dated Mar. 10, 2008, 6 pages.
Partial European Search Report for EP Patent Appl. Serial No. 10163478.0, dated Nov. 2, 2010, 6 pages.
Partial International Search Report for International Application No. PCT/EP2014/055044, filed Mar. 13, 2014, 7 pages.
Pavcnik D., et al., "Aortic and Venous Valve for Percutaneous Insertion," Minimally Invasive Therapy & Allied Technologies, Jan. 2000, vol. 9(3/4), pp. 287-292.
Pavcnik D., et al., "Development and Initial Experimental Evaluation of a Prosthetic Aortic Valve for Transcatheter Placement." Radiology, 183:151-154 (Apr. 1992).
Pavcnik et al., "Percutaneous Bioprosthetic Venous Valve: A Long-term Study in Sheep," Jounal of Vascular Surg., vol. 35, No. 3, Mar. 2002, pp. 598-603.
Pawelec-Wojtalk M., "Closure of left ventricle perforation with the use of muscular VSD occluder," European Journal of Cardia-Thoracic Surgery, 27(4):714-716 (Apr. 2005).
Pelton A.R., et al., "Medical Uses of Nitinol," Materials Science Forum, Jan. 2000, vol. 327-328, pp. 63-70.

(56) References Cited

OTHER PUBLICATIONS

Phillips et al., "A Temporary Catheter-Tip Aortic Valve: Hemodynamic Effects on Experimental Acute Aortic Insufficiency", Annals of Thoracic Surg., Feb. 1976, 21(2), pp. 134-136.
Phillips S.J., et al., "Improvement in Forward Coronary Blood Flow by Using a Reversed Saphenous Vein with a Competent Valve," The Annals of Thoracic Surgery, vol. 21 (1), Jan. 1976, pp. 12-15.
Preliminary Search Report (Rapport De Recherche Preliminaire) dated Jul. 8, 2002 in French Patent Application No. 0110444 (2 pages).
Raillat et al., "Treatment of Iliac Artery Stenosis with the Wallstent Endoprosthesis." AJR, Mar. 1990, vol. 154(3), pp. 613-616.
Remadi et al., "Preliminary results of 130 aortic valve replacements with a new mechanical bileaflet prosthesis: The Edwards MIRA valve," Interactive Cardiovasc. and Thorac. Surg., 2:80-83 (Mar. 2003).
Rogers J.H., et al., "The Tricuspid Valve: Current Perspective and Evolving Management of Tricuspid Regurgitation," Circulation, 119(20):2718-2725 (May 2009).
Ruiz C.E., "Transcatheter Aortic Valve Implantation and Mitral Valve Repair: State of the Art," Pediatric Cardiology, Jun. 2005, vol. 26(3), pp. 289-294.
Saliba Z., et al., "Treatment of Obstructions of Prosthetic Conduits by Percutaneous Implantation of Stents," Archives Des Maladies Du Coeur Et Des Vaisseaux, May 1999, pp. 591-596.
Schurink et al., "Stent Attachment Site-related Endoleakage after Stent Graft Treatment: An in vitro study of the effects of graft size, stent type, and atherosclerotic wall changes", J. Vasc. Surg., vol. 30(4), Oct. 1999, pp. 658-667.
Search Report dated Oct. 15, 2003 from the European Patent Office for European Patent Application No. EP 02291953.4, 2 pages.
Search Report from the European Patent Office for European Patent Application No. EP 02291954.4, 4 pages.
Sochman et al., "Percutaneous Transcatheter Aortic Disc Valve Prosthesis Implantation: A Feasibility Study." Cardiovasc. Intervent. Radiol., Sep. 2000, 23: 384-388.
Stanley et al., "Evaluation of Patient Selection Guidelines for Endoluminal AAA Repair With the Zenith Stent Graft: The Australasian Experience." J. Endovasc. Ther., 8:457-464 (Oct. 2001).
Stassano P., et al., "Mid-term Results of the Valve-on-Valve Technique for Bioprosthetic Failure," European Journal of Cardiothoracic Surgery, Oct. 2000, vol. 18, pp. 453-457.
Stein D.P., et al., "Turbulent blood flow in the ascending aorta of humans with normal and diseased aortic valves", Circulation Research by American Heart Association, 39:58-65 (Jul. 1976).
Steinhoff et al., "Tissue Engineering of Pulmonary Heart Valves on Allogenic Acellular Matrix Conduits." Circulation102 [suppl. III], pp. III-50-III-55 (Nov. 2000).
Supplemental Search Report from EP Patent Office for EP Application No. 04813777.2, dated Aug. 19, 2011.
Supplemental Search Report from EP Patent Office for EP Application No. 04815634.3, dated Aug. 19, 2011.
Supplemental Search Report from EP Patent Office for EP Application No. 05758878.2, dated Oct. 24, 2011.
Supplementary European Search Report dated Jan. 2, 2012 in EP Patent Appl. Serial No. 09820051.2.
Thompson et al., "Endoluminal stent grafting of the thoracic aorta: Initial experience with the Gore Excluder," Journal of Vascular Surgery, Jun. 2002, pp. 1163-1170.
Topol, Eric., Textbook of Interventional Cardiology, 4th Ed; Chapter 24: "Endovascular Options For Peripheral Arterial Occlusive and Aneurysmal Disease," Saunders, pp. 499-503, 949-953 (Dec. 2003).
Triennial Review of the National Nanotechnology Initiative: "A Matter of Size", The National Academies Press, Washington DC, V-13, Retrieved from the Internet: URL: http://www.nap.edu/catalog/11752/a-matter-of-size-triennial-review-of-the-national-nanotechnology, 200 pages (Mar. 2006) (Parts 1-5).
Vahanian et al., "Percutaneous Approaches to Valvular Disease", Circulation, Apr. 6, 2004, 109: 1572-1579.
Van Herwerden et al., "Percutaneous Valve Implantation: Back to the Future?", Euro. Heart J., Sep. 2002, 23(18): 1415-1416.
Walther et al., "Transapical approach for sutureless stent-fixed aortic valve implantation: experimental results", European Journal of Cardio-thoracic Surgery 29, 703-708 (May 2006).
Webb J.G., et al., "Percutaneous Aortic Valve Implantation Retrograde from the Femoral Artery," Circulation, American Heart Association, Feb. 14, 2006, vol. 113, pp. 842-850.
Weerasinghe A., et al., "First Redo Heart Valve Replacement: A 10-Year Analysis," Circulation, 99(5):655-658 (Feb. 1999).
Weyman AB et al., "Aortic Stenosis: Physics and Physiology—What Do the Numbers Really Mean?", Rev Cardiovasc Med., 6(1):23-32 (Jan. 2005).
White et al., "Endoleak as a Complication of Endoluminal Grafting of Abdominal Aortic Aneurysms: Classification, Incidence, Diagnosis, and Management," J. Endovasc. Surg., 4:152-168 (May 1997).
Written Opinion dated Mar. 30, 2007 in Int'l PCT Application Serial No. PCT/EP2006/010023, 10 Pages.
Written Opinion dated Sep. 27, 2007 in Int'l Application No. PCT/EP2006/012455, 11 pages.
Written Opinion for Application No. PCT/EP2007/007413, dated Jan. 28, 2008, 5 pages.
Written Opinion for Application No. PCT/EP2011/058506, dated Nov. 3, 2011, 5 pages.
Written Opinion for Application No. PCT/EP2014/065817, dated Jan. 7, 2015, 7 pages.
Written Opinion for PCT/EP2012/067714 dated Dec. 18, 2012, 5 Pages.
Yonga G.O., et al., "Percutaneous Transvenous Mitral Commissurotomy in Juvenile Mitral Stenosis", East African Medical Journal, 80(4):172-174 (Apr. 2003).
Yoshioka et al., "Self-Expanding Endovascular Graft: An Experimental Study in Dogs." AJR 151, Oct. 1988, pp. 673-676.

MEDICAL DEVICE FOR TREATING A HEART VALVE INSUFFICIENCY

This application is a continuation of U.S. application Ser. No. 15/889,959, filed on Feb. 6, 2018, which is a continuation of U.S. application Ser. No. 15/098,410, filed on Apr. 14, 2016, now U.S. Pat. No. 9,918,835, which is a continuation of U.S. application Ser. No. 14/174,441, filed on Feb. 6, 2014, now U.S. Pat. No. 9,339,386, which is a continuation of U.S. application Ser. No. 13/030,708, filed on Feb. 18, 2011, now U.S. Pat. No. 8,685,085, which is a continuation of U.S. application Ser. No. 12/572,340, filed on Oct. 2, 2009, now U.S. Pat. No. 7,914,575, which is a divisional of U.S. application Ser. No. 11/785,072, filed on Apr. 13, 2007, now U.S. Pat. No. 7,896,915, each of which is incorporated by reference herein in its entirety.

This invention relates to a medical device for treating a heart valve insufficiency, with an endoprosthesis which can be introduced into a patient's body with minimal invasion and automatically expanded in order to position and secure a heart valve prosthesis in the patient's aorta, which endoprosthesis has at least three positioning arches for automatically positioning the medical device in the patient's aorta and a retaining segment with retaining arches for accommodating a heart valve prosthesis, and the endoprosthesis assumes a first pre definable mode during the process of introducing it into the patient's body and a second pre-definable mode in the state when the medical device is implanted, and when the medical device is in a collapsed state when the endoprosthesis is in the first mode and in an expanded state when the endoprosthesis is in the second mode.

The operating principle of such a device is known from medical technology. Biological or mechanical valve models am currently available as a means of replacing human heart valves, which are securely stitched in the heart valve base through an opening in the thorax during surgery once the diseased heart valve has been removed. In order to undertake this intervention, the patient's circulation must be supported by a heart and lung machine and the heart is arrested whilst the heart valve prosthesis is being implanted. This is a risky surgical intervention which places the patient at risk accordingly and which involves a long post-operative phase of treatment. In multi-morbid patients in particular, the risk of carrying out such intervention is no longer justifiable.

In more recent times, treatment methods which are minimally invasive have been developed, which are distinctive due to the fact that the intervention can be carried out with a local anaesthetic. This option is based on the use of a self-expanding stent with a collapsible heart valve prosthesis, which is implanted in the human body by means of an appropriate catheter system. A self-expanding heart valve prosthesis of this type can be fed by means of a catheter system through a main artery or vein to the implantation site at the heart. Once the implantation site is reached, the stent, which is made up of several self-expanding gent segments which can be angled relative to one another, is successively unfolded. Once unfolded, the heart valve prosthesis can be anchored in the respective blood vessel at least in the vicinity of the heart with the assistance of anchoring hooks for example. The actual heart valve prosthesis is then disposed directly in the proximal region of the stent or endoprosthesis.

Patent publication DE 100 10 074 A1, for example, discloses a device for securing and anchoring heart valve prostheses, which essentially comprises shaped wire elements connected to one another. In this instance, different arches are used as a means of reliably securing and anchoring the heart valve prosthesis. To this end, the device described in this specification has three identical pairs of arches respectively disposed at a distance of 120° apart. These arches are connected to one another by fixed body joints, and the fixed body joints assume the function of pivot bearings. Arches bent in the opposite direction are also provided, which form lever arms which are of identical length as far as possible, to enable a reliable seating of the arches, even in the event of peristaltic movements of the heart and blood vessel, and afford a reliable seal for an implanted and secured heart valve prosthesis.

With the known solution, however, there is still a risk of heart valves being incorrectly implanted. In particular, this is attributable to the fact that the heart valve prosthesis must be exactly positioned and longitudinally oriented. In particular, it requires enormous skill on the part of the surgeon performing the treatment—if it is possible at all—to position a stent which has a heart valve prosthesis at its proximal end and to do so accurately enough in the vicinity of the patient's diseased heart valve to ensure both correct lateral positioning accuracy and a correct longitudinal position of the heart valve prosthesis as far as possible.

Amongst other things, incorrect implantation of a heart valve prosthesis that is not optimally positioned can lead to inadequate sealing or valve insufficiency, which places considerable stress on the ventricle. If a heart valve prosthesis is implanted too far above the actual heart valve plane, for example, this can cause the outlets of the coronary vessels (coronaries) to close, thus leading to fatal coronary ischaemia due to heart infarction. This being the case, it is absolutely vital that both the lateral positioning accuracy and longitudinal positioning accuracy of a heart valve prosthesis meet requirements.

In the case of conventional implantation techniques whereby self-expandable heart valve prostheses are fed to the implantation site at the heart through a main artery of the patient requiring minimal invasion, for example, the prosthesis is usually introduced by means of a guide wire and with the aid of catheters, in which case it is standard practice to use a balloon catheter for this intervention. Although it is possible to monitor and control the introduction process during such an intervention, for example with the aid of an X-ray system (heart catheter laboratory=HCL) or with the aid of ultrasound (trans-oesophageal echocardiogram=TEE), the heart valve prosthesis is still of relatively large dimensions in spite of being collapsed whilst it is being introduced and it is often not possible to obtain the required positioning accuracy due to restricted ability to manoeuvre, and in particular to ensure correct longitudinal positioning of the heart valve prosthesis to be implanted with the fixing elements attached to it accordingly. Especially if there is a risk that the coronary vessels might close, implanting the heart valve prosthesis in a position angularly offset from the optimum implantation site represents a particular risk for the patient.

When designing a heart valve prosthesis, allowance must specifically be made for the considerable forces which act on the prosthesis, including during the filling phase of the heart cycle (diastole), and reliable anchoring is necessary in order to prevent the implanted heart valve prosthesis from becoming detached.

Accordingly, it must be possible to manoeuvre the heart valve prosthesis in the relevant access vessel as efficiently as possible during the implantation process in order to ensure optimum positioning accuracy on the one hand, and on the other hand, the implanted heart valve prosthesis must be firmly anchored at the implantation site in order effectively to prevent the prosthesis from shifting subsequently.

The underlying problem addressed by this invention is the fact that known devices used for the transvascular implantation of heart valve prostheses are often not suitable for implanting a heart valve prosthesis easily to the required degree of positioning accuracy. Furthermore, until now, it has only been possible to correct an incorrectly positioned heart valve prosthesis that has already been partially implanted with great difficulty—if at all.

Against this background, the objective of the invention is to improve a medical device for treating heart valve insufficiency of the type outlined above so that manoeuvring of the device is optimised during the implantation process on the one hand, and whilst achieving optimum positioning accuracy and anchoring of the implanted heart valve prosthesis on the other hand, thereby permitting a routine treatment of heart valve insufficiency without subjecting the patient to excessive stress.

This objective is achieved by means of a medical device oldie type outlined above due to the fact that the endoprosthesis of the medical device is of an integral structure cut from a metal tube, and every end portion of the positioning arch at the distal end of the endoprosthesis is joined to the terminal portion of the associated retaining arch.

Accordingly, a medical device is proposed which essentially comprises a self-expandable endoprosthesis (hereafter referred to simply as stent), and this stent has a valve-supporting retaining segment for accommodating a heart valve prosthesis. The stent design is distinctive due to the fact that at least three positioning arches are provided, which project radially outwards and are open when the endoprosthesis assumes the second pre-definable mode, in which the original (old) heart valves of the heart valve to be replaced engage, thereby resulting in an automatic fixing and positioning of the medical device as regards the axial rotation on the one hand and the horizontal position on the other hand.

Since the endoprosthesis (stent) of the medical device has an integral structure cut from a metal tube incorporating the positioning arches on the one hand and the retaining segment with the retaining arches on the other hand, the endoprosthesis and hence also the medical device can be made particularly inexpensively and in large numbers. Specifically, it would be conceivable to cut the stent structure from a metal tube by means of a laser, after which the structure is subjected to an appropriate shaping and heat treatment process so that the endoprosthesis and hence also the medical device can be transferred from the collapsed sate during implantation to the expanded state at the implantation site. This shaping and heat treatment process is advantageously operated in steps in order to prevent damage to the stent structure.

Since the endoprosthesis of the medical device is of an integral structure cut from a metal tube as proposed by the invention and a retaining arch is associated with every positioning arch and every end portion of the positioning arch at the distal end of the endoprosthesis is joined to the terminal portion of the associated retaining arch, them is no need to provide fixed body joints or similar connecting devices. On the other hand, the endoprosthesis of the medical device proposed by the invention is a stent which, on the one hand, offers a positioning function due to the positioning arches with a minimal longitudinal extension and, on the other hand, offers a function of retaining a heart valve prosthesis due to the retaining arches.

As will be seen, when transferring the endoprosthesis from the first pre-definable mode to the second pre-definable mode by widening the cross-section of the entire stent, the retaining arches on the one hand and the positioning arches on the other hand are opened out in the radial direction. The second mode of the endoprosthesis is advantageously selected so that as the retaining and positioning arches open up, they hit against the vessel wall of the aorta and form a positive connection with it, thereby anchoring the medical device firmly at the implantation site.

Due to the fact that the structure of the endoprosthesis imparts a particularly short shape to the medical device, the medical device is particularly easy to manoeuvre in the collapsed state, which is of particular advantage if the implantation route to the heart valve to be replaced leads through the arch of the aorta. The minimum length of the medical device is made possible in particular by the special structure of the endoprosthesis due to the fact that every end portion of the positioning arch at the distal end is joined to the end portion of the associated retaining arch, and both the positioning arch and the retaining arch extend to the proximal retaining region of the medical device or endoprosthesis. The retaining segment for accommodating the heart valve prosthesis therefore lies at the proximal retaining region of the endoprosthesis.

Advantageous embodiments of the medical device are specified in the dependent claims, especially as regards the endoprosthesis (stent).

In one particular embodiment of the endoprosthesis used with the medical device proposed by the invention, every positioning arch and its associated retaining arch is respectively of an essentially U-shaped or V-shaped structure, which is closed towards the proximal end of the endoprosthesis. By particular preference, every positioning arch is cut from the material blank of the metal tube which is accommodated by the essentially U-shaped or V-shaped structure of the associated retaining arch. In this preferred embodiment of the stent structure, therefore, the respective retaining arches of the retaining segment form the proximal retaining region of the endoprosthesis and the respective positioning arches are of a design symmetrical with the retaining arches but lie slightly in front of the distal retaining region of the medical device. The respective distal ends of the positioning arches are joined to the respective distal ends of the co-operating retaining arches in the distal retaining region of the medical device or endoprosthesis. When the medical device is in the expanded state, not only the proximal retaining region with the heart valve prosthesis fitted to it and the positioning arches disposed between the proximal and the distal retaining regions of the medical device open out, but also the joining points between the respective positioning arches and retaining arches at the distal end of the medical device, so that a radially acting force is also applied to the vessel wall via the distal retaining region of the medical device, which further assists anchoring of the medical device at the implantation site.

Since the medical device is in a (an expanded) state in which the distal and proximal retaining region as well as the positioning arches are radially opened out when the endoprosthesis assumes the second mode, the expanded medical device has as shorter length than it does in its collapsed state. To enable the length of the medical device in its expanded state to be set beforehand, it would be conceivable to connect the respective distal end portions of the positioning arches to the distal end portions of the associated retaining arches using a connecting web extending essentially in the longitudinal direction of the endoprosthesis rather than directly. The length of the medical device in the expanded state can therefore be adapted by selecting the length of this connecting web accordingly. However, it is preferable, especially with a view to ensuring good manoeuvrability of the medical device during the implantation process, i.e. when the endoprosthesis is in its first (collapsed) mode, if the connecting web between the respective end portions of the positioning arches and retaining arches is selected so that it is as short as possible.

In one particularly preferred embodiment of the medical device, the endoprosthesis has other fixing means at its distal end, which can be engaged with an introduction catheter system. In a preferred embodiment of the fixing, means, it would be conceivable for the latter to have a respective anchoring eye disposed between two adjacent positioning arches, in which case the respective arms of the adjacent positioning arches on the one hand and the respective arms of the retaining arches associated with the adjacent positioning arches on the other hand are connected to the anchoring eye. It would likewise be conceivable for the respective arms of the adjacent positioning arches to be directly and the respective arms of the retaining arches associated with the adjacent positioning arches to be indirectly connected via a connecting web extending essentially in the longitudinal direction of the endoprosthesis. Generally speaking, the purpose of the fixing means provided on the distal end of the endoprosthesis is to accommodate appropriate mechanisms on the introduction catheter system and these mechanisms are of a design complementing that of the fixing means of the endoprosthesis. The engagement between the catheter system on the one hand and the fixing means on the distal end of the endoprosthesis on the other hand can be released by means of an external manipulation in order to release the medical device at the implantation site, thereby ensuring that the medical device expands and is thus reliably anchored. Naturally, however, other fixing means could also be used.

As mentioned above, because of the special structure of the endoprosthesis, it is possible to use a self-expandable medical device which is distinctive due to its short overall length in the collapsed state, thereby ensuring improved manoeuvrability during the implantation process, whilst simultaneously affording a self-positioning function in the pockets of the old heart valve with the aid of the positioning arches so that the endoprosthesis is reliably anchored by the proximal and distal retaining regions of the endoprosthesis pressing radially against the vessel wall in the expanded state.

As an alternative to the preferred embodiment of the medical device outlined above, in which the respective arms of the adjacent positioning arches axe joined directly and the respective arms of the retaining arches associated with the adjacent positioning arches are joined indirectly to the fixing eye by means of a connecting web extending essentially in the longitudinal direction of the endoprosthesis, it would however also be conceivable for the respective arms of the adjacent positioning arches to be joined to the fixing eye indirectly via a connecting web extending essentially in the longitudinal direction of the endoprosthesis, in which case the respective arms of the retaining arches associated with the adjacent positioning arches are joined to the fixing eye indirectly via a connecting web extending essentially in the longitudinal direction of the endoprosthesis, and the connecting web of the retaining arches merges into the connecting web of the positioning arches at the end portion of the positioning arches. Providing the respective connecting webs for connecting the arms of the positioning arches to the fixing eye and for connecting the arms of the retaining arches to the end portion of the positioning arches offers a particularly simple but effective way of adapting the length of the endoprosthesis to respective requirements and does so because the respective lengths of the connecting webs can be selected accordingly.

In a preferred embodiment of the solution proposed by the invention, in order to ensure that the distal retaining region of the endoprosthesis can be retained at the implantation site in its expanded state particularly reliably, the endoprosthesis is provided with fixing eyes or similar at its distal retaining region, and these fixing eyes, which are preferably disposed between two adjacent positioning arches, are respectively provided with at least one barb, the tip of which points in the direction of the proximal end of the endoprosthesis. In this preferred embodiment, therefore, the endoprosthesis is secured at the implantation site due to the radial force exerted on the vessel wall by the endoprosthesis and in particular by the distal retaining region of the endoprosthesis, but also due to the barb hooking into the vessel wall. As regards the barb, it would naturally also be possible to use other appropriate design options.

As an alternative to or in addition to the barbs, which are preferably provided on the fixing eyes, another conceivable way of securing the endoprosthesis reliably at the implantation site is for the respective arms of the retaining arches of the endoprosthesis to be respectively provided with an anchoring support in the shape of a bow, which projects out from the relevant arm of the retaining arch when the endoprosthesis is in the expanded state, the tip of which points in the direction of the distal end of the endoprosthesis. This embodiment therefore provides additional fixing means for the endoprosthesis and accordingly additionally secures the medical device to prevent it from becoming dislocated.

In a preferred embodiment of the anchoring support, it would be conceivable for the anchoring support to be of an essentially U-shaped or V-shaped structure which is closed at the distal end of the endoprosthesis or the distal end of the medical device, in which case the distal region of the anchoring support constitutes the tip of the anchoring support and the respective arms of the anchoring support are joined to the respective arms of two adjacent retaining arches at the proximal end of the anchoring support.

Alternatively, in another preferred embodiment, the respective arms of retaining arches have continuous slots or elongate holes extending in the longitudinal direction of the retaining arches, the purpose of which is to enable and assist the expansion of the endoprosthesis from the collapsed state into the expanded state because these slots or elongate holes are preferably designed to permit a particularly easy cross-sectional expansion of the stent (endoprosthesis) whilst simultaneously reducing the length. Such slots or elongate holes have the additional advantage of saving on material.

In the case of the latter embodiment in which the respective retaining arches incorporate slots extending in the longitudinal direction of the retaining arches designed to influence the shape of the endoprosthesis in the second mode, it would be conceivable for the respective retaining arches to be additionally provided with reinforcing portions which interrupt the slots extending in the longitudinal direction of the retaining arches and which prevent components of the retaining arches from projecting outwards when the endoprosthesis is in the expanded state, which is of particular advantage in preventing explantation of the medical device.

In a preferred embodiment, the endoprosthesis has an external diameter of approximately 5.0 mm and a length of between 33.0 mm and 40.0 mm, preferably between 34.0 and 39.0 mm, and even more preferably between 34.37 mm and 38.37 mm, in its first mode, which means that the medical device can be introduced by means of a 21 F introduction system, for example, and heart valve prostheses with a diameter of 21 mm to 28 mm may be used. The length specifications given above are currently preferred values, on the basis of which the medical device is suitable for the majority of patients to be treated.

In order to obtain a particularly reliable anchoring of the implanted medical device in its expanded state, the endoprosthesis is subjected to a shaping and heat treatment process during its manufacture so that when the endoprosthesis is in the finished state, it has a slightly concave shape tapering in the direction of the proximal retaining region of the endoprosthesis in its second mode.

In other words, this means that the proximal retaining region of the endoprosthesis, i.e. the region to which the heart valve prosthesis is attached, has a slightly narrower diameter than the distal retaining region. It has effectively been found that if the distal retaining region of the endoprosthesis in the second mode has an approximately 10% to 25% bigger diameter than the proximal retaining region of the endoprosthesis, radial forces are generated at the distal retaining region of the endoprosthesis in particular which enable the medical device to be securely retained in the vessel without causing damage to the vessel wall, and due allowance is also made for the peristaltic movements of the heart and vessel wall. The slightly lower radial force expended by the proximal retaining region of the endoprosthesis not only serves as a means of anchoring the medical device in the aorta but in particular also opens out the heart valve prosthesis fitted on the proximal retaining region of the endoprosthesis and imparts to it a reliable seal with respect to the vessel wall. Naturally, however, it would also be conceivable for the concave shape to be more or less pronounced when the endoprosthesis assumes the second mode.

In particular, however, it is preferable if the retaining region of the endoprosthesis has a diameter of between 22 mm and 33 mm, and preferably between 25 mm and 31 mm, in the second mode. This being the case, it would be conceivable for the endoprosthesis to be made in two or more differently dimensioned sizes, in which case an optimum size of endoprosthesis could be selected depending on the patient, and the exact dimensions of the endoprosthesis are adapted to the patient to be treated—starting from a pre-defined stent size—by an appropriate finishing treatment of the endoprosthesis (stent), in particular by tempering.

In one, particularly preferred embodiment of the medical device, not only does it have the endoprosthesis (stent) but also a heart valve prosthesis, preferably a bio-heart valve prosthesis, which is attached to the retaining segment of the endoprosthesis by means of a thread or similar, in which case orifices are provided in the retaining arches of the endoprosthesis through which the thread or similar is inserted. Accordingly, it would also be conceivable for the heart valve prosthesis to be connected to the retaining segment of the endoprosthesis immediately prior to the medical intervention. As a result, the medical device can be made in a modular design, which is of particular advantage in terms of transporting and storing the medical device.

As regards the preferred material used for the endoprosthesis of the medical device, a shape memory material is used, which is designed so that the endoprosthesis is transformed from a temporary shape to a permanent shape by means of an external stimulus, in which case the endoprosthesis assumes the temporary shape in the first mode (when the medical device is in the collapsed state) and the endoprosthesis assumes the permanent shape in the second mode (when the medical device is in the expanded state). Especially if a shape memory material such as Nitinol is used, i.e. an equal atomic alloy of nickel and titanium, the implantation process will be particularly gentle during the operation of implanting the medical device.

During production of an endoprosthesis made from a shape memory material, after the stent structure has been cut from the metal tube, it is deformed and fixed in the desired permanent shape, a process which is known as programming. This operation may be performed on the one hand by heating, deforming and then cooling the stent structure. Alternatively, the stent structure may also be deformed at low temperature by an operation known as cold stretching. As a result, the permanent shape is memorised whilst the temporary shape actually prevails. If the stent structure is then subjected to an external stimulus, the shape memory effect is triggered and the memorised permanent shape is restored.

In a particularly preferred embodiment, the external stimulus is a settable switching temperature. It is therefore conceivable for the endoprosthesis material to be heated to a temperature high than the switching temperature in order to trigger the shape memory effect and thus restore the memorised permanent shape of the endoprosthesis. By selecting the chemical composition of the shape memory material accordingly, a specific switching temperature can be fixed beforehand.

This being the case, the switching temperature is set so that it falls within the range of room temperature and the body temperature of the patient. This is of particular advantage in applications where the medical device is to be implanted in a patient's body. Accordingly, when implanting the medical device, it is merely necessary to ensure that the instrument is not heated and thus triggers the shape memory effect of the endoprosthesis material until it is in the implanted state on the patient's body (36° C.).

Preferred embodiments of an endoprosthesis of a medical device proposed by the invention will be described in more detail below with reference to the appended drawings.

Of these:

Figure 1A:
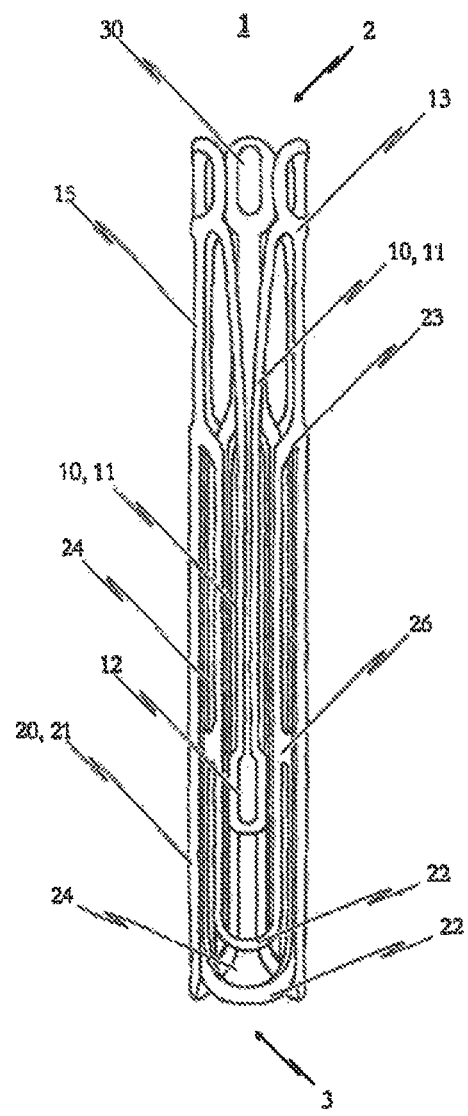
FIG. 1a illustrates a first, preferred embodiment of a self-expandable endoprosthesis for the medical device proposed by the invention in its first predefined mode in which the medical device is in its collapsed state.
Figure 1B:
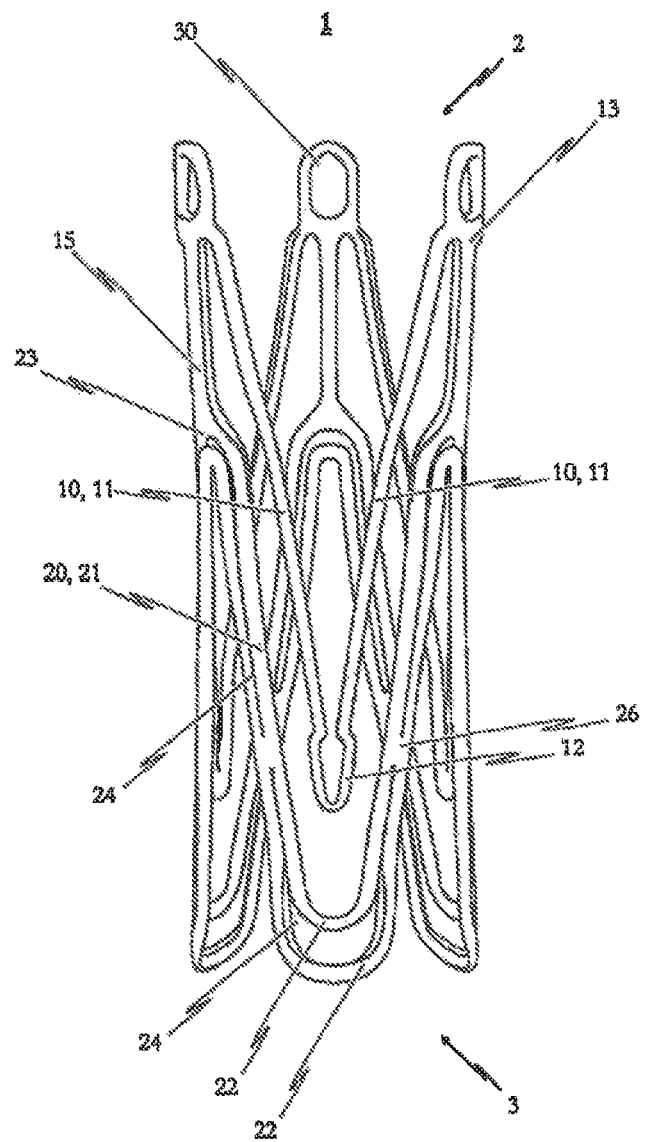
FIG. 1b shows the endoprosthesis illustrated in FIG. 1a but in a state between its first pre-definable mode and its second mode in which the medical device is in its expanded state.
Figure 1C:
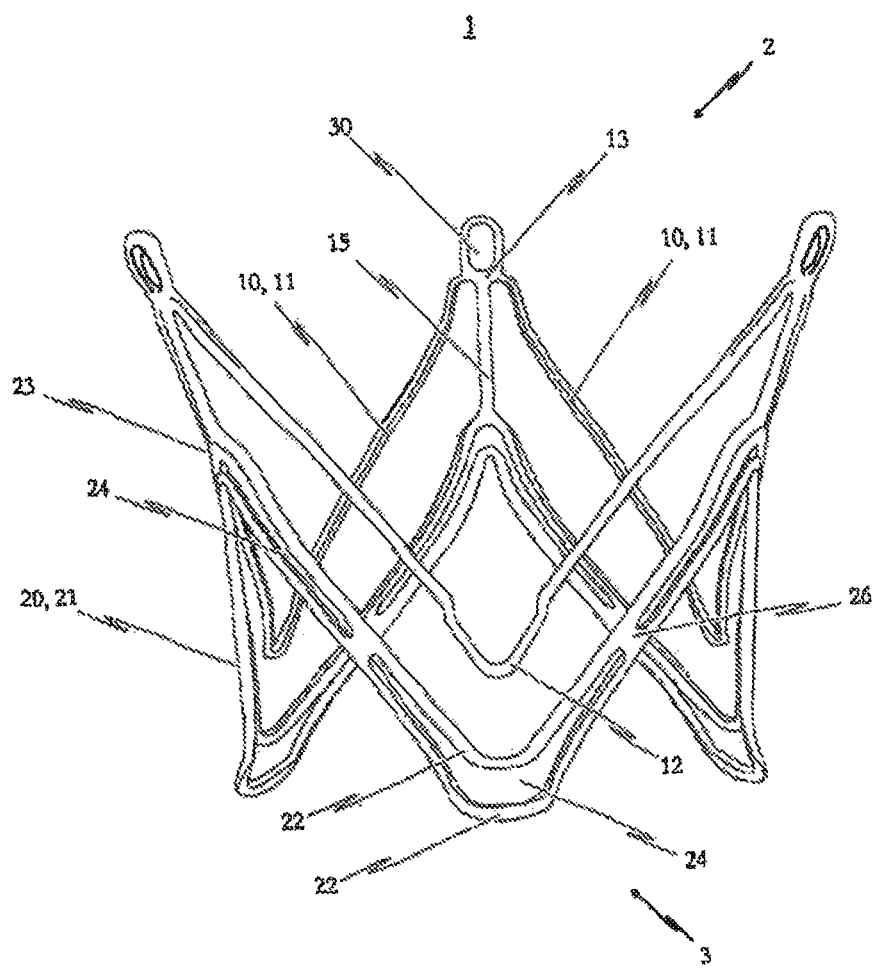
FIG. 1c shows the endoprosthesis illustrated in FIG. 1a but in its second mode in which the medical device is in its expanded state.
Figure 1D:
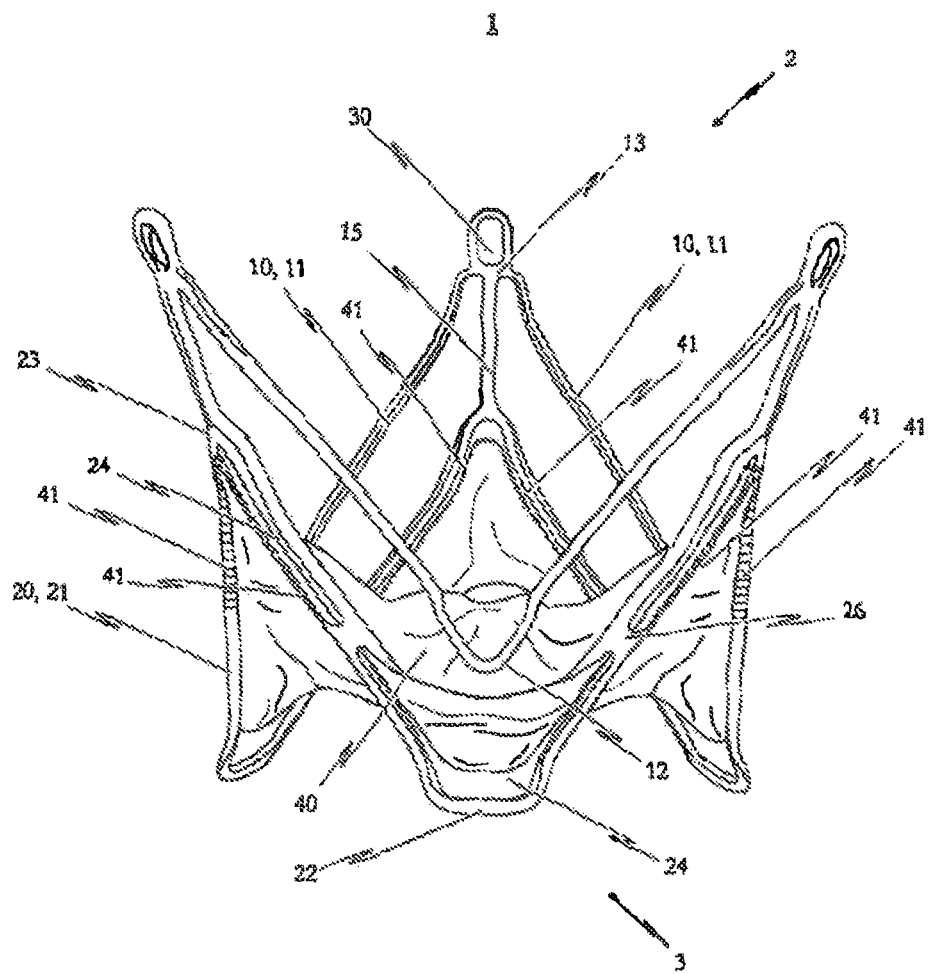
FIG. 1d shows a first, preferred embodiment of the medical device proposed by the invention in its expanded state, with an endoprosthesis of the type illustrated in FIG. 1c with a heart valve prosthesis attached to it and opened out.
Figure 1E:
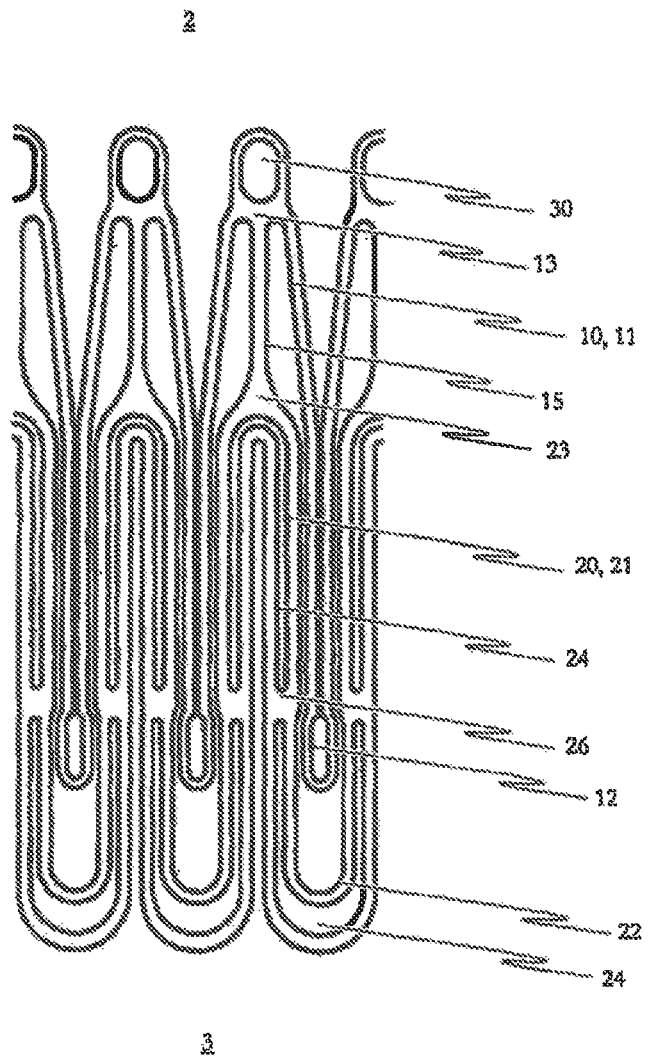
FIG. 1e is a flat projection of a cutting pattern which can be used for the production of the first, preferred, self-expandable endoprosthesis in order to cut the endoprosthesis illustrated in FIG. 1a integrally from a metal tube.

A first preferred embodiment of the self-expandable endoprosthesis 1 for the medical device proposed by the invention will be described first of all with reference to FIG. 1a to 1e. FIG. 1a illustrates the endoprosthesis 1 in its first pre-definable mode in which the medical device (not explicitly illustrated) is in a collapsed state and can therefore be introduced into a patient's body with minimal invasion by means of a catheter system. FIG. 1c illustrates the endoprosthesis 1 in its second mode in which the medical device is in its expanded state. FIG. 1b illustrates the endoprosthesis 1 in a state between the first mode (see FIG. 1a) and the second mode (see FIG. 1c). FIG. 1d illustrates a first preferred embodiment of the medical device proposed by the invention in its expanded state with an endoprosthesis of the type illustrated to FIG. 1c and a heart valve prosthesis 40 attached to it and secured.

The endoprosthesis 1 based on the first preferred embodiment is distinctive due to the fact that it has a structure which is cut integrally from a metal tube. The cutting pattern used to produce the stent design is illustrated in a flat projection in FIG. 1e. Specifically, the endoprosthesis 1 comprises a total of three positioning arches 10, which assume the function of automatically positioning the medical device in the patient's aorta. The positioning arches 10 have a rounded head portion 12, which engages in the pockets of the insufficient heart valve to be replaced by the medical device when the medical device is positioned at the implantation site. Providing three positioning arches 10 in total ensures that the requisite positioning accuracy can be obtained in the direction of rotation.

The head portions 12 of the positioning arches 10 pointing respectively towards the proximal end 3 of the endoprosthesis 1 are appropriately rounded so that the vessel wall is not damaged when the positioning arches 10 engage in the pockets of the heart valve to be replaced. Extending from the head portion 12 of the positioning arch 10 to the distal end 2 of the endoprosthesis 1 are two positioning webs or arms 11 in total for each positioning arch 10, which merge into an eye-shaped element 30 at the distal end 2 of the endoprosthesis 1. This eye-shaped element 30 serves as a fixing means for attaching the endoprosthesis 1 and hence the medical device to an introduction catheter system.

Specifically, the respective fixing eyes 30 are disposed between the two arms 11 of two mutually adjacent positioning arches 10. Opening into the transition portion 13 between the two arms 11 of two mutually adjacent positioning arches 10 incorporating the fixing eye 30 is a connecting web 15 extending essentially in the longitudinal direction of the endoprosthesis 1. At the proximal end, the connecting web 15 merges into the respective retaining arms 21 of two mutually adjacent retaining arches 20.

As a result of this stent design, an axially symmetrical structure is obtained, whereby a retaining arch 20 is associated with each positioning arch 10. The endoprosthesis 1 in the preferred embodiment illustrated in FIGS. 1a to 1c therefore has a total of three retaining arms 20, which form the base for a retaining segment of the endoprosthesis 1 for accommodating a heart valve prosthesis 40 (illustrated in FIG. 1d, for example). Providing the respective connecting webs 15 between the distally lying transition portieres 23 of two mutually adjacent retaining arches 20 and the transition portions 13 of two mutually adjacent positioning arches 10 results in a stent structure whereby the respective arms 11 of a positioning arch 10 extend essentially parallel with the respective arms 21 of a retaining arch 21 associated with the positioning arch 10.

When the endoprosthesis 1 is in the state illustrated in FIG. 1a in which it assumes its first mode, the respective arms 11 of the positioning arches 10 directly bound the respective arms 21 of the associated retaining arches 20.

Particular attention should be paid to FIG. 1c in which the endoprosthesis 1 based on the first preferred embodiment is illustrated its second anode. Particularly worth mentioning in respect of this diagram is the fact that every positioning arch 10 and its associated retaining arch 20 has an essentially U-shaped or V-shaped structure which is closed towards the proximal end 3 of the endoprosthesis 1. Specifically, every positioning arch 10 is cut from the material portion of the metal tube which is accommodated in the essentially U-shaped or V-shaped structure of the associated retaining arch 20, as may be seen from the cutting pattern illustrated in FIG. 1e.

As may be seen by comparing FIGS. 1a and 1c, during the transition from the first mode into the second mode, the endoprosthesis becomes shorter in the longitudinal direction whilst the cross-section simultaneously becomes wider, in particular at the distal and the proximal retaining regions 2, 3. When the endoprosthesis 1 is in the expanded state, the respective positioning arches 10 are specifically opened out to a more pronounced degree in the radial direction than is the case at the distal retaining region 2 of the stent 1. The positioning arches 10 which assume the function of positioning the medical device in the implanted state by engaging in the pockets of the old heart valve to be replaced can therefore project farther out in the radial direction and can be inserted in the heart valve pockets of the heart valve to be replaced in a particularly easy manner.

FIG. 1d illustrates a first preferred embodiment of the medical device proposed by the invention in its expanded state, with an endoprosthesis 1 of the type illustrated in FIG. 1c and a heart valve prosthesis 40 attached to with the aid of a thread 41 and opened out. As illustrated, opening out the proximal retaining region 3 of the endoprosthesis 1 in which the heart valve prosthesis 40 is disposed causes the heart valve prosthesis 40 to open out, whilst a radial force is simultaneously applied to the vessel wall (not illustrated) by the proximal end portions 22 of the retaining arches 21, thereby affording a reliable seal of the heart valve prosthesis 40 with respect to the vessel wall.

Although the force exerted by the retaining arches 21 in the radial direction onto the vessel wall causes the medical device to be secured at the implantation site to a certain extent, the distal retaining region 2 is expanded by a further 10% to 25% in the radial direction than is the case at the proximal retaining region 3 of the endoprosthesis 1 when the medical device is in the expanded state in order to obtain a permanently stable implantation of the medical device, especially in view of the unavoidable peristaltic movement of the vessel wall and the relatively high fluid pressures which prevail. As a result, a slightly concave shape is imparted to the endoprosthesis 1, which tapers in the direction of the proximal retaining region 3 of the endoprosthesis 1, thereby ensuring that the medical device is firmly anchored in the vessel due to the distal retaining region 2 of the endoprosthesis 1 pressing against the vessel wall.

In the embodiment illustrated, the respective arms 21 of the retaining arches 20 have uninterrupted slots or elongate holes 24, the purpose of which is to enable or assist expansion of the endoprosthesis 1 from the collapsed state into the expanded state, because these slots or elongate holes 24 make it easy to widen the cross-section of the stent 1 whilst simultaneously reducing its length. Naturally, however, it would also be conceivable for these slots or elongate holes 24 to accommodate a thread 41 or similar used to attach the heart valve prosthesis 40 (illustrated in FIG. 1d) to the proximal region 3 of the endoprosthesis 1.

The solution proposed by the invention is a medical device of a modular design essentially comprising the two separately manufactured components, endoprosthesis 1 and heart valve prosthesis 40, and the endoprosthesis 1 assumes the function of positioning and securing the heart valve prosthesis 40 in the patient's aorta. It may be preferable if the two components (endoprosthesis 1 and heart valve prosthesis 40) are not connected to one another until immediately prior to performing the surgical intervention; this is of advantage in terms of transporting and storing the endoprosthesis 1 as such since the endoprosthesis 1 is a relatively robust component from a mechanical point of view and in particular can be stored for a longer period. This applies in particular if the endoprosthesis 1 is stored in its second mode, i.e. in the expanded state, and is not switched to its first (collapsed) mode until immediately prior to undertaking the surgical intervention.

The state of the endoprosthesis 1 illustrated in FIG. 1a in which the endoprosthesis 1 is in its first mode and the medical device is in its collapsed state is the so-called "temporary" mode of the endoprosthesis sure made from a memory shape material. When an external stimulus acts on the endoprosthesis body illustrated in FIG. 15, the shape memory effect is triggered and the fixed permanent shape memorised during production of the endoprosthesis 1 illustrated in FIG. 1c is restored. This external stimulus is preferably a settable switching temperature and the body must be heated to a temperature higher than the switching temperature in order to trigger the shape memory effect and thus restore the memorised permanent shape of the endoprosthesis 1. By selecting the chemical composition of the material used for the endoprosthesis 1 accordingly, a specific switching temperature can be fixed beforehand; in the case of the preferred embodiment of the solution proposed by the invention, it lies in a range of between 20° C. and the body temperature of the patient.

When the medical device is being implanted, it would therefore be conceivable for the medical device to be cooled accordingly during the introduction process. When the medical device has been moved to the desired implantation site, in other words in front of the native heart valve, preferably by means of an appropriate introduction system, cooling can be interrupted so that the endoprosthesis 1 of the medical device is heated to the body temperature (36° C.) of the patient, thereby triggering the shape memory effect of the endoprosthesis material. Having triggered the self-expanding property of the endoprosthesis 1, radial forces are generated which act on the individual components of the endoprosthesis 1 and in particular on the respective positioning arches 10, 11 and retaining arches 20, 21 of the endoprosthesis 1. Since the endoprosthesis 1 of the medical device is still disposed in the introduction catheter system as before, the radial forces which build up once the critical switch temperature exceeded and act on the individual components of the endoprosthesis 1 are still compensated by the introduction port of the introduction catheter system so that—in spite of the shape memory effect having been triggered—the endoprosthesis 1 of the medical device is forcibly retained in its first (collapsed) mode.

By releasing the endoprosthesis 1 from the introduction catheter system in appropriate steps, it is then possible to release the positioning arches 10, 11 of the endoprosthesis 1 through the introduction port of the introduction catheter system first, as a result of which it opens up due to the radial forces acting in the radial direction. The opened positioning arches 10, 11 can then be positioned in the pockets of the native heart valve.

The remaining components of the endoprosthesis 1 and the medical device can then be released through the introduction port of the introduction catheter system. As this happens, the retaining arches 20, 21 open in the radial direction and the heart valve prosthesis 40 attached to the retaining arches 20, 21 by means of a thread 41, etc., for example, thus unfolds in the manner of an umbrella. The radial forces acting on the retaining arches 20, 21 but also on the distal retaining region 2 of the endoprosthesis 1 cause the endoprosthesis 1 to be pressed in the radial direction against the vessel wall, which guarantees a reliable anchoring of the medical device at the implantation site on the one hand and ensures a reliable seal of the heart valve prosthesis 40 at the proximal retaining region 3 of the endoprosthesis 1 on the other hand.

Figure 2A:
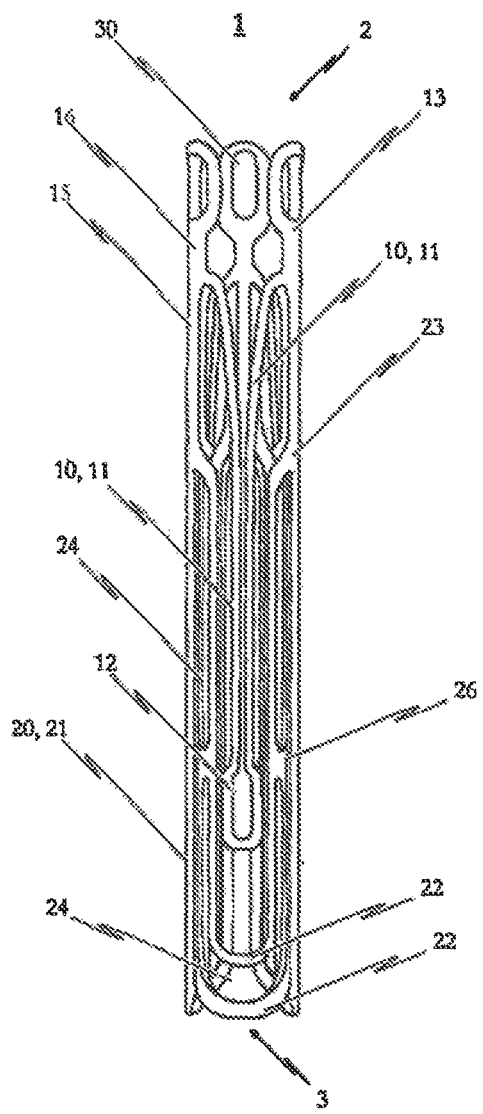
FIG. 2a shows a second, preferred embodiment of a self-expandable endoprosthesis for the medical device proposed by the invention in its first, pre-determined mode in which the medical device is in its collapsed state.
Figure 2B:
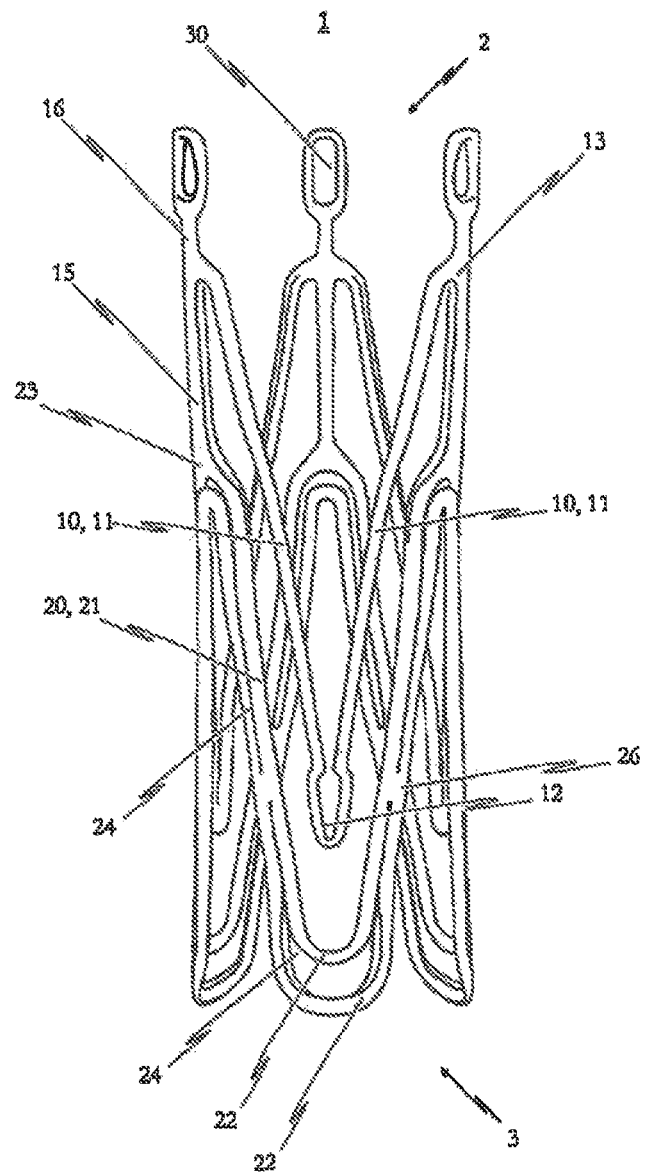
FIG. 2b shows the endoprosthesis illustrated in FIG. 2a in a state between its first, pre-definable mode and its second mode in which the medical device is in its expanded state.
Figure 2C:
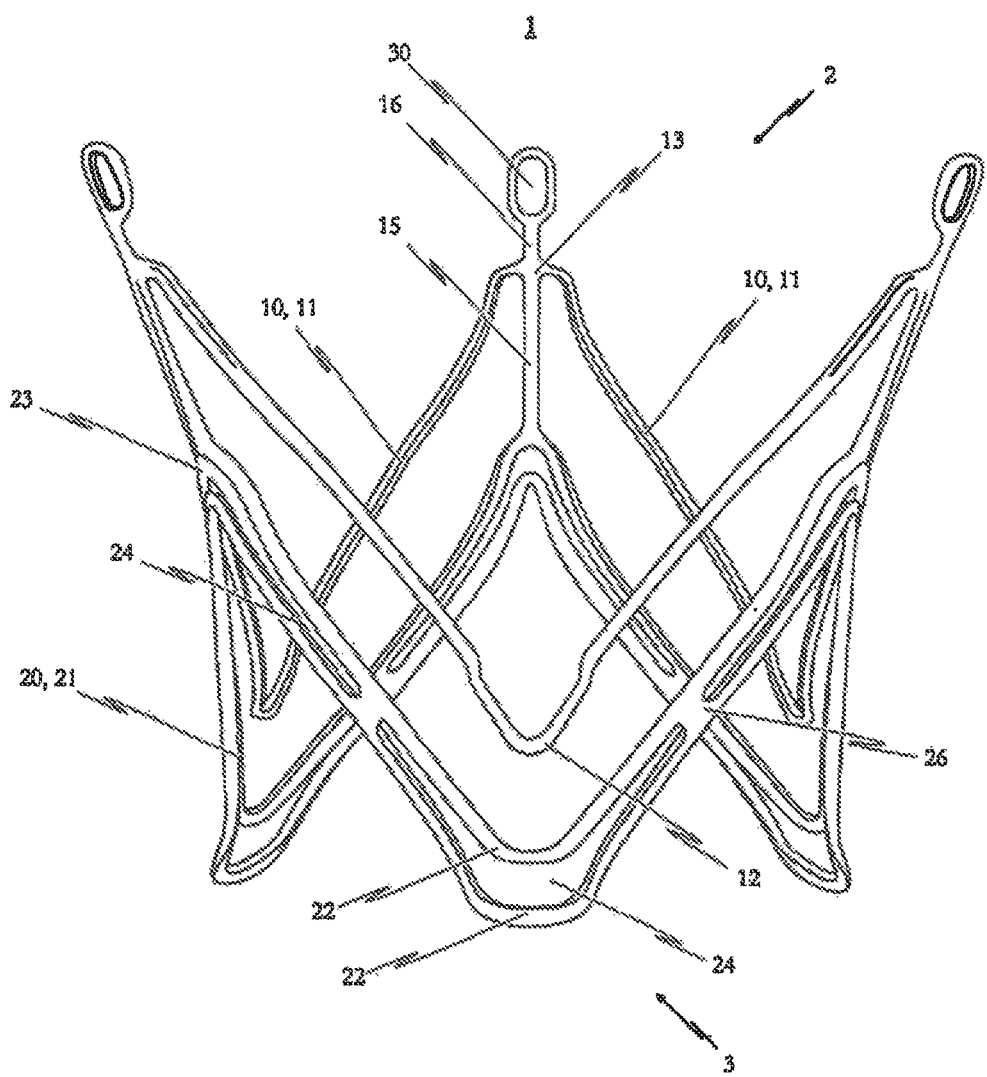
FIG. 2c shows the endoprosthesis illustrated in FIG. 2a in its second mode in which the medical device is in its expanded state.

FIGS. 2a to 2c illustrate a second preferred embodiment of a self-expandable endoprosthesis 1 for the medical device proposed by the invention in its first, pre-definable mode (see FIG. 2a) in its second pre-definable mode (see FIG. 2c) as well as in a state in between (see FIG. 2b).

Figure 2D:
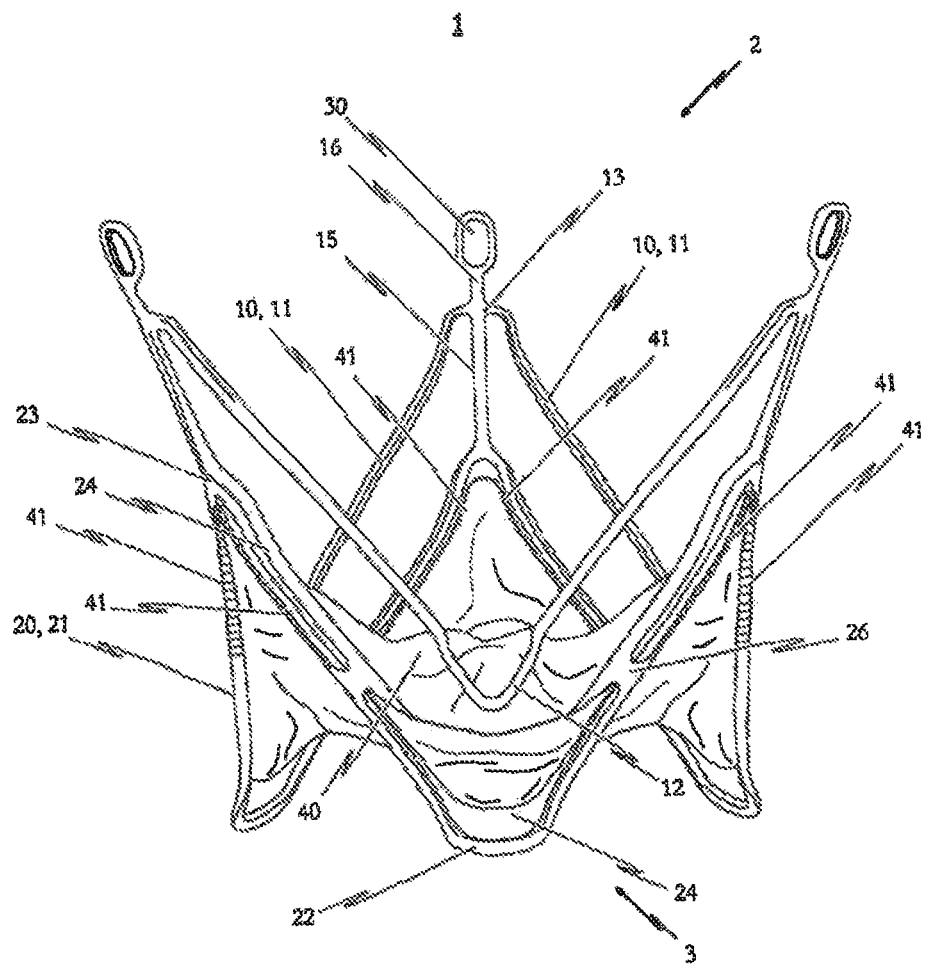
FIG. 2d illustrates a second preferred embodiment of the medical device proposed by the invention in its expanded state, with an endoprosthesis of the type illustrated in FIG. 2c and a heart valve prosthesis attached to it and opened out.
Figure 2E:
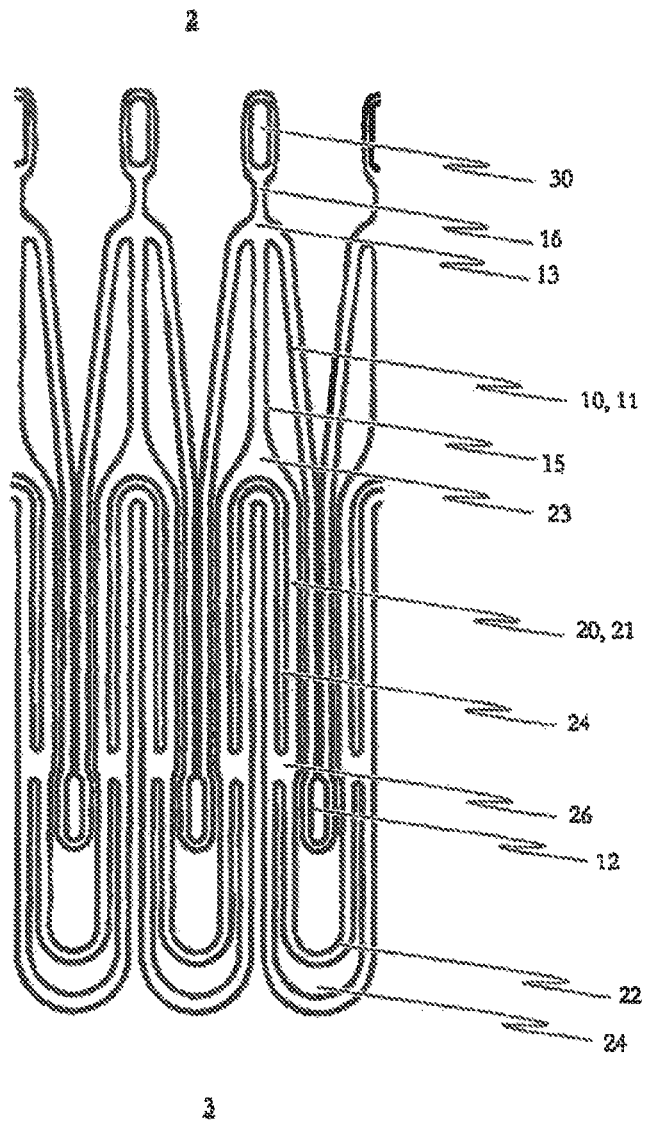
FIG. 2e is a flat projection of a cutting pattern which can be used for the production of the second preferred, self-expandable endoprosthesis in order to cut the endoprosthesis illustrated in FIG. 2a integrally from a metal tube.

FIG. 2d illustrates a second preferred embodiment of the medical device proposed by the invention in its expanded state with an endoprosthesis of the type illustrated in FIG. 2c and a heart valve prosthesis 40 attached to it and opened out. A flat projection of a cutting pattern which may be used for the production of the second preferred embodiment of the self-expendable endoprosthesis is illustrated in FIG. 2e. This cutting pattern is suitable for cutting the endoprosthesis illustrated in FIG. 2a integrally from a metal tube.

The endoprosthesis 1 based on the second preferred embodiment essentially corresponds to the first preferred embodiment described above with reference to FIGS. 1a to 1e. The second embodiment differs from the first preferred embodiment of the endoprosthesis due to the fact that the respective arms 11 of the adjacent positioning arches 10 are joined indirectly via a connecting web 16 extending essentially in the longitudinal direction of the endoprosthesis 1 to the fixing eye 30, and the respective arms 21 of the retaining arches 20 associated with the adjacent positioning arches 10 are indirectly joined via a connecting web 15 extending essentially in the longitudinal direction of the endoprosthesis 1 to the fixing eye 30. Specifically, the connecting web 15 of the retaining arches 20 merges into the connecting web 16 of the positioning arches 10 at the end portion 13 of the positioning arches 10. By selecting the respective lengths of the two connecting webs 15 and 16 accordingly, therefore, the overall length of the stent 1 can be adjusted in an easy manner.

Figure 3A:
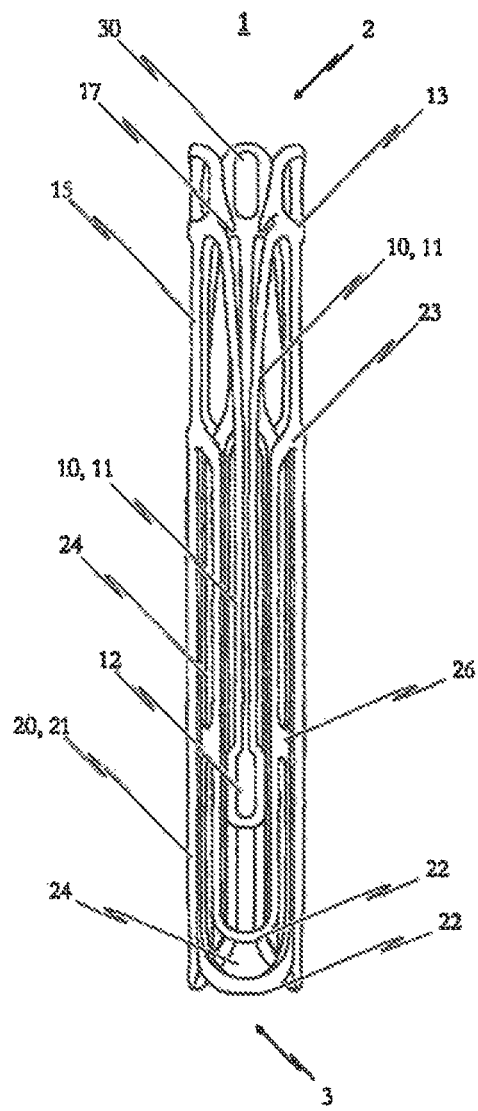
FIG. 3a shows a third, preferred embodiment of a self-expandable endoprosthesis for the medical device proposed by the invention in its first, pre-determined mode in which the medical device is in its collapsed state.
Figure 3H:
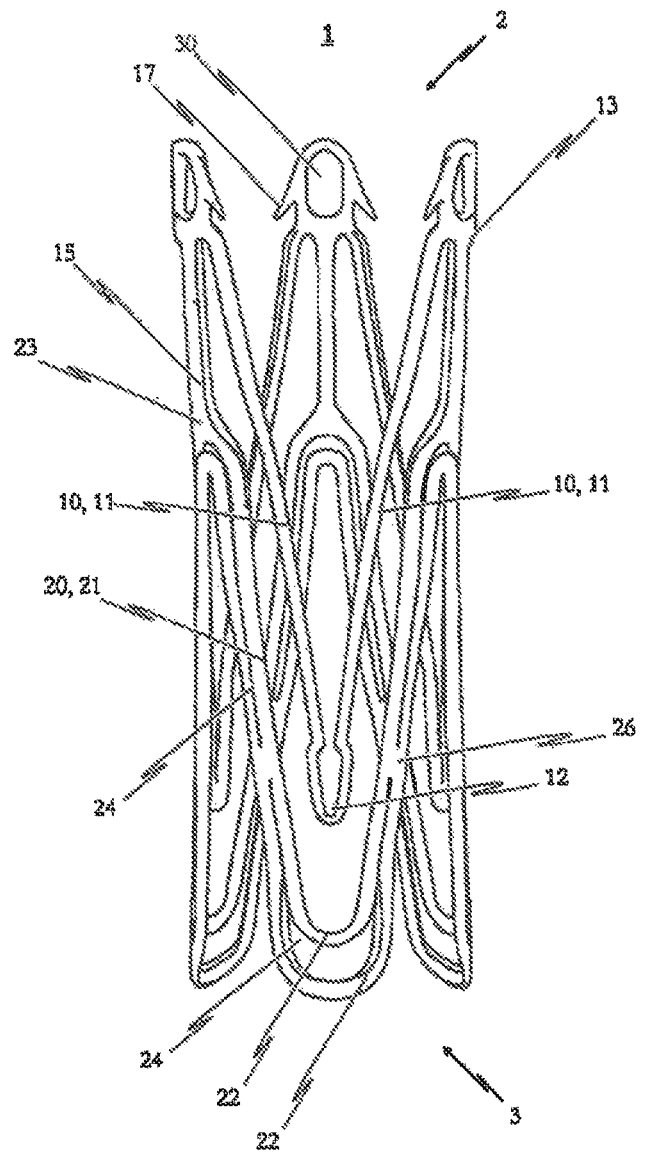
FIG. 3b shows the endoprosthesis illustrated in FIG. 3a in a state between its first, pre-definable mode and its second mode in which the medical device is in its expanded state.
FIG. 3c shows the endoprosthesis illustrated in FIG. 3a in its second mode in which the medical device is in its expanded state.
FIG. 3d illustrates a third preferred embodiment of the medical device proposed by the invention in its expanded state, with an endoprosthesis of the type illustrated in FIG. 3c and a heart valve prosthesis attached to it and opened out.
FIG. 3e is a flat projection of a cutting pattern which can be used for the production of the third preferred, self-expandable endoprosthesis in order to cut the endoprosthesis illustrated in FIG. 3a integrally from a metal tube.
Figure 3C:
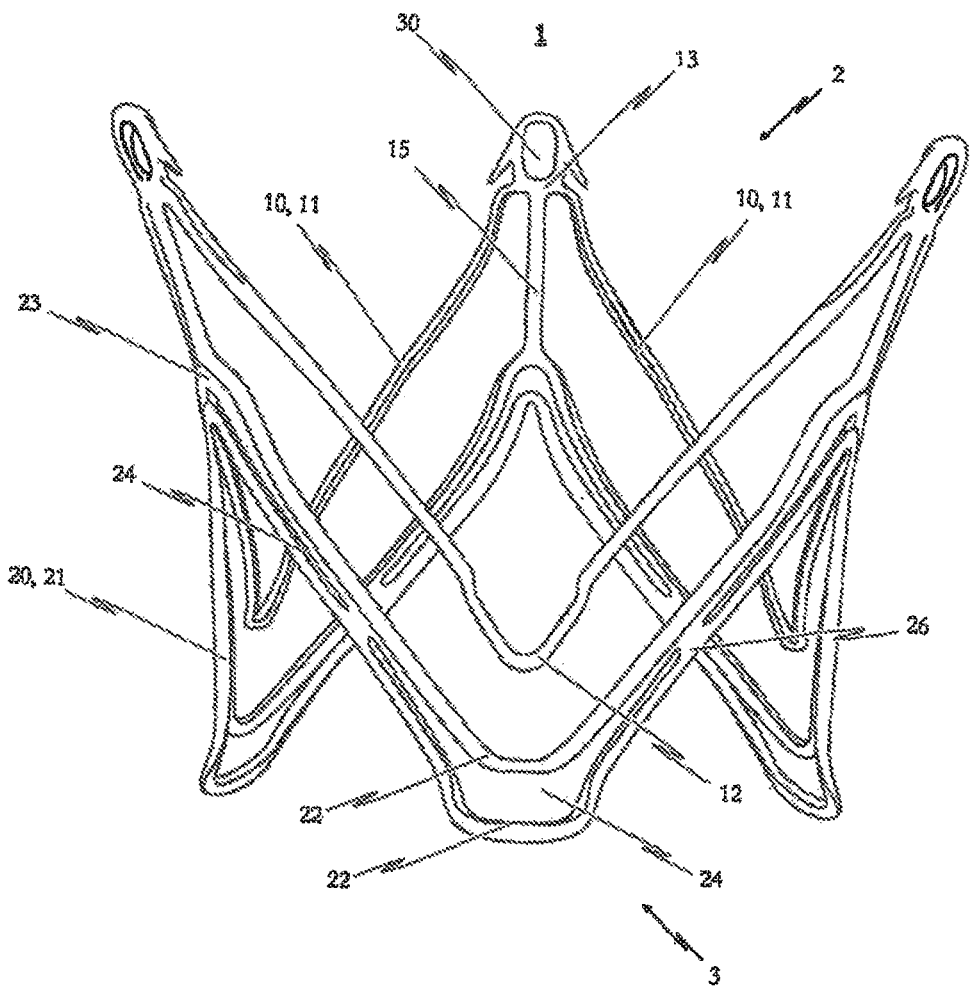

The third preferred embodiment of a self-expandable endoprosthesis for the medical device proposed by the invention illustrated in FIGS. 3a to 3c essentially corresponds to the first preferred embodiment illustrated in FIGS. 1a to 1c; the difference, however, is that in the third preferred embodiment the fixing eyes 30 disposed between two adjacent positioning arches 10 are provided with barbs 17, the respective tips of which point in the direction of the proximal end 3 of the endoprosthesis 1. With this modification to the design of the heart valve-stent 1 based on the first preferred embodiment, therefore, additional anchoring is provided for the system to prevent the stent 1 from being dislocated in the direction of the left ventricle.

Figure 3D:
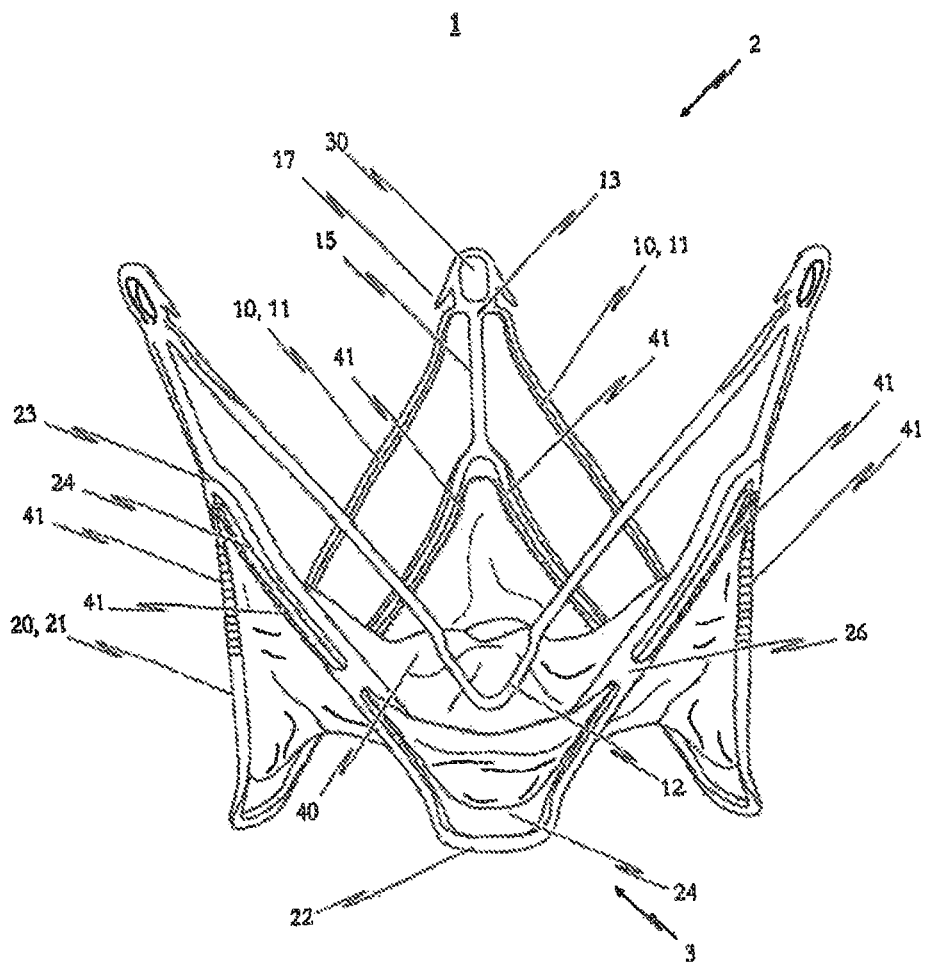

FIG. 3d illustrates a third preferred embodiment of the medical device proposed by the invention in its expanded state with an endoprosthesis of the type illustrated in FIG. 3c and a heart valve prosthesis 40 attached to it and opened out. This diagram essentially corresponds to that of FIG. 1d; the exception, however, is the fact that the barb elements 17 described above are provided on the respective fixing eyes 30.

Figure 3E:
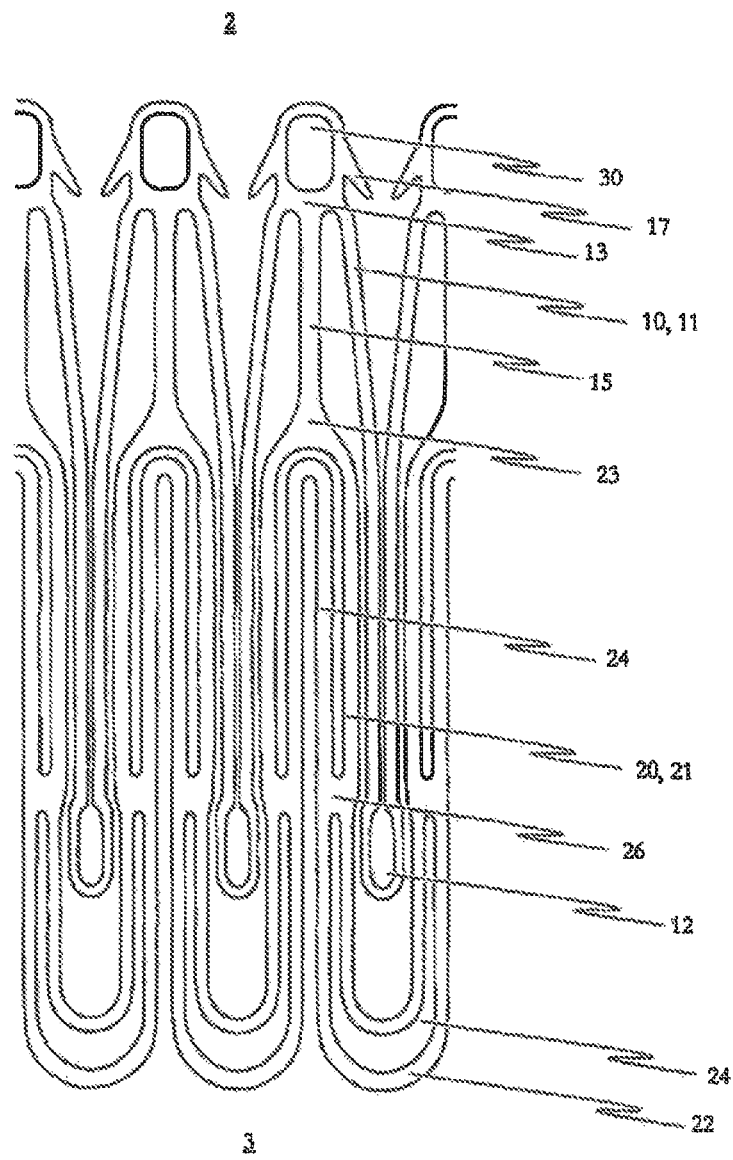

A flat projection of a cutting pattern which may be used for the production of the third preferred embodiment of the self-expandable endoprosthesis 1 is illustrated in FIG. 3e. This cutting pattern is suitable for cutting the endoprosthesis illustrated in FIG. 3a integrally from a metal tube.

Figure 4A:
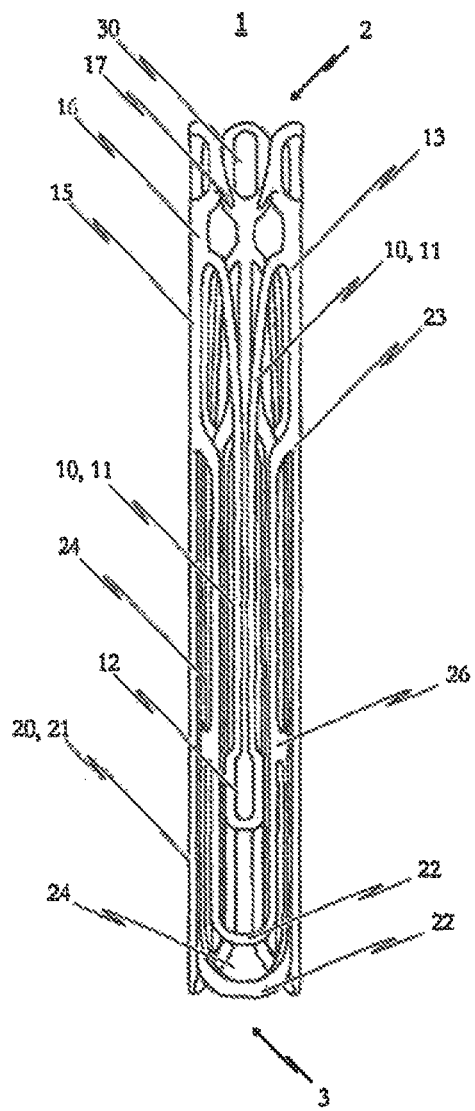
FIG. 4a shows a fourth, preferred embodiment of a self-expandable endoprosthesis for the medical device proposed by the invention in its first, pro-determined mode in which the medical device is in its collapsed state.
Figure 4B:
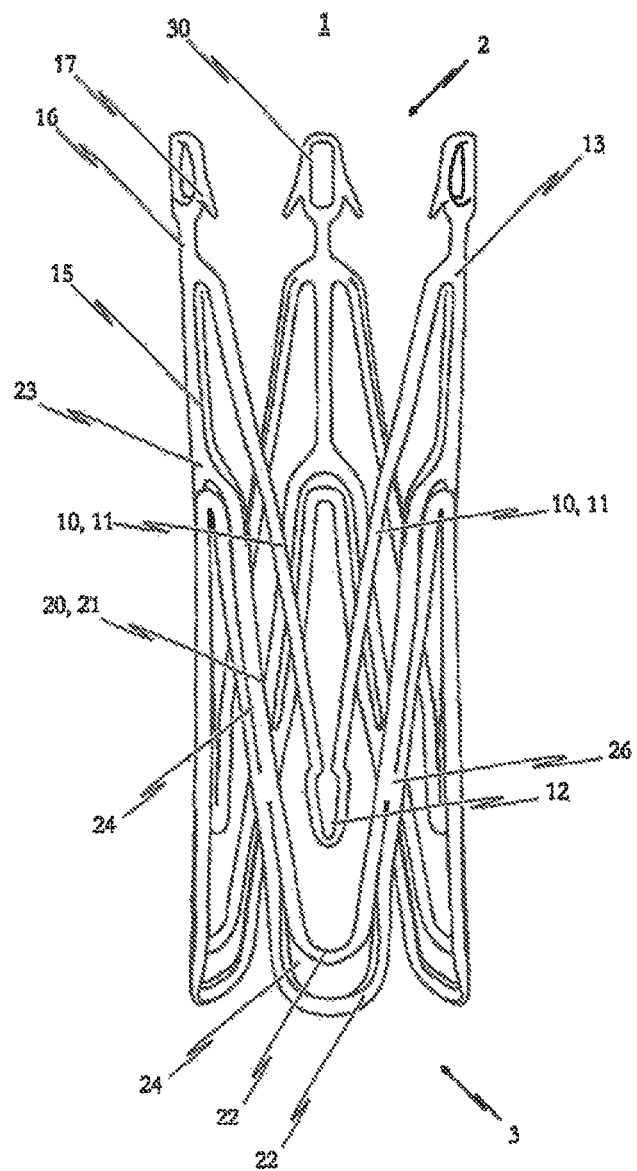
FIG. 4b shows the endoprosthesis illustrated in FIG. 4a in a state between its first, pre-definable mode and its second mode in which the medical device is in its expanded state.
Figure 4C:
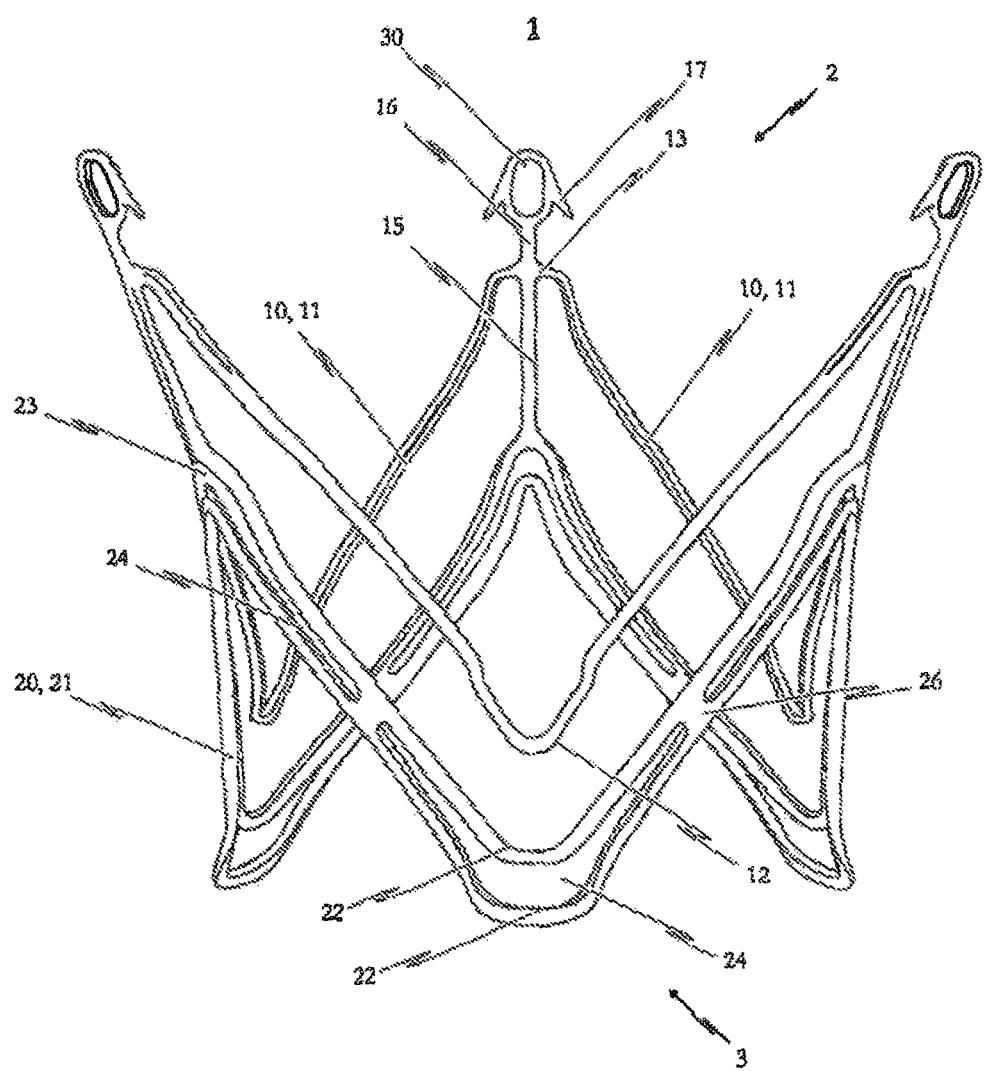
FIG. 4c shows the endoprosthesis illustrated in FIG. 4a in its second mode in which the medical device is in its expanded state.
Figure 4D:
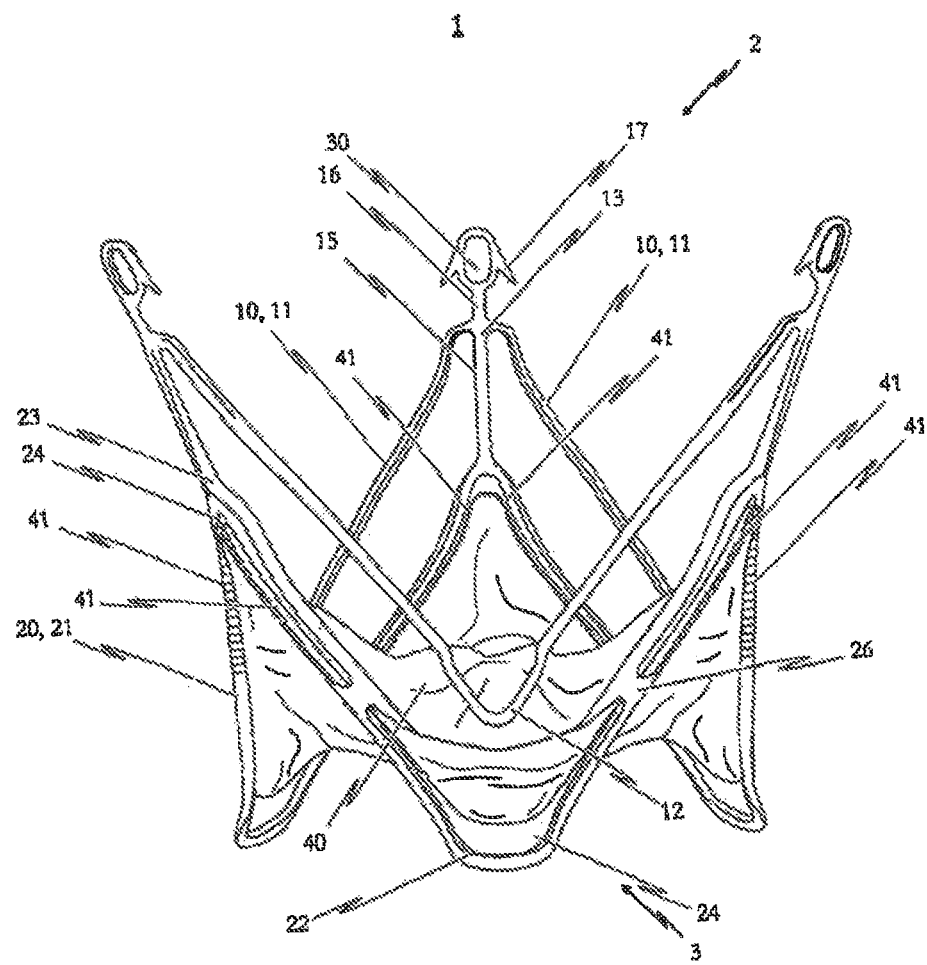
FIG. 4d illustrates a fourth preferred embodiment of the medical device proposed by the invention in its expanded state, with an endoprosthesis of the type illustrated in FIG. 4c and a heart valve prosthesis attached to it and opened out.
Figure 4E:
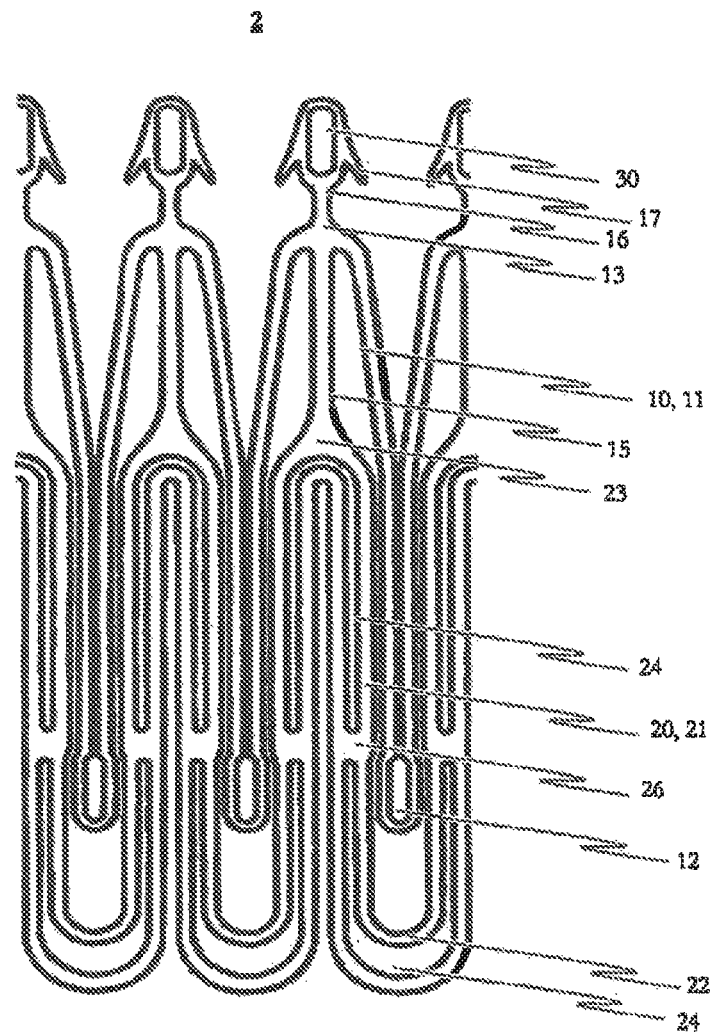
FIG. 4e is a flat projection of a cutting pattern, which can be used for the production of the fourth, preferred, self-expandable endoprosthesis in order to cut the endoprosthesis illustrated in FIG. 4a integrally from a metal tube.

FIG. 4a to FIG. 4c illustrate a fourth preferred embodiment of a self expandable endoprosthesis 1 for the medical device proposed by the invention. A fourth preferred embodiment of the medical device proposed by the invention is illustrated in its expanded state with an endoprosthesis in FIG. 4c and an opened out heart valve prosthesis 40 attached to it is illustrated in FIG. 4d, whilst FIG. 4e illustrates a flat projection of a cutting pattern, which may be used for the production of the fourth preferred embodiment of the self-expandable endoprosthesis 1. The cutting pattern illustrated in FIG. 4c is specifically suitable for cutting the endoprosthesis illustrated in FIG. 4a integrally from a metal tube.

The fourth preferred embodiment of the self-expandable prosthesis 1 corresponds to a combination of the second and third preferred embodiments described above. Specifically, the respective arms 11 of the adjacent positioning arches 10 are indirectly joined via the connecting web 16 extending essentially in the longitudinal direction of the endoprosthesis to the fixing eye 30, whilst barbs 17 are provided on the respective fixing eyes 30, the tips of which point in the direction of the proximal end 3 of the endoprosthesis 1. The advantages which can be achieved as a result of the features provided on the fourth preferred embodiment were described above and will not be reiterated at this stage.

The fifth preferred embodiment of a self-expandable endoprosthesis 1 and a medical device proposed by the invention illustrated in FIG. 5a to FIG. 5e essentially corresponds to the first preferred embodiment described with reference to FIG. 1a to FIG. 1e, except that in this instance, the respective retaining arches 21 of the endoprosthesis 1 are provided with reinforcing portions 26, which interrupt the slots 24 extending in the longitudinal direction of the retaining arches 21. The purpose of these reinforcing portions 26 is to open out the individual components of the retaining arches 21, and in particular to break the anchoring support 25 radially out of the retaining arches 20. Accordingly, a retaining portion for the stent 1 can be obtained with the reinforcing portions 26, which has no components which might explant the medical device when it is in the expanded state.

Figure 5A:
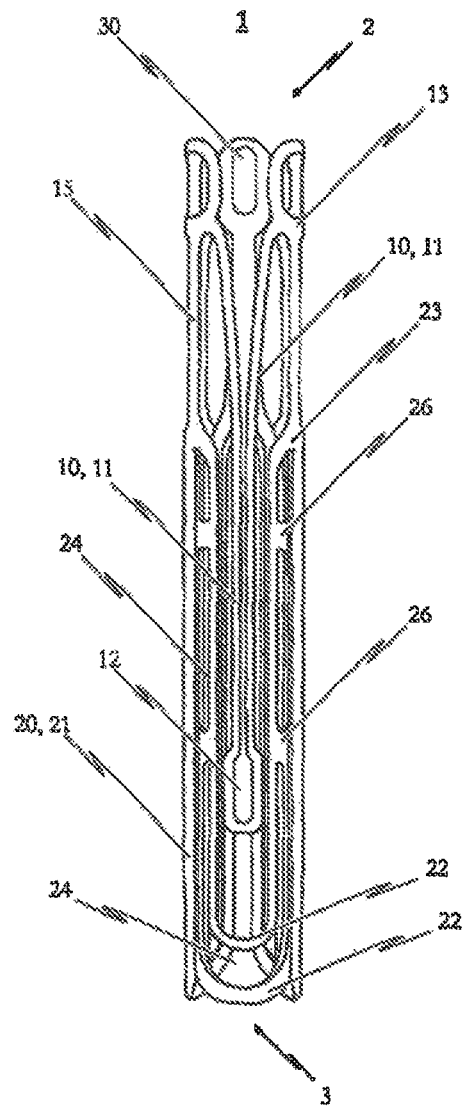
FIG. 5a shows a fifth preferred embodiment of a self-expandable endoprosthesis for the medical device proposed by the invention in its first, pre-determined mode in which the medical device is in its collapsed state.
Figure 5B:
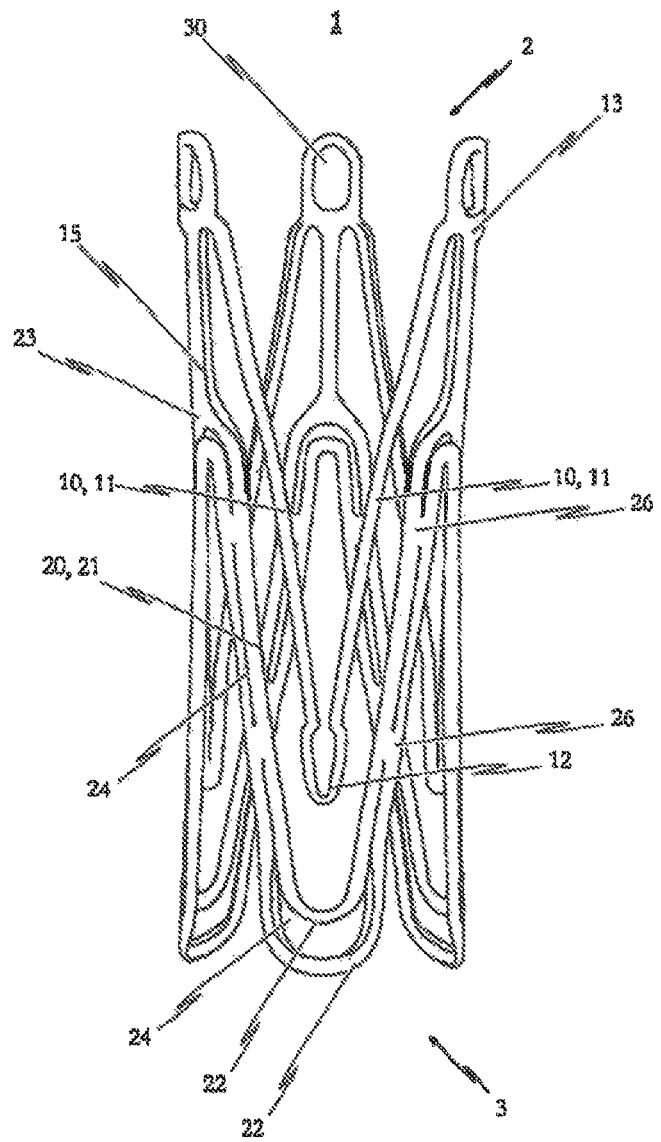
FIG. 5b shows the endoprosthesis illustrated in FIG. 5a in a state between its first, pre-definable mode and its second mode in which the medical device is in its expanded state.
Figure 5C:
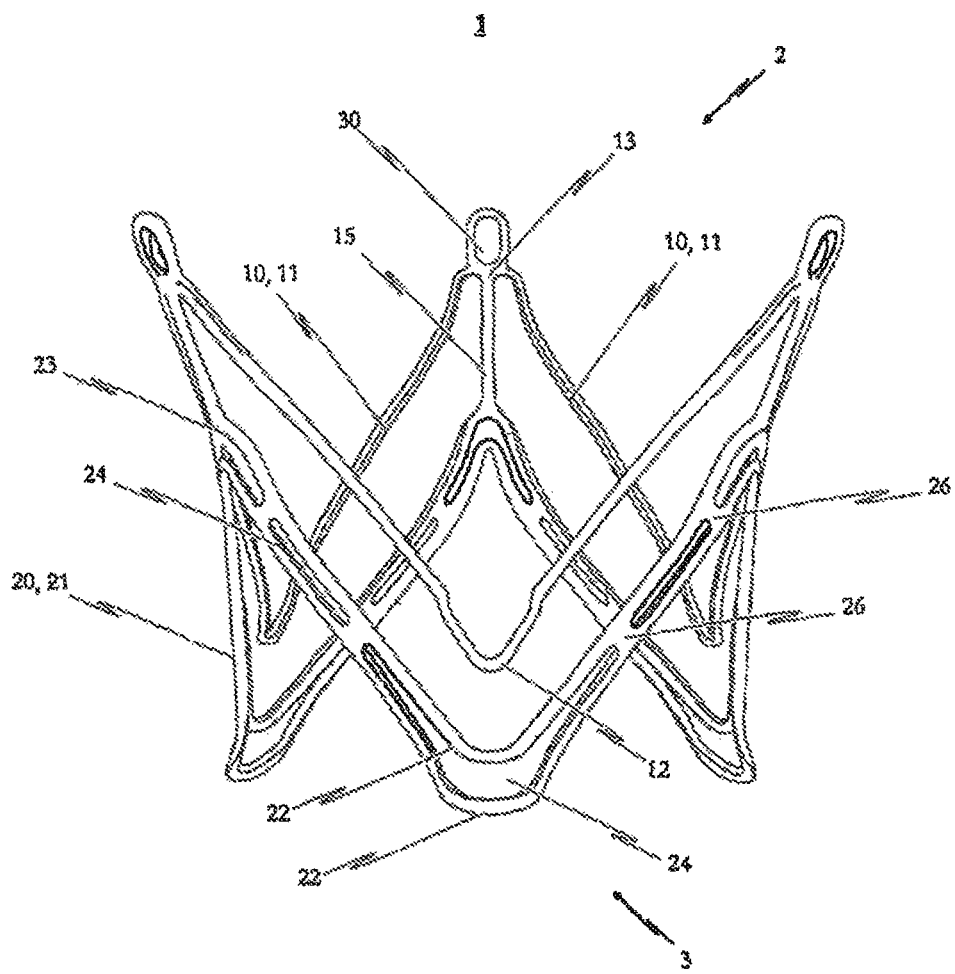
FIG. 5c shows the endoprosthesis illustrated in FIG. 5a in its second mode in which the medical device is in its expanded state.
Figure 5D:
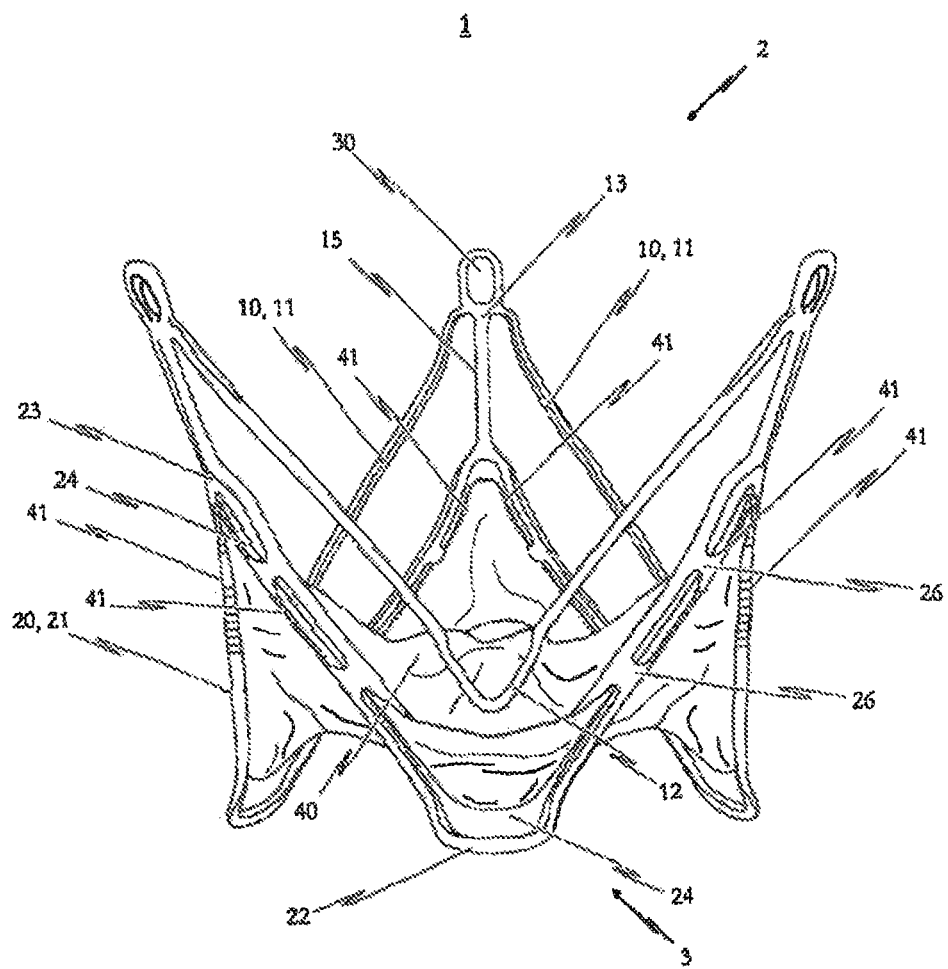
FIG. 5d illustrates a fifth preferred embodiment of the medical device proposed by the invention in its expanded state, with an endoprosthesis of the type illustrated in FIG. 5c and a heart valve prosthesis attached to it and opened out.
Figure 5E:
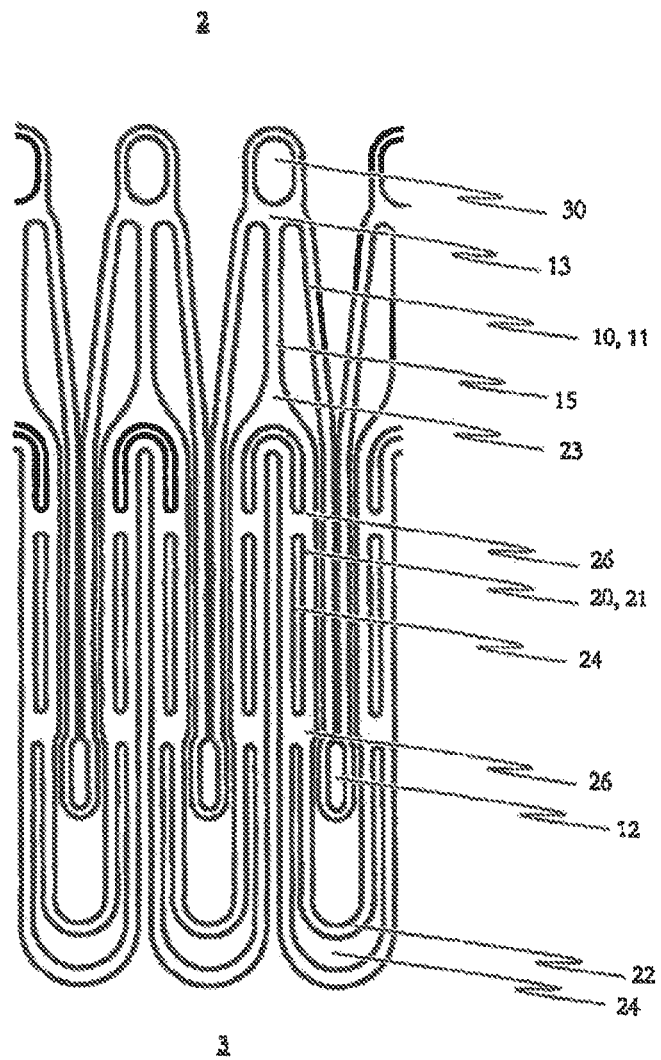
FIG. 5e is a flat projection of a cutting pattern which can be used for the production of the fifth, preferred, self-expandable endoprosthesis in order to cut the endoprosthesis illustrated in FIG. 5a integrally from a metal tube.
Figure 6A:
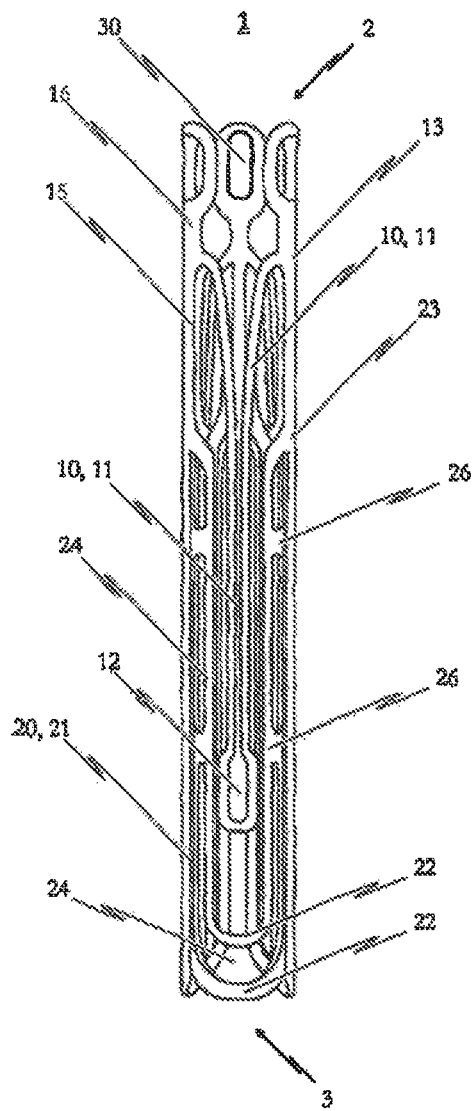
FIG. 6a shows a sixth preferred embodiment of a self-expandable endoprosthesis for the medical device proposed by the invention in its first, pre-determined mode in which the medical device is in its collapsed state.
Figure 6B:
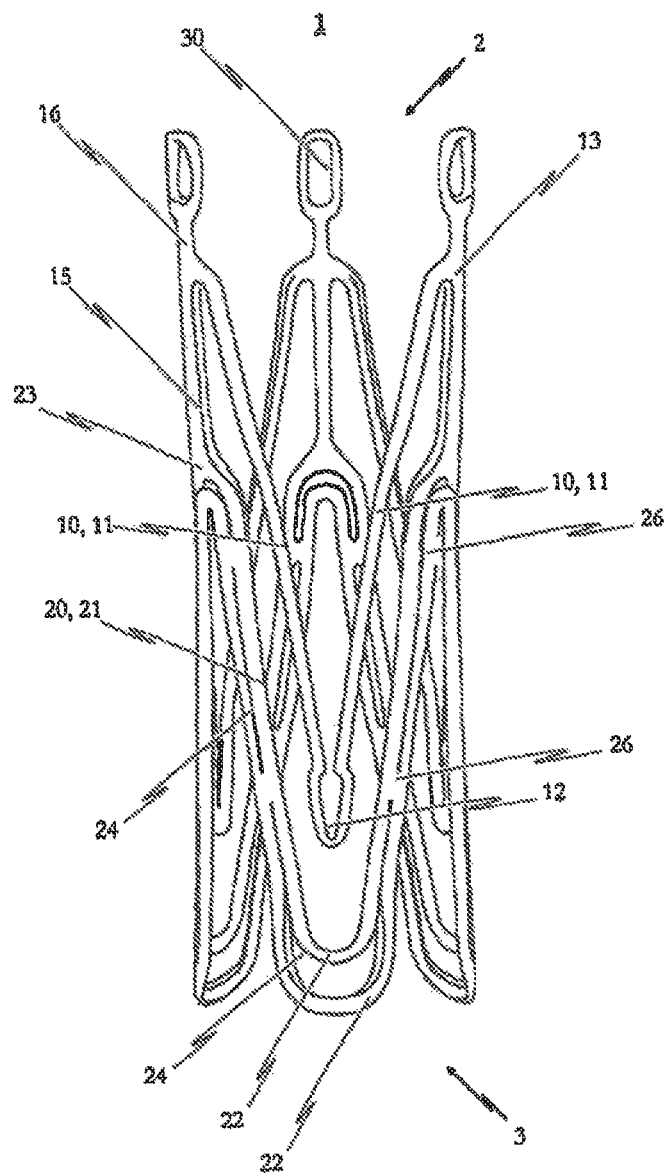
FIG. 6b shows the endoprosthesis illustrated in FIG. 6a in a state between its first, pre-definable mode and its second mode in which the medical device is in its expanded state.
Figure 6C:
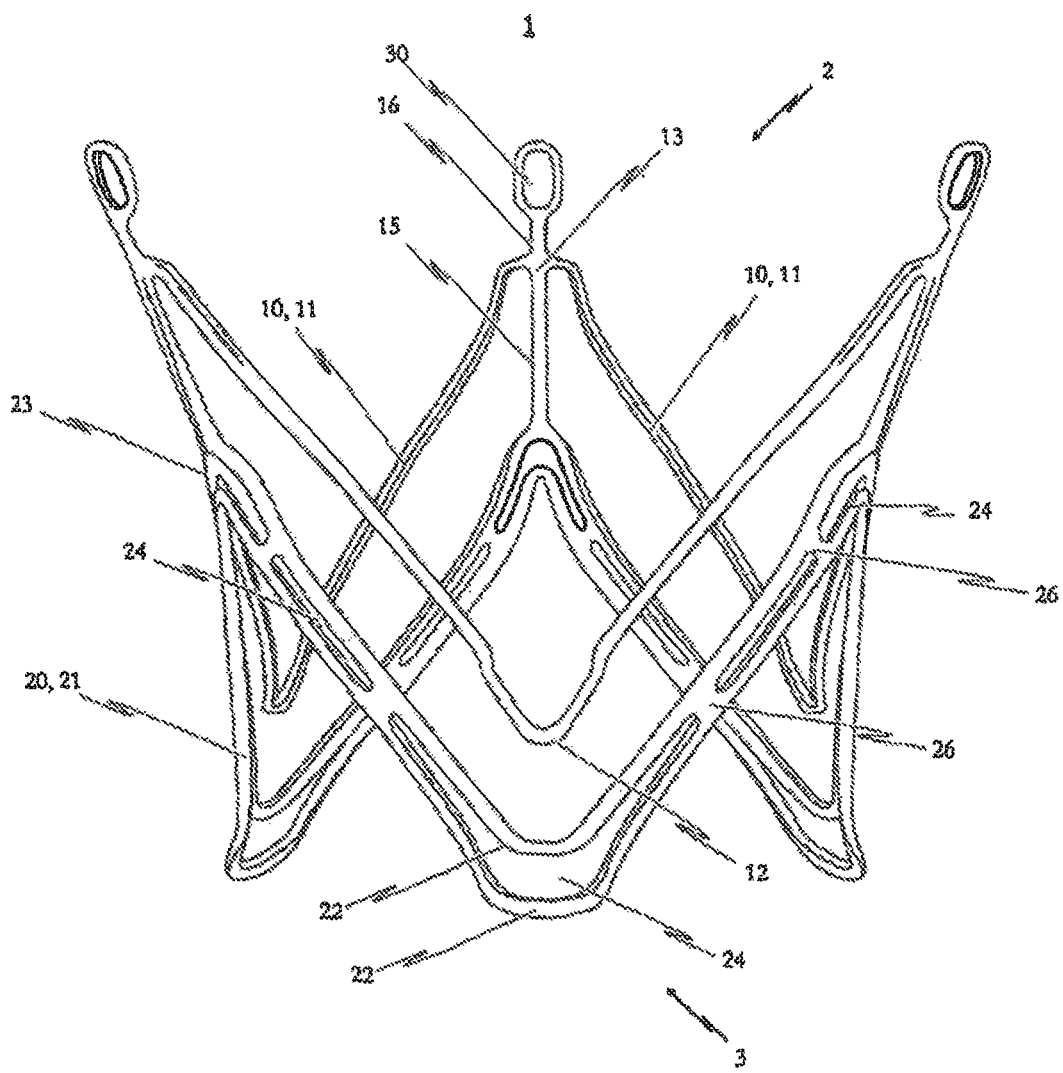
FIG. 6c shows the endoprosthesis illustrated in FIG. 6a in its second mode in which the medical device is in its expanded state.
Figure 6D:
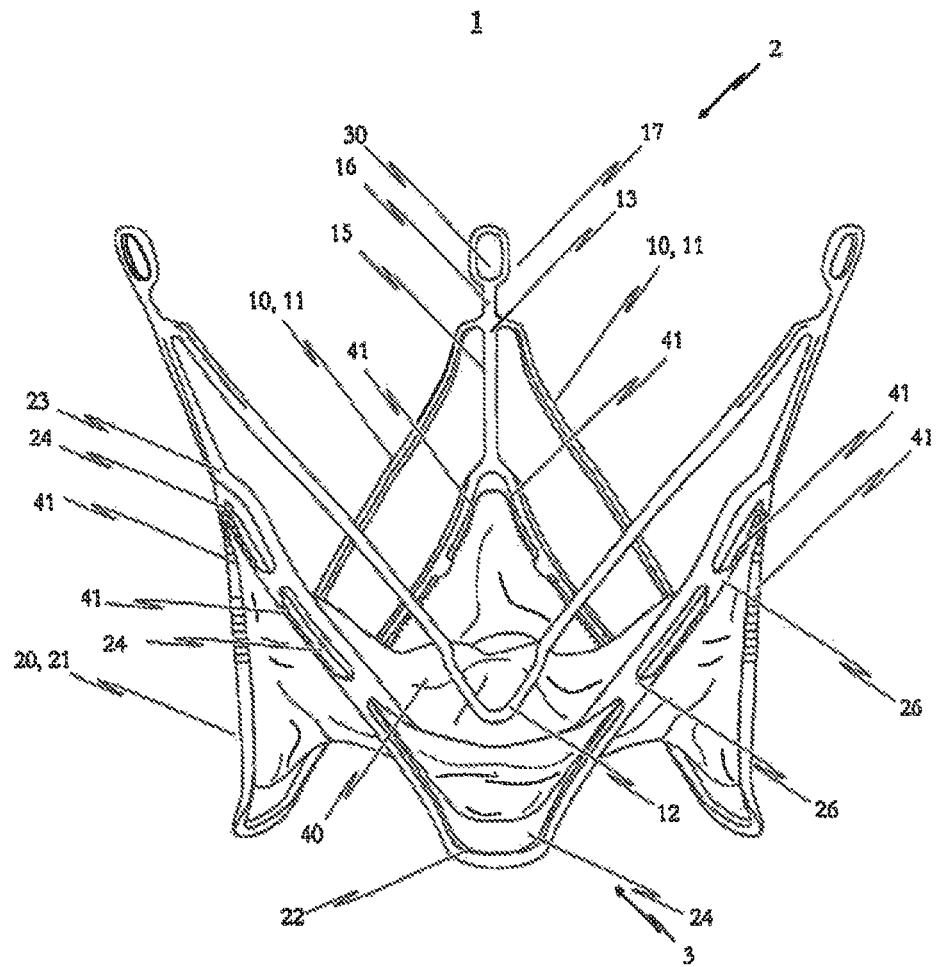
FIG. 6d illustrates a sixth preferred embodiment of the medical device proposed by the invention in its expanded state, with an endoprosthesis of the type illustrated in FIG. 6c and a heart valve prosthesis attached to it and opened out.
Figure 6E:
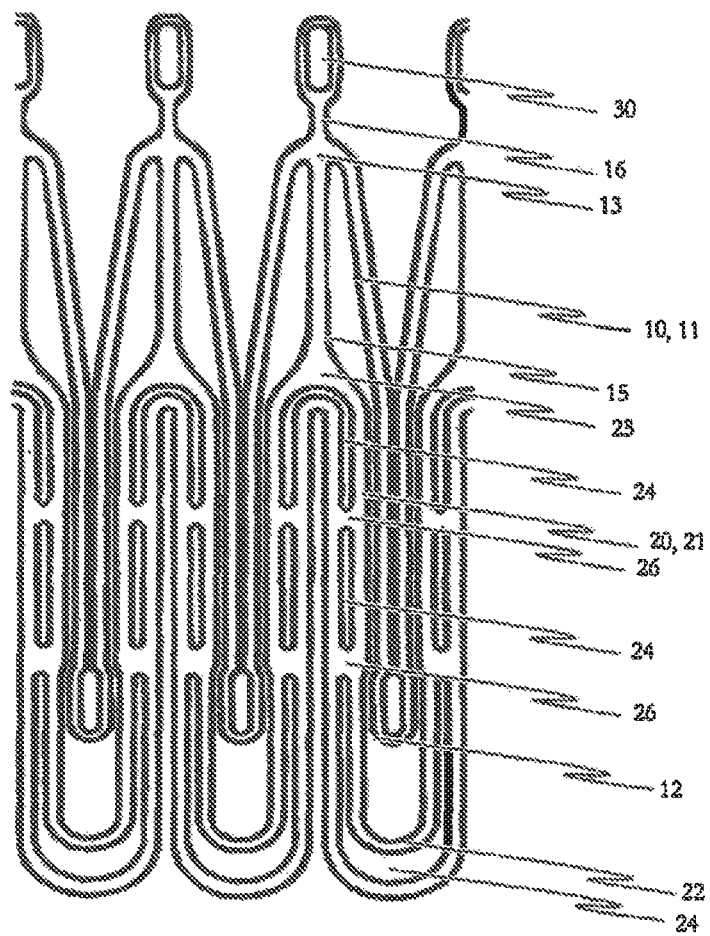
FIG. 6e is a flat projection of a cutting pattern which can be used for the production of the sixth, preferred, self-expandable endoprosthesis in order to cut the endoprosthesis illustrated in FIG. 6a integrally from a metal tube.
Figure 7A:
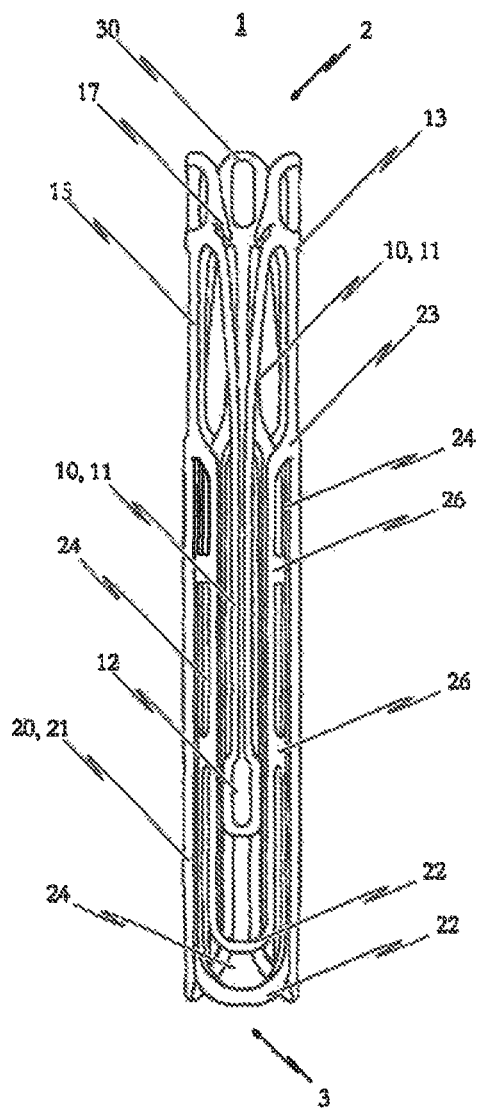
FIG. 7a shows a seventh, preferred embodiment of a self-expandable endoprosthesis for the medical device proposed by the invention in its first, pre-determined mode in which the medical device is in its collapsed state.
Figure 7B:
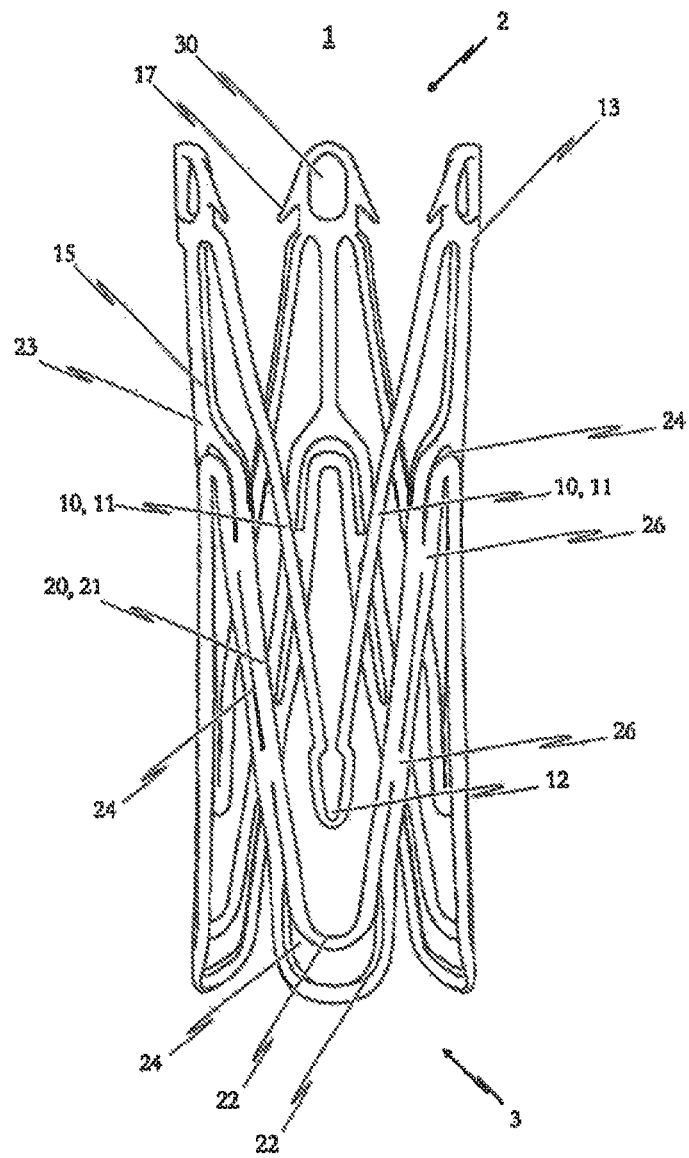
FIG. 7b shows the endoprosthesis illustrated in FIG. 7a in a state between its first, pre-definable mode and its second mode in which the medical device is in its expanded state.
Figure 7C:
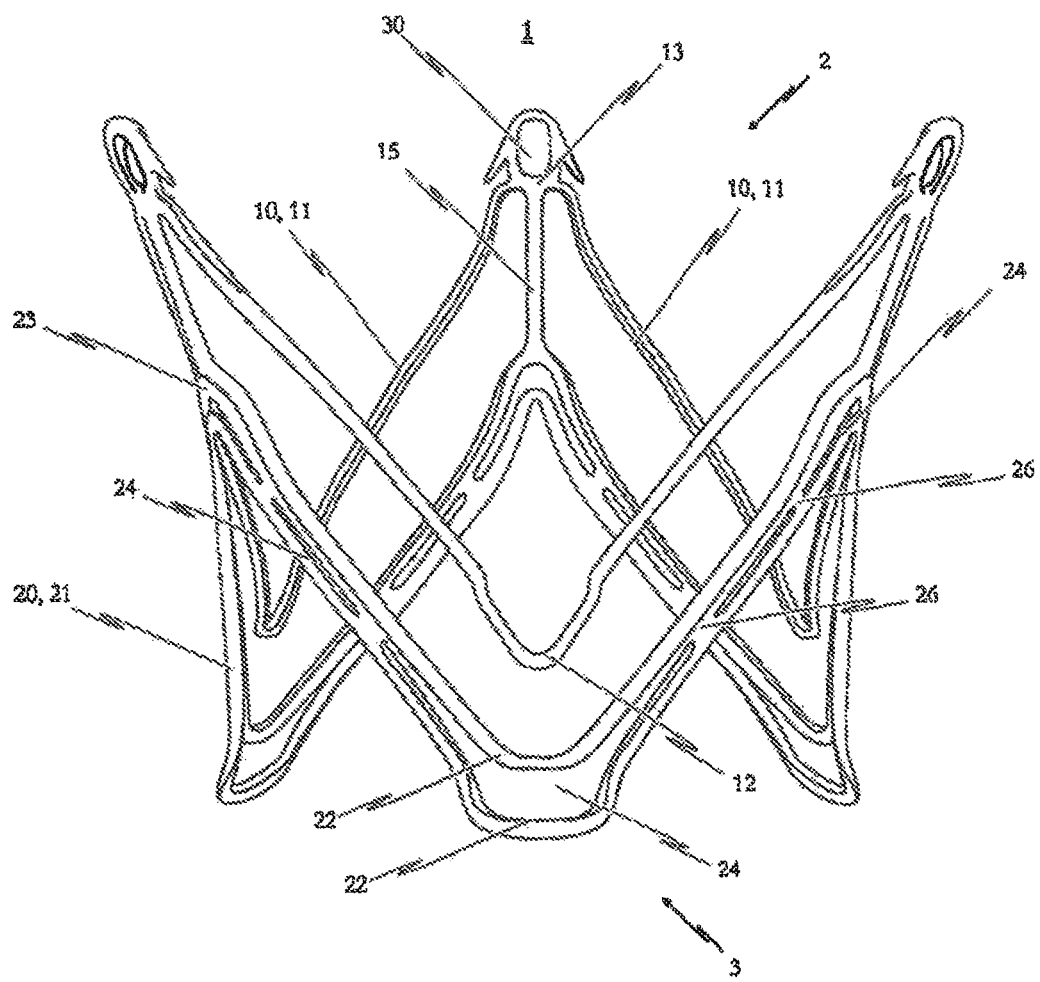
FIG. 7c shows the endoprosthesis illustrated in FIG. 7a in its second mode in which the medical device is in its wended state.
Figure 7D:
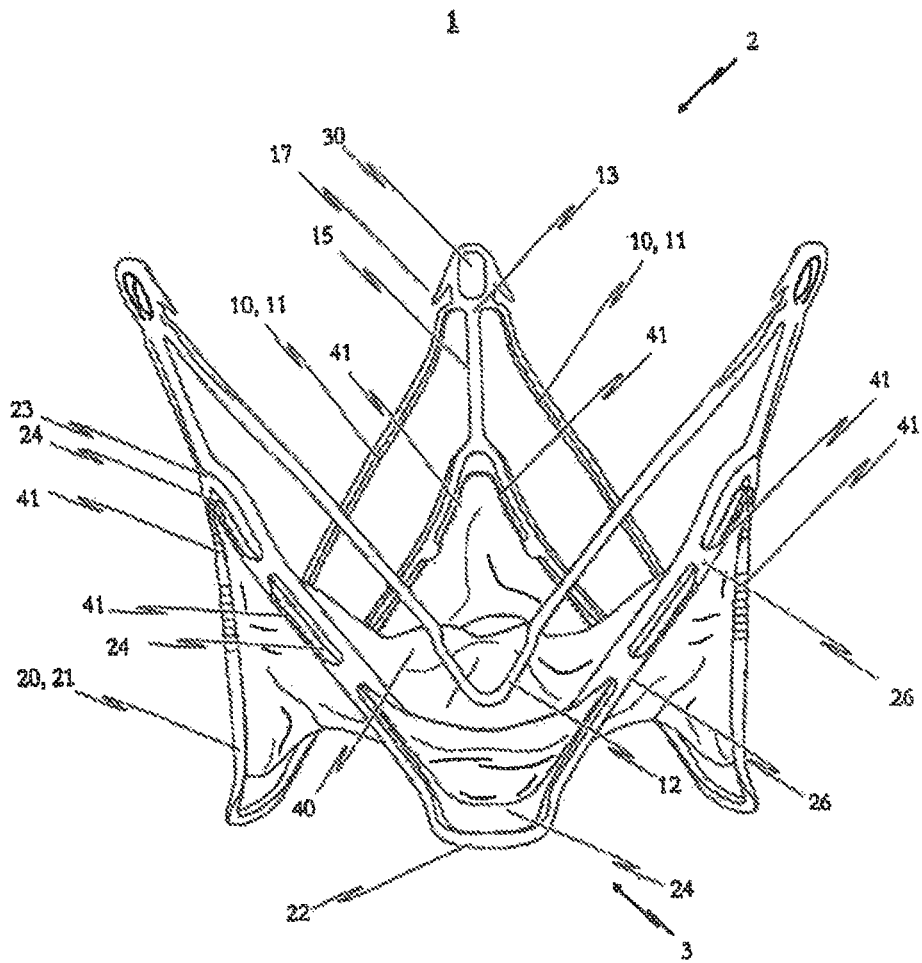
FIG. 7d illustrates a seventh preferred embodiment of the medical device proposed by the invention in its expanded state, with an endoprosthesis of the type illustrated in FIG. 7c and a heart valve prosthesis attached to it and opened out.
Figure 7E:
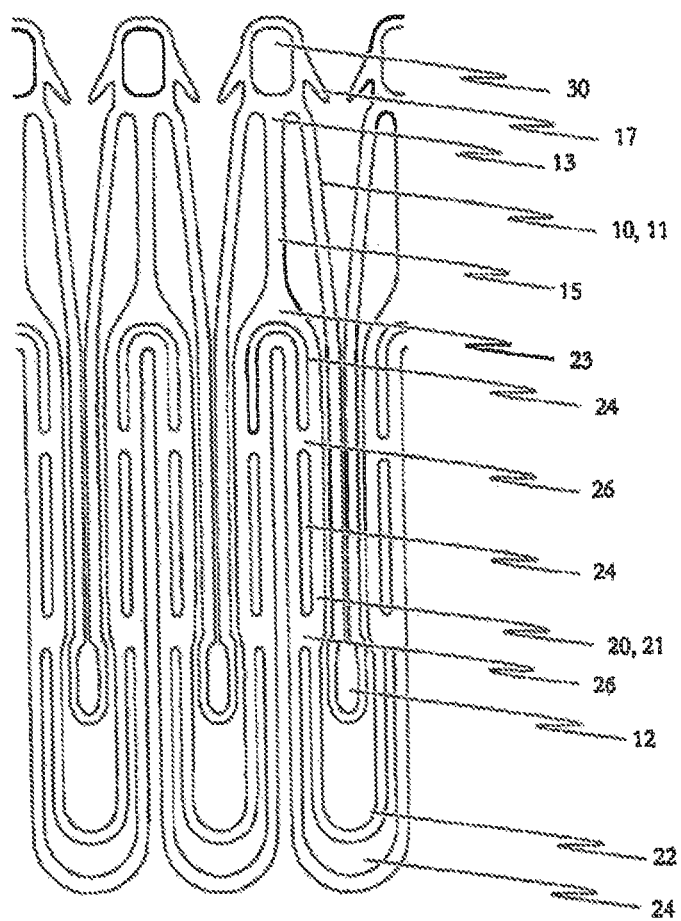
FIG. 7e is a flat projection of a cutting pattern which can be used for the production of the seventh preferred, self-expandable endoprosthesis in order to cut the endoprosthesis illustrated in FIG. 7a integrally from a metal tube.

FIG. 5e illustrates a flat projection of a cutting pattern which may be used for production of the fifth preferred embodiment of the self-expandable endoprosthesis 1 in order to cut the endoprosthesis 1 illustrated in FIG. 5a integrally from a metal tube.

The sixth preferred embodiment of the self-expandable endoprosthesis and the medical device proposed by the invention illustrated in FIGS. 6a to 6e corresponds to a combination of the second preferred embodiment illustrated in FIGS. 2a to 2c and the fifth preferred embodiment described above with reference to FIGS. 5a to 5e. Specifically, therefore, the endoprosthesis 1 based on the second preferred embodiment is provided with additional anchoring portions 26 at the respective retaining arches 21, which interrupt the slots 24 extending in the longitudinal direction of the retaining arches 21.

The seventh preferred embodiment of the endoprosthesis 1 and the medical device proposed by the invention illustrated in FIGS. 7a to 7e corresponds to a combination of the third and fifth embodiments described above, in which case the respective fixing eyes 30 are provided with barbs 17 and the respective retaining arches 21 are provided with reinforcing portions 26.

Figure 8A:
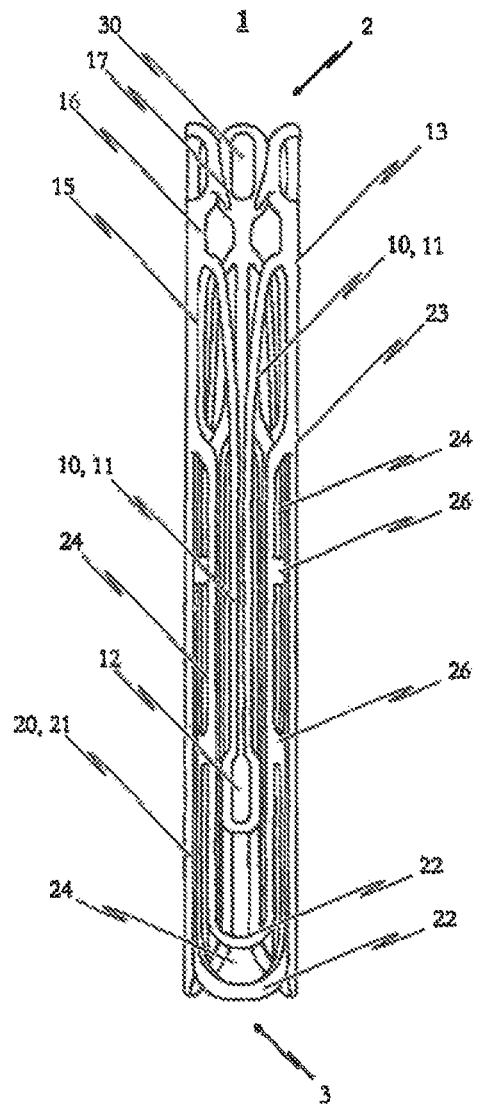
FIG. 8a shows an eighth, preferred embodiment of a self-expandable endoprosthesis for the medical device proposed by the invention in its first, pre-determined mode in which the medical device is in its collapsed state.
Figure 8B:
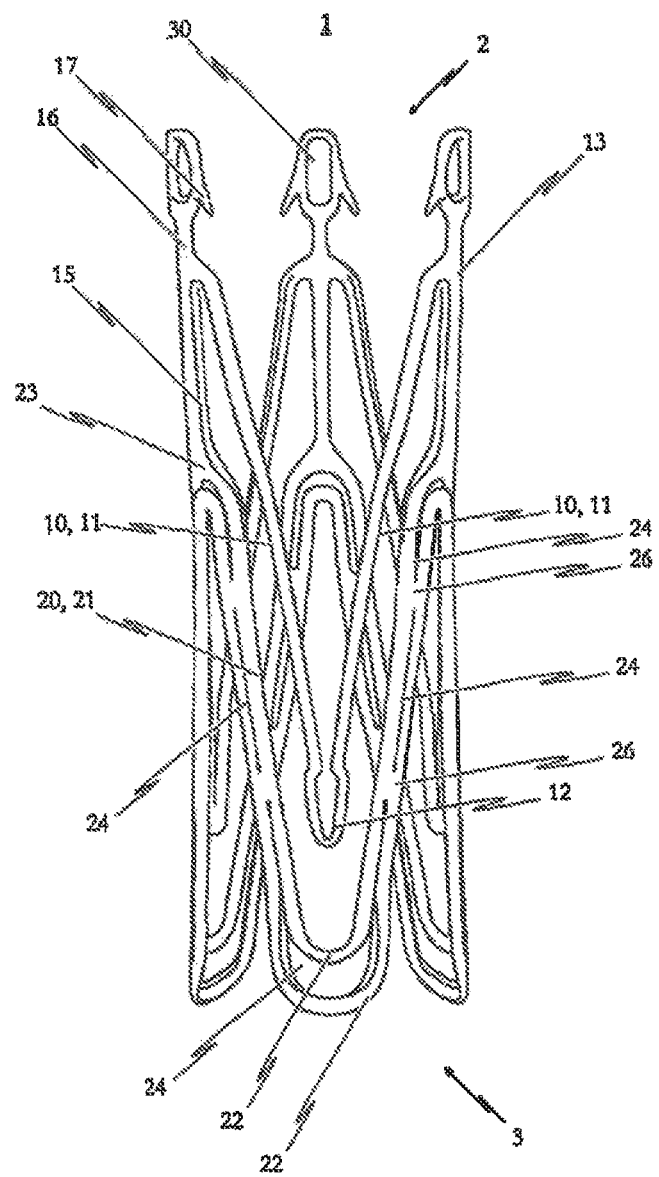
FIG. 8b shows the endoprosthesis illustrated in iso FIG. 8a in a state between its first, pre-definable mode and its second mode in which the medical device is in its expanded state.
Figure 8C:
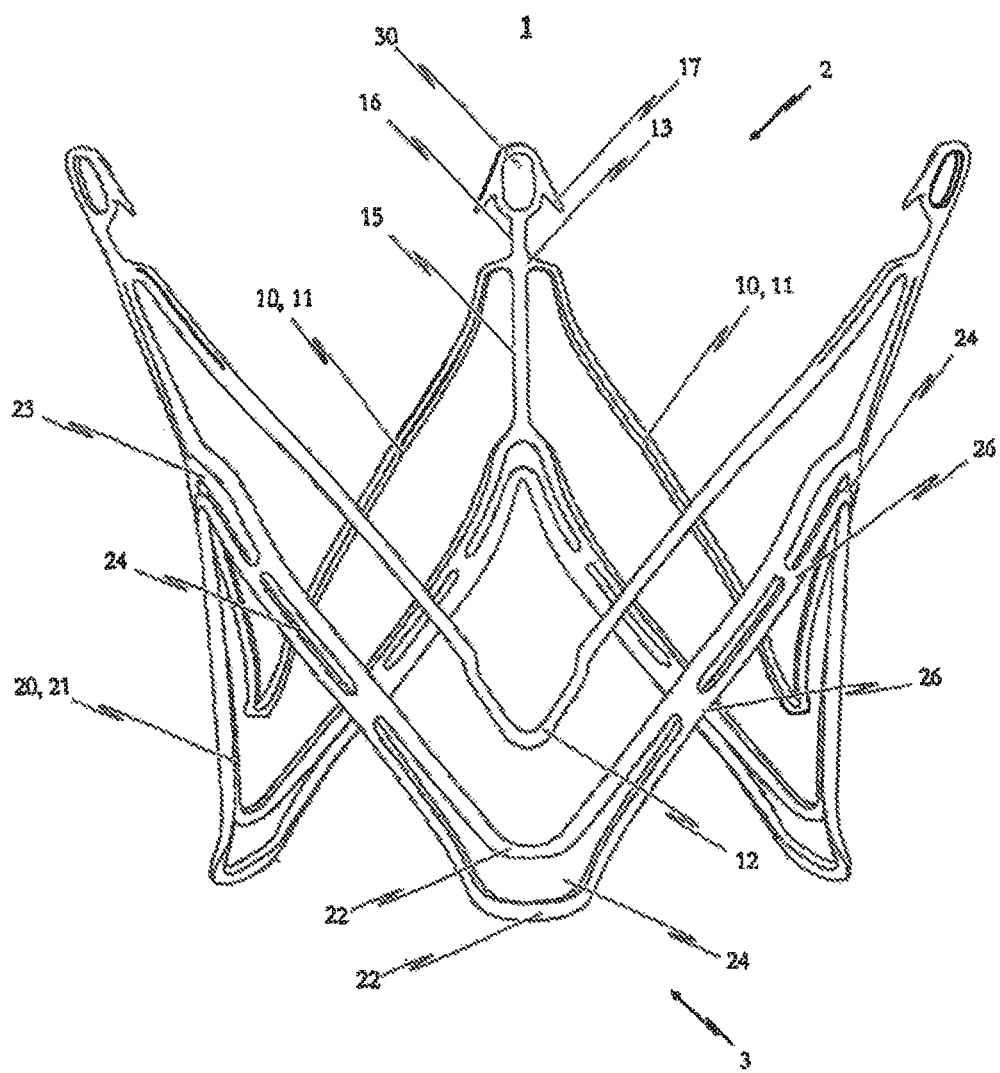
FIG. 8c shows the endoprosthesis illustrated in FIG. 8a in its second mode in which the medical device is in its expanded state.
Figure 8D:
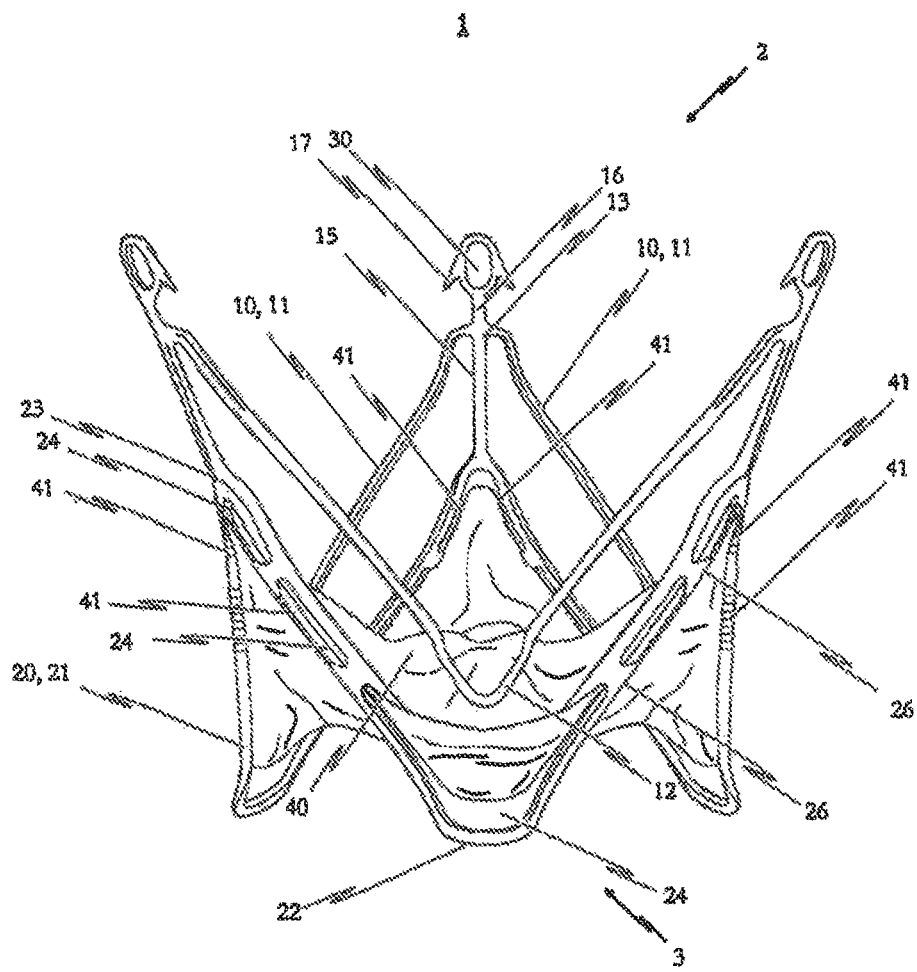
FIG. 8d illustrates an eighth preferred embodiment of the medical device proposed by the invention in its expanded state, with an endoprosthesis of the type illustrated in FIG. 8c and a heart valve prosthesis attached to it and opened out.
Figure 8E:
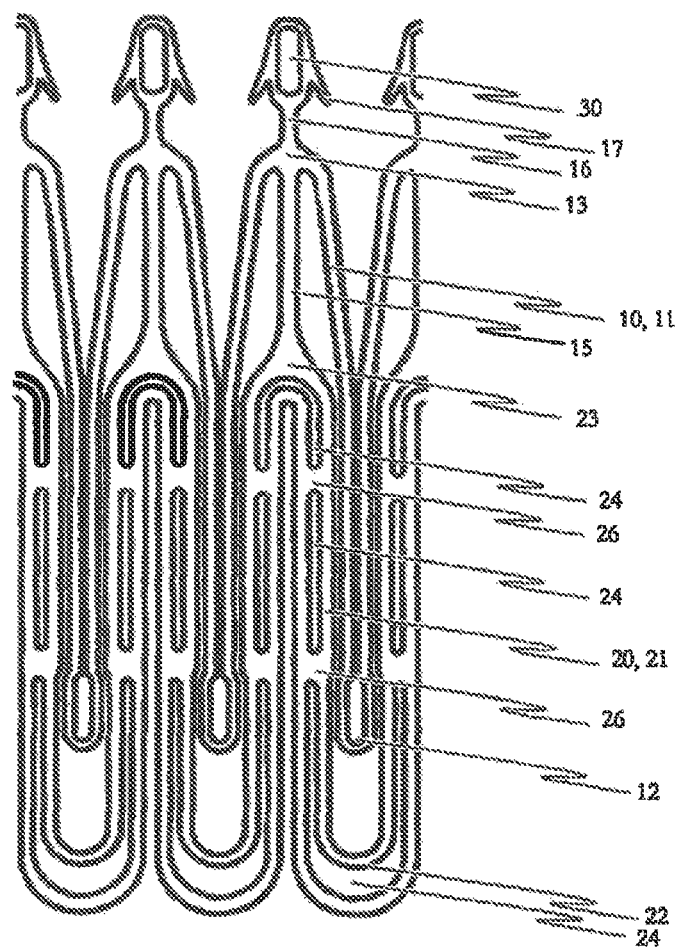
FIG. 8e is a flat projection of a cutting pattern which can be used for the production of the eighth preferred, self-expandable endoprosthesis in order to cut the endoprosthesis illustrated in FIG. 8a integrally from a metal tube.

The eighth preferred embodiment of the self-expandable endoprosthesis and the medical device proposed by the invention illustrated in FIGS. 8a to 8c corresponds to a combination of the fourth and fifth embodiments, in which case the respective retaining arches 21 are provided with reinforcing portions 26 and the fixing eyes 30 provided with barbs 17 are connected to the respective arms 11 of the adjacent positioning arches 10 by means of a connecting web 16 extending essentially in the longitudinal direction of the endoprosthesis 1.

Figure 9A:
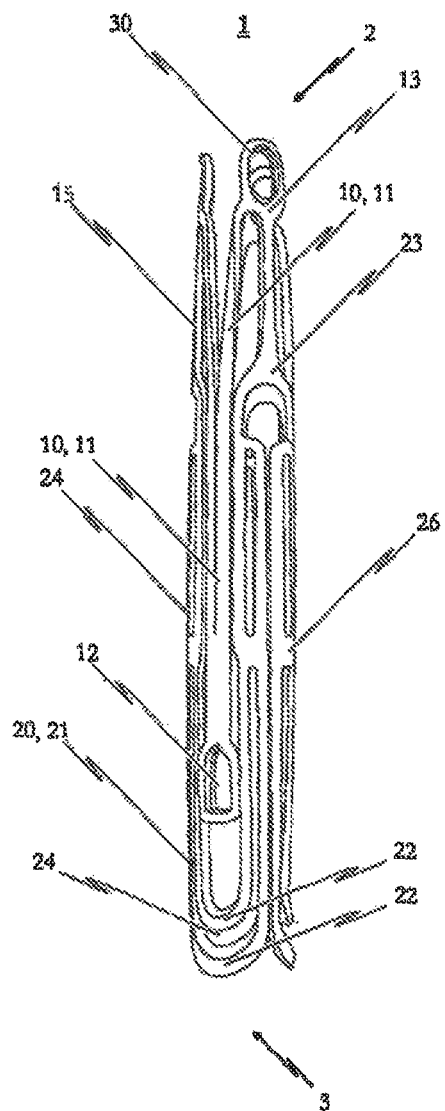
FIG. 9a shows a ninth, preferred embodiment of a self-expandable endoprosthesis for the medical device proposed by the invention in its first, pre-determined mode in which the medical device is in its collapsed state.
Figure 9B:
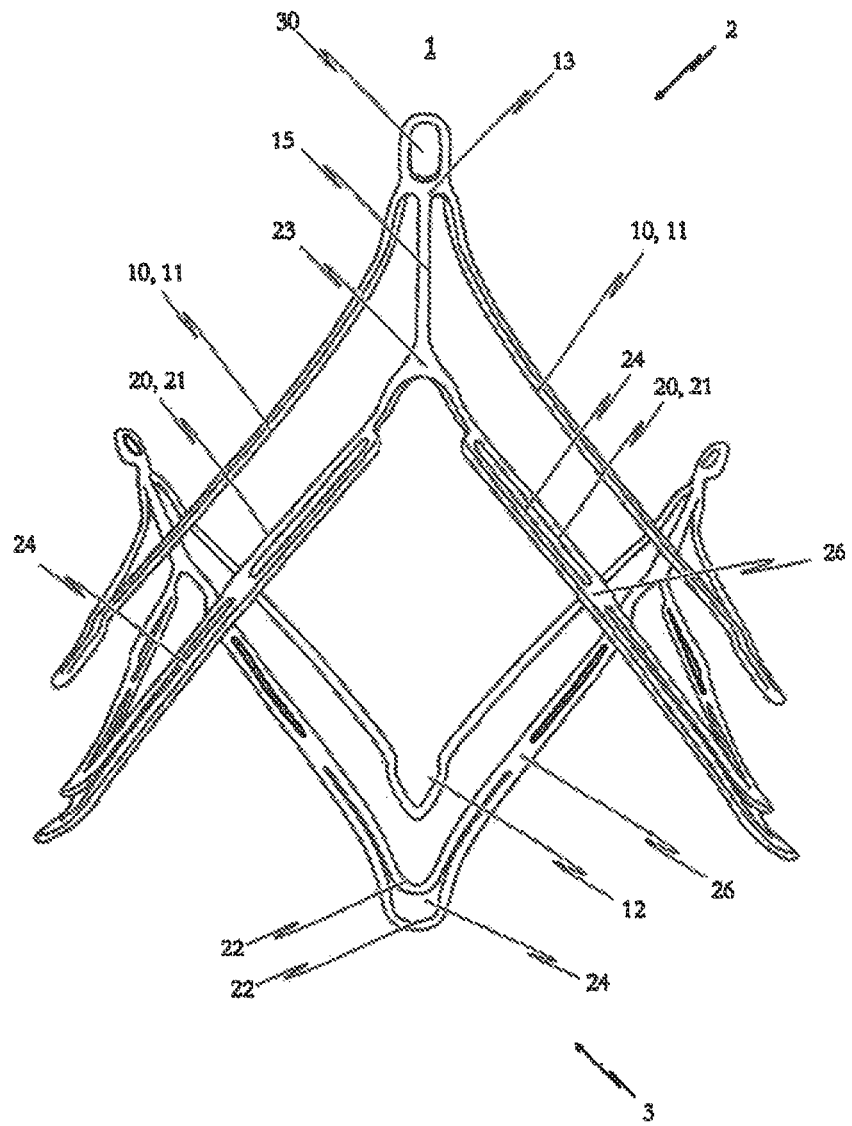
FIG. 9b is a perspective side view of a connecting web between an end portion of a positioning arch and an end portion of an associated retaining arch of the endoprosthesis illustrated in FIG. 9a in its second mode in which the medical device is in its expanded state.
Figure 9C:
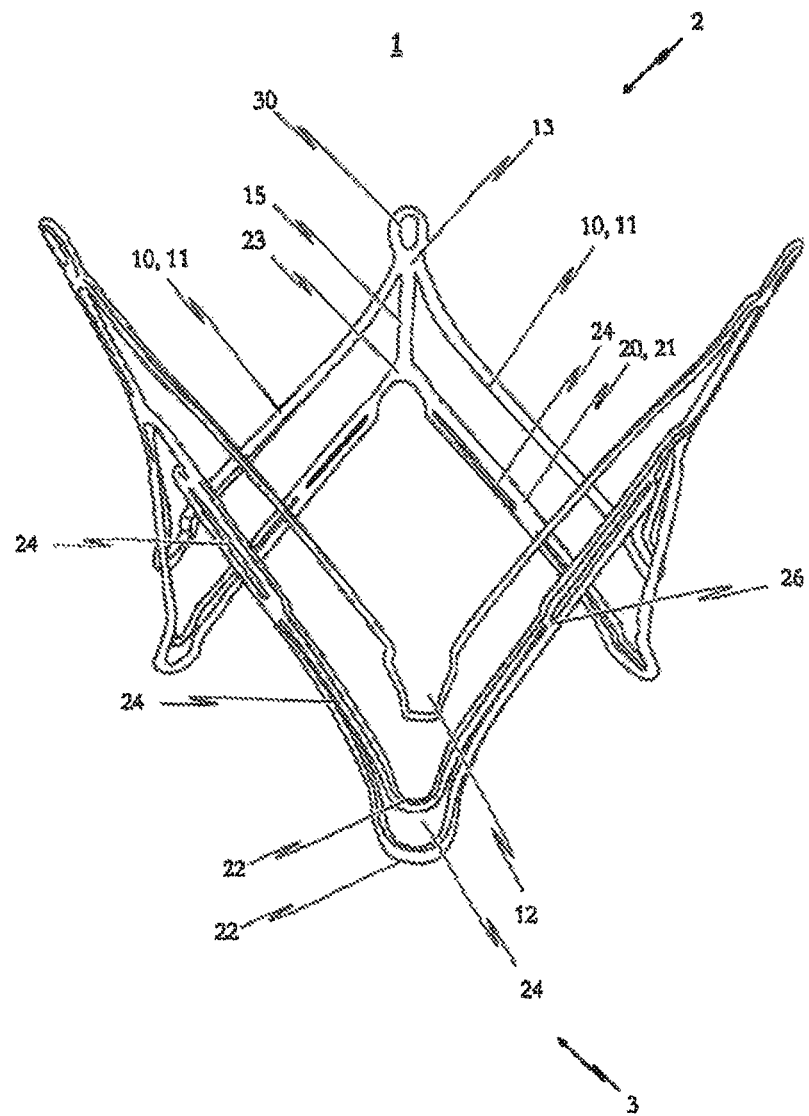
FIG. 9o is a perspective side view of a positioning arch and the associated retaining arch of the endoprosthesis illustrated in FIG. 9a in its second mode in which the medical device is in its expanded state.
FIG. 9d is a perspective plan view of the distal region of the endoprosthesis illustrated in FIG. 9a in its second mode in which the medical device is in its expended state.
FIG. 9e is a flat projection of a cutting pattern which can be used for the production of the ninth preferred embodiment of the self-expandable endoprosthesis in order to cut the endoprosthesis illustrated in FIG. 9a integrally from a metal tube.
Figure 9D:
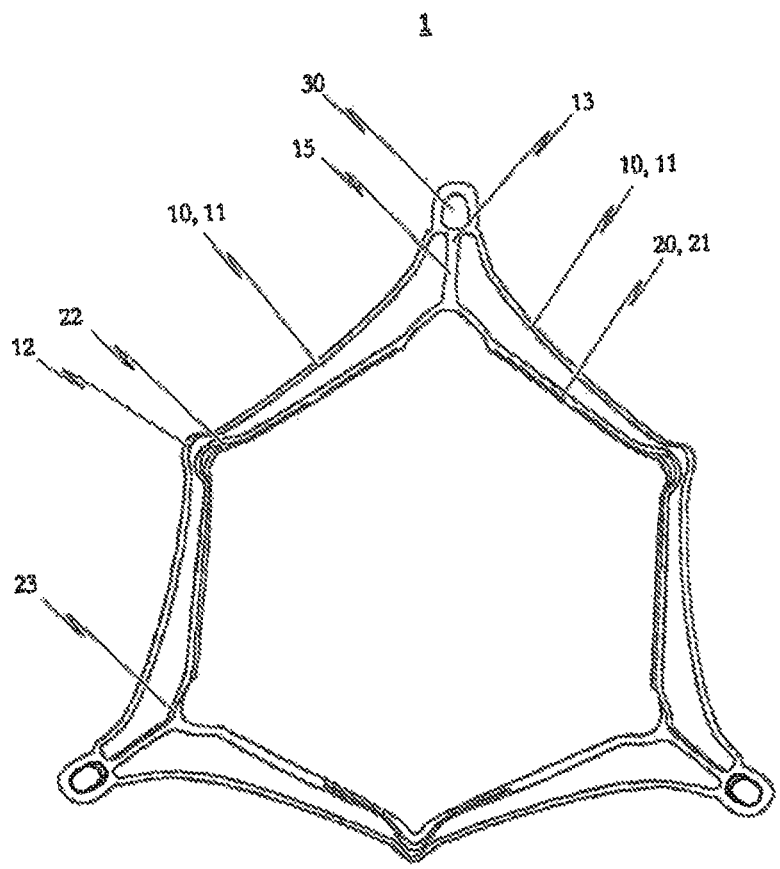

The ninth preferred embodiment of the self-expandable endoprosthesis for the medical device proposed by the invention illustrated in FIGS. 9a to 9d is of a slightly modified shape compared with the first embodiment (see FIGS. 1a to 1c). The endoprosthesis 1 based on the ninth embodiment is illustrated in its first pre-defined mode in FIG. 9a. FIGS. 9b and 9c respectively show a perspective side view of the endoprosthesis 1 based on the ninth embodiment in its second mode. Specifically, the connecting web 15 between the end portion 13 of a positioning arch 10, 11 and the end portion 23 of an associated retaining arch 20, 21 is illustrated in FIG. 9b. FIG. 9c, on the other hand, illustrates the positioning arches 10, 11 and the associated retaining arches 20, 21 of the endoprosthesis 1 illustrated in FIG. 9a.

Figure 9E:
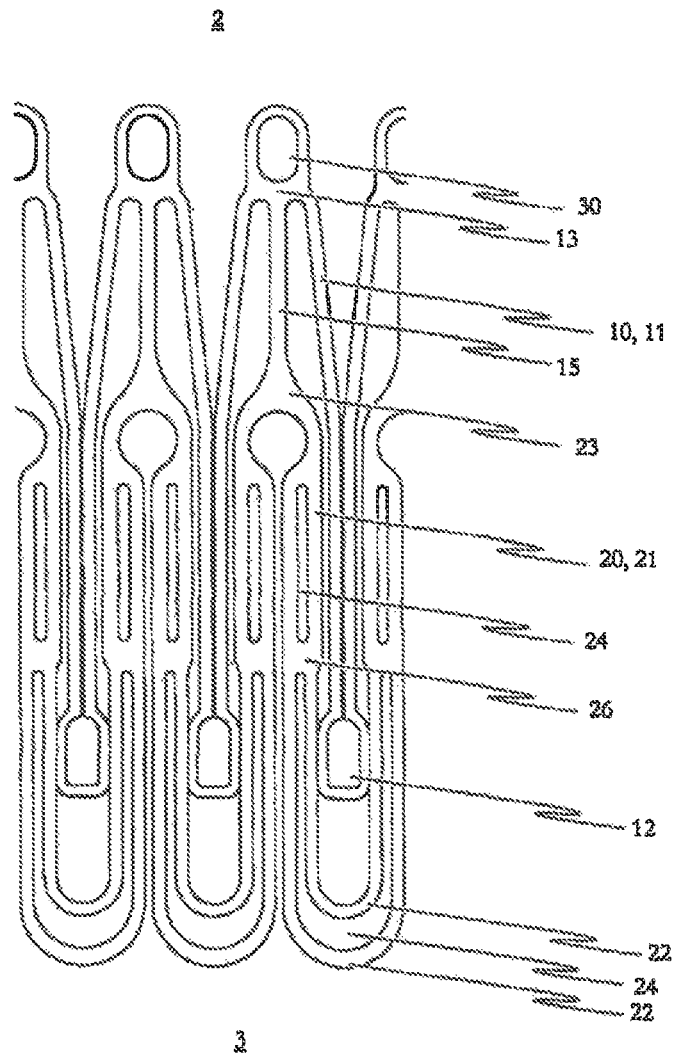

FIG. 9e illustrates a flat projection of a cutting pattern which may be used to produce the ninth preferred embodiment of the self-expandable endoprosthesis in order to cut the endoprosthesis illustrated in FIG. 9a integrally from a metal tube.

Unlike the first embodiment, the respective head portions 12 of the positioning arches 10 pointing towards the proximal end 3 of the endoprosthesis are of a slightly wider design at the proximal end in the ninth embodiment of the endoprosthesis 1. Although the head portions 12 of the positioning arches 10 have a slightly rectangular in shape compared with the first embodiment, all the respective corners of the head portions 12 are rounded so that the vessel wall is not damaged when the positioning arches 10 engage in the pockets of the heart valve to be replaced. The advantage of the slightly wider design of the head portions 12 of the positioning arches 10 is that the positioning arches 10 can be placed in the pockets of the native heart valve with the smallest possible clearance during the implantation operation, thereby enabling even more accurate positioning of the medical device at the implantation site.

As with the embodiments described above, a total of two positioning webs or arms 11 extend from the head portion 12 of the positioning arches 10 to the distal end 2 of the endoprosthesis 1 for every positioning arch 10 in the ninth embodiment of the endoprosthesis 1, which merge at the distal end 2 of the endoprosthesis 1 into an eye-shaped element 30. This eye-shaped element 30 serves as a fixing means for attaching the endoprosthesis 1 and hence the medical device to an introduction catheter system.

Specifically in the case of the ninth embodiment of the endoprosthesis 1, the respective fixing eyes 30 are disposed between the two arms 11 of two mutually adjacent positioning arches 10. The connecting web 15 extending essentially in the longitudinal direction of the endoprosthesis 1 opens into the transition portion 13 between the two arms 11 of two mutually adjacent positioning arches 10 where the fixing eye 30 is formed. At the proximal end of the connecting web 15, the latter merges into the respective retaining arms 21 of two mutually adjacent retaining arches 20. This design is illustrated particularly clearly in FIG. 9d, which shows a perspective plan view of the distal region of the endoprosthesis illustrated in FIG. 9a in its second mode.

By contrast with the embodiments described above, the respective retaining arms 21 of the retaining arches 20 on the transition portion 23 between the two arms 21 of two mutually adjacent retaining arches 20 are not provided with slots or elongate holes 24 in the ninth embodiment of the endoprosthesis 1. Due to the fact that only one arm web 21 actually opens into the transition portion 23 between the two arms 21 of two mutually adjacent retaining arches 20 for each retaining arch, there are advantageously no components belonging to the retaining arches 20 which project out from the respective retaining arches 20 in the radial direction when the endoprosthesis 1 is in the expanded state (see FIG. 9b for example). Especially when the endoprosthesis 1 is in the expanded state, no barb portion such as usually extends through the slots 24 projects out in the radial direction at the transition portions 23 between the two arms 21 of two mutually adjacent retaining arches 20, the tip of which points in the direction of the distal retaining region 2 of the endoprosthesis 1. Due to the fact that a barb portion of this type is dispensed with in the ninth embodiment, the endoprosthesis 1 can be explanted particularly easily and removed from the patient's body again.

Although the ninth embodiment of the endoprosthesis 1 does not have slots or elongate holes 24 at the respective transition portions 23 between the two arms 21 of two mutually adjacent retaining arches 20, the respective retaining arms 21 of the endoprosthesis 1 have reinforcing portions 26, which are respectively provided on portions of the retaining arms 21 that are not congruent with the transition portions 23 between the two arms 21 of two mutually adjacent retaining arches 20.

Figure 10:
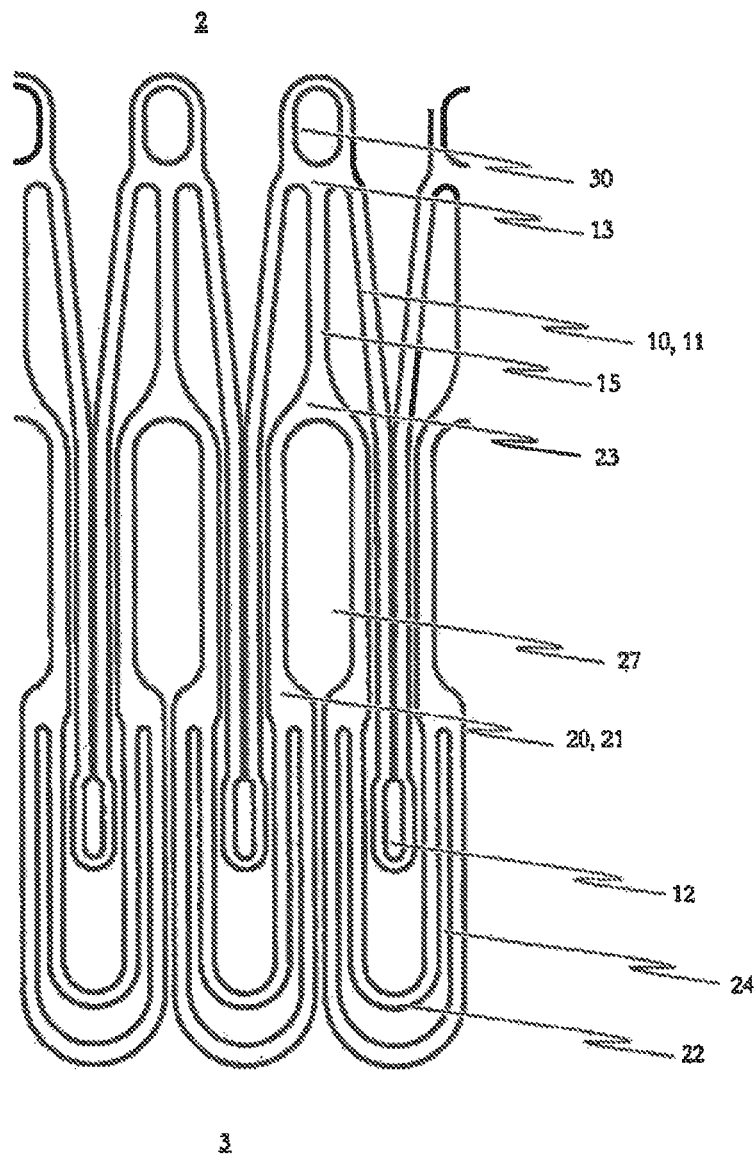
FIG. 10 is a flat projection of a cutting pattern which can be used for the production of another preferred embodiment of the self-expandable endoprosthesis in order to cut an endoprosthesis integrally from a metal tube.
Figure 11:
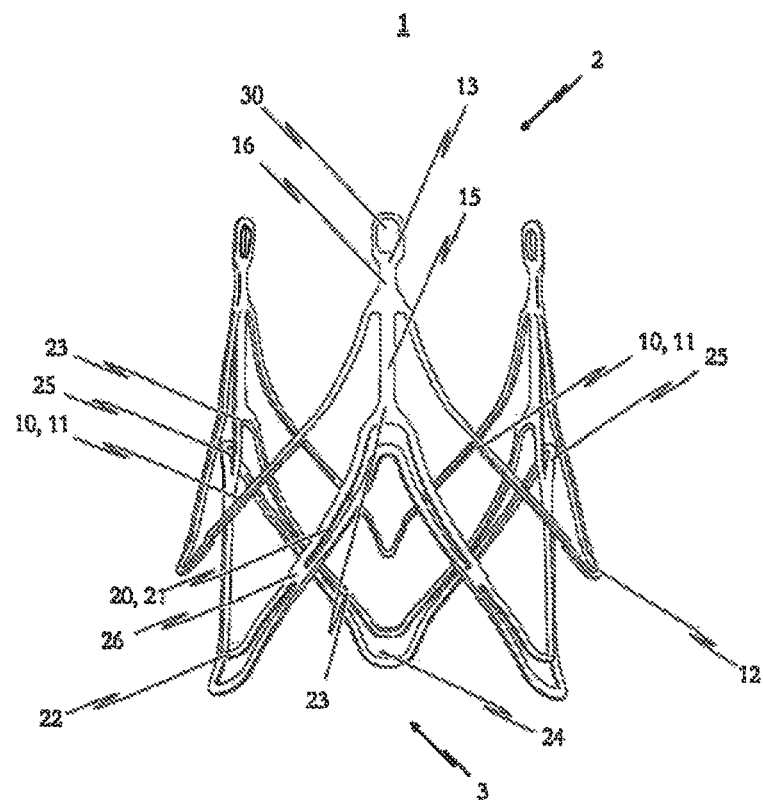
FIG. 11 shows another preferred embodiment of a self-expandable endoprosthesis for the medical device, proposed by the invention in its second mode in which the medical device is in its expanded state.

FIG. 10 illustrates a flat projection of a cutting pattern, which may be used for the production of another preferred embodiment of the self-expandable endoprosthesis 1 in order to cut an endoprosthesis integrally from a metal tube. The cutting pattern illustrated in FIG. 9 differs from the cutting pattern illustrated in FIG. 1e due to the fact that the distally disposed slots 24 extending in the longitudinal direction of the retaining arches 21 have been omitted from the respective retaining arches 21 on the one hand, and a bigger space 27 is cut from between the adjacent retaining arches 21 in order to save on material on the other hand, FIG. 11 illustrates another preferred embodiment of a self expandable endoprosthesis 1 for an alternative design of the medical device proposed by the invention. Specifically, the endoprosthesis 1 of the other preferred embodiment illustrated in FIG. 11 has assumed its second mode in which the medical device is in its expanded state and contains a different embodiment of the endoprosthesis 1 for the medical device proposed by the invention. Specifically, this is an endoprosthesis 1 which is in its second mode, i.e. after triggering the shape memory effect.

The endoprosthesis 1 illustrated in FIG. 11 differs from the endoprosthesis 1 illustrated in FIG. 1c due to the fact that in the case of the stent 1 illustrated in FIG. 11, an interconnecting web 16 extending essentially in the longitudinal direction of the endoprosthesis 1 is provided between the fixing eyes 30 and the transition portion 13 between the positioning arms 11 of two adjacent positioning arches 10, and the total length of the endoprosthesis 1 and hence the medical device is made longer. In order to ensure optimum ability to manoeuvre the medical device in the collapsed state, however, it is of advantage if the endoprosthesis 1 has as short a longitudinal extension as possible, especially if the implantation route to the heart valve leads through the arch of the aorta, in which case it is of advantage if the medical device is as short as possible (and the endoprosthesis 1 is also as short as possible) so that it can overcome this bend.

The endoprosthesis 1 illustrated in FIG. 11 also differs from the endoprosthesis of the embodiments described above due to the fact that when the endoprosthesis 1 is in the expanded state, a barb portion 25 projects through the slots 24 in the radial direction at the respective transition portions 23 between the two arms 21 of two mutually adjacent retaining arches 20, the tip of which points in the direction of the distal retaining region 2 of the endoprosthesis 1.

A more detailed description will be given below with reference to FIGS. 12a ad 12b, explaining how the medical device proposed by the invention is used to treat a condition of heart valve insufficiency.

The medical device proposed by the invention, and in particular the endoprosthesis 1 with the heart valve prosthesis 40 contained in it, is designed to be introduced into the patient's body either backwards or topically, i.e. coming from the heart apex, via a special catheter, positioned percutaneously orthotopically in vivo and assume the function of an insufficient or narrowed heart valve. FIG. 12a provides a schematic illustration of one possible implantation operation for the medical device proposed by the invention, whereby the medical device in this instance is introduced into the patient's body backwards using a special catheter. FIG. 12b provides a schematic view of the medical device proposed by the invention in the implanted state.

Figure 12A:
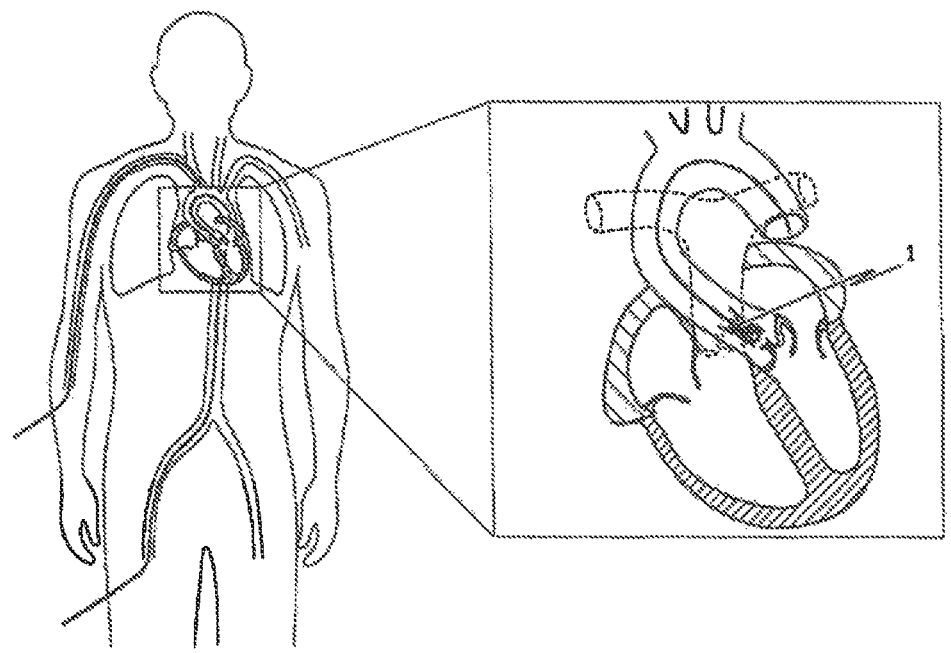
FIG. 12a is a schematic view intended to illustrate one possible implantation operation of the medical device proposed by this invention.
Figure 12B:
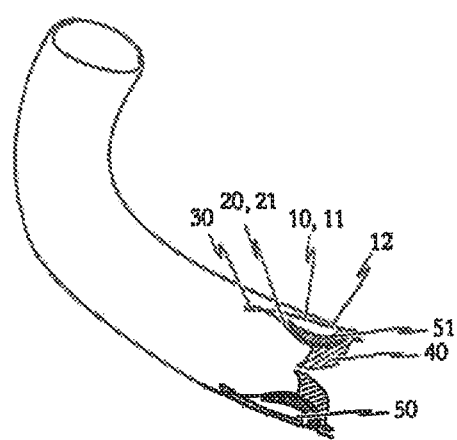
FIG. 12b is a schematic view of the medical device proposed by the invention in the implanted state.

In the case of the implantation route illustrated in FIG. 12a, the special catheter system, which is not specifically illustrated, containing the medical device with the heart valve prosthesis 40 and the endoprosthesis 1 serving as an anchoring stent are introduced by puncturing the A. femoris communis (inguinal artery). This catheter system is preferably moved forward to the aortal valve position assisted by angiographic (vessel display) and echocardiographic. (ultrasound) control, where the actual heart valve implantation then takes place.

Alternatively, a special catheter system can be pushed transapically from the heart apex through the left ventricle to the aortal valve, where a similar implantation of the endoprosthesis 1 with the heart valve prosthesis 40 is possible using a catheter tube modified accordingly.

As the special catheter system is being fed forwards, the medical device is preferably appropriately cooled, for example by rinsing the special catheter system with an appropriate coolant, such as a salt solution. When the medical device has been moved forward to the desired implantation site, cooling is interrupted, as a result of which the endoprosthesis 1 of the medical device is warmed to the body temperature (36° C.) of the patient, thereby triggering the shape memory effect of the endoprosthesis material.

Due to the triggering of the self-expanding property of the endoprosthesis 1, radial forces develop which act on the individual components of the endoprosthesis 1 and in particular on the respective positioning arches 10, 11 and retaining arches 20, 21 of the endoprosthesis 1. Since the endoprosthesis 1 of the medical device is still disposed in the introduction catheter system as before, the radial forces which develop once the critical switching temperature is exceeded and act on the individual components of the endoprosthesis 1 are still compensated by the introduction port of the introduction catheter system so that—in spite of the shape memory effect having been triggered—the endoprosthesis 1 of the medical device is forcibly held in its first (collapsed) shape.

By releasing the endoprosthesis 1 from the introduction catheter system in appropriate steps, the positioning arches 10, 11 of the endoprosthesis 1 are then moved out though the introduction port of the introduction catheter system. The positioning arches 10, 11 open out due to the radial forces acting in the radial direction. The opened positioning arches 10, 11 are then positioned in the pockets 50 of the native heart valve 51.

The other components of the endoprosthesis 1 and the medical device are then released through the introduction port of the introduction catheter system. As illustrated in FIG. 12b, the retaining arches 20, 21 open in the radial direction at the same time and thus cause the heart valve prosthesis 40 attached to the to the retaining arches 20, 21 by means of a thread 41, etc., for example, top open out in the manner of an umbrella. However, the radial forces acting on the retaining arches 20, 21 also act on the distal retaining region 2 of the endoprosthesis 1, causing the endoprosthesis 1 to be pressed in the radial direction against the vessel wall, which on the one hand guarantees a reliable anchoring of the medical device at the implantation site and on the other hand ensures a reliable seal of the heart valve prosthesis 40 at the proximal retaining region 3 of the endoprosthesis 1.

When the medical device is in the implanted state illustrated in FIG. 12b, the heart valve prosthesis 40 is opened out at the proximal retaining region 3 of the endoprosthesis 1 whilst the old (insufficient) heart valve 51 is pressed against the vessel wall due to the self-expanding property of the endoprosthesis 1. The distal retaining region of the endoprosthesis 1 affords additional mechanical support for the system and reliable anchoring.

As may specifically be seen from FIG. 12b, when the endoprosthesis 1 is in the expanded state, the respective positioning arms 21 of the positioning arches 20 locate in the pockets of the diseased heart valve and thus guarantee secure and error-free positioning of the medical device. The pocket flaps of the diseased heart valve are clamped between the positioning arches 10 and the retaining arches 20 due to the expansion of the endoprosthesis 1, which further assists in achieving optimum positioning and a stable anchoring of the heart valve prosthesis 40 disposed at the proximal retaining region 3 of the endoprosthesis 1. Optimum lateral sealing of the implanted valve prosthesis 40 is guaranteed at the same time.

The system is afforded additional mechanical support and reliable anchoring can also be achieved by providing barbs 17 on the fixing eyes 30 disposed at the distal retaining region 2 of the endoprosthesis 1 and/or by appropriate anchoring supports 25. When the endoprosthesis 1 is in the expanded state, the anchoring supports 25 stand proud of the co-operating arm 21 of the retaining arches 20, and their tips point in the direction of the distal end 2 of the endoprosthesis 1.

In principle, the special design of the endoprosthesis 1 offers the possibility of gripping the endoprosthesis 1 subsequently by means of the fixing eyes 30 and collapsing the medical device by the longitudinal extension of the endoprosthesis 1 so that the medical device can be removed from the patient's body again by means of a catheter tube.

Due to the modular integration of retaining elements (fixing eyes) on the self-expandable endoprosthesis 1, it can also be explanted again by means of a special catheter once it has been implanted. To this end, the distal retaining region 2 of the endoprosthesis 1 is pulled into a catheter by several retaining points using guide wires. This being the case, in the reverse of the implantation operation, the endoprosthesis 1 is pulled from its expanded state into the collapsed state and released from the anchoring in the packets of the actual heart valve.

In summary, it remains to be said that the solution proposed by the invention is based on a metal endoprosthesis 1 with a heart valve prosthesis which can be stitched to it or is stitched to it, designed for use in treating diseases of the heart valve which make replacement of the old heart valve necessary. The heart valve stent 1 (endoprosthesis) may be introduced in the inverted position and thus positioned orthotopically in vivo percutaneously and assume the function of the insufficient or defective native heart valve. The radial forces created due to the self-expanding property of the endoprosthesis 1 guarantee reliable anchoring in the region of the aorta.

Specifically, a medical instrument comprising an endoprosthesis 1 for positioning and securing a heart valve prosthesis in the aorta of the patient is described, and a specially developed endoprosthesis 1 made from a base of Nitinol is provided as a means of accommodating a heart valve prosthesis for implantation in the aorta. The ready-to-use medical device proposed by the invention consists of the components comprising the self-expandable Nitinol stent 1 with the valve-supporting segment 20, valve and system for introducing it to the desired site in the body.

In terms of design, the endoprosthesis 1 has three positioning arches for positioning and fixing the medical device in the vessel of the patient and retaining webs for accommodating/attaching the heart valve prosthesis by means of a thread, for example. From a functional point of view, the endoprosthesis 1 exerts high radial forces in its second mode to ensure that the medical device is anchored in the aorta. Eyes 30 are preferably provided on the distal retaining region of the endoprosthesis 1 or medical device, which can be releasably engaged with corresponding components of an introduction catheter system.

The material used to trigger the shape memory effect of the endoprosthesis has a switching temperature between 20° C. and 36° C. and is preferably 22° C. In the cooled state, therefore, the medical device can be introduced into the patient's body by means of a 21 F introduction system.

As regards the exact dimensions of the endoprosthesis 1, it is designed to accommodate heart valve prostheses with a valve diameter of 21 mm to 25 mm, in which case the distal retaining region 2 of the endoprosthesis 1 in particular has a diameter that is approximately 10% to 15% bigger than this in order to ensure that the medical device is reliably anchored.

The medical device proposed by the invention has an endoprosthesis which is readily visible by X-ray, which can be achieved by applying markers at the proximal and/or distal region of the endoprosthesis if necessary.

The materials used for the endoprosthesis 1 are materials that have been tried and tested for implantation purposes, for example Nitinol and Tantal. As regards the dimensions of the endoprosthesis, two different stent sizes are currently preferred, which are set out in the table below together with the diameter of the proximal retaining region and the distal retaining region.

| Stent size | Diameter of the proximal retaining region | Diameter of the distal retaining region |
|---|---|---|
| Stent No. 1 | 21 to 25 mm | 32 to 34 mm |
| Stent No. 2 | 26 to 31 mm | 35 to 38 mm |

By applying an appropriate finishing treatment, in particular tempering, other dimensions of the stent can be achieved—starting from the two currently preferred stent sizes.

The invention is not restricted to the features described in connection with the preferred embodiments illustrated in the drawings. All combinations of the features described in the specification would be conceivable.

The invention claimed is:

1. An endoprosthesis comprising:
a plurality of first arches configured to be respectively positioned within a plurality of pockets of a native heart valve on a first side of a plurality of native valve leaflets, each first arch having an apex oriented in a first direction and an open end joined to an open end of an adjacent first arch;
a plurality of second arches configured to be positioned on a second side of the plurality of native valve leaflets, such that the plurality of native valve leaflets are positioned radially inward of at least a portion of the plurality of first arches and radially outward of at least a portion of the plurality of second arches when the endoprosthesis is implanted; and
a prosthetic valve attached to the plurality of second arches such that at least part of the prosthetic valve extends from the plurality of second arches transversely across an interior of the endoprosthesis;
wherein the plurality of first arches are self-expandable independently of the plurality of second arches.

2. The endoprosthesis of claim 1, wherein the plurality of first arches includes exactly three first arches.

3. The endoprosthesis of claim 1, wherein each first arch of the plurality of first arches has a U-shaped structure.

4. The endoprosthesis of claim 1, wherein each second arch of the plurality of second arches has a V-shaped structure.

5. The endoprosthesis of claim 1, wherein the endoprosthesis includes exactly three first arches.

6. The endoprosthesis of claim 1, wherein the plurality of first arches is connected to the plurality of second arches by a plurality of connecting webs.

7. The endoprosthesis of claim 6, wherein each connecting web of the plurality of connecting webs is oriented in a longitudinal direction of the endoprosthesis and disposed between two adjacent first arches.

8. The endoprosthesis of claim 6, wherein the plurality of connecting webs includes exactly three connecting webs.

9. The endoprosthesis of claim 1, wherein the prosthetic valve is sutured directly to the plurality of second arches.

10. An endoprosthesis comprising:
a plurality of first arches configured to be respectively positioned within a plurality of pockets of a native heart valve on a first side of a plurality of native valve leaflets, each first arch having a U-shaped or V-shaped apex oriented in a first direction and an open end joined to an open end of an adjacent first arch;
a plurality of second arches configured to be positioned on a second side of the plurality of native valve leaflets, such that the plurality of native valve leaflets are positioned radially inward of at least a portion of the plurality of first arches and radially outward of at least a portion of the plurality of second arches when the endoprosthesis is implanted; and
a prosthetic valve attached to the plurality of second arches such that at least part of the prosthetic valve extends from the plurality of second arches transversely across an interior of the endoprosthesis;
wherein the plurality of first arches and the plurality of second arches each comprise a shape memory material, the plurality of first arches being self-expandable independently of the plurality of second arches.

11. The endoprosthesis of claim 10, wherein the endoprosthesis includes exactly three first arches.

12. The endoprosthesis of claim 10, wherein the open end of each first arch is joined to an open end of an adjacent first arch at a commis sure region of the endoprosthesis.

13. The endoprosthesis of claim 10, wherein the plurality of first arches is indirectly connected to the plurality of second arches.

14. The endoprosthesis of claim 13, wherein the plurality of first arches is connected to the plurality of second arches by three connecting webs.

15. The endoprosthesis of claim 10, wherein the plurality of second arches includes a pair of second arches having apices spaced apart along a longitudinal direction of the endoprosthesis.

16. The endoprosthesis of claim 15, wherein the plurality of second arches includes three pairs of second arches having apices spaced apart along a longitudinal direction of the endoprosthesis.

17. An endoprosthesis comprising:
a plurality of first arches configured to be respectively positioned within a plurality of pockets of a native heart valve on a first side of a plurality of native valve leaflets, each first arch having an apex oriented in a first direction and an open end joined to an open end of an adjacent first arch;
a plurality of second arches configured to be positioned on a second side of the plurality of native valve leaflets, such that the plurality of native valve leaflets are positioned radially inward of at least a portion of the plurality of first arches and radially outward of at least a portion of the plurality of second arches when the endoprosthesis is implanted; and a prosthetic valve sutured to the plurality of second arches such that at least part of the prosthetic valve extends from the plurality of second arches transversely across an interior of the endoprosthesis;

wherein the plurality of first arches is connected to the plurality of second arches by three connecting webs; and wherein the plurality of first arches are self-expandable independently of the plurality of second arches.

18. The endoprosthesis of claim 17, wherein each connecting web is oriented in a longitudinal direction of the endoprosthesis and disposed between two adjacent first arches.

19. The endoprosthesis of claim 17, wherein the apex of each first arch has a U-shaped or V-shaped structure.

20. The endoprosthesis of claim 17, wherein the plurality of second arches includes a pair of second arches having apices spaced apart along a longitudinal direction of the endoprosthesis.

* * * * *